United States Patent
Zhang et al.

(10) Patent No.: US 11,453,711 B2
(45) Date of Patent: Sep. 27, 2022

(54) FUSION PROTEINS OF GLP-1 AND GDF15 AND CONJUGATES THEREOF

(71) Applicant: BEIJING QL BIOPHARMACEUTICAL CO., LTD., Beijing (CN)

(72) Inventors: Yuanyuan Zhang, Beijing (CN); Haixia Zou, Beijing (CN); Xinyu Zhao, Beijing (CN); Yaoguang Jin, Beijing (CN); Xu Chen, Beijing (CN); Peng Zhai, Beijing (CN); Wei Guo, Beijing (CN)

(73) Assignee: BEIJING QL BIOPHARMACEUTICAL CO., LTD., Beijing (CN)

( * ) Notice: Subject to any disclaimer, the term of this patent is extended or adjusted under 35 U.S.C. 154(b) by 0 days.

(21) Appl. No.: 17/467,288

(22) Filed: Sep. 6, 2021

(65) Prior Publication Data

US 2022/0017589 A1    Jan. 20, 2022

Related U.S. Application Data

(63) Continuation-in-part of application No. PCT/CN2020/140532, filed on Dec. 29, 2020.

(30) Foreign Application Priority Data

Dec. 31, 2019 (WO) ............... PCT/CN2019/130668
Jul. 18, 2020 (WO) ............... PCT/CN2020/102884

(51) Int. Cl.
| | |
|---|---|
| *C07K 14/605* | (2006.01) |
| *C07K 14/475* | (2006.01) |
| *A61K 38/00* | (2006.01) |
| *A61K 47/64* | (2017.01) |

(52) U.S. Cl.
CPC ............ *C07K 14/605* (2013.01); *A61K 47/64* (2017.08); *C07K 14/475* (2013.01); *A61K 38/00* (2013.01)

(58) Field of Classification Search
None
See application file for complete search history.

(56) References Cited

U.S. PATENT DOCUMENTS

| | | |
|---|---|---|
| 5,208,020 A | 5/1993 | Chari et al. |
| 5,545,618 A | 8/1996 | Buckley et al. |
| 5,869,602 A | 2/1999 | Jonassen et al. |
| 6,191,102 B1 | 2/2001 | DiMarchi et al. |
| 6,268,343 B1 | 7/2001 | Knudsen et al. |
| 6,441,163 B1 | 8/2002 | Chari et al. |
| 6,458,924 B2 | 10/2002 | Knudsen et al. |
| 6,737,236 B1 | 5/2004 | Pieken et al. |
| 7,083,970 B2 | 8/2006 | Schultz et al. |
| 7,576,059 B2 | 8/2009 | Jonassen et al. |
| 8,067,554 B2 | 11/2011 | Staby |
| 8,097,698 B2 | 1/2012 | Knudsen et al. |
| 8,129,343 B2 | 3/2012 | Lau et al. |
| 8,445,433 B2 | 5/2013 | Werbitzky et al. |
| 8,536,122 B2 | 9/2013 | Lau et al. |
| 8,563,521 B2 | 10/2013 | Skerra et al. |
| 8,603,972 B2 | 12/2013 | Lau et al. |
| 8,648,041 B2 | 2/2014 | Garibay et al. |
| 8,791,236 B2 | 7/2014 | Christensen et al. |
| 8,815,802 B2 | 8/2014 | Kalthoff et al. |
| 8,895,694 B2 | 11/2014 | Spetzler et al. |
| 9,006,178 B2 | 4/2015 | Kofoed et al. |
| 9,040,480 B2 | 5/2015 | Werbitzky et al. |
| 9,067,977 B2 | 6/2015 | Spetzler et al. |
| 9,175,083 B2 | 11/2015 | Cho et al. |
| 9,266,940 B2 | 2/2016 | Wieczorek et al. |
| 9,409,966 B2 | 8/2016 | Spetzler et al. |
| 9,527,900 B2 | 12/2016 | Linderoth et al. |
| 9,556,250 B2 | 1/2017 | Garibay et al. |
| 9,708,383 B2 | 7/2017 | Madsen et al. |
| 9,732,137 B2 | 8/2017 | Lau et al. |
| 9,758,560 B2 | 9/2017 | Lau et al. |
| 9,797,908 B2 | 10/2017 | Deiters et al. |
| 9,938,331 B2 | 4/2018 | Schellenberger et al. |
| 9,956,264 B2 | 5/2018 | Shaw et al. |
| 10,000,542 B2 | 6/2018 | Kofoed et al. |
| 10,005,827 B2 | 6/2018 | Spetzler et al. |
| 10,010,614 B2 | 7/2018 | Reedtz-Runge et al. |
| 10,035,839 B2 | 7/2018 | Baldwin et al. |
| 10,308,700 B2 | 6/2019 | Lau et al. |
| 10,370,426 B2 | 8/2019 | Oh et al. |
| 10,400,020 B2 | 9/2019 | Oh et al. |
| 10,407,482 B2 | 9/2019 | Grabstein et al. |
| 10,421,798 B2 | 9/2019 | Schellenberger et al. |

(Continued)

FOREIGN PATENT DOCUMENTS

| | | | | |
|---|---|---|---|---|
| WO | WO 2019/048660 | * | 3/2019 | ............ A61K 38/19 |
| WO | 2020/084496 A1 | | 4/2020 | |

OTHER PUBLICATIONS

Bhattacharya et al., PLoS ONE 12(3): e0171355. https://doi.org/10.1371/journal.pone.0171355; 22 pages total (Year: 2017).*

(Continued)

*Primary Examiner* — Christina M Borgeest
(74) *Attorney, Agent, or Firm* — Jun He Law Offices P.C.; James J. Zhu

(57) ABSTRACT

The present disclosure provides fusion polypeptides comprising GLP-1 and GDF15, the polypeptide complexes, and the conjugates thereof. Pharmaceutical compositions comprising the same and methods of treating diseases are also provided.

26 Claims, 56 Drawing Sheets

Specification includes a Sequence Listing.

(56) References Cited

U.S. PATENT DOCUMENTS

| | | | |
|---|---|---|---|
| 10,548,953 B2 | 2/2020 | Liu et al. | |
| 10,604,554 B2 | 3/2020 | Kofoed et al. | |
| 10,610,568 B2 | 4/2020 | Matern et al. | |
| 10,669,323 B2 | 6/2020 | Boettcher et al. | |
| 10,844,135 B2 | 11/2020 | Chari et al. | |
| 10,869,909 B2 | 12/2020 | Lindhout et al. | |
| 10,953,073 B2 | 3/2021 | Schellenberger et al. | |
| 10,961,287 B2 | 3/2021 | Schellenberger et al. | |
| 11,034,746 B2 | 6/2021 | Wieczorek et al. | |
| 2003/0199672 A1 | 10/2003 | Knudsen et al. | |
| 2003/0224983 A1 | 12/2003 | Nielsen | |
| 2007/0203058 A1 | 8/2007 | Lau et al. | |
| 2009/0005312 A1 | 1/2009 | Hansen et al. | |
| 2010/0239554 A1 | 9/2010 | Schellenberger et al. | |
| 2010/0305032 A1 | 12/2010 | Lau et al. | |
| 2011/0166321 A1 | 7/2011 | Garibay et al. | |
| 2011/0312881 A1 | 12/2011 | Silverman et al. | |
| 2012/0004183 A1 | 1/2012 | Deiters et al. | |
| 2013/0040884 A1 | 2/2013 | Lau et al. | |
| 2013/0053315 A1 | 2/2013 | Lau et al. | |
| 2013/0244931 A1 | 9/2013 | Lau et al. | |
| 2014/0378665 A1 | 12/2014 | Xiong et al. | |
| 2015/0037359 A1 | 2/2015 | Schellenberger et al. | |
| 2015/0152157 A1 | 6/2015 | Kofoed et al. | |
| 2015/0210745 A1 | 7/2015 | Kofoed et al. | |
| 2015/0259431 A1 | 9/2015 | Stemmer et al. | |
| 2016/0108102 A1 | 4/2016 | Lau et al. | |
| 2016/0129083 A1* | 5/2016 | Shaw | C07K 14/475 514/4.8 |
| 2016/0158321 A1 | 6/2016 | Cleland et al. | |
| 2016/0237132 A1* | 8/2016 | Alvarez | A61P 9/00 |
| 2017/0145069 A1 | 5/2017 | Lau et al. | |
| 2018/0000962 A1 | 1/2018 | Eigenbrot, Jr. et al. | |
| 2018/0051063 A1 | 2/2018 | Cleland et al. | |
| 2018/0125988 A1 | 5/2018 | Yang et al. | |
| 2018/0251512 A1 | 9/2018 | Wieczorek et al. | |
| 2018/0291076 A1 | 10/2018 | Kjeldsen et al. | |
| 2018/0339057 A1* | 11/2018 | Gao | C07K 14/475 |
| 2019/0000923 A1 | 1/2019 | Chutkow et al. | |
| 2019/0025332 A1 | 1/2019 | Su et al. | |
| 2019/0085043 A1 | 3/2019 | Boscheinen et al. | |
| 2019/0153115 A1 | 5/2019 | Schellenberger et al. | |
| 2019/0169267 A1 | 6/2019 | Chhabra et al. | |
| 2019/0218269 A1 | 7/2019 | Oh et al. | |
| 2019/0292241 A1 | 9/2019 | Armstrong et al. | |
| 2019/0315822 A1 | 10/2019 | Xiong et al. | |
| 2020/0024318 A1 | 1/2020 | Kim et al. | |
| 2020/0079829 A1 | 3/2020 | Gao et al. | |
| 2020/0079834 A1 | 3/2020 | Wieczorek et al. | |
| 2020/0165314 A1 | 5/2020 | Lindhout et al. | |
| 2020/0181216 A1 | 6/2020 | Chopra et al. | |
| 2020/0197491 A1 | 6/2020 | Joergensen | |
| 2020/0231645 A1 | 7/2020 | Tornoee et al. | |
| 2020/0325200 A1 | 10/2020 | Xiong et al. | |
| 2020/0347149 A1 | 11/2020 | Doronina et al. | |
| 2020/0392195 A1 | 12/2020 | Schellenberger et al. | |
| 2021/0000964 A1 | 1/2021 | Barnes et al. | |
| 2021/0079051 A1 | 3/2021 | Xiong et al. | |
| 2021/0164011 A1 | 6/2021 | Schellenberger et al. | |
| 2021/0198331 A1 | 7/2021 | Zhang et al. | |

OTHER PUBLICATIONS

Fenton et al., Medicinal Chemistry Research (2020) 29:1133-1146 (Year: 2020).*

The website Medline Plus: https://medlineplus.gov/metabolicdisorders.html (Year: 2022).*

David Benton and Hayley A. Young, Perspectives on Psychological Science 2017, vol. 12(5) 703-714 (Year: 2017).*

* cited by examiner

Linkers with 80 amino acid residues

| SEQ ID NO | Sequence |
|---|---|
| 1 | GQEPGAQPGQEPGAQPGAQPGAQPGAQPGAQPGAQPGAQPGAQPGAQPGAQPGAQPGAQPGAQPGAQPGAQPGAQPGAQP |
| 2 | GQEPGAQPGQEPGAQPGQEPGAQPGAQPGAQPGAQPGAQPGAQPGAQPGAQPGAQPGAQPGAQPGAQPGAQPGAQPGAQP |
| 3 | GQEPGAQPGQEPGAQPGQEPGAQPGQEPGAQPGAQPGAQPGAQPGAQPGAQPGAQPGAQPGAQPGAQPGAQPGAQPGAQP |
| 4 | GQEPGAQPGQEPGAQPGQEPGAQPGQEPGAQPGQEPGAQPGAQPGAQPGAQPGAQPGAQPGAQPGAQPGAQPGAQPGAQP |
| 5 | GQEPGAQPGQEPGAQPGQEPGAQPGQEPGAQPGQEPGAQPGQEPGAQPGAQPGAQPGAQPGAQPGAQPGAQPGAQPGAQP |
| 6 | GQEPGAQPGQEPGAQPGQEPGAQPGQEPGAQPGQEPGAQPGQEPGAQPGQEPGAQPGAQPGAQPGAQPGAQPGAQPGAQP |
| 7 | GQEPGAQPGQEPGAQPGQEPGAQPGQEPGAQPGQEPGAQPGQEPGAQPGQEPGAQPGQEPGAQPGAQPGAQPGAQPGAQP |
| 8 | GQEPGAQPGQEPGAQPGQEPGAQPGQEPGAQPGQEPGAQPGQEPGAQPGQEPGAQPGQEPGAQPGQEPGAQPGAQPGAQP |
| 9 | GQEPGAQPGQEPGAQPGQEPGAQPGQEPGAQPGQEPGAQPGQEPGAQPGQEPGAQPGQEPGAQPGQEPGAQPGQEPGAQP |
| 10 | GQEPGQEPGQEPGQEPGQEPGQEPGQEPGQEPGQEPGQEPGQEPGQEPGQEPGQEPGAQPGAQPGAQPGAQP |
| 11 | GQEPGQEPGQEPGQEPGQEPGQEPGQEPGQEPGQEPGQEPGQEPGQEPGQEPGAQPGAQPGAQPGAQPGAQP |
| 12 | GQEPGQEPGQEPGQEPGQEPGQEPGQEPGQEPGQEPGQEPGQEPGQEPGAQPGAQPGAQPGAQPGAQPGAQP |
| 13 | GQEPGQEPGQEPGQEPGQEPGQEPGQEPGQEPGQEPGQEPGQEPGAQPGAQPGAQPGAQPGAQPGAQPGAQP |
| 14 | GQEPGQEPGQEPGQEPGQEPGQEPGQEPGQEPGQEPGQEPGAQPGAQPGAQPGAQPGAQPGAQPGAQPGAQP |
| 15 | GQEPGQEPGQEPGQEPGQEPGQEPGQEPGQEPGQEPGQEPGAQPGAQPGAQPGAQPGAQPGAQPGAQPGAQP |
| 16 | GQEPGQEPGQEPGQEPGQEPGQEPGQEPGQEPGQEPGAQPGAQPGAQPGAQPGAQPGAQPGAQPGAQPGAQP |
| 17 | GQEPGQEPGQEPGQEPGQEPGQEPGQEPGQEPGAQPGAQPGAQPGAQPGAQPGAQPGAQPGAQPGAQPGAQP |
| 18 | GQEPGQEPGQEPGQEPGQEPGQEPGQEPGAQPGAQPGAQPGAQPGAQPGAQPGAQPGAQPGAQPGAQPGAQP |
| 19 | GQEPGQEPGQEPGQEPGQEPGQEPGAQPGAQPGAQPGAQPGAQPGAQPGAQPGAQPGAQPGAQPGAQPGAQP |
| 20 | GQEPGQEPGQEPGQEPGQEPGAQPGAQPGAQPGAQPGAQPGAQPGAQPGAQPGAQPGAQPGAQPGAQPGAQP |
| 21 | GQEPGQEPGQEPGQEPGAQPGAQPGAQPGAQPGAQPGAQPGAQPGAQPGAQPGAQPGAQPGAQPGAQPGAQP |

Fig. 11A

| | |
|---|---|
| 22 | GQEPGQEPGQEPGQEPGAQPGAQPGAQPGAQPGAQPGAQPGAQPG AQPGAQPGAQPGAQPGAQPGAQPGAQPGAQPGAQPGAQP |
| 23 | GQEPGQEPGQEPGAQPGAQPGAQPGAQPGAQPGAQPGAQPGAQPG AQPGAQPGAQPGAQPGAQPGAQPGAQPGAQPGAQP |
| 24 | GQEPGQEPGAQPGAQPGAQPGAQPGAQPGAQPGAQPGAQPGAQPG AQPGAQPGAQPGAQPGAQPGAQPGAQPGAQP |
| 25 | GAQPGAQPGAQPGAQPGQEPGQEPGQEPGQEPGQEPGQEPG QEPGQEPGQEPGQEPGQEPGQEPGQEPGQEP |
| 26 | GAQPGAQPGAQPGAQPGAQPGQEPGQEPGQEPGQEPGQEPG QEPGQEPGQEPGQEPGQEPGQEPGQEPGQEP |
| 27 | GAQPGAQPGAQPGAQPGAQPGAQPGQEPGQEPGQEPGQEPG QEPGQEPGQEPGQEPGQEPGQEPGQEPGQEP |
| 28 | GAQPGAQPGAQPGAQPGAQPGAQPGAQPGQEPGQEPGQEPG QEPGQEPGQEPGQEPGQEPGQEPGQEPGQEP |
| 29 | GAQPGAQPGAQPGAQPGAQPGAQPGAQPGAQPGQEPGQEPG QEPGQEPGQEPGQEPGQEPGQEPGQEPGQEP |
| 30 | GAQPGAQPGAQPGAQPGAQPGAQPGAQPGAQPGAQPGQEPG QEPGQEPGQEPGQEPGQEPGQEPGQEPGQEP |
| 31 | GAQPGAQPGAQPGAQPGAQPGAQPGAQPGAQPGAQPGAQPGQEPG QEPGQEPGQEPGQEPGQEPGQEPGQEPGQEP |
| 32 | GAQPGAQPGAQPGAQPGAQPGAQPGAQPGAQPGAQPGAQPG QEPGQEPGQEPGQEPGQEPGQEPGQEPGQEP |
| 33 | GAQPGAQPGAQPGAQPGAQPGAQPGAQPGAQPGAQPGAQPGAQPG AQPGQEPGQEPGQEPGQEPGQEPGQEPGQEPGQEP |
| 34 | GAQPGAQPGAQPGAQPGAQPGAQPGAQPGAQPGAQPGAQPGAQPG AQPGAQPGQEPGQEPGQEPGQEPGQEPGQEPGQEP |
| 35 | GAQPGAQPGAQPGAQPGAQPGAQPGAQPGAQPGAQPGAQPG AQPGAQPGAQPGQEPGQEPGQEPGQEPGQEPGQEP |
| 36 | GAQPGAQPGAQPGAQPGAQPGAQPGAQPGAQPGAQPGAQPGAQPG AQPGAQPGAQPGAQPGQEPGQEPGQEPGQEPGQEP |
| 37 | GAQPGAQPGAQPGAQPGAQPGAQPGAQPGAQPGAQPGAQPGAQPG AQPGAQPGAQPGAQPGAQPGQEPGQEPGQEPGQEP |
| 38 | GAQPGAQPGAQPGAQPGAQPGAQPGAQPGAQPGAQPGAQPGAQPG AQPGAQPGAQPGAQPGAQPGAQPGQEPGQEPGQEP |
| 39 | GAQPGAQPGAQPGAQPGAQPGAQPGAQPGAQPGAQPGAQPGAQPG AQPGAQPGAQPGAQPGAQPGAQPGAQPGQEPGQEP |
| 40 | GAQPGAQPGAQPGAQPGAQPGAQPGAQPGAQPGAQPGAQPGAQPG AQPGAQPGAQPGAQPGAQPGQEPGAQPGQEPGAQP |
| 41 | GAQPGAQPGAQPGAQPGAQPGAQPGAQPGAQPGAQPGAQPGAQPG AQPGAQPGAQPGQEPGAQPGQEPGAQPGQEPGAQP |
| 42 | GAQPGAQPGAQPGAQPGAQPGAQPGAQPGAQPGAQPGAQPGAQPG AQPGQEPGAQPGQEPGAQPGQEPGAQPGQEPGAQP |
| 43 | GAQPGAQPGAQPGAQPGAQPGAQPGAQPGAQPGAQPGAQPGQEPG AQPGQEPGAQPGQEPGAQPGQEPGAQPGQEPGAQP |
| 44 | GAQPGAQPGAQPGAQPGAQPGAQPGAQPGAQPGQEPGAQPGQEPG AQPGQEPGAQPGQEPGAQPGQEPGAQPGQEPGAQP |
| 45 | GAQPGAQPGAQPGAQPGAQPGAQPGQEPGAQPGQEPGAQPGQEPG AQPGQEPGAQPGQEPGAQPGQEPGAQPGQEPGAQP |

Fig. 11A Continued

| | |
|---|---|
| 46 | GAQPGAQPGAQPGAQPGQEPGAQPGQEPGAQPGQEPGAQPGQEPG AQPGQEPGAQPGQEPGAQPGQEPGAQPGQEPGAQP |
| 47 | GAQPGAQPGQEPGAQPGQEPGAQPGQEPGAQPGQEPGAQPGQEPG AQPGQEPGAQPGQEPGAQPGQEPGAQPGQEPGAQP |
| 48 | GAQPGQEPGAQPGAQPGQEPGAQPGAQPGQEPGAQPGAQPGQEPG AQPGAQPGQEPGAQPGAQPGQEPGAQPGAQPGAQP |
| 49 | GAQPGAQPGQEPGAQPGAQPGQEPGAQPGAQPGQEPGAQPGAQPG QEPGAQPGAQPGQEPGAQPGAQPGQEPGAQPGAQP |
| 50 | GAQPGQEPGAQPGAQPGQEPGAQPGAQPGQEPGAQPGAQPGQEPG AQPGAQPGQEPGAQPGAQPGAQPGAQPGAQPGAQP |
| 51 | GAQPGAQPGAQPGAQPGAQPGAQPGAQPGAQPGAQPGAQPGQEPG QEPGQEPGQEPGQEPGQEPGQEPGAQPGAQP |
| 52 | GAQPGAQPGAQPGAQPGAQPGAQPGAQPGAQPGAQPGAQPGAQPG QEPGQEPGQEPGQEPGQEPGQEPGAQPGAQP |
| 53 | GAQPGAQPGAQPGAQPGAQPGAQPGAQPGAQPGAQPGAQPGAQPG AQPGQEPGQEPGQEPGQEPGQEPGQEPGAQPGAQP |
| 54 | GAQPGAQPGAQPGAQPGAQPGAQPGAQPGAQPGAQPGAQPGAQPG AQPGAQPGQEPGQEPGQEPGQEPGQEPGAQPGAQP |
| 55 | GAQPGAQPGAQPGAQPGAQPGAQPGAQPGAQPGAQPGAQPGAQPG AQPGAQPGAQPGQEPGQEPGQEPGQEPGAQPGAQP |
| 56 | GAQPGAQPGAQPGAQPGAQPGAQPGAQPGAQPGAQPGAQPGAQPG AQPGAQPGAQPGAQPGQEPGQEPGQEPGAQPGAQP |
| 57 | GAQPGAQPGAQPGAQPGAQPGAQPGAQPGAQPGAQPGAQPGAQPG AQPGAQPGAQPGAQPGAQPGQEPGQEPGAQPGAQP |
| 58 | GAQPGAQPGAQPGAQPGAQPGAQPGAQPGAQPGQEPGAQPGQEPG AQPGQEPGQEPGQEPGQEPGQEPGQEPGAQPGAQP |
| 59 | GAQPGAQPGAQPGAQPGAQPGAQPGAQPGAQPGAQPGAQPGQEPG AQPGQEPGQEPGQEPGQEPGQEPGQEPGAQPGAQP |
| 61 | GAQPGAQPGAQPGAQPGAQPGAQPGAQPGAQPGAQPGAQPGAQPG AQPGAQPGQEPGQEPGQEPGQEPGQEPGAQPGAQP |
| 62 | GAQPGAQPGAQPGAQPGAQPGAQPGQEPGAQPGQEPGAQPGQEPG AQPGQEPGQEPGQEPGQEPGQEPGQEPGAQPGAQP |
| 63 | GAQPGAQPGAQPGAQPGQEPGAQPGQEPGAQPGQEPGAQPGQEPG AQPGQEPGQEPGQEPGQEPGQEPGQEPGAQPGAQP |
| 64 | GAQPGAQPGAQPGAQPGAQPGAQPGAQPGAQPGAQPGQEPGAQPG QEPGQEPGQEPGQEPGQEPGQEPGQEPGAQPGAQP |
| 65 | SEPATSGSETPGTSESATPESGPGTSTEPSEGGAQPGAQPGAQPGAQP GAQPGAQPGAQPGAQPGAQPGAQPGAQPGAQP |
| 66 | SEPATSGSETPGTSESATPESGPGTSTEPSEGGQEPGAQPGAQPGAQP GAQPGAQPGAQPGAQPGAQPGAQPGAQPGAQP |
| 67 | SEPATSGSETPGTSESATPESGPGTSTEPSEGGQEPGQEPGAQPGAQP GAQPGAQPGAQPGAQPGAQPGAQPGAQPGAQP |
| 68 | SEPATSGSETPGTSESATPESGPGTSTEPSEGGQEPGQEPGQEPGAQP GAQPGAQPGAQPGAQPGAQPGAQPGAQPGAQP |
| 69 | SEPATSGSETPGTSESATPESGPGTSTEPSEGGQEPGQEPGQEPGQEP GAQPGAQPGAQPGAQPGAQPGAQPGAQPGAQP |
| 70 | SEPATSGSETPGTSESATPESGPGTSTEPSEGGQEPGQEPGQEPGQEP GQEPGAQPGAQPGAQPGAQPGAQPGAQPGAQP |

Fig. 11A Continued

| | |
|---|---|
| 71 | SEPATSGSETPGTSESATPESGPGTSTEPSEGGQEPGQEPGQEPGQEP GQEPGQEPGAQPGAQPGAQPGAQPGAQPGAQP |
| 72 | SEPATSGSETPGTSESATPESGPGTSTEPSEGGQEPGQEPGQEPGQEP GQEPGQEPGQEPGAQPGAQPGAQPGAQPGAQP |
| 73 | SEPATSGSETPGTSESATPESGPGTSTEPSEGGQEPGQEPGQEPGQEP GQEPGQEPGQEPGQEPGAQPGAQPGAQPGAQP |
| 74 | SEPATSGSETPGTSESATPESGPGTSTEPSEGGQEPGQEPGQEPGQEP GQEPGQEPGQEPGQEPGQEPGAQPGAQPGAQP |
| 75 | SEPATSGSETPGTSESATPESGPGTSTEPSEGGQEPGQEPGQEPGQEP GQEPGQEPGQEPGQEPGQEPGQEPGAQPGAQP |
| 76 | SEPATSGSETPGTSESATPESGPGTSTEPSEGGQEPGQEPGQEPGQEP GQEPGQEPGQEPGQEPGQEPGQEPGQEPGAQP |
| 77 | SEPATSGSETPGTSESATPESGPGTSTEPSEGGQEPGQEPGQEPGQEP GQEPGQEPGQEPGQEPGQEPGQEPGQEPGQEP |
| 78 | SEPATSGSETPGTSESATPESGPGTSTEPSEGGAQPGAQPGAQPGAQP GAQPGAQPGAQPGAQPGAQPGAQPGAQPGQEP |
| 79 | SEPATSGSETPGTSESATPESGPGTSTEPSEGGAQPGAQPGAQPGAQP GAQPGAQPGAQPGAQPGAQPGAQPGQEPGQEP |
| 80 | SEPATSGSETPGTSESATPESGPGTSTEPSEGGAQPGAQPGAQPGAQP GAQPGAQPGAQPGAQPGAQPGQEPGQEPGQEP |
| 81 | SEPATSGSETPGTSESATPESGPGTSTEPSEGGAQPGAQPGAQPGAQP GAQPGAQPGAQPGAQPGQEPGQEPGQEPGQEP |
| 82 | SEPATSGSETPGTSESATPESGPGTSTEPSEGGAQPGAQPGAQPGAQP GAQPGAQPGAQPGQEPGQEPGQEPGQEPGQEP |
| 83 | SEPATSGSETPGTSESATPESGPGTSTEPSEGGAQPGAQPGAQPGAQP GAQPGAQPGQEPGQEPGQEPGQEPGQEPGQEP |
| 84 | SEPATSGSETPGTSESATPESGPGTSTEPSEGGAQPGAQPGAQPGAQP GAQPGQEPGQEPGQEPGQEPGQEPGQEPGQEP |
| 85 | SEPATSGSETPGTSESATPESGPGTSTEPSEGGAQPGAQPGAQPGAQP GQEPGQEPGQEPGQEPGQEPGQEPGQEPGQEP |
| 86 | SEPATSGSETPGTSESATPESGPGTSTEPSEGGAQPGAQPGAQPGQEP GQEPGQEPGQEPGQEPGQEPGQEPGQEPGQEP |
| 87 | SEPATSGSETPGTSESATPESGPGTSTEPSEGGAQPGAQPGQEPGQEP GQEPGQEPGQEPGQEPGQEPGQEPGQEPGQEP |
| 88 | SEPATSGSETPGTSESATPESGPGTSTEPSEGGAQPGQEPGQEPGQEP GQEPGQEPGQEPGQEPGQEPGQEPGQEPGQEP |
| 90 | GAQPGQEPGAQPGQEPGAQPGQEPGAQPGQEPGAQPGQEPGAQPG QEPGAQPGAQPGAQPGAQPGAQPGAQPGAQPGAQP |
| 91 | GAQPGQEPGAQPGQEPGAQPGQEPGAQPGQEPGAQPGQEPGAQPG QEPGAQPGQEPGAQPGAQPGAQPGAQPGAQPGAQP |
| 92 | GAQPGQEPGAQPGQEPGAQPGQEPGAQPGQEPGAQPGQEPGAQPG QEPGAQPGQEPGAQPGQEPGAQPGAQPGAQPGAQP |
| 93 | GAQPGQEPGAQPGQEPGAQPGQEPGAQPGQEPGAQPGQEPGAQPG QEPGAQPGQEPGAQPGQEPGAQPGQEPGAQPGAQP |
| 454 | GQEPGAQPGQEPGAQPGQEPGAQPGQEPGAQPGQEPGAQPGQEPG AQPGQAPGAQPGAQPGAQPGAQPGAQPGAQPGAQP |
| 455 | GQEPGAQPGQEPGAQPGQEPGAQPGQEPGAQPGQEPGAQPGQAPGQEPG AQPGAQPGAQPGAQPGAQPGAQPGAQPGAQPGAQP |

Fig. 11A Continued

| 456 | GAQPGAQPGAQPGAQPGAQPGAQPGAQPGAQPGQEPGQAPGQEPGAQPGQEPGAQPGQEPGAQPGQEPGAQPGQEPGAQP |
|---|---|
| 457 | GQEPGAQPGQEPGAQPGQEPGAQPGQEPGQAPGQEPGAQPGQEPGAQPGAQPGAQPGAQPGAQPGAQPGAQPGAQP |
| 463 | GQEPGAQPGQEPGAQPGQEPGAQPGQEPGAQPGAQPGAQPGQAPGQEPGAQPGAQPGAQPGAQPGAQPGAQPGAQPGAQP |
| 464 | GAQPGAQPGAQPGAQPGQAPGAQPGAQPGAQPGQEPGAQPGQEPGAQPGQEPGAQPGQEPGAQPGQEPGAQPGQEPGAQP |
| 465 | GAQPGAQPGAQPGAQPGAQPGQAPGAQPGAQPGQEPGAQPGQEPGAQPGQEPGAQPGQEPGAQPGQEPGAQPGQEPGAQP |
| 466 | GAQPGAQPGAQPGAQPGAQPGAQPGQAPGAQPGQEPGAQPGQEPGAQPGQEPGAQPGQEPGAQPGQEPGAQPGQEPGAQP |
| 467 | GAQPGAQPGAQPGAQPGAQPGAQPGAQPGAQPGQEPGAQPGQEPGQAPGQEPGQAPGQEPGQAPGQEPGQAPGQEPGQAP |
| 468 | GAQPGAQPGAQPGAQPGAQPGAQPGAQPGAQPGQEPGAQPGQEPGAQPGQAPGQEPGQEPGQAPGQEPGQAPGQEPGQAP |
| 469 | GAQPGAQPGAQPGAQPGAQPGAQPGAQPGAQPGQEPGQAPGQEPGQAPGQEPGQAPGQEPGQAPGQEPGQAPGQEPGQAP |
| 470 | GAQPGQAPGAQPGAQPGAQPGAQPGAQPGAQPGQEPGAQPGQEPGAQPGQEPGAQPGQEPGAQPGQEPGAQPGQEPGAQP |
| 471 | GAQPGAQPGAQPGAQPGAQPGAQPGAQPGAQPGQEPGAQPGQEPGAQPGQEPGAQPGQEPGAQPGQEPGAQPGQEPGQAP |

Fig. 11A Continued

Linkers with 60 amino acids

| SEQ ID NO | Sequence |
|---|---|
| 94 | GQEPGQEPGQEPGQEPGQEPGQEPGQEPGQEPGQEPGQEPGQEPGQEPGQEPGQEP |
| 95 | GQEPGQEPGQEPGQEPGQEPGQEPGQEPGQEPGQEPGQEPGQEPGQEPGQEPGAQP |
| 96 | GQEPGQEPGQEPGQEPGQEPGQEPGQEPGQEPGQEPGQEPGQEPGQEPGAQPGAQP |
| 97 | GQEPGQEPGQEPGQEPGQEPGQEPGQEPGQEPGQEPGQEPGQEPGAQPGAQPGAQP |
| 98 | GQEPGQEPGQEPGQEPGQEPGQEPGQEPGQEPGQEPGQEPGAQPGAQPGAQPGAQP |
| 99 | GQEPGQEPGQEPGQEPGQEPGQEPGQEPGQEPGQEPGAQPGAQPGAQPGAQPGAQP |
| 100 | GQEPGQEPGQEPGQEPGQEPGQEPGQEPGQEPGAQPGAQPGAQPGAQPGAQPGAQP |
| 101 | GQEPGQEPGQEPGQEPGQEPGQEPGQEPGAQPGAQPGAQPGAQPGAQPGAQPGAQP |
| 102 | GQEPGQEPGQEPGQEPGQEPGQEPGAQPGAQPGAQPGAQPGAQPGAQPGAQPGAQP |
| 103 | GQEPGQEPGQEPGQEPGQEPGAQPGAQPGAQPGAQPGAQPGAQPGAQPGAQPGAQP |

Fig. 11B

| | |
|---|---|
| 104 | GQEPGQEPGQEPGQEPGQEPGAQPGAQPGAQPGAQPGAQPGAQPGAQPGAQPGAQPGAQP |
| 105 | GQEPGQEPGQEPGQEPGAQPGAQPGAQPGAQPGAQPGAQPGAQPGAQPGAQPGAQP |
| 106 | GQEPGQEPGQEPGAQPGAQPGAQPGAQPGAQPGAQPGAQPGAQPGAQPGAQPGAQP |
| 107 | GQEPGQEPGAQPGAQPGAQPGAQPGAQPGAQPGAQPGAQPGAQPGAQPGAQPGAQP |
| 108 | GQEPGAQPGQEPGAQPGQEPGAQPGQEPGAQPGQEPGAQPGQEPGAQPGQEPGAQPGQEP |
| 109 | GQEPGAQPGQEPGAQPGQEPGAQPGQEPGAQPGQEPGAQPGQEPGAQPGQEPGQEPGQEPGQEP |
| 110 | GQEPGAQPGQEPGAQPGQEPGAQPGQEPGAQPGQEPGAQPGQEPGAQPGQEPGQEPGQEPGQEP |
| 111 | GQEPGAQPGQEPGAQPGQEPGAQPGQEPGAQPGQEPGAQPGQEPGQEPGQEPGQEPGQEP |
| 112 | GQEPGAQPGQEPGAQPGQEPGAQPGQEPGQEPGQEPGQEPGQEPGQEPGQEPGQEP |
| 113 | GQEPGAQPGQEPGAQPGQEPGQEPGQEPGQEPGQEPGQEPGQEPGQEPGQEPGQEP |
| 114 | GQEPGAQPGQEPGQEPGQEPGQEPGQEPGQEPGQEPGQEPGQEPGQEPGQEPGQEP |
| 115 | GQEPGAQPGQEPGAQPGQEPGAQPGQEPGAQPGQEPGAQPGQEPGAQPGQEPGAQPGAQP |
| 116 | GQEPGAQPGQEPGAQPGQEPGAQPGQEPGAQPGQEPGAQPGQEPGAQPGQEPGAQPGAQPGAQP |
| 117 | GQEPGAQPGQEPGAQPGQEPGAQPGQEPGAQPGQEPGAQPGQEPGAQPGAQPGAQPGAQPGAQP |
| 118 | GQEPGAQPGQEPGAQPGQEPGAQPGQEPGAQPGQEPGAQPGAQPGAQPGAQPGAQPGAQPGAQP |
| 119 | GQEPGAQPGQEPGAQPGQEPGAQPGQEPGAQPGAQPGAQPGAQPGAQPGAQPGAQPGAQPGAQP |
| 120 | GQEPGAQPGQEPGAQPGAQPGAQPGAQPGAQPGAQPGAQPGAQPGAQPGAQPGAQPGAQP |
| 121 | GAQPGAQPGAQPGAQPGAQPGQEPGQEPGQEPGQEPGQEPGQEPGQEPGAQPGAQP |
| 122 | GAQPGAQPGAQPGAQPGAQPGAQPGQEPGQEPGQEPGQEPGQEPGQEPGAQPGAQP |
| 123 | GAQPGAQPGAQPGAQPGAQPGAQPGAQPGQEPGQEPGQEPGQEPGQEPGAQPGAQP |
| 124 | GAQPGAQPGAQPGAQPGAQPGAQPGAQPGAQPGQEPGQEPGQEPGQEPGAQPGAQP |
| 125 | GAQPGAQPGAQPGQEPGAQPGQEPGAQPGQEPGQEPGQEPGQEPGQEPGAQPGAQP |
| 126 | GAQPGQEPGAQPGQEPGAQPGQEPGAQPGQEPGQEPGQEPGQEPGQEPGAQPGAQP |
| 127 | GAQPGQEPGAQPGQEPGAQPGQEPGAQPGQEPGQEPGQEPGQEPGQEPGQEPGAQPGAQP |

Fig. 11B Continued

| | |
|---|---|
| 128 | GAQPGQEPGAQPGQEPGAQPGQEPGAQPGQEPGAQPGQEPGAQPGQEPGQEPGAQPGAQP |
| 129 | GAQPGAQPGAQPGAQPGQEPGAQPGQEPGQEPGQEPGQEPGQEPGQEPGAQPGAQP |
| 130 | GAQPGQEPGQEPGQEPGQEPGQEPGQEPGQEPGQEPGQEPGQEPGQEPGQEPGQEP |
| 131 | GAQPGAQPGQEPGQEPGQEPGQEPGQEPGQEPGQEPGQEPGQEPGQEPGQEPGQEP |
| 132 | GAQPGAQPGAQPGQEPGQEPGQEPGQEPGQEPGQEPGQEPGQEPGQEPGQEPGQEP |
| 133 | GAQPGAQPGAQPGAQPGQEPGQEPGQEPGQEPGQEPGQEPGQEPGQEPGQEPGQEP |
| 134 | GAQPGAQPGAQPGAQPGAQPGQEPGQEPGQEPGQEPGQEPGQEPGQEPGQEPGQEP |
| 135 | GAQPGAQPGAQPGAQPGAQPGAQPGQEPGQEPGQEPGQEPGQEPGQEPGQEPGQEP |
| 136 | GAQPGAQPGAQPGAQPGAQPGAQPGAQPGQEPGQEPGQEPGQEPGQEPGQEPGQEP |
| 137 | GAQPGAQPGAQPGAQPGAQPGAQPGAQPGAQPGQEPGQEPGQEPGQEPGQEPGQEP |
| 138 | GAQPGAQPGAQPGAQPGAQPGAQPGAQPGAQPGAQPGQEPGQEPGQEPGQEPGQEP |
| 139 | GAQPGAQPGAQPGAQPGAQPGAQPGAQPGAQPGAQPGAQPGQEPGQEPGQEPGQEP |
| 140 | GAQPGAQPGAQPGAQPGAQPGAQPGAQPGAQPGAQPGAQPGAQPGQEPGQEPGQEP |
| 141 | GAQPGAQPGAQPGAQPGAQPGAQPGAQPGAQPGAQPGAQPGAQPGAQPGQEPGQEPGQEP |
| 142 | GAQPGAQPGAQPGAQPGAQPGAQPGAQPGAQPGAQPGAQPGAQPGAQPGAQPGQEPGQEP |
| 143 | GAQPGQEPGAQPGQEPGAQPGQEPGAQPGQEPGAQPGQEPGAQPGQEPGAQPGQEPGQEP |
| 144 | GAQPGQEPGAQPGQEPGAQPGQEPGAQPGQEPGAQPGQEPGAQPGQEPGQEPGQEP |
| 145 | GAQPGQEPGAQPGQEPGAQPGQEPGAQPGQEPGAQPGQEPGQEPGQEPGQEPGQEP |
| 146 | GAQPGQEPGAQPGQEPGAQPGQEPGAQPGQEPGAQPGQEPGAQPGQEPGAQPGQEPGAQP |
| 147 | GAQPGQEPGAQPGQEPGAQPGQEPGAQPGQEPGAQPGQEPGAQPGQEPGAQPGAQPGAQP |
| 148 | GAQPGQEPGAQPGQEPGAQPGQEPGAQPGQEPGAQPGQEPGAQPGQEPGAQPGAQPGAQPGAQP |
| 149 | SEPATSGSETPGTSESATPESGPGTSTEPSEGGAQPGAQPGAQPGAQPGAQPGAQPGAQP |
| 150 | SEPATSGSETPGTSESATPESGPGTSTEPSEGGQEPGAQPGAQPGAQPGAQPGAQPGAQP |
| 151 | SEPATSGSETPGTSESATPESGPGTSTEPSEGGQEPGQEPGAQPGAQPGAQPGAQPGAQP |

Fig. 11B Continued

| SEQ ID NO | Sequence |
|---|---|
| 152 | SEPATSGSETPGTSESATPESGPGTSTEPSEGGQEPGQEPGQEPGAQPGAQPGAQPGAQP |
| 153 | SEPATSGSETPGTSESATPESGPGTSTEPSEGGQEPGQEPGQEPGQEPGAQPGAQPGAQP |
| 154 | SEPATSGSETPGTSESATPESGPGTSTEPSEGGQEPGQEPGQEPGQEPGQEPGAQPGAQP |
| 155 | SEPATSGSETPGTSESATPESGPGTSTEPSEGGQEPGQEPGQEPGQEPGQEPGQEPGAQP |
| 156 | SEPATSGSETPGTSESATPESGPGTSTEPSEGGQEPGQEPGQEPGQEPGQEPGQEPGQEP |

Fig. 11B Continued

Linkers with 40 amino acids

| SEQ ID NO | Sequence |
|---|---|
| 157 | GQEPGQEPGQEPGQEPGQEPGQEPGQEPGQEPGAQPGAQP |
| 158 | GQEPGAQPGQEPGAQPGQEPGAQPGQEPGAQPGQEPGQEP |
| 159 | GQEPGQEPGQEPGQEPGQEPGQEPGQEPGQEPGQEPGQEP |
| 160 | GQEPGQEPGQEPGQEPGQEPGQEPGQEPGQEPGQEPGAQP |
| 161 | GQEPGQEPGQEPGQEPGQEPGQEPGQEPGAQPGAQPGAQP |
| 162 | GQEPGQEPGQEPGQEPGQEPGQEPGAQPGAQPGAQPGAQP |
| 163 | GQEPGQEPGQEPGQEPGQEPGAQPGAQPGAQPGAQPGAQP |
| 164 | GQEPGQEPGQEPGQEPGAQPGAQPGAQPGAQPGAQPGAQP |
| 165 | GQEPGQEPGQEPGAQPGAQPGAQPGAQPGAQPGAQPGAQP |
| 166 | GQEPGQEPGAQPGAQPGAQPGAQPGAQPGAQPGAQPGAQP |
| 167 | GQEPGAQPGQEPGAQPGQEPGAQPGQEPGAQPGQEPGAQP |
| 168 | GQEPGAQPGQEPGAQPGQEPGAQPGQEPGQEPGQEPGQEP |
| 169 | GQEPGAQPGQEPGAQPGQEPGQEPGQEPGQEPGQEPGQEP |
| 170 | GQEPGAQPGQEPGQEPGQEPGQEPGQEPGQEPGQEPGQEP |
| 171 | GAQPGQEPGQEPGQEPGQEPGQEPGQEPGQEPGQEPGQEP |
| 172 | GAQPGAQPGQEPGQEPGQEPGQEPGQEPGQEPGQEPGQEP |
| 173 | GAQPGAQPGAQPGQEPGQEPGQEPGQEPGQEPGQEPGQEP |

Fig. 11C

| 174 | GAQPGAQPGAQPGAQPGQEPGQEPGQEPGQEPGQEP |
| --- | --- |
| 175 | GAQPGAQPGAQPGAQPGAQPGQEPGQEPGQEPGQEP |
| 176 | GAQPGAQPGAQPGAQPGAQPGAQPGQEPGQEPGQEP |
| 177 | GAQPGAQPGAQPGAQPGAQPGAQPGAQPGQEPGQEP |
| 178 | GAQPGAQPGAQPGAQPGAQPGAQPGAQPGAQPGQEP |
| 179 | GAQPGQEPGQEPGQEPGQEPGQEPGQEPGQEPGAQP |
| 180 | GAQPGQEPGQEPGQEPGQEPGQEPGQEPGAQPGAQP |
| 181 | GAQPGAQPGQEPGQEPGQEPGQEPGQEPGQEPGAQP |
| 182 | GAQPGAQPGQEPGQEPGQEPGQEPGQEPGAQPGAQP |
| 183 | GAQPGQEPGQEPGQEPGQEPGQEPGAQPGAQPGAQP |
| 184 | GAQPGAQPGAQPGQEPGQEPGQEPGQEPGQEPGAQP |
| 185 | GQEPGQEPGQEPGAQPGQEPGAQPGQEPGAQPGAQP |
| 186 | GQEPGQEPGAQPGQEPGAQPGQEPGAQPGQEPGAQPGQEP |
| 187 | GQEPGQEPGQEPGQEPGQEPGAQPGQEPGAQPGQEPGAQP |
| 188 | GQEPGQEPGQEPGAQPGQEPGAQPGQEPGAQPGQEPGQEP |
| 189 | GQEPGQEPGAQPGQEPGAQPGQEPGAQPGQEPGQEP |
| 190 | GQEPGQEPGQEPGQEPGAQPGQEPGAQPGQEPGAQPGQEP |
| 191 | GQEPGQEPGQEPGQEPGQEPGQEPGAQPGQEPGAQP |
| 192 | GQEPGQEPGQEPGQEPGAQPGQEPGAQPGQEPGQEP |
| 193 | GQEPGQEPGQEPGAQPGQEPGAQPGQEPGQEPGQEP |
| 194 | GQEPGQEPGQEPGQEPGAQPGQEPGAQPGQEPGQEP |
| 195 | GQEPGQEPGAQPGQEPGAQPGQEPGQEPGQEPGQEP |
| 196 | GQEPGQEPGQEPGQEPGQEPGQEPGAQPGQEPGAQPGQEP |
| 197 | GQEPGAQPGQEPGQEPGQEPGQEPGQEPGQEPGQEP |

| SEQ ID NO | Sequence |
|---|---|
| 199 | GQEPGQEPGQEPGQEPGQEPGAQPGQEPGQEPGQEPGQEP |
| 200 | GQEPGQEPGQEPGAQPGQEPGQEPGQEPGQEPGQEPGQEP |
| 201 | GQEPGQEPGQEPGQEPGQEPGQEPGQEPGAQPGQEPGQEP |
| 202 | GQEPGQEPGQEPGQEPGAQPGQEPGQEPGQEPGQEPGQEP |
| 203 | GQEPGQEPGQEPGQEPGQEPGQEPGAQPGQEPGQEPGQEP |
| 204 | GQEPGQEPGQEPGQEPGQEPGQEPGQEPGQEPGAQPGQEP |
| 205 | GQEPGQEPGAQPGQEPGQEPGQEPGQEPGQEPGQEPGQEP |
| 206 | SEPATSGSETPGTSESATPESGPGTSTEPSEGGAQPGAQP |
| 207 | SEPATSGSETPGTSESATPESGPGTSTEPSEGGAQPGQEP |
| 208 | SEPATSGSETPGTSESATPESGPGTSTEPSEGGQEPGQEP |
| 209 | SEPATSGSETPGTSESATPESGPGTSTEPSEGGQEPGAQP |

Fig. 11C Continued

Other Linkers

| SEQ ID NO | Sequence |
|---|---|
| 210 | GQEPGQEPGQEPGQEPGQEPGQEP |
| 211 | GQEPGQEPGQEP |
| 212 | SEPATSGSETPGTSESATPESGPGTSTEPSEG |
| 460 | GQEP |
| 461 | GQEPGAQPGQEPGAQPGQEPGAQPGQEPGAQPGQEPGAQPGQEP GAQPGAQPGAQPGAQPGAQPGAQPGAQPGAQPGAQPGAQPGAQP GAQPGAQPGAQPGAQPGAQPGAQPGAQPGAQP |
| 462 | GAQPGAQPGAQPGAQPGAQPGAQPGAQPGAQPGAQPGAQPGAQP GAQPGQEPGAQPGQEPGAQPGQEPGAQPGQEPGAQPGQEPGAQP CQEPGAQPGAQPGAQPGAQPGAQPGAQPGAQPGAQPGAQPGAQP GAQPGAQPGAQPGAQPGAQPGAQPGAQPGAQPGAQPGAQP |
| 458 | GAQPGAQPGAQPGAQPGAQPGAQPGAQPGAQPGQEPGAQPGQEP GAQPGQEPGAQPGQEPGAQPGQEPGAQPGQEPGAQPGAQP |
| 459 | GAQPGAQPGAQPGAQPGAQPGAQPGAQPGAQPGQEPGQAPGQEP GAQPGQEPGAQPGQEPGAQPGQEPGAQPGQEPGAQPGAQP |

Fig. 11D

Linkers Repeats

| SEQ ID NO | Linker repeats |
|---|---|
| 213 | GQEPGAQP |
| 214 | GAQPGAQP |
| 215 | GQEP |

Fig. 11E

| 216 | GAQP |
|---|---|
| 217 | SEPATSGSETPGTSESATPESGPGTSTEPSEG |
| 218 | GAQPGQEPGAQP |
| 219 | GAQPGQEP |
| 220 | GEQP |
| 221 | GPQE |
| 222 | GPEQ |
| 223 | GSEP |
| 224 | GESP |
| 225 | GPSE |
| 226 | GPES |
| 227 | GQAP |
| 228 | GPAQ |
| 229 | GPQA |
| 230 | GSQP |
| 231 | GASP |
| 232 | GPAS |
| 233 | GPSA |
| 234 | GGGS |
| 235 | GSGS |
| 236 | GGGGS |
| 237 | SEPATS |
| 238 | GSETPG |
| 239 | TSESAT |
| 240 | PESGPG |
| 241 | TSTEPS |
| 453 | GQEPGQAP |
| 476 | GQAPGQEP |

Fig. 11E Continued

GLP-1

| SEQ ID NO | GLP-1 amino acid sequence |
|---|---|
| 242 | HAEGTFTSDVSSYLEGQAAKEFIAWLVKGRG |
| 243 | HGEGTFTSDVSSYLEEQAAKEFIAWLVRGGG |
| 244 | HGEGTFTSDVSSYLEEQAAREFIAWLVRGGG |
| 245 | HGEGTFTSDVSSYLEEQAAREFIAWLVRGKG |
| 325 | $X_7X_8$EGTFTSDVSSYLEX$_{22}$QAAX$_{26}$X$_{27}$FIAWLVX$_{34}$GX$_{36}$G |
| 336 | HGEGTFTSDVSSYLEEQAAKEFIAWLVKGGG |
| 448 | HGEGTFTSDVSSYLEEQAACEFIAWLVRGGG |
| 450 | EGTFTSDVSSYLEEQAAKEFIAWLVRGGG |
| 478 | H-Aib-EGTFTSDVSSYLEEQAAKEFIAWLVRGGG |

Fig. 11F

GDF15

| SEQ ID NO | GDF15 amino acid sequence |
|---|---|
| 246 | ARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 247 | ARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 248 | ARNGDHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI |
| 290 | ARQGDHCPLGPGRCCRLHTVRASLEDLGWADWVLSPREVQVTMCIGACPSQFRAANLHAQIKTSLHRLKPDTVPAPCCVPASYNPMVLIQRTDTGVSLQTYDDLLARDCHCI |
| 271 | GDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 291 | ARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLAKDCHCI |
| 292 | ARQGDHCPLGPGRCCRLHTVRASLEDLGWADWVLSPREVQVTMCIGACPSQFRAANLHAQIKTSLHRLKPDTVPAPCCVPASYNPMVLIQRTDTGVSLQTYDDLLAKDCHCI |
| 293 | ARQGDHCPLGPGRCCRLHTVRASLEDLGWADWVLSPREVQVTMCIGACPSQFRAANMHAQIKTSLHRLRPDTVPAPCCVPASYNPMVLIQRTDTGVSLQTYDDLLARDCHCI |
| 294 | ARQGDHCPLGPGRCCRLHTVRASLEDLGWADWVLSPREVQVTMCIGACPSQFRAANMHAQIKTSLHRLKPDTVPAPCCVPASYNPMVLIQKTDTGVSLQTYDDLLAKDCHCI |
| 295 | ARQGDHCPLGPGRCCRLHTVRASLEDLGWADWVLSPREVQVTMCIGACPSQFRAANMHAQIKTSLHRLKPDTVPAPCCVPASYNPMVLIQRTDTGVSLQTYDDLLARDCHCI |
| 296 | ARQGDHCPLGPGRCCRLHTVRASLEDLGWADWVLSPREVQVTMCIGACPSQFRAANMHAQIKTSLHRLRPDTVPAPCCVPASYNPMVLIQRTDTGVSLQTYDDLLAKDCHCI |

Fig. 11F Continued

| 297 | ARQGDHCPLGPGRCCRLHTVRASLEDLGWADWVLSPREVQVTMCIGACPSQFRAANMHAQIKTSLHRLKPDTVPAPCCVPASYNPMVLIQRTDTGVSLQTYDDLLAKDCHCI |
| --- | --- |
| 358 | ARQGDHCPLGPGRCCRLHTVRASLEDLGWADWVLSPREVQVTMCIGACPSQFRAANLHAQIKTSLHRLRPDTVPAPCCVPASYNPMVLIQKTDTGVSLQTYDDLLARDCHCI |
| 451 | ARQGDHCPLGPGRCCRLHTVRASLEDLGWADWVLSPREVQVTMCIGACPSQFRAANLHAQIKTSLHRLRPDTVPAPCCVPASYNPLVLIQRTDTGVSLQTYDDLLARDCHCI |
| 452 | ARQGDHCPLGPGRCCRLHTVRASLEDLGWADWVLSPREVQVTMCIGACPSQFRAANLHAQIKTSLHRLKPDTVPAPCCVPASYNPMRLIQKTDTGVSLQTYDDLLAKDCHCI |
| 479 | ARNGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 480 | ARNGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |

Fig. 11F Continued

Fusion protein

| SEQ ID NO | fusion protein full length |
|---|---|
| 249 | HGEGTFTSDVSSYLEEQAAKEFIAWLVRGGGGQEPGQEPGQEPGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 250 | HGEGTFTSDVSSYLEEQAAKEFIAWLVRGGGGQEPGQEPGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 251 | HGEGTFTSDVSSYLEEQAAKEFIAWLVRGGGGQEPGAQPGQEPGAQPGQEPGAQPGQEPGAQPGQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 252 | HGEGTFTSDVSSYLEEQAAREFIAWLVRGGGGQEPGQEPGQEKGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 253 | HGEGTFTSDVSSYLEEQAAREFIAWLVRGKGGQEPGQEPGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 254 | HGEGTFTSDVSSYLEEQAAREFIAWLVRGGGKQEPGQEPGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 255 | HGEGTFTSDVSSYLEEQAAREFIAWLVRGGGGQEPGKEPGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 256 | HGEGTFTSDVSSYLEEQAAREFIAWLVRGGGGQEPGQEPGQEPGQKPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 257 | HGEGTFTSDVSSYLEEQAAREFIAWLVRGGGSEPKTSGSETPGTSESATPESGPGTSTEPSEGARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |

Fig. 11G

| | |
|---|---|
| 258 | HGEGTFTSDVSSYLEEQAAREFIAWLVRGGGGQEPGAQPGQEP GAQPGQEKGAQPGQEPGAQPGQEPGQEPARQGDHCPLGPGRC CRLHTVRASLEDLGWADWVLSPREVQVTMCIGACPSQFRAANLH AQIKTSLHRLRPDTVPAPCCVPASYNPMVLIQRTDTGVSLQTYDD LLARDCHCI |
| 259 | HGEGTFTSDVSSYLEEQAAREFIAWLVRGGGGQEPGQEPGQEK GQEPGQEPGQEPGQEPGQEPGQEPGQEPARQGDHCPLGPGRC CRLHTVRASLEDLGWADWVLSPREVQVTMCIGACPSQFRAANLH AQIKTSLHRLRPDTVPAPCCVPASYNPMVLIQRTDTGVSLQTYDD LLARDCHCI |
| 260 | HGEGTFTSDVSSYLEEQAAREFIAWLVRGGGKQEPGAQPGQEP GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 261 | SEPATSGQEKGQEPGQEPGQEPGQEPGQEPGAQPGAQPARQG DHCPLGPGRCCRLHTVRASLEDLGWADWVLSPREVQVTMCIGA CPSQFRAANLHAQIKTSLHRLRPDTVPAPCCVPASYNPMVLIQRT DTGVSLQTYDDLLARDCHCI |
| 262 | HGEGTFTSDVSSYLEEQAAREFIAWLVRGGGGQEPGAQPGQEK GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 263 | HGEGTFTSDVSSYLEEQAAREFIAWLVRGGGGQEPGAQPGQEP GAQPGQEPGAQPGQEPGAQPGQEPGAQPGQEPGAQPGAQKG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 264 | HGEGTFTSDVSSYLEEQAAREFIAWLVRGGGGQEPGAQPGQEP GAQPGQEPGAQPGQEPGAQPGQEPGAQPGQEPGAQPGAQPG AKPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 265 | HGEGTFTSDVSSYLEEQAAREFIAWLVRGGGGQEPGAQPGQEP GAQPGQEPGAQPGQEPGAQPGQEPGAQPGQEPGAQPGQEKG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 266 | HGEGTFTSDVSSYLEEQAAKEFIAWLVRGGGGQEPGAQPGQEP GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA |

Fig. 11G Continued

| | |
|---|---|
| | QIKTSLHRLRPDTVPAPCCVPASYNPMVLIQRTDTGVSLQTYDDLLARDCHCI |
| 267 | HGEGTFTSDVSSYLEEQAAKEFIAWLVRGGGGQEPGQEPGQEPGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 268 | HGEGTFTSDVSSYLEEQAAKEFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 269 | HGEGTFTSDVSSYLEEQAAKEFIAWLVRGGGGQEPGQEPGQEPGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 270 | HGEGTFTSDVSSYLEEQAAKEFIAWLVRGGGGQEPGQEPGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 273 | HGEGTFTSDVSSYLEEQAAREFIAWLVRGGGGAQPGAQPGAQPGAQPGAQPGAQPGAQPGAQPGAQPGAQPGQEPGQEPGQEPGQKPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 274 | HGEGTFTSDVSSYLEEQAAREFIAWLVRGGGGAQPGAQPGAQPGAQPGAQPGAQPGAQPGAQPGQEPGAQPGQEPGAQPGQEPGQKPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 275 | HGEGTFTSDVSSYLEEQAAREFIAWLVRGGGGAQPGAQPGAQPGAQPGAQPGAQPGAQPGAQPGAQPGQEPGQEPGQEKGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 276 | HGEGTFTSDVSSYLEEQAAREFIAWLVRGGGGAQPGAQPGAQPGAQPGAQPGAQPGAQPGAQPGAQPGQEPGAQPGQEPGQEKGQEPGQEPGQEPGQEPGQEPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |

Fig. 11G Continued

| | |
|---|---|
| 277 | HGEGTFTSDVSSYLEEQAAREFIAWLVRGGGGQEPGQEPGQEPGQKPGQEPGQEPGQEPGQEPGAQPGAQPGAQPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 278 | HGEGTFTSDVSSYLEEQAAREFIAWLVRGGGGQEPGQEPGQEKGQEPGQEPGQEPGQEPGQEPGAQPGAQPGAQPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 279 | HGEGTFTSDVSSYLEEQAAREFIAWLVRGGGSEPATSGSETPGTKESATPESGPGTSTEPSEGGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 280 | HGEGTFTSDVSSYLEEQAAREFIAWLVRGGGGAQPGAQPGAQPGAQPGAQPGAQPGAQPGAQPGAQPGAQPGQEPGQKPGQEPGQEPGQEPGQEPGQEPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 281 | HGEGTFTSDVSSYLEEQAAREFIAWLVRGGGGAQPGAQPGAQPGAQPGAQPGAQPGAQPGAQPGAQPGAQPGAQPGQEKGQEPGQEPGQEPGQEPGQEPGQEPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 282 | HGEGTFTSDVSSYLEEQAAREFIAWLVRGGGGAQPGAQPGAQPGAKPGAQPGAQPGAQPGAQPGAQPGAQPGAQPGQEPGQEPGQEPGQEPGQEPGQEPGQEPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 283 | HGEGTFTSDVSSYLEEQAAREFIAWLVRGGGGAQPGAQPGAQKGAQPGAQPGAQPGAQPGAQPGAQPGAQPGAQPGAQPGQEPGQEPGQEPGQEPGQEPGQEPGQEPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 284 | HGEGTFTSDVSSYLEEQAAREFIAWLVRGGGKQEPGAQPGQEPGAQPGQEPGAQPGQEPGAQPGQEPGAQPGQEPGAQPGQEPAQPGQEPGAQPGQEPGAQPGQEPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |

Fig. 11G Continued

| | |
|---|---|
| 285 | HGEGTFTSDVSSYLEEQAAREFIAWLVRGGGKAQPGAQPGAQP GAQPGAQPGAQPGAQPGAQPGAQPGAQPGQEPGQEPGQEPG QEPGQEPGQEPGQEPGQEPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 286 | HGEGTFTSDVSSYLEEQAAREFIAWLVRGGGKAQPGAQPGAQP GAQPGAQPGAQPGAQPGAQPGQEPGAQPGQEPGAQPGQEPG QEPGQEPGQEPGQEPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 287 | HGEGTFTSDVSSYLEEQAAREFIAWLVRGGGKAQPGAQPGAQP GAQPGAQPGAQPGAQPGAQPGAQPGQEPGAQPGQEPGQEPG QEPGQEPGQEPGQEPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 288 | HGEGTFTSDVSSYLEEQAAREFIAWLVRGGGKQEPGQEPGQEP GQEPGQEPGQEPGQEPGQEPGAQPGAQPGAQPGAQPGAQPG AQPGAQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 289 | HGEGTFTSDVSSYLEEQAAREFIAWLVRGGGKAQPGAQPGAQP GAQPGAQPGAQPGAQPGAQPGAQPGAQPGAQPGAQPGQEPG QEPGQEPGQEPGQEPGQEPGQEPGARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 326 | HGEGTFTSDVSSYLEEQAAKEFIAWLVRGGGGQEPGAQPGQEP GAQPGQEPGAQPGQEPGAQPGQEPGAQPGQEPGAQPGAQPG AQPGAQPARQGDHCPLGPGRCCRLHTVRASLEDLGWADWVLSP REVQVTMCIGACPSQFRAANLHAQIKTSLHRLRPDTVPAPCCVPA SYNPMVLIQRTDTGVSLQTYDDLLARDCHCI |
| 327 | HGEGTFTSDVSSYLEEQAAKEFIAWLVRGGGGQEPGAQPGQEP GAQPGQEPGAQPGQEPGAQPGQEPGAQPGQEPGAQPGAQPG AKPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 328 | HGEGTFTSDVSSYLEEQAAREFIAWLVRGGGKQEPGAQPGQEP GAQPGQEPGAQPGQEPGAQPGQEPGAQPGQEPGAQPGAQPG AKPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |

Fig. 11G Continued

| | |
|---|---|
| 329 | HGEGTFTSDVSSYLEEQAAREFIAWLVRGGGGQEPGAQPGQEPGAQPGQEPGAQPGQEPGAQPGQEPGAQPGQEPGAQPGAQPGAQPGAQKGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 330 | HGEGTFTSDVSSYLEEQAAREFIAWLVRGGGGQEPGAQPGQEPGAQPGQEPGAQPGQEPGAQPGQEPGAQKGQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 331 | HGEGTFTSDVSSYLEEQAAKEFIAWLVRGGGGAQPGQEPGAQPGQEPGAQPGQEPGAQPGQEPGAQPGQEPGAQPGQEPGAQPGQEPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 337 | HGEGTFTSDVSSYLEEQAAREFIAWLVRGGGKQEPGAQPGQEPGAQPGQEPGAQPGQEPGAQPGQEPGAQPGQEPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 338 | HGEGTFTSDVSSYLEEQAAREFIAWLVRGGGGQEPGAQPGQEPGAQPGQEPGAQPGQEPGAQKGQEPGAQPGQEPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 339 | HGEGTFTSDVSSYLEEQAAREFIAWLVRGGGGQEPGAQPGQEPGAQPGQEPGAQPGQEPGAQPGQKPGAQPGQEPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 340 | HGEGTFTSDVSSYLEEQAAREFIAWLVRGGGGQEPGAQPGQEKGAQPGQEPGAQPGQEPGAQPGQEPGAQPGQEPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 341 | HGEGTFTSDVSSYLEEQAAREFIAWLVRGGGGQEPGAQPGQEPGAKPGQEPGAQPGQEPGAQPGQEPGAQPGQEPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |

Fig. 11G Continued

| | |
|---|---|
| 347 | HGEGTFTSDVSSYLEEQAAKEFIAWLVRGGGGQEPGAQPGQEPGAQPGQEPGAQPGQEPGAQPGQEPGAQPGQEPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| | |
| 349 | HGEGTFTSDVSSYLEEQAAREFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQKTDTGVSLQTYDDLLARDCHCI |
| 350 | HGEGTFTSDVSSYLEEQAAREFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLAKDCHCI |
| | |
| 352 | HGEGTFTSDVSSYLEEQAAKEFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQKTDTGVSLQTYDDLLARDCHCI |
| 353 | HGEGTFTSDVSSYLEEQAAKEFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLAKDCHCI |
| 354 | HGEGTFTSDVSSYLEEQAAREFIAWLVRGGGKQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQRTDTGVSLQTYDDLLARDCHCI |

Fig. 11G Continued

| 355 | HGEGTFTSDVSSYLEEQAAKEFIAWLVRGGGGQEPGAQPGQEP GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLKPDTVPAPCCVPASYNPMVLIQRTDTGVSLQTYDDLL ARDCHCI |
|---|---|
| 356 | HGEGTFTSDVSSYLEEQAAREFIAWLVRGGGGQEPGAQPGQEP GAQPGQEPGAQPGQEPGAQPGQEPGAQPGQEPGAQPGAQPG AKPGAQPGAQPGAQPGAQPGAQPGAQPARQGDHCPLGPGRCC RLHTVRASLEDLGWADWVLSPREVQVTMCIGACPSQFRAANLHA QIKTSLHRLKPDTVPAPCCVPASYNPMVLIQRTDTGVSLQTYDDLL ARDCHCI |
| 357 | HGEGTFTSDVSSYLEEQAAREFIAWLVRGGGGQEPGAQPGQEP GAQPGQEPGAQPGQEPGAQPGQEPGAQPGQEPGAQPGQEKG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQRTDTGVSLQTYDDLL ARDCHCI |
| 359 | HGEGTFTSDVSSYLEEQAAREFIAWLVRGGGGQEPGAQPGQEP GAQPGQEPGAQPGQEPGAQPGQEPGAQPGQEPGAQPGAKPGA QPGAQPGAQPGAQPGAQPGAQPGAQPARQGDHCPLGPGRCCR LHTVRASLEDLGWADWVLSPREVQVTMCIGACPSQFRAANLHAQ IKTSLHRLRPDTVPAPCCVPASYNPMVLIQRTDTGVSLQTYDDLLA RDCHCI |
| 360 | HGEGTFTSDVSSYLEEQAAREFIAWLVRGGGGAQPGAQPGAQP GAQPGAQPGAQPGAQPGAQPGAQPGAQPGQEPGQEPGQKPG QEPGQEPGQEPGQEPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 361 | HGEGTFTSDVSSYLEEQAAKEFIAWLVRGGGKQEPGAQPGQEP GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPMVLIQRTDTGVSLQTYDDLL ARDCHCI |
| 362 | HGEGTFTSDVSSYLEEQAAKEFIAWLVRGGGGQEPGAQPGQEP GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPLVLIQRTDTGVSLQTYDDLL ARDCHCI |
| 363 | HGEGTFTSDVSSYLEEQAAREFIAWLVRGGGKQEPGAQPGQEP GAQPGQEPGAQPGQEPGAQPGQEPGAQPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLRPDTVPAPCCVPASYNPLVLIQRTDTGVSLQTYDDLL ARDCHCI |

Fig. 11G Continued

| | |
|---|---|
| 364 | HGEGTFTSDVSSYLEEQAAREFIAWLVRGGGGQEPGAQPGQEPGAQPGQEPGAQPGQEPGAQPGQEPGAQPGQEPGAQPGAQPGAKPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPLVLIQRTDTGVSLQTYDDLLARDCHCI |
| 365 | HGEGTFTSDVSSYLEEQAAREFIAWLVRGGGGQEPGAQPGQEPGAQPGQEPGAQPGQEPGAQPGQEPGAQPGQEPGAQPGAQKGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPLVLIQRTDTGVSLQTYDDLLARDCHCI |
| 366 | HGEGTFTSDVSSYLEEQAACEFIAWLVRGGGGQEPGAQPGQEPGAQPGQEPGAQPGQEPGAQPGQEPGAQPGQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 367 | HGEGTFTSDVSSYLEEQAAKEFIAWLVRGGGCQEPGAQPGQEPGAQPGQEPGAQPGQEPGAQPGQEPGAQPGQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 368 | HGEGTFTSDVSSYLEEQAAKEFIAWLVRGGGGQEPGAQPGQEPGAQPGQEPGAQPGQEPGAQPGQEPGAQPGQEPGAQPGAQPGACPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 369 | HGEGTFTSDVSSYLEEQAAKEFIAWLVRGGGGQEPGAQPGQEPGAQPGQEPGAQPGQEPGAQPGQEPGAQPCQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 370 | HGEGTFTSDVSSYLEEQAAREFIAWLVRGGGGQEPGAQPGQEPGAQPGQEPGAQPGQEPGAQPGQKPGAQPGQEPGAQPGQEPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 371 | HGEGTFTSDVSSYLEEQAAREFIAWLVRGGGGQEPGAQPGQEPGAQPGQEPGAQPGQEPKQAPGQEPGAQPGQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |

Fig. 11G Continued

| 372 | HGEGTFTSDVSSYLEEQAAREFIAWLVRGGGGQEPGAQPGQEP GAQPGQEPGAQPKQEPGAQPGQEPGAQPGQEPGAQPGAQPGA QPGAQPGAQPGAQPGAQPGAQPGAQPARQGDHCPLGPGRCCR LHTVRASLEDLGWADWVLSPREVQVTMCIGACPSQFRAANLHAQ IKTSLHRLRPDTVPAPCCVPASYNPMVLIQRTDTGVSLQTYDDLLA RDCHCI |
|---|---|
| 373 | HGEGTFTSDVSSYLEEQAAREFIAWLVRGGGGQEPGAQPGQEP GAQPGQEPKQAPGQEPGAQPGQEPGAQPGQEPGAQPGAQPGA QPGAQPGAQPGAQPGAQPGAQPGAQPARQGDHCPLGPGRCCR LHTVRASLEDLGWADWVLSPREVQVTMCIGACPSQFRAANLHAQ IKTSLHRLRPDTVPAPCCVPASYNPMVLIQRTDTGVSLQTYDDLLA RDCHCI |
| 374 | HGEGTFTSDVSSYLEEQAAKEFIAWLVRGGGGQEPGAQPGQEP GAQPGQEPGAQPGQEPGAQPGQCPGAQPGQEPGAQPGQEPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 375 | HGEGTFTSDVSSYLEEQAAKEFIAWLVRGGGGQEPGAQPGQEP GAQPGQEPGAQPGQEPGAQPGQEPGAQPGQEPGAQPGQCPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 376 | HGEGTFTSDVSSYLEEQAAKEFIAWLVRGGGGQEPGAQPGQEP GAQPGQEPGAQPGQEPGAQPGQEPGQCPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 377 | HGEGTFTSDVSSYLEEQAAKEFIAWLVRGGGGQEPGAQPGQEP GAQPGQEPGAQPGQEPGAQPGQEPCQAPGQEPGAQPGAQPG AQPGAQPGAQPGAQPGAQPGAQPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 378 | HGEGTFTSDVSSYLEEQAAKEFIAWLVRGGGGAQPGAQPGAQP GAQPGAQPGAQPGAQPGAQPGQEPGAQPCQEPGAQPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 379 | HGEGTFTSDVSSYLEEQAAKEFIAWLVRGGGGAQPGAQPGAQP GAQPGAQPGAQPGAQPGAQPGQEPGQCPGQEPGAQPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |

Fig. 11G Continued

| | |
|---|---|
| 380 | HGEGTFTSDVSSYLEEQAAKEFIAWLVRGGGGAQPGAQPGAQPGAQPGAQPGAQPGAQPGAQPGQCPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 381 | HGEGTFTSDVSSYLEEQAAKEFIAWLVRGGGGAQPGAQPGAQPGAQPGAQPGAQPGAQPGAQPCQEPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 383 | HGEGTFTSDVSSYLEEQAAKEFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMRLIQKTDTGVSLQTYDDLLAKDCHCI |
| 384 | EGTFTSDVSSYLEEQAAKEFIAWLVRGGGGQEPGAQPGQEPGAQPGQEPGAQPGQEPGAQPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 385 | HGEGTFTSDVSSYLEEQAAREFIAWLVRGGGGAQPGAQPGAQPGAQPGAQPGAQPGAQPGQEPGQKPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 386 | HGEGTFTSDVSSYLEEQAAREFIAWLVRGGGGAQPGAQPGAQPGAQPGAQPGAQPGQEPGAQPGQKPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 387 | HGEGTFTSDVSSYLEEQAAKEFIAWLVRGGGGQEPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 388 | HGEGTFTSDVSSYLEEQAAKEFIAWLVRGGGARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |

Fig. 11G Continued

| | |
|---|---|
| 389 | HGEGTFTSDVSSYLEEQAAKEFIAWLVRGGGGQEPGAQPGQEPGAQPGQEPGAQPGQEPGAQPGQEPGAQPGQEPGAQPGAQPGAQPGAQPGAQPGAQPGAQPGAQPGAQPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 390 | HGEGTFTSDVSSYLEEQAAREFIAWLVRGGGGQEPGAQPGQEPGAQPGQEPGAQPGQEPGAQPGQEPGAQPGQEPGAQPGAQPGAQPGAQPGAQPGAQPGAKPGAQPGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 391 | HGEGTFTSDVSSYLEEQAAREFIAWLVRGGGGQEPGAQPGQEPGAQPGQEPGAQPGQEPGAQPGQEPGAQPGAQPGAQPGAQPGAQPGAQPGAQPGAQKGAQPARQGDHCPLGPGRCCRLHTVRASLEDLGWADWVLSPREVQVTMCIGACPSQFRAANLHAQIKTSLHRLRPDTVPAPCCVPASYNPMVLIQRTDTGVSLQTYDDLLARDCHCI |
| 392 | HGEGTFTSDVSSYLEEQAAKEFIAWLVRGGGGAQPGAQPGAQPGAQPCQAPGAQPGAQPGAQPGQEPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 393 | HGEGTFTSDVSSYLEEQAAKEFIAWLVRGGGGAQPGAQPGAQPGAQPGAQPCQAPGAQPGAQPGQEPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 394 | HGEGTFTSDVSSYLEEQAAKEFIAWLVRGGGGAQPGAQPGAQPGAQPGAQPGAQPCQAPGAQPGQEPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 395 | HGEGTFTSDVSSYLEEQAAKEFIAWLVRGGGGQEPGAQPGQEPGAQPGQEPGAQPGQEPGAQPGQCPGQEPGAQPGQEPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 396 | HGEGTFTSDVSSYLEEQAAKEFIAWLVRGGGGQEPGAQPGQEPGAQPGQEPGAQPCQEPGAQPGQEPGAQPGQEPGAQPGAQPGAQPGAQPGAQPGAQPGAQPGAQPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |

Fig. 11G Continued

| | |
|---|---|
| 397 | HGEGTFTSDVSSYLEEQAAKEFIAWLVRGGGGAQPGAQPGAQP GAQPGAQPGAQPGAQPGAQPGQEPGAQPGQEPCQAPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 398 | HGEGTFTSDVSSYLEEQAAKEFIAWLVRGGGGAQPGAQPGAQP GAQPGAQPGAQPGAQPGAQPGQEPGAQPGQEPGAQPGQCPG QEPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 399 | HGEGTFTSDVSSYLEEQAAKEFIAWLVRGGGGAQPGAQPGAQP GAQPGAQPGAQPGAQPCAQPGQEPGAQPGQEPGQAPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 400 | HGEGTFTSDVSSYLEEQAAKEFIAWLVRGGGGAQPGAQPGAQP GAQPGAQPGAQPGAQPGAQPCQEPGAQPGQEPGAQPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMRLIQKTDTGVSLQTYDDLL AKDCHCI |
| 401 | EGTFTSDVSSYLEEQAAKEFIAWLVRGGGGAQPGAQPGAQPGA QPGAQPGAQPGAQPGAQPCQEPGAQPGQEPGAQPGQEPGAQ PGQEPGAQPGQEPGAQPGQEPGAQPARQGDHCPLGPGRCCRL HTVRASLEDLGWADWVLSPREVQVTMCIGACPSQFRAANLHAQI KTSLHRLKPDTVPAPCCVPASYNPMVLIQKTDTGVSLQTYDDLLA KDCHCI |
| 402 | HGEGTFTSDVSSYLEEQAAKEFIAWLVRGGGGAQPGAQPGAQP GAQPGAQPGAQPGAQPGAQPCQEPGAQPGQEPGAQPGQEPG AQPGQEPGAQPGQEPGAQPGQEPGAQPGAQPGDHCPLGPGRC CRLHTVRASLEDLGWADWVLSPREVQVTMCIGACPSQFRAANLH AQIKTSLHRLKPDTVPAPCCVPASYNPMVLIQKTDTGVSLQTYDDL LAKDCHCI |
| 403 | HGEGTFTSDVSSYLEEQAAKEFIAWLVRGGGGAQPGAQPGAQP GAQPGAQPGAQPGAQPGAQPGQEPGQCPGQEPGAQPGQEPG AQPGQEPGAQPGQEPGAQPGQEPGAQPGAQPGDHCPLGPGRC CRLHTVRASLEDLGWADWVLSPREVQVTMCIGACPSQFRAANLH AQIKTSLHRLKPDTVPAPCCVPASYNPMVLIQKTDTGVSLQTYDDL LAKDCHCI |
| 404 | HGEGTFTSDVSSYLEEQAAKEFIAWLVKGGGGAQPGAQPGAQP GAQPGAQPGAQPGAQPGAQPCQEPGAQPGQEPGAQPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |

Fig. 11G Continued

| | |
|---|---|
| 405 | HGEGTFTSDVSSYLEEQAAKEFIAWLVKGGGGAQPGAQPGAQP GAQPGAQPGAQPGAQPGAQPGQEPGQCPGQEPGAQPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 406 | HGEGTFTSDVSSYLEEQAAKEFIAWLVRGGGGAQPGAQPGAQP GAQPGAQPGAQPGAQPGAQPGQEPGQCPGQEPGAQPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMRLIQKTDTGVSLQTYDDLL AKDCHCI |
| 407 | EGTFTSDVSSYLEEQAAKEFIAWLVRGGGGAQPGAQPGAQPGA QPGAQPGAQPGAQPGAQPGQEPGQCPGQEPGAQPGQEPGAQ PGQEPGAQPGQEPGAQPGQEPGAQPARQGDHCPLGPGRCCRL HTVRASLEDLGWADWVLSPREVQVTMCIGACPSQFRAANLHAQI KTSLHRLKPDTVPAPCCVPASYNPMVLIQKTDTGVSLQTYDDLLA KDCHCI |
| 408 | HGEGTFTSDVSSYLEEQAAKEFIAWLVRGGGGAQPGAQPGAQP GAQPGAQPGAQPGAQPGAQPGAQPGAQPGAQPGAQPGQEPG AQPGQEPGAQPGQEPGAQPGQEPGAQPGQEPGAQPCQEPGA QPGAQPGAQPGAQPGAQPGAQPGAQPGAQPGAQPGAQPGAQ PGAQPGAQPGAQPGAQPGAQPGAQPGAQPGAQPGAQPARQG DHCPLGPGRCCRLHTVRASLEDLGWADWVLSPREVQVTMCIGA CPSQFRAANLHAQIKTSLHRLKPDTVPAPCCVPASYNPMVLIQKT DTGVSLQTYDDLLAKDCHCI |
| 472 | HGEGTFTSDVSSYLEEQAAKEFIAWLVRGGGGAQPCQAPGAQP GAQPGAQPGAQPGAQPGQEPGAQPGQEPGAQPGQEPGQEPG AQPGQEPGAQPGQEPGAQPGQEPGAQPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 473 | HGEGTFTSDVSSYLEEQAAKEFIAWLVRGGGGAQPGAQPGAQP GAQPGAQPGAQPGAQPGAQPGQEPGAQPGQEPGAQPGQEPG AQPGQEPGAQPGQEPGAQPGQEPGQCPARQGDHCPLGPGRCC RLHTVRASLEDLGWADWVLSPREVQVTMCIGACPSQFRAANLHA QIKTSLHRLKPDTVPAPCCVPASYNPMVLIQKTDTGVSLQTYDDLL AKDCHCI |
| 477 | H-Aib-EGTFTSDVSSYLEEQAAKEFIAWLVRGGGGAQPGAQPGAQPGA QPGAQPGAQPGAQPGAQPCQEPGAQPGQEPGAQPGQEPGAQ PGQEPGAQPGQEPGAQPGQEPGAQPARQGDHCPLGPGRCCRL HTVRASLEDLGWADWVLSPREVQVTMCIGACPSQFRAANLHAQI KTSLHRLRPDTVPAPCCVPASYNPMVLIQRTDTGVSLQTYDDLLA RDCHCI |

Fig. 11G Continued

| SEQ ID NO | |
|---|---|
| 481 | HGEGTFTSDVSSYLEEQAAKEFIAWLVRGGGGAQPGAQPGAQPGAQPGAQPGAQPGAQPGAQPGQEPGAQPGQEPGAQPGQEPGAQPGQEPGAQPGQEPGAQPCQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |
| 482 | HGEGTFTSDVSSYLEEQAACEFIAWLVRGGGGAQPGAQPGAQPGAQPGAQPGAQPGAQPGAQPGQEPGAQPGQEPGAQPGQEPGAQPGQEPGAQPGQEPGAQPGQEPGAQPARQGDHCPLGPGRCCRLHTVRASLEDLGWADWVLSPREVQVTMCIGACPSQFRAANLHAQIKTSLHRLKPDTVPAPCCVPASYNPMVLIQKTDTGVSLQTYDDLLAKDCHCI |

Fig. 11G Continued

K or C mutated linkers

| SEQ ID NO | Linker amino acid sequence |
|---|---|
| 298 | GQEPGQEPGQEKGQEPGQEPGQEPGQEPGQEPGAQPGAQP |
| 299 | KQEPGQEPGQEPGQEPGQEPGQEPGQEPGQEPGAQPGAQP |
| 300 | GQEPGKEPGQEPGQEPGQEPGQEPGQEPGQEPGAQPGAQP |
| 301 | GQEPGQEPGQEPGQKPGQEPGQEPGQEPGQEPGAQPGAQP |
| 302 | SEPKTSGSETPGTSESATPESGPGTSTEPSEG |
| 303 | GQEPGAQPGQEPGAQPGQEKGAQPGQEPGAQPGQEPGQEP |
| 304 | GQEPGQEPGQEKGQEPGQEPGQEPGQEPGQEPGQEPGQEP |
| 305 | KQEPGAQPGQEPGAQPGQEPGAQPGQEPGAQPGQEPGAQPGQEPGAQPGAQPGAQPGAQPGAQPGAQPGAQPGAQPGAQP |
| 306 | SEPATSGQEKGQEPGQEPGQEPGQEPGQEPGAQPGAQP |
| 307 | GQEPGAQPGQEKGAQPGQEPGAQPGQEPGAQPGQEPGAQPGQEPGAQPGAQPGAQPGAQPGAQPGAQPGAQPGAQPGAQP |
| 308 | GQEPGAQPGQEPGAQPGQEPGAQPGQEPGAQPGQEPGAQPGQEPGAQPGAQKGAQPGAQPGAQPGAQPGAQPGAQPGAQP |
| 309 | GQEPGAQPGQEPGAQPGQEPGAQPGQEPGAQPGQEPGAQPGQEPGAQPGAQPGAKPGAQPGAQPGAQPGAQPGAQPGAQP |
| 310 | GQEPGAQPGQEPGAQPGQEPGAQPGQEPGAQPGQEPGAQPGQEPGAQPGQEKGAQPGQEPGAQPGQEPGAQPGQEPGAQP |
| 311 | GAQPGAQPGAQPGAQPGAQPGAQPGAQPGAQPGAQPGAQPGQEPGQEPGQEPGQKPGQEPGQEPGQEPGQEPGAQPGAQP |
| 312 | GAQPGAQPGAQPGAQPGAQPGAQPGAQPGAQPGQEPGAQPGQEPGAQPGQEPGQKPGQEPGQEPGQEPGQEPGAQPGAQP |
| 313 | GAQPGAQPGAQPGAQPGAQPGAQPGAQPGAQPGAQPGAQPGQEPGQEPGQEKGQEPGQEPGQEPGQEPGQEPGAQPGAQP |
| 314 | GAQPGAQPGAQPGAQPGAQPGAQPGAQPGAQPGAQPGQEPGAQPGQEPGQEKGQEPGQEPGQEPGQEPGQEPGAQPGAQP |

Fig. 11H

| | |
|---|---|
| 315 | GQEPGQEPGQEPGQKPGQEPGQEPGQEPGQEPGAQPGAQP GAQPGAQPGAQPGAQPGAQPGAQPGAQPGAQPGAQPGAQP |
| 316 | GQEPGQEPGQEKGQEPGQEPGQEPGQEPGQEPGAQPGAQP GAQPGAQPGAQPGAQPGAQPGAQPGAQPGAQPGAQPGAQP |
| 317 | SEPATSGSETPGTKESATPESGPGTSTEPSEGGAQPGAQP |
| 318 | GAQPGAQPGAQPGAQPGAQPGAQPGAQPGAQPGAQPGAQP GAQPGAQPGQEPGQKPGQEPGQEPGQEPGQEPGQEPGQEP |
| 319 | GAQPGAQPGAQPGAQPGAQPGAQPGAQPGAQPGAQPGAQP GAQPGAQPGQEKGQEPGQEPGQEPGQEPGQEPGQEPGQEP |
| 320 | GAQPGAQPGAQPGAKPGAQPGAQPGAQPGAQPGAQPGAQPG AQPGAQPGQEPGQEPGQEPGQEPGQEPGQEPGQEPGQEP |
| 321 | GAQPGAQPGAQKGAQPGAQPGAQPGAQPGAQPGAQPGAQP GAQPGAQPGQEPGQEPGQEPGQEPGQEPGQEPGQEPGQEP |
| 322 | KQEPGAQPGQEPGAQPGQEPGAQPGQEPGAQPGQEPGAQPG QEPGAQPGQEPGAQPGQEPGAQPGQEPGAQPGQEPGAQP |
| 323 | KAQPGAQPGAQPGAQPGAQPGAQPGAQPGAQPGAQPGAQPG QEPGQEPGQEPGQEPGQEPGQEPGQEPGQEPGAQPGAQP |
| 324 | KAQPGAQPGAQPGAQPGAQPGAQPGAQPGAQPGQEPGAQPG QEPGAQPGQEPGQEPGQEPGQEPGQEPGQEPGAQPGAQP |
| 89 | KAQPGAQPGAQPGAQPGAQPGAQPGAQPGAQPGAQPGQEPG AQPGQEPGQEPGQEPGQEPGQEPGQEPGQEPGAQPGAQP |
| 60 | KQEPGQEPGQEPGQEPGQEPGQEPGQEPGQEPGAQPGAQPG AQPGAQPGAQPGAQPGAQPGAQPGAQPGAQPGAQPGAQP |
| 198 | KAQPGAQPGAQPGAQPGAQPGAQPGAQPGAQPGAQPGAQPG AQPGAQPGQEPGQEPGQEPGQEPGQEPGQEPGQEPGQEP |
| 332 | KQEPGAQPGQEPGAQPGQEPGAQPGQEPGAQPGQEPGAQPG QEPGAQPGAQPGAKPGAQPGAQPGAQPGAQPGAQPGAQP |
| 333 | GQEPGAQPGQEPGAQPGQEPGAQPGQEPGAQPGQEPGAQP GQEPGAQPGAQPGAQPGAQKGAQPGAQPGAQPGAQPGAQP |
| 334 | GQEPGAQPGQEPGAQPGQEPGAQPGQEPGAQPGQEPGAQK GQEPGAQPGAQPGAQPGAQPGAQPGAQPGAQPGAQPGAQP |
| 342 | KQEPGAQPGQEPGAQPGQEPGAQPGQEPGAQPGQEPGAQPG QEPGAQPGAQPGAQPGAQP |

Fig. 11H Continued

| | |
|---|---|
| 343 | GQEPGAQPGQEPGAQPGQEPGAQPGQEPGAQKGQEPGAQPGQEPGAQPGAQPGAQPGAQP |
| 344 | GQEPGAQPGQEPGAQPGQEPGAQPGQEPGAQPGQKPGAQPGQKPGAQPGAQPGAQPGAQP |
| 345 | GQEPGAQPGQEKGAQPGQEPGAQPGQEPGAQPGQEPGAQPGQEPGAQPGAQPGAQPGAQP |
| 346 | GQEPGAQPGQEPGAKPGQEPGAQPGQEPGAQPGQEPGAQPGQEPGAQPGAQPGAQPGAQP |
| 409 | GQEPGAQPGQEPGAQPGQEPGAQPGQEPGAQPGQEPGAQPGQEPGAQPGAKPGAQPGAQPGAQPGAQPGAQPGAQP |
| 410 | GAQPGAQPGAQPGAQPGAQPGAQPGAQPGAQPGAQPGAQPGQEPGQEPGQKPGQEPGQEPGQEPGQEPGQEPGAQPGAQP |
| 411 | CQEPGAQPGQEPGAQPGQEPGAQPGQEPGAQPGQEPGAQPGQEPGAQPGAQPGAQPGAQPGAQPGAQPGAQPGAQP |
| 412 | GQEPGAQPGQEPGAQPGQEPGAQPGQEPGAQPGQEPGAQPGQEPGAQPGAQPGACPGAQPGAQPGAQPGAQPGAQPGAQP |
| 413 | GQEPGAQPGQEPGAQPGQEPGAQPGQEPGAQPGQEPGAQPGAQPCQEPGAQPGAQPGAQPGAQPGAQPGAQPGAQPGAQP |
| 414 | GQEPGAQPGQEPGAQPGQEPGAQPGQEPGAQPGQKPGAQPGQEPGAQPGQEPGAQPGAQPGAQPGAQPGAQPGAQPGAQP |
| 415 | GQEPGAQPGQEPGAQPGQEPGAQPGQEPKQAPGQEPGAQPGQEPGAQPGAQPGAQPGAQPGAQPGAQPGAQPGAQP |
| 416 | GQEPGAQPGQEPGAQPGQEPGAQPKQEPGAQPGQEPGAQPGQEPGAQPGAQPGAQPGAQPGAQPGAQPGAQPGAQP |
| 417 | GQEPGAQPGQEPGAQPGQEPKQAPGQEPGAQPGQEPGAQPGQEPGAQPGAQPGAQPGAQPGAQPGAQPGAQPGAQP |

Fig. 11H Continued

| | |
|---|---|
| 418 | GQEPGAQPGQEPGAQPGQEPGAQPGQEPGAQPGQCPGAQPGQEPGAQPGQEPGAQPGAQPGAQPGAQPGAQPGAQPGAQP |
| 419 | GQEPGAQPGQEPGAQPGQEPGAQPGQEPGAQPGQEPGAQPGQEPGAQPGQCPGAQPGAQPGAQPGAQPGAQPGAQP |
| 420 | GQEPGAQPGQEPGAQPGQEPGAQPGQEPGAQPGQEPGQCPGQEPGAQPGAQPGAQPGAQPGAQPGAQPGAQPGAQPGAQP |
| 421 | GQEPGAQPGQEPGAQPGQEPGAQPGQEPGAQPGQEPCQAPGQEPGAQPGAQPGAQPGAQPGAQPGAQPGAQPGAQPGAQP |
| 422 | GAQPGAQPGAQPGAQPGAQPGAQPGAQPGAQPGQEPGAQPCQEPGAQPGQEPGAQPGQEPGAQPGQEPGAQPGQEPGAQP |
| 423 | GAQPGAQPGAQPGAQPGAQPGAQPGAQPGAQPGQEPGQCPGQEPGAQPGQEPGAQPGQEPGAQPGQEPGAQPGQEPGAQP |
| 424 | GAQPGAQPGAQPGAQPGAQPGAQPGAQPGAQPGQCPGAQPGQEPGAQPGQEPGAQPGQEPGAQPGQEPGAQPGQEPGAQP |
| 425 | GAQPGAQPGAQPGAQPGAQPGAQPGAQPGAQPCQEPGAQPGQEPGAQPGQEPGAQPGQEPGAQPGQEPGAQPGQEPGAQP |
| 426 | GAQPGAQPGAQPGAQPGAQPGAQPGAQPGAQPGQEPGQKPGQEPGAQPGQEPGAQPGQEPGAQPGQEPGAQPGQEPGAQP |
| 427 | GAQPGAQPGAQPGAQPGAQPGAQPGQEPGAQPGQKPGAQPGQEPGAQPGQEPGAQPGQEPGAQPGQEPGAQPGQEPGAQP |
| 428 | GQEPGAQPGQEPGAQPGQEPGAQPGQEPGAQPGQEPGAQPGQEPGAQPGAQPGAQPGAQPGAQPGAQPGAKPGAQPGAQP |
| 429 | GQEPGAQPGQEPGAQPGQEPGAQPGQEPGAQPGQEPGAQPGQEPGAQPGAQPGAQPGAQPGAQPGAQPGAQPGAQKGAQP |

Fig. 11H Continued

| | |
|---|---|
| 430 | GAQPGAQPGAQPGAQPCQAPGAQPGAQPGAQPGQEP GAQPGQEPGAQPGQEPGAQPGQEPGAQPGQEPGAQPGQEP GAQP |
| 431 | GAQPGAQPGAQPGAQPGAQPCQAPGAQPGAQPGQEP GAQPGQEPGAQPGQEPGAQPGQEPGAQPGQEPGAQPGQEP GAQP |
| 432 | GAQPGAQPGAQPGAQPGAQPGAQPCQAPGAQPGQEP GAQPGQEPGAQPGQEPGAQPGQEPGAQPGQEPGAQPGQEP GAQP |
| 433 | GQEPGAQPGQEPGAQPGQEPGAQPGQEPGQCPGQEP GAQPGQEPGAQPGAQPGAQPGAQPGAQPGAQPGAQPGAQP GAQP |
| 434 | GQEPGAQPGQEPGAQPGQEPGAQPCQEPGAQPGQEP GAQPGQEPGAQPGAQPGAQPGAQPGAQPGAQPGAQPGAQP GAQP |
| 435 | GAQPGAQPGAQPGAQPGAQPGAQPGAQPGAQPGQEP GAQPGQEPCQAPGQEPCQAPGQEPCQAPGQEPCQAPGQEPC QAP |
| 436 | GAQPGAQPGAQPGAQPGAQPGAQPGAQPGAQPGQEP GAQPGQEPGAQPGQCPGQEPGQEPCQAPGQEPCQAPGQEPC QAP |
| 437 | GAQPGAQPGAQPGAQPGAQPGAQPGAQPCAQPGQEP CQAPGQEPCQAPGQEPCQAPGQEPCQAPGQEPCQAPGQEPC QAP |
| 438 | GAQPGAQPGAQPGAQPGAQPGAQPGAQPGAQPCQEP GAQPGQEPGAQPGQEPGAQPGQEPGAQPGQEPGAQPGQEP GAQP |
| 439 | GAQPGAQPGAQPGAQPGAQPGAQPGAQPGAQPCQEP GAQPGQEPGAQPGQEPGAQPGQEPGAQPGQEPGAQPGQEP GAQP |
| 440 | GAQPGAQPGAQPGAQPGAQPGAQPGAQPGAQPCQEP GAQPGQEPGAQPGQEPGAQPGQEPGAQPGQEPGAQPGQEP GAQPGAQP |
| 441 | GAQPGAQPGAQPGAQPGAQPGAQPGAQPGAQPGQEP GQCPGQEPGAQPGQEPGAQPGQEPGAQPGQEPGAQPGQEP GAQPGAQP |

Fig. 11H Continued

| | |
|---|---|
| 442 | GAQPGAQPGAQPGAQPGAQPGAQPGAQPGAQPCQEP GAQPGQEPGAQPGQEPGAQPGQEPGAQPGQEPGAQPGQEP GAQP |
| 443 | GAQPGAQPGAQPGAQPGAQPGAQPGAQPGAQPGQEP GQCPGQEPGAQPGQEPGAQPGQEPGAQPGQEPGAQPGQEP GAQP |
| 444 | GAQPGAQPGAQPGAQPGAQPGAQPGAQPGAQPGQEP GQCPGQEPGAQPGQEPGAQPGQEPGAQPGQEPGAQPGQEP GAQP |
| 445 | GAQPGAQPGAQPGAQPGAQPGAQPGAQPGAQPGQEP GQCPGQEPGAQPGQEPGAQPGQEPGAQPGQEPGAQPGQEP GAQP |
| 446 | GAQPGAQPGAQPGAQPGAQPGAQPGAQPGAQPGAQP GAQPGAQPGAQPGQEPGAQPGQEPGAQPGQEPGAQPGQEP GAQPGQEPGAQPCQEPGAQPGAQPGAQPGAQPGAQPGAQPG AQPGAQPGAQPGAQPGAQPGAQPGAQPGAQPGAQPGAQPGA QPGAQPGAQPGAQP |
| 447 | GAQPCQAPGAQPGAQPGAQPGAQPGAQPGAQPGQEP GAQPGQEPGAQPGQEPGAQPGQEPGAQPGQEPGAQPGQEP GAQP |
| 475 | GAQPGAQPGAQPGAQPGAQPGAQPGAQPGAQPGQEP GAQPGQEPGAQPGQEPGAQPGQEPGAQPGQEPGAQPGQEP GQCP |
| 483 | (GAQP)8(GQEPGAQP)5(CQEPGAQP) |

Fig. 11H Continued

SEQUENCE LISTING

<160> NUMBER OF SEQ ID NOS: 483

<210> SEQ ID NO 1
<211> LENGTH: 80
<212> TYPE: PRT
<213> ORGANISM: Artificial Sequence
<220> FEATURE:
<223> OTHER INFORMATION: Synthetic

<400> SEQUENCE: 1

```
Gly Gln Glu Pro Gly Ala Gln Pro Gly Gln Glu Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
                35                  40                  45
```

```
Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 2
<211> LENGTH: 80
<212> TYPE: PRT
<213> ORGANISM: Artificial Sequence
<220> FEATURE:
<223> OTHER INFORMATION: Synthetic

<400> SEQUENCE: 2

Gly Gln Glu Pro Gly Ala Gln Pro Gly Gln Glu Pro Gly Ala Gln Pro
1               5                  10                  15

Gly Gln Glu Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 3
<211> LENGTH: 80
<212> TYPE: PRT
<213> ORGANISM: Artificial Sequence
<220> FEATURE:
<223> OTHER INFORMATION: Synthetic

<400> SEQUENCE: 3

Gly Gln Glu Pro Gly Ala Gln Pro Gly Gln Glu Pro Gly Ala Gln Pro
1               5                  10                  15

Gly Gln Glu Pro Gly Ala Gln Pro Gly Gln Glu Pro Gly Ala Gln Pro
                20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 4
<211> LENGTH: 80
<212> TYPE: PRT
<213> ORGANISM: Artificial Sequence
<220> FEATURE:
<223> OTHER INFORMATION: Synthetic

<400> SEQUENCE: 4

Gly Gln Glu Pro Gly Ala Gln Pro Gly Gln Glu Pro Gly Ala Gln Pro
1               5                  10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
```

```
                65                  70                  75                  80

<210> SEQ ID NO 5
<211> LENGTH: 80
<212> TYPE: PRT
<213> ORGANISM: Artificial Sequence
<220> FEATURE:
<223> OTHER INFORMATION: Synthetic

<400> SEQUENCE: 5

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 6
<211> LENGTH: 80
<212> TYPE: PRT
<213> ORGANISM: Artificial Sequence
<220> FEATURE:
<223> OTHER INFORMATION: Synthetic

<400> SEQUENCE: 6

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 7
<211> LENGTH: 80
<212> TYPE: PRT
<213> ORGANISM: Artificial Sequence
<220> FEATURE:
<223> OTHER INFORMATION: Synthetic

<400> SEQUENCE: 7

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 8
```

-continued

```
<211> LENGTH: 80
<212> TYPE: PRT
<213> ORGANISM: Artificial Sequence
<220> FEATURE:
<223> OTHER INFORMATION: Synthetic

<400> SEQUENCE: 8

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Ala Gln Pro Gly Ala Gln Pro
65                  70                  75                  80

<210> SEQ ID NO 9
<211> LENGTH: 80
<212> TYPE: PRT
<213> ORGANISM: Artificial Sequence
<220> FEATURE:
<223> OTHER INFORMATION: Synthetic

<400> SEQUENCE: 9

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 10
<211> LENGTH: 80
<212> TYPE: PRT
<213> ORGANISM: Artificial Sequence
<220> FEATURE:
<223> OTHER INFORMATION: Synthetic

<400> SEQUENCE: 10

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro Gly Gln Glu Pro
    50                  55                  60

Gly Ala Gln Pro Gly Ala Gln Pro Gly Ala Gln Pro Gly Ala Gln Pro
65                  70                  75                  80

<210> SEQ ID NO 11
<211> LENGTH: 80
<212> TYPE: PRT
<213> ORGANISM: Artificial Sequence
<220> FEATURE:
```

<223> OTHER INFORMATION: Synthetic

<400> SEQUENCE: 11

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 12
<211> LENGTH: 80
<212> TYPE: PRT
<213> ORGANISM: Artificial Sequence
<220> FEATURE:
<223> OTHER INFORMATION: Synthetic

<400> SEQUENCE: 12

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 13
<211> LENGTH: 80
<212> TYPE: PRT
<213> ORGANISM: Artificial Sequence
<220> FEATURE:
<223> OTHER INFORMATION: Synthetic

<400> SEQUENCE: 13

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 14
<211> LENGTH: 80
<212> TYPE: PRT
<213> ORGANISM: Artificial Sequence
<220> FEATURE:
<223> OTHER INFORMATION: Synthetic

<400> SEQUENCE: 14

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 15
<211> LENGTH: 80
<212> TYPE: PRT
<213> ORGANISM: Artificial Sequence
<220> FEATURE:
<223> OTHER INFORMATION: Synthetic

<400> SEQUENCE: 15

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 16
<211> LENGTH: 80
<212> TYPE: PRT
<213> ORGANISM: Artificial Sequence
<220> FEATURE:
<223> OTHER INFORMATION: Synthetic

<400> SEQUENCE: 16

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 17
<211> LENGTH: 80
<212> TYPE: PRT
<213> ORGANISM: Artificial Sequence
<220> FEATURE:
<223> OTHER INFORMATION: Synthetic

<400> SEQUENCE: 17

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro

-continued

```
                 20                  25                  30

Gly Gln Glu Pro Gly Ala Gln Pro Gly Ala Gln Pro Gly Ala Gln Pro
             35                  40                  45

Gly Ala Gln Pro Gly Ala Gln Pro Gly Ala Gln Pro Gly Ala Gln Pro
         50                  55                  60

Gly Ala Gln Pro Gly Ala Gln Pro Gly Ala Gln Pro Gly Ala Gln Pro
 65                  70                  75                  80

<210> SEQ ID NO 18
<211> LENGTH: 80
<212> TYPE: PRT
<213> ORGANISM: Artificial Sequence
<220> FEATURE:
<223> OTHER INFORMATION: Synthetic

<400> SEQUENCE: 18

Gly Gln Glu Pro Gly Gln Glu Pro Gly Gln Glu Pro Gly Gln Glu Pro
 1               5                  10                  15

Gly Gln Glu Pro Gly Gln Glu Pro Gly Gln Glu Pro Gly Gln Glu Pro
             20                  25                  30

Gly Ala Gln Pro Gly Ala Gln Pro Gly Ala Gln Pro Gly Ala Gln Pro
             35                  40                  45

Gly Ala Gln Pro Gly Ala Gln Pro Gly Ala Gln Pro Gly Ala Gln Pro
         50                  55                  60

Gly Ala Gln Pro Gly Ala Gln Pro Gly Ala Gln Pro Gly Ala Gln Pro
 65                  70                  75                  80

<210> SEQ ID NO 19
<211> LENGTH: 80
<212> TYPE: PRT
<213> ORGANISM: Artificial Sequence
<220> FEATURE:
<223> OTHER INFORMATION: Synthetic

<400> SEQUENCE: 19

Gly Gln Glu Pro Gly Gln Glu Pro Gly Gln Glu Pro Gly Gln Glu Pro
 1               5                  10                  15

Gly Gln Glu Pro Gly Gln Glu Pro Gly Gln Glu Pro Gly Ala Gln Pro
             20                  25                  30

Gly Ala Gln Pro Gly Ala Gln Pro Gly Ala Gln Pro Gly Ala Gln Pro
             35                  40                  45

Gly Ala Gln Pro Gly Ala Gln Pro Gly Ala Gln Pro Gly Ala Gln Pro
         50                  55                  60

Gly Ala Gln Pro Gly Ala Gln Pro Gly Ala Gln Pro Gly Ala Gln Pro
 65                  70                  75                  80

<210> SEQ ID NO 20
<211> LENGTH: 80
<212> TYPE: PRT
<213> ORGANISM: Artificial Sequence
<220> FEATURE:
<223> OTHER INFORMATION: Synthetic

<400> SEQUENCE: 20

Gly Gln Glu Pro Gly Gln Glu Pro Gly Gln Glu Pro Gly Gln Glu Pro
 1               5                  10                  15

Gly Gln Glu Pro Gly Gln Glu Pro Gly Ala Gln Pro Gly Ala Gln Pro
             20                  25                  30

Gly Ala Gln Pro Gly Ala Gln Pro Gly Ala Gln Pro Gly Ala Gln Pro
             35                  40                  45
```

Gly Ala Gln Pro Gly Ala Gln Pro Gly Ala Gln Pro Gly Ala Gln Pro
            50                  55                  60

Gly Ala Gln Pro Gly Ala Gln Pro Gly Ala Gln Pro Gly Ala Gln Pro
65                  70                  75                  80

<210> SEQ ID NO 21
<211> LENGTH: 80
<212> TYPE: PRT
<213> ORGANISM: Artificial Sequence
<220> FEATURE:
<223> OTHER INFORMATION: Synthetic

<400> SEQUENCE: 21

Gly Gln Glu Pro Gly Gln Glu Pro Gly Gln Glu Pro Gly Gln Glu Pro
1               5                   10                  15

Gly Gln Glu Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 22
<211> LENGTH: 80
<212> TYPE: PRT
<213> ORGANISM: Artificial Sequence
<220> FEATURE:
<223> OTHER INFORMATION: Synthetic

<400> SEQUENCE: 22

Gly Gln Glu Pro Gly Gln Glu Pro Gly Gln Glu Pro Gly Gln Glu Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 23
<211> LENGTH: 80
<212> TYPE: PRT
<213> ORGANISM: Artificial Sequence
<220> FEATURE:
<223> OTHER INFORMATION: Synthetic

<400> SEQUENCE: 23

Gly Gln Glu Pro Gly Gln Glu Pro Gly Gln Glu Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 24
<211> LENGTH: 80
<212> TYPE: PRT
<213> ORGANISM: Artificial Sequence
<220> FEATURE:
<223> OTHER INFORMATION: Synthetic

<400> SEQUENCE: 24

Gly Gln Glu Pro Gly Gln Glu Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 25
<211> LENGTH: 80
<212> TYPE: PRT
<213> ORGANISM: Artificial Sequence
<220> FEATURE:
<223> OTHER INFORMATION: Synthetic

<400> SEQUENCE: 25

Gly Ala Gln Pro Gly Ala Gln Pro Gly Ala Gln Pro Gly Ala Gln Pro
1               5                   10                  15

Gly Gln Glu Pro Gly Gln Glu Pro Gly Gln Glu Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 26
<211> LENGTH: 80
<212> TYPE: PRT
<213> ORGANISM: Artificial Sequence
<220> FEATURE:
<223> OTHER INFORMATION: Synthetic

<400> SEQUENCE: 26

Gly Ala Gln Pro Gly Ala Gln Pro Gly Ala Gln Pro Gly Ala Gln Pro
1               5                   10                  15

Gly Ala Gln Pro Gly Gln Glu Pro Gly Gln Glu Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 27
<211> LENGTH: 80
<212> TYPE: PRT
<213> ORGANISM: Artificial Sequence
<220> FEATURE:
<223> OTHER INFORMATION: Synthetic

<400> SEQUENCE: 27

```
Gly Ala Gln Pro Gly Ala Gln Pro Gly Ala Gln Pro Gly Ala Gln Pro
1               5                   10                  15

Gly Ala Gln Pro Gly Ala Gln Pro Gly Gln Glu Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80
```

<210> SEQ ID NO 28
<211> LENGTH: 80
<212> TYPE: PRT
<213> ORGANISM: Artificial Sequence
<220> FEATURE:
<223> OTHER INFORMATION: Synthetic

<400> SEQUENCE: 28

```
Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80
```

<210> SEQ ID NO 29
<211> LENGTH: 80
<212> TYPE: PRT
<213> ORGANISM: Artificial Sequence
<220> FEATURE:
<223> OTHER INFORMATION: Synthetic

<400> SEQUENCE: 29

```
Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80
```

<210> SEQ ID NO 30
<211> LENGTH: 80
<212> TYPE: PRT
<213> ORGANISM: Artificial Sequence
<220> FEATURE:
<223> OTHER INFORMATION: Synthetic

<400> SEQUENCE: 30

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Gln Glu Pro Gly Gln Glu Pro Gly Gln Glu Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

<210> SEQ ID NO 31
<211> LENGTH: 80
<212> TYPE: PRT
<213> ORGANISM: Artificial Sequence
<220> FEATURE:
<223> OTHER INFORMATION: Synthetic

<400> SEQUENCE: 31

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Gln Glu Pro Gly Gln Glu Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

<210> SEQ ID NO 32
<211> LENGTH: 80
<212> TYPE: PRT
<213> ORGANISM: Artificial Sequence
<220> FEATURE:
<223> OTHER INFORMATION: Synthetic

<400> SEQUENCE: 32

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Gln Glu Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

<210> SEQ ID NO 33
<211> LENGTH: 80
<212> TYPE: PRT
<213> ORGANISM: Artificial Sequence
<220> FEATURE:
<223> OTHER INFORMATION: Synthetic

<400> SEQUENCE: 33

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 34
<211> LENGTH: 80
<212> TYPE: PRT
<213> ORGANISM: Artificial Sequence
<220> FEATURE:
<223> OTHER INFORMATION: Synthetic

<400> SEQUENCE: 34

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Gln Glu Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 35
<211> LENGTH: 80
<212> TYPE: PRT
<213> ORGANISM: Artificial Sequence
<220> FEATURE:
<223> OTHER INFORMATION: Synthetic

<400> SEQUENCE: 35

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Gln Glu Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 36
<211> LENGTH: 80
<212> TYPE: PRT
<213> ORGANISM: Artificial Sequence
<220> FEATURE:
<223> OTHER INFORMATION: Synthetic

<400> SEQUENCE: 36

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 37
<211> LENGTH: 80
<212> TYPE: PRT
<213> ORGANISM: Artificial Sequence
<220> FEATURE:
<223> OTHER INFORMATION: Synthetic

<400> SEQUENCE: 37

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
        50                  55                  60

Gly Gln Glu Pro Gly Gln Glu Pro Gly Gln Glu Pro Gly Gln Glu Pro
65                  70                  75                  80

<210> SEQ ID NO 38
<211> LENGTH: 80
<212> TYPE: PRT
<213> ORGANISM: Artificial Sequence
<220> FEATURE:
<223> OTHER INFORMATION: Synthetic

<400> SEQUENCE: 38

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
        50                  55                  60

Gly Ala Gln Pro Gly Gln Glu Pro Gly Gln Glu Pro Gly Gln Glu Pro
65                  70                  75                  80

<210> SEQ ID NO 39
<211> LENGTH: 80
<212> TYPE: PRT
<213> ORGANISM: Artificial Sequence
<220> FEATURE:
<223> OTHER INFORMATION: Synthetic

<400> SEQUENCE: 39

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro

```
                    35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Gln Glu Pro Gly Gln Glu Pro
65                  70                  75                  80

<210> SEQ ID NO 40
<211> LENGTH: 80
<212> TYPE: PRT
<213> ORGANISM: Artificial Sequence
<220> FEATURE:
<223> OTHER INFORMATION: Synthetic

<400> SEQUENCE: 40

Gly Ala Gln Pro Gly Ala Gln Pro Gly Ala Gln Pro Gly Ala Gln Pro
1               5                  10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 41
<211> LENGTH: 80
<212> TYPE: PRT
<213> ORGANISM: Artificial Sequence
<220> FEATURE:
<223> OTHER INFORMATION: Synthetic

<400> SEQUENCE: 41

Gly Ala Gln Pro Gly Ala Gln Pro Gly Ala Gln Pro Gly Ala Gln Pro
1               5                  10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 42
<211> LENGTH: 80
<212> TYPE: PRT
<213> ORGANISM: Artificial Sequence
<220> FEATURE:
<223> OTHER INFORMATION: Synthetic

<400> SEQUENCE: 42

Gly Ala Gln Pro Gly Ala Gln Pro Gly Ala Gln Pro Gly Ala Gln Pro
1               5                  10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Ala Gln Pro Gly Ala Gln Pro
            35                  40                  45

Gly Gln Glu Pro Gly Ala Gln Pro Gly Gln Glu Pro Gly Ala Gln Pro
    50                  55                  60
```

```
Gly Gln Glu Pro Gly Ala Gln Pro Gly Gln Glu Pro Gly Ala Gln Pro
 65                  70                  75                  80

<210> SEQ ID NO 43
<211> LENGTH: 80
<212> TYPE: PRT
<213> ORGANISM: Artificial Sequence
<220> FEATURE:
<223> OTHER INFORMATION: Synthetic

<400> SEQUENCE: 43

Gly Ala Gln Pro Gly Ala Gln Pro Gly Ala Gln Pro Gly Ala Gln Pro
  1               5                  10                  15

Gly Ala Gln Pro Gly Ala Gln Pro Gly Ala Gln Pro Gly Ala Gln Pro
                 20                  25                  30

Gly Ala Gln Pro Gly Ala Gln Pro Gly Gln Glu Pro Gly Ala Gln Pro
                 35                  40                  45

Gly Gln Glu Pro Gly Ala Gln Pro Gly Gln Glu Pro Gly Ala Gln Pro
         50                  55                  60

Gly Gln Glu Pro Gly Ala Gln Pro Gly Gln Glu Pro Gly Ala Gln Pro
 65                  70                  75                  80

<210> SEQ ID NO 44
<211> LENGTH: 80
<212> TYPE: PRT
<213> ORGANISM: Artificial Sequence
<220> FEATURE:
<223> OTHER INFORMATION: Synthetic

<400> SEQUENCE: 44

Gly Ala Gln Pro Gly Ala Gln Pro Gly Ala Gln Pro Gly Ala Gln Pro
  1               5                  10                  15

Gly Ala Gln Pro Gly Ala Gln Pro Gly Ala Gln Pro Gly Ala Gln Pro
                 20                  25                  30

Gly Gln Glu Pro Gly Ala Gln Pro Gly Gln Glu Pro Gly Ala Gln Pro
                 35                  40                  45

Gly Gln Glu Pro Gly Ala Gln Pro Gly Gln Glu Pro Gly Ala Gln Pro
         50                  55                  60

Gly Gln Glu Pro Gly Ala Gln Pro Gly Gln Glu Pro Gly Ala Gln Pro
 65                  70                  75                  80

<210> SEQ ID NO 45
<211> LENGTH: 80
<212> TYPE: PRT
<213> ORGANISM: Artificial Sequence
<220> FEATURE:
<223> OTHER INFORMATION: Synthetic

<400> SEQUENCE: 45

Gly Ala Gln Pro Gly Ala Gln Pro Gly Ala Gln Pro Gly Ala Gln Pro
  1               5                  10                  15

Gly Ala Gln Pro Gly Ala Gln Pro Gly Gln Glu Pro Gly Ala Gln Pro
                 20                  25                  30

Gly Gln Glu Pro Gly Ala Gln Pro Gly Gln Glu Pro Gly Ala Gln Pro
                 35                  40                  45

Gly Gln Glu Pro Gly Ala Gln Pro Gly Gln Glu Pro Gly Ala Gln Pro
         50                  55                  60

Gly Gln Glu Pro Gly Ala Gln Pro Gly Gln Glu Pro Gly Ala Gln Pro
 65                  70                  75                  80
```

<210> SEQ ID NO 46
<211> LENGTH: 80
<212> TYPE: PRT
<213> ORGANISM: Artificial Sequence
<220> FEATURE:
<223> OTHER INFORMATION: Synthetic

<400> SEQUENCE: 46

Gly Ala Gln Pro Gly Ala Gln Pro Gly Ala Gln Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Ala Gln Pro Gly Gln Glu Pro Gly Ala Gln Pro
        50                  55                  60

Gly Gln Glu Pro Gly Ala Gln Pro Gly Gln Glu Pro Gly Ala Gln Pro
65                  70                  75                  80

<210> SEQ ID NO 47
<211> LENGTH: 80
<212> TYPE: PRT
<213> ORGANISM: Artificial Sequence
<220> FEATURE:
<223> OTHER INFORMATION: Synthetic

<400> SEQUENCE: 47

Gly Ala Gln Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Ala Gln Pro Gly Gln Glu Pro Gly Ala Gln Pro
        50                  55                  60

Gly Gln Glu Pro Gly Ala Gln Pro Gly Gln Glu Pro Gly Ala Gln Pro
65                  70                  75                  80

<210> SEQ ID NO 48
<211> LENGTH: 80
<212> TYPE: PRT
<213> ORGANISM: Artificial Sequence
<220> FEATURE:
<223> OTHER INFORMATION: Synthetic

<400> SEQUENCE: 48

Gly Ala Gln Pro Gly Gln Glu Pro Gly Ala Gln Pro Gly Ala Gln Pro
1               5                   10                  15

Gly Gln Glu Pro Gly Ala Gln Pro Gly Ala Gln Pro Gly Gln Glu Pro
                20                  25                  30

Gly Ala Gln Pro Gly Ala Gln Pro Gly Gln Glu Pro Gly Ala Gln Pro
            35                  40                  45

Gly Ala Gln Pro Gly Gln Glu Pro Gly Ala Gln Pro Gly Ala Gln Pro
        50                  55                  60

Gly Gln Glu Pro Gly Ala Gln Pro Gly Ala Gln Pro Gly Ala Gln Pro
65                  70                  75                  80

<210> SEQ ID NO 49
<211> LENGTH: 80
<212> TYPE: PRT

<213> ORGANISM: Artificial Sequence
<220> FEATURE:
<223> OTHER INFORMATION: Synthetic

<400> SEQUENCE: 49

```
Gly Ala Gln Pro Gly Ala Gln Pro Gly Gln Glu Pro Gly Ala Gln Pro
1               5                   10                  15
Gly Ala Gln Pro Gly Gln Glu Pro Gly Ala Gln Pro Gly Ala Gln Pro
                20                  25                  30
Gly Gln Glu Pro Gly Ala Gln Pro Gly Ala Gln Pro Gly Gln Glu Pro
                35                  40                  45
Gly Ala Gln Pro Gly Ala Gln Pro Gly Gln Glu Pro Gly Ala Gln Pro
        50                  55                  60
Gly Ala Gln Pro Gly Gln Glu Pro Gly Ala Gln Pro Gly Ala Gln Pro
65                  70                  75                  80
```

<210> SEQ ID NO 50
<211> LENGTH: 80
<212> TYPE: PRT
<213> ORGANISM: Artificial Sequence
<220> FEATURE:
<223> OTHER INFORMATION: Synthetic

<400> SEQUENCE: 50

```
Gly Ala Gln Pro Gly Gln Glu Pro Gly Ala Gln Pro Gly Ala Gln Pro
1               5                   10                  15
Gly Gln Glu Pro Gly Ala Gln Pro Gly Ala Gln Pro Gly Gln Glu Pro
                20                  25                  30
Gly Ala Gln Pro Gly Ala Gln Pro Gly Gln Glu Pro Gly Ala Gln Pro
                35                  40                  45
Gly Ala Gln Pro Gly Gln Glu Pro Gly Ala Gln Pro Gly Ala Gln Pro
        50                  55                  60
Gly Ala Gln Pro Gly Ala Gln Pro Gly Ala Gln Pro Gly Ala Gln Pro
65                  70                  75                  80
```

<210> SEQ ID NO 51
<211> LENGTH: 80
<212> TYPE: PRT
<213> ORGANISM: Artificial Sequence
<220> FEATURE:
<223> OTHER INFORMATION: Synthetic

<400> SEQUENCE: 51

```
Gly Ala Gln Pro Gly Ala Gln Pro Gly Ala Gln Pro Gly Ala Gln Pro
1               5                   10                  15
Gly Ala Gln Pro Gly Ala Gln Pro Gly Ala Gln Pro Gly Ala Gln Pro
                20                  25                  30
Gly Ala Gln Pro Gly Ala Gln Pro Gly Gln Glu Pro Gly Gln Glu Pro
                35                  40                  45
Gly Gln Glu Pro Gly Gln Glu Pro Gly Gln Glu Pro Gly Gln Glu Pro
        50                  55                  60
Gly Gln Glu Pro Gly Gln Glu Pro Gly Ala Gln Pro Gly Ala Gln Pro
65                  70                  75                  80
```

<210> SEQ ID NO 52
<211> LENGTH: 80
<212> TYPE: PRT
<213> ORGANISM: Artificial Sequence
<220> FEATURE:
<223> OTHER INFORMATION: Synthetic

<400> SEQUENCE: 52

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Gln Glu Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Ala Gln Pro Gly Ala Gln Pro
65                  70                  75                  80

<210> SEQ ID NO 53
<211> LENGTH: 80
<212> TYPE: PRT
<213> ORGANISM: Artificial Sequence
<220> FEATURE:
<223> OTHER INFORMATION: Synthetic

<400> SEQUENCE: 53

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Ala Gln Pro Gly Ala Gln Pro
65                  70                  75                  80

<210> SEQ ID NO 54
<211> LENGTH: 80
<212> TYPE: PRT
<213> ORGANISM: Artificial Sequence
<220> FEATURE:
<223> OTHER INFORMATION: Synthetic

<400> SEQUENCE: 54

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Gln Glu Pro Gly Gln Glu Pro Gly Gln Glu Pro
    50                  55                  60

Gly Gln Glu Pro Gly Gln Glu Pro Gly Ala Gln Pro Gly Ala Gln Pro
65                  70                  75                  80

<210> SEQ ID NO 55
<211> LENGTH: 80
<212> TYPE: PRT
<213> ORGANISM: Artificial Sequence
<220> FEATURE:
<223> OTHER INFORMATION: Synthetic

<400> SEQUENCE: 55

Gly Ala Gln Pro Gly Ala Gln Pro Gly Ala Gln Pro Gly Ala Gln Pro
1               5                   10                  15

-continued

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Gln Glu Pro Gly Gln Glu Pro
 50                  55                  60

Gly Gln Glu Pro Gly Gln Glu Pro Gly Ala Gln Pro Gly Ala Gln Pro
65                  70                  75                  80

<210> SEQ ID NO 56
<211> LENGTH: 80
<212> TYPE: PRT
<213> ORGANISM: Artificial Sequence
<220> FEATURE:
<223> OTHER INFORMATION: Synthetic

<400> SEQUENCE: 56

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Gln Glu Pro Gly Gln Glu Pro
 50                  55                  60

Gly Gln Glu Pro Gly Gln Glu Pro Gly Ala Gln Pro Gly Ala Gln Pro
65                  70                  75                  80

<210> SEQ ID NO 57
<211> LENGTH: 80
<212> TYPE: PRT
<213> ORGANISM: Artificial Sequence
<220> FEATURE:
<223> OTHER INFORMATION: Synthetic

<400> SEQUENCE: 57

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
 50                  55                  60

Gly Gln Glu Pro Gly Gln Glu Pro Gly Ala Gln Pro Gly Ala Gln Pro
65                  70                  75                  80

<210> SEQ ID NO 58
<211> LENGTH: 80
<212> TYPE: PRT
<213> ORGANISM: Artificial Sequence
<220> FEATURE:
<223> OTHER INFORMATION: Synthetic

<400> SEQUENCE: 58

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

```
Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Gln Glu Pro Gly Gln Glu Pro Gly Ala Gln Pro Gly Ala Gln Pro
65                  70                  75                  80
```

<210> SEQ ID NO 59
<211> LENGTH: 80
<212> TYPE: PRT
<213> ORGANISM: Artificial Sequence
<220> FEATURE:
<223> OTHER INFORMATION: Synthetic

<400> SEQUENCE: 59

```
Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Gln Glu Pro Gly Ala Gln Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Ala Gln Pro Gly Ala Gln Pro
65                  70                  75                  80
```

<210> SEQ ID NO 60
<211> LENGTH: 80
<212> TYPE: PRT
<213> ORGANISM: Artificial Sequence
<220> FEATURE:
<223> OTHER INFORMATION: Synthetic

<400> SEQUENCE: 60

```
Lys Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80
```

<210> SEQ ID NO 61
<211> LENGTH: 80
<212> TYPE: PRT
<213> ORGANISM: Artificial Sequence
<220> FEATURE:
<223> OTHER INFORMATION: Synthetic

<400> SEQUENCE: 61

```
Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Gln Glu Pro Gly Gln Glu Pro Gly Gln Glu Pro
```

```
                50                  55                  60

Gly Gln Glu Pro Gly Gln Glu Pro Gly Ala Gln Pro Gly Ala Gln Pro
 65                  70                  75                  80

<210> SEQ ID NO 62
<211> LENGTH: 80
<212> TYPE: PRT
<213> ORGANISM: Artificial Sequence
<220> FEATURE:
<223> OTHER INFORMATION: Synthetic

<400> SEQUENCE: 62

Gly Ala Gln Pro Gly Ala Gln Pro Gly Ala Gln Pro Gly Ala Gln Pro
 1               5                  10                  15

Gly Ala Gln Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Gln Glu Pro Gly Gln Glu Pro Gly Gln Glu Pro
         50                  55                  60

Gly Gln Glu Pro Gly Gln Glu Pro Gly Ala Gln Pro Gly Ala Gln Pro
 65                  70                  75                  80

<210> SEQ ID NO 63
<211> LENGTH: 80
<212> TYPE: PRT
<213> ORGANISM: Artificial Sequence
<220> FEATURE:
<223> OTHER INFORMATION: Synthetic

<400> SEQUENCE: 63

Gly Ala Gln Pro Gly Ala Gln Pro Gly Ala Gln Pro Gly Ala Gln Pro
 1               5                  10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Gln Glu Pro Gly Gln Glu Pro Gly Gln Glu Pro
         50                  55                  60

Gly Gln Glu Pro Gly Gln Glu Pro Gly Ala Gln Pro Gly Ala Gln Pro
 65                  70                  75                  80

<210> SEQ ID NO 64
<211> LENGTH: 80
<212> TYPE: PRT
<213> ORGANISM: Artificial Sequence
<220> FEATURE:
<223> OTHER INFORMATION: Synthetic

<400> SEQUENCE: 64

Gly Ala Gln Pro Gly Ala Gln Pro Gly Ala Gln Pro Gly Ala Gln Pro
 1               5                  10                  15

Gly Ala Gln Pro Gly Ala Gln Pro Gly Ala Gln Pro Gly Ala Gln Pro
                20                  25                  30

Gly Ala Gln Pro Gly Gln Glu Pro Gly Ala Gln Pro Gly Gln Glu Pro
            35                  40                  45

Gly Gln Glu Pro Gly Gln Glu Pro Gly Gln Glu Pro Gly Gln Glu Pro
         50                  55                  60

Gly Gln Glu Pro Gly Gln Glu Pro Gly Ala Gln Pro Gly Ala Gln Pro
 65                  70                  75                  80
```

<210> SEQ ID NO 65
<211> LENGTH: 80
<212> TYPE: PRT
<213> ORGANISM: Artificial Sequence
<220> FEATURE:
<223> OTHER INFORMATION: Synthetic

<400> SEQUENCE: 65

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 66
<211> LENGTH: 80
<212> TYPE: PRT
<213> ORGANISM: Artificial Sequence
<220> FEATURE:
<223> OTHER INFORMATION: Snythetic

<400> SEQUENCE: 66

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 67
<211> LENGTH: 80
<212> TYPE: PRT
<213> ORGANISM: Artificial Sequence
<220> FEATURE:
<223> OTHER INFORMATION: Synthetic

<400> SEQUENCE: 67

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 68
<211> LENGTH: 80

```
<212> TYPE: PRT
<213> ORGANISM: Artificial Sequence
<220> FEATURE:
<223> OTHER INFORMATION: Synthetic

<400> SEQUENCE: 68

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Gly Gln Glu Pro Gly Gln Glu Pro Gly Gln Glu Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 69
<211> LENGTH: 80
<212> TYPE: PRT
<213> ORGANISM: Artificial Sequence
<220> FEATURE:
<223> OTHER INFORMATION: Synthetic

<400> SEQUENCE: 69

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Gly Gln Glu Pro Gly Gln Glu Pro Gly Gln Glu Pro Gly Gln Glu Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 70
<211> LENGTH: 80
<212> TYPE: PRT
<213> ORGANISM: Artificial Sequence
<220> FEATURE:
<223> OTHER INFORMATION: Synthetic

<400> SEQUENCE: 70

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Gly Gln Glu Pro Gly Gln Glu Pro Gly Gln Glu Pro Gly Gln Glu Pro
            35                  40                  45

Gly Gln Glu Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 71
<211> LENGTH: 80
<212> TYPE: PRT
<213> ORGANISM: Artificial Sequence
<220> FEATURE:
<223> OTHER INFORMATION: Synthetic
```

<400> SEQUENCE: 71

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 72
<211> LENGTH: 80
<212> TYPE: PRT
<213> ORGANISM: Artificial Sequence
<220> FEATURE:
<223> OTHER INFORMATION: Synthetic

<400> SEQUENCE: 72

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 73
<211> LENGTH: 80
<212> TYPE: PRT
<213> ORGANISM: Artificial Sequence
<220> FEATURE:
<223> OTHER INFORMATION: Synthetic

<400> SEQUENCE: 73

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro Gly Gln Glu Pro
    50                  55                  60

Gly Ala Gln Pro Gly Ala Gln Pro Gly Ala Gln Pro Gly Ala Gln Pro
65                  70                  75                  80

<210> SEQ ID NO 74
<211> LENGTH: 80
<212> TYPE: PRT
<213> ORGANISM: Artificial Sequence
<220> FEATURE:
<223> OTHER INFORMATION: Synthetic

<400> SEQUENCE: 74

Ser Glu Pro Ala Thr Ser Gly Ser Glu Thr Pro Gly Thr Ser Glu Ser

```
                1               5                  10                 15
Ala Thr Pro Glu Ser Gly Pro Gly Thr Ser Thr Glu Pro Ser Glu Gly
                20                 25                 30

Gly Gln Glu Pro Gly Gln Glu Pro Gly Gln Glu Pro Gly Gln Glu Pro
            35                 40                 45

Gly Gln Glu Pro Gly Gln Glu Pro Gly Gln Glu Pro Gly Gln Glu Pro
 50                 55                 60

Gly Gln Glu Pro Gly Ala Gln Pro Gly Ala Gln Pro Gly Ala Gln Pro
 65                 70                 75                 80
```

<210> SEQ ID NO 75
<211> LENGTH: 80
<212> TYPE: PRT
<213> ORGANISM: Artificial Sequence
<220> FEATURE:
<223> OTHER INFORMATION: Synthetic

<400> SEQUENCE: 75

```
Ser Glu Pro Ala Thr Ser Gly Ser Glu Thr Pro Gly Thr Ser Glu Ser
 1               5                  10                 15

Ala Thr Pro Glu Ser Gly Pro Gly Thr Ser Thr Glu Pro Ser Glu Gly
                20                 25                 30

Gly Gln Glu Pro Gly Gln Glu Pro Gly Gln Glu Pro Gly Gln Glu Pro
            35                 40                 45

Gly Gln Glu Pro Gly Gln Glu Pro Gly Gln Glu Pro Gly Gln Glu Pro
 50                 55                 60

Gly Gln Glu Pro Gly Gln Glu Pro Gly Ala Gln Pro Gly Ala Gln Pro
 65                 70                 75                 80
```

<210> SEQ ID NO 76
<211> LENGTH: 80
<212> TYPE: PRT
<213> ORGANISM: Artificial Sequence
<220> FEATURE:
<223> OTHER INFORMATION: Synthetic

<400> SEQUENCE: 76

```
Ser Glu Pro Ala Thr Ser Gly Ser Glu Thr Pro Gly Thr Ser Glu Ser
 1               5                  10                 15

Ala Thr Pro Glu Ser Gly Pro Gly Thr Ser Thr Glu Pro Ser Glu Gly
                20                 25                 30

Gly Gln Glu Pro Gly Gln Glu Pro Gly Gln Glu Pro Gly Gln Glu Pro
            35                 40                 45

Gly Gln Glu Pro Gly Gln Glu Pro Gly Gln Glu Pro Gly Gln Glu Pro
 50                 55                 60

Gly Gln Glu Pro Gly Gln Glu Pro Gly Gln Glu Pro Gly Ala Gln Pro
 65                 70                 75                 80
```

<210> SEQ ID NO 77
<211> LENGTH: 80
<212> TYPE: PRT
<213> ORGANISM: Artificial Sequence
<220> FEATURE:
<223> OTHER INFORMATION: Synthetic

<400> SEQUENCE: 77

```
Ser Glu Pro Ala Thr Ser Gly Ser Glu Thr Pro Gly Thr Ser Glu Ser
 1               5                  10                 15

Ala Thr Pro Glu Ser Gly Pro Gly Thr Ser Thr Glu Pro Ser Glu Gly
                20                 25                 30
```

Gly Gln Glu Pro Gly Gln Glu Pro Gly Gln Glu Pro Gly Gln Glu Pro
       35                  40                  45

Gly Gln Glu Pro Gly Gln Glu Pro Gly Gln Glu Pro Gly Gln Glu Pro
 50                  55                  60

Gly Gln Glu Pro Gly Gln Glu Pro Gly Gln Glu Pro Gly Gln Glu Pro
65                   70                  75                  80

<210> SEQ ID NO 78
<211> LENGTH: 80
<212> TYPE: PRT
<213> ORGANISM: Artificial Sequence
<220> FEATURE:
<223> OTHER INFORMATION: Synthetic

<400> SEQUENCE: 78

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
       35                  40                  45

Gly Ala Gln Pro Gly Ala Gln Pro Gly Ala Gln Pro Gly Ala Gln Pro
 50                  55                  60

Gly Ala Gln Pro Gly Ala Gln Pro Gly Ala Gln Pro Gly Gln Glu Pro
65                   70                  75                  80

<210> SEQ ID NO 79
<211> LENGTH: 80
<212> TYPE: PRT
<213> ORGANISM: Artificial Sequence
<220> FEATURE:
<223> OTHER INFORMATION: Synthetic

<400> SEQUENCE: 79

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
       35                  40                  45

Gly Ala Gln Pro Gly Ala Gln Pro Gly Ala Gln Pro Gly Ala Gln Pro
 50                  55                  60

Gly Ala Gln Pro Gly Ala Gln Pro Gly Gln Glu Pro Gly Gln Glu Pro
65                   70                  75                  80

<210> SEQ ID NO 80
<211> LENGTH: 80
<212> TYPE: PRT
<213> ORGANISM: Artificial Sequence
<220> FEATURE:
<223> OTHER INFORMATION: Synthetic

<400> SEQUENCE: 80

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
       35                  40                  45

Gly Ala Gln Pro Gly Ala Gln Pro Gly Ala Gln Pro Gly Ala Gln Pro
        50                  55                  60

Gly Ala Gln Pro Gly Gln Glu Pro Gly Gln Glu Pro Gly Gln Glu Pro
65                  70                  75                  80

<210> SEQ ID NO 81
<211> LENGTH: 80
<212> TYPE: PRT
<213> ORGANISM: Artificial Sequence
<220> FEATURE:
<223> OTHER INFORMATION: Synthetic

<400> SEQUENCE: 81

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
        50                  55                  60

Gly Gln Glu Pro Gly Gln Glu Pro Gly Gln Glu Pro Gly Gln Glu Pro
65                  70                  75                  80

<210> SEQ ID NO 82
<211> LENGTH: 80
<212> TYPE: PRT
<213> ORGANISM: Artificial Sequence
<220> FEATURE:
<223> OTHER INFORMATION: Synthetic

<400> SEQUENCE: 82

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Gln Glu Pro
        50                  55                  60

Gly Gln Glu Pro Gly Gln Glu Pro Gly Gln Glu Pro Gly Gln Glu Pro
65                  70                  75                  80

<210> SEQ ID NO 83
<211> LENGTH: 80
<212> TYPE: PRT
<213> ORGANISM: Artificial Sequence
<220> FEATURE:
<223> OTHER INFORMATION: Synthetic

<400> SEQUENCE: 83

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Gln Glu Pro Gly Gln Glu Pro
        50                  55                  60

Gly Gln Glu Pro Gly Gln Glu Pro Gly Gln Glu Pro Gly Gln Glu Pro

```
<210> SEQ ID NO 84
<211> LENGTH: 80
<212> TYPE: PRT
<213> ORGANISM: Artificial Sequence
<220> FEATURE:
<223> OTHER INFORMATION: Synthetic

<400> SEQUENCE: 84

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Gly Ala Gln Pro Gly Ala Gln Pro Gly Ala Gln Pro Gly Ala Gln Pro
        35                  40                  45
Gly Ala Gln Pro Gly Gln Glu Pro Gly Gln Glu Pro Gly Gln Glu Pro
    50                  55                  60
Gly Gln Glu Pro Gly Gln Glu Pro Gly Gln Glu Pro Gly Gln Glu Pro
65                  70                  75                  80

<210> SEQ ID NO 85
<211> LENGTH: 80
<212> TYPE: PRT
<213> ORGANISM: Artificial Sequence
<220> FEATURE:
<223> OTHER INFORMATION: Synthetic

<400> SEQUENCE: 85

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Gly Ala Gln Pro Gly Ala Gln Pro Gly Ala Gln Pro Gly Ala Gln Pro
        35                  40                  45
Gly Gln Glu Pro Gly Gln Glu Pro Gly Gln Glu Pro Gly Gln Glu Pro
    50                  55                  60
Gly Gln Glu Pro Gly Gln Glu Pro Gly Gln Glu Pro Gly Gln Glu Pro
65                  70                  75                  80

<210> SEQ ID NO 86
<211> LENGTH: 80
<212> TYPE: PRT
<213> ORGANISM: Artificial Sequence
<220> FEATURE:
<223> OTHER INFORMATION: Synthetic

<400> SEQUENCE: 86

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Gly Ala Gln Pro Gly Ala Gln Pro Gly Ala Gln Pro Gly Gln Glu Pro
        35                  40                  45
Gly Gln Glu Pro Gly Gln Glu Pro Gly Gln Glu Pro Gly Gln Glu Pro
    50                  55                  60
Gly Gln Glu Pro Gly Gln Glu Pro Gly Gln Glu Pro Gly Gln Glu Pro
65                  70                  75                  80

<210> SEQ ID NO 87
```

```
<211> LENGTH: 80
<212> TYPE: PRT
<213> ORGANISM: Artificial Sequence
<220> FEATURE:
<223> OTHER INFORMATION: Synthetic

<400> SEQUENCE: 87

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Gly Ala Gln Pro Gly Ala Gln Pro Gly Gln Glu Pro Gly Gln Glu Pro
        35                  40                  45
Gly Gln Glu Pro Gly Gln Glu Pro Gly Gln Glu Pro Gly Gln Glu Pro
    50                  55                  60
Gly Gln Glu Pro Gly Gln Glu Pro Gly Gln Glu Pro Gly Gln Glu Pro
65                  70                  75                  80

<210> SEQ ID NO 88
<211> LENGTH: 80
<212> TYPE: PRT
<213> ORGANISM: Artificial Sequence
<220> FEATURE:
<223> OTHER INFORMATION: Synthetic

<400> SEQUENCE: 88

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30
Gly Ala Gln Pro Gly Gln Glu Pro Gly Gln Glu Pro Gly Gln Glu Pro
        35                  40                  45
Gly Gln Glu Pro Gly Gln Glu Pro Gly Gln Glu Pro Gly Gln Glu Pro
    50                  55                  60
Gly Gln Glu Pro Gly Gln Glu Pro Gly Gln Glu Pro Gly Gln Glu Pro
65                  70                  75                  80

<210> SEQ ID NO 89
<211> LENGTH: 80
<212> TYPE: PRT
<213> ORGANISM: Artificial Sequence
<220> FEATURE:
<223> OTHER INFORMATION: Synthetic

<400> SEQUENCE: 89

Lys Ala Gln Pro Gly Ala Gln Pro Gly Ala Gln Pro Gly Ala Gln Pro
1               5                   10                  15
Gly Ala Gln Pro Gly Ala Gln Pro Gly Ala Gln Pro Gly Ala Gln Pro
            20                  25                  30
Gly Ala Gln Pro Gly Gln Glu Pro Gly Ala Gln Pro Gly Gln Glu Pro
        35                  40                  45
Gly Gln Glu Pro Gly Gln Glu Pro Gly Gln Glu Pro Gly Gln Glu Pro
    50                  55                  60
Gly Gln Glu Pro Gly Gln Glu Pro Gly Ala Gln Pro Gly Ala Gln Pro
65                  70                  75                  80

<210> SEQ ID NO 90
<211> LENGTH: 80
<212> TYPE: PRT
<213> ORGANISM: Artificial Sequence
<220> FEATURE:
```

<223> OTHER INFORMATION: Synthetic

<400> SEQUENCE: 90

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 91
<211> LENGTH: 80
<212> TYPE: PRT
<213> ORGANISM: Artificial Sequence
<220> FEATURE:
<223> OTHER INFORMATION: Synthetic

<400> SEQUENCE: 91

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Ala Gln Pro Gly Gln Glu Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 92
<211> LENGTH: 80
<212> TYPE: PRT
<213> ORGANISM: Artificial Sequence
<220> FEATURE:
<223> OTHER INFORMATION: Synthetic

<400> SEQUENCE: 92

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Ala Gln Pro Gly Gln Glu Pro Gly Ala Gln Pro Gly Gln Glu Pro
    50                  55                  60

Gly Ala Gln Pro Gly Ala Gln Pro Gly Ala Gln Pro Gly Ala Gln Pro
65                  70                  75                  80

<210> SEQ ID NO 93
<211> LENGTH: 80
<212> TYPE: PRT
<213> ORGANISM: Artificial Sequence
<220> FEATURE:
<223> OTHER INFORMATION: Synthetic

<400> SEQUENCE: 93

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Ala Gln Pro Gly Gln Glu Pro Gly Ala Gln Pro Gly Gln Glu Pro
    50                  55                  60

Gly Ala Gln Pro Gly Gln Glu Pro Gly Ala Gln Pro Gly Ala Gln Pro
65                  70                  75                  80

<210> SEQ ID NO 94
<211> LENGTH: 60
<212> TYPE: PRT
<213> ORGANISM: Artificial Sequence
<220> FEATURE:
<223> OTHER INFORMATION: Synthetic

<400> SEQUENCE: 94

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 95
<211> LENGTH: 60
<212> TYPE: PRT
<213> ORGANISM: Artificial Sequence
<220> FEATURE:
<223> OTHER INFORMATION: Synthetic

<400> SEQUENCE: 95

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Ala Gln Pro
    50                  55                  60

<210> SEQ ID NO 96
<211> LENGTH: 60
<212> TYPE: PRT
<213> ORGANISM: Artificial Sequence
<220> FEATURE:
<223> OTHER INFORMATION: Synthetic

<400> SEQUENCE: 96

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro

<210> SEQ ID NO 97
<211> LENGTH: 60
<212> TYPE: PRT
<213> ORGANISM: Artificial Sequence
<220> FEATURE:
<223> OTHER INFORMATION: Synthetic

<400> SEQUENCE: 97

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Ala Gln Pro Gly Ala Gln Pro Gly Ala Gln Pro
    50                  55                  60

<210> SEQ ID NO 98
<211> LENGTH: 60
<212> TYPE: PRT
<213> ORGANISM: Artificial Sequence
<220> FEATURE:
<223> OTHER INFORMATION: Synthetic

<400> SEQUENCE: 98

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Ala Gln Pro
        35                  40                  45

Gly Ala Gln Pro Gly Ala Gln Pro Gly Ala Gln Pro
    50                  55                  60

<210> SEQ ID NO 99
<211> LENGTH: 60
<212> TYPE: PRT
<213> ORGANISM: Artificial Sequence
<220> FEATURE:
<223> OTHER INFORMATION: Synthetic

<400> SEQUENCE: 99

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 100
<211> LENGTH: 60
<212> TYPE: PRT
<213> ORGANISM: Artificial Sequence
<220> FEATURE:
<223> OTHER INFORMATION: Synthetic

<400> SEQUENCE: 100

Gly Gln Glu Pro Gly Gln Glu Pro Gly Gln Glu Pro Gly Gln Glu Pro

```
1               5                   10                  15
Gly Gln Glu Pro Gly Gln Glu Pro Gly Gln Glu Pro Gly Gln Glu Pro
            20                  25                  30
Gly Gln Glu Pro Gly Ala Gln Pro Gly Ala Gln Pro Gly Ala Gln Pro
            35                  40                  45
Gly Ala Gln Pro Gly Ala Gln Pro Gly Ala Gln Pro
        50                  55                  60

<210> SEQ ID NO 101
<211> LENGTH: 60
<212> TYPE: PRT
<213> ORGANISM: Artificial Sequence
<220> FEATURE:
<223> OTHER INFORMATION: Synthetic

<400> SEQUENCE: 101

Gly Gln Glu Pro Gly Gln Glu Pro Gly Gln Glu Pro Gly Gln Glu Pro
1               5                   10                  15
Gly Gln Glu Pro Gly Gln Glu Pro Gly Gln Glu Pro Gly Gln Glu Pro
            20                  25                  30
Gly Ala Gln Pro Gly Ala Gln Pro Gly Ala Gln Pro Gly Ala Gln Pro
            35                  40                  45
Gly Ala Gln Pro Gly Ala Gln Pro Gly Ala Gln Pro
        50                  55                  60

<210> SEQ ID NO 102
<211> LENGTH: 60
<212> TYPE: PRT
<213> ORGANISM: Artificial Sequence
<220> FEATURE:
<223> OTHER INFORMATION: Synthetic

<400> SEQUENCE: 102

Gly Gln Glu Pro Gly Gln Glu Pro Gly Gln Glu Pro Gly Gln Glu Pro
1               5                   10                  15
Gly Gln Glu Pro Gly Gln Glu Pro Gly Gln Glu Pro Gly Ala Gln Pro
            20                  25                  30
Gly Ala Gln Pro Gly Ala Gln Pro Gly Ala Gln Pro Gly Ala Gln Pro
            35                  40                  45
Gly Ala Gln Pro Gly Ala Gln Pro Gly Ala Gln Pro
        50                  55                  60

<210> SEQ ID NO 103
<211> LENGTH: 60
<212> TYPE: PRT
<213> ORGANISM: Artificial Sequence
<220> FEATURE:
<223> OTHER INFORMATION: Synthetic

<400> SEQUENCE: 103

Gly Gln Glu Pro Gly Gln Glu Pro Gly Gln Glu Pro Gly Gln Glu Pro
1               5                   10                  15
Gly Gln Glu Pro Gly Gln Glu Pro Gly Ala Gln Pro Gly Ala Gln Pro
            20                  25                  30
Gly Ala Gln Pro Gly Ala Gln Pro Gly Ala Gln Pro Gly Ala Gln Pro
            35                  40                  45
Gly Ala Gln Pro Gly Ala Gln Pro Gly Ala Gln Pro
        50                  55                  60

<210> SEQ ID NO 104
```

```
<211> LENGTH: 60
<212> TYPE: PRT
<213> ORGANISM: Artificial Sequence
<220> FEATURE:
<223> OTHER INFORMATION: Synthetic

<400> SEQUENCE: 104

Gly Gln Glu Pro Gly Gln Glu Pro Gly Gln Glu Pro Gly Gln Glu Pro
1               5                   10                  15

Gly Gln Glu Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 105
<211> LENGTH: 60
<212> TYPE: PRT
<213> ORGANISM: Artificial Sequence
<220> FEATURE:
<223> OTHER INFORMATION: Synthetic

<400> SEQUENCE: 105

Gly Gln Glu Pro Gly Gln Glu Pro Gly Gln Glu Pro Gly Gln Glu Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 106
<211> LENGTH: 60
<212> TYPE: PRT
<213> ORGANISM: Artificial Sequence
<220> FEATURE:
<223> OTHER INFORMATION: Synthetic

<400> SEQUENCE: 106

Gly Gln Glu Pro Gly Gln Glu Pro Gly Gln Glu Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 107
<211> LENGTH: 60
<212> TYPE: PRT
<213> ORGANISM: Artificial Sequence
<220> FEATURE:
<223> OTHER INFORMATION: Synthetic

<400> SEQUENCE: 107

Gly Gln Glu Pro Gly Gln Glu Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30
```

```
Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60
```

<210> SEQ ID NO 108
<211> LENGTH: 60
<212> TYPE: PRT
<213> ORGANISM: Artificial Sequence
<220> FEATURE:
<223> OTHER INFORMATION: Synthetic

<400> SEQUENCE: 108

```
Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
        20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro
    50                  55                  60
```

<210> SEQ ID NO 109
<211> LENGTH: 60
<212> TYPE: PRT
<213> ORGANISM: Artificial Sequence
<220> FEATURE:
<223> OTHER INFORMATION: Synthetic

<400> SEQUENCE: 109

```
Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
        20                  25                  30

Gly Gln Glu Pro Gly Ala Gln Pro Gly Gln Glu Pro Gly Ala Gln Pro
        35                  40                  45

Gly Gln Glu Pro Gly Gln Glu Pro Gly Gln Glu Pro
    50                  55                  60
```

<210> SEQ ID NO 110
<211> LENGTH: 60
<212> TYPE: PRT
<213> ORGANISM: Artificial Sequence
<220> FEATURE:
<223> OTHER INFORMATION: Synthetic

<400> SEQUENCE: 110

```
Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
        20                  25                  30

Gly Gln Glu Pro Gly Ala Gln Pro Gly Gln Glu Pro Gly Gln Glu Pro
        35                  40                  45

Gly Gln Glu Pro Gly Gln Glu Pro Gly Gln Glu Pro
    50                  55                  60
```

<210> SEQ ID NO 111
<211> LENGTH: 60
<212> TYPE: PRT
<213> ORGANISM: Artificial Sequence
<220> FEATURE:

<223> OTHER INFORMATION: Synthetic

<400> SEQUENCE: 111

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 112
<211> LENGTH: 60
<212> TYPE: PRT
<213> ORGANISM: Artificial Sequence
<220> FEATURE:
<223> OTHER INFORMATION: Synthetic

<400> SEQUENCE: 112

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 113
<211> LENGTH: 60
<212> TYPE: PRT
<213> ORGANISM: Artificial Sequence
<220> FEATURE:
<223> OTHER INFORMATION: Synthetic

<400> SEQUENCE: 113

Gly Gln Glu Pro Gly Ala Gln Pro Gly Gln Glu Pro Gly Ala Gln Pro
1               5                   10                  15

Gly Gln Glu Pro Gly Gln Glu Pro Gly Gln Glu Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 114
<211> LENGTH: 60
<212> TYPE: PRT
<213> ORGANISM: Artificial Sequence
<220> FEATURE:
<223> OTHER INFORMATION: Synthetic

<400> SEQUENCE: 114

Gly Gln Glu Pro Gly Ala Gln Pro Gly Gln Glu Pro Gly Gln Glu Pro
1               5                   10                  15

Gly Gln Glu Pro Gly Gln Glu Pro Gly Gln Glu Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro
    50                  55                  60

<210> SEQ ID NO 115
<211> LENGTH: 60
<212> TYPE: PRT
<213> ORGANISM: Artificial Sequence
<220> FEATURE:
<223> OTHER INFORMATION: Synthetic

<400> SEQUENCE: 115

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Ala Gln Pro
    50                  55                  60

<210> SEQ ID NO 116
<211> LENGTH: 60
<212> TYPE: PRT
<213> ORGANISM: Artificial Sequence
<220> FEATURE:
<223> OTHER INFORMATION: Synthetic

<400> SEQUENCE: 116

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro
    50                  55                  60

<210> SEQ ID NO 117
<211> LENGTH: 60
<212> TYPE: PRT
<213> ORGANISM: Artificial Sequence
<220> FEATURE:
<223> OTHER INFORMATION: Synthetic

<400> SEQUENCE: 117

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 118
<211> LENGTH: 60
<212> TYPE: PRT
<213> ORGANISM: Artificial Sequence
<220> FEATURE:
<223> OTHER INFORMATION: Synthetic

<400> SEQUENCE: 118

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 119
<211> LENGTH: 60
<212> TYPE: PRT
<213> ORGANISM: Artificial Sequence
<220> FEATURE:
<223> OTHER INFORMATION: Synthetic

<400> SEQUENCE: 119

Gly Gln Glu Pro Gly Ala Gln Pro Gly Gln Glu Pro Gly Ala Gln Pro
1               5                   10                  15

Gly Gln Glu Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 120
<211> LENGTH: 60
<212> TYPE: PRT
<213> ORGANISM: Artificial Sequence
<220> FEATURE:
<223> OTHER INFORMATION: Synthetic

<400> SEQUENCE: 120

Gly Gln Glu Pro Gly Ala Gln Pro Gly Gln Glu Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 121
<211> LENGTH: 60
<212> TYPE: PRT
<213> ORGANISM: Artificial Sequence
<220> FEATURE:
<223> OTHER INFORMATION: Synthetic

<400> SEQUENCE: 121

Gly Ala Gln Pro Gly Ala Gln Pro Gly Ala Gln Pro Gly Ala Gln Pro
1               5                   10                  15

Gly Ala Gln Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 122
<211> LENGTH: 60
<212> TYPE: PRT
<213> ORGANISM: Artificial Sequence
<220> FEATURE:
<223> OTHER INFORMATION: Synthetic

<400> SEQUENCE: 122

Gly Ala Gln Pro Gly Ala Gln Pro Gly Ala Gln Pro Gly Ala Gln Pro
1               5                   10                  15

Gly Ala Gln Pro Gly Ala Gln Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 123
<211> LENGTH: 60
<212> TYPE: PRT
<213> ORGANISM: Artificial Sequence
<220> FEATURE:
<223> OTHER INFORMATION: Synthetic

<400> SEQUENCE: 123

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 124
<211> LENGTH: 60
<212> TYPE: PRT
<213> ORGANISM: Artificial Sequence
<220> FEATURE:
<223> OTHER INFORMATION: Synthetic

<400> SEQUENCE: 124

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 125
<211> LENGTH: 60
<212> TYPE: PRT
<213> ORGANISM: Artificial Sequence
<220> FEATURE:
<223> OTHER INFORMATION: Synthetic

<400> SEQUENCE: 125

Gly Ala Gln Pro Gly Ala Gln Pro Gly Ala Gln Pro Gly Gln Glu Pro
1               5                   10                  15

Gly Ala Gln Pro Gly Gln Glu Pro Gly Ala Gln Pro Gly Gln Glu Pro 20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 126
<211> LENGTH: 60
<212> TYPE: PRT
<213> ORGANISM: Artificial Sequence
<220> FEATURE:
<223> OTHER INFORMATION: Synthetic

<400> SEQUENCE: 126

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 127
<211> LENGTH: 60
<212> TYPE: PRT
<213> ORGANISM: Artificial Sequence
<220> FEATURE:
<223> OTHER INFORMATION: Synthetic

<400> SEQUENCE: 127

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Gln Glu Pro Gly Ala Gln Pro Gly Ala Gln Pro
    50                  55                  60

<210> SEQ ID NO 128
<211> LENGTH: 60
<212> TYPE: PRT
<213> ORGANISM: Artificial Sequence
<220> FEATURE:
<223> OTHER INFORMATION: Synthetic

<400> SEQUENCE: 128

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Gln Glu Pro Gly Ala Gln Pro Gly Ala Gln Pro
    50                  55                  60

<210> SEQ ID NO 129
<211> LENGTH: 60
<212> TYPE: PRT
<213> ORGANISM: Artificial Sequence

```
<220> FEATURE:
<223> OTHER INFORMATION: Synthetic

<400> SEQUENCE: 129

Gly Ala Gln Pro Gly Ala Gln Pro Gly Ala Gln Pro Gly Ala Gln Pro
1               5                   10                  15

Gly Gln Glu Pro Gly Ala Gln Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 130
<211> LENGTH: 60
<212> TYPE: PRT
<213> ORGANISM: Artificial Sequence
<220> FEATURE:
<223> OTHER INFORMATION: Synthetic

<400> SEQUENCE: 130

Gly Ala Gln Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 131
<211> LENGTH: 60
<212> TYPE: PRT
<213> ORGANISM: Artificial Sequence
<220> FEATURE:
<223> OTHER INFORMATION: Synthetic

<400> SEQUENCE: 131

Gly Ala Gln Pro Gly Ala Gln Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 132
<211> LENGTH: 60
<212> TYPE: PRT
<213> ORGANISM: Artificial Sequence
<220> FEATURE:
<223> OTHER INFORMATION: Synthetic

<400> SEQUENCE: 132

Gly Ala Gln Pro Gly Ala Gln Pro Gly Ala Gln Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45
```

Gly Gln Glu Pro Gly Gln Glu Pro Gly Gln Glu Pro
        50                  55                  60

<210> SEQ ID NO 133
<211> LENGTH: 60
<212> TYPE: PRT
<213> ORGANISM: Artificial Sequence
<220> FEATURE:
<223> OTHER INFORMATION: Synthetic

<400> SEQUENCE: 133

Gly Ala Gln Pro Gly Ala Gln Pro Gly Ala Gln Pro Gly Ala Gln Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 134
<211> LENGTH: 60
<212> TYPE: PRT
<213> ORGANISM: Artificial Sequence
<220> FEATURE:
<223> OTHER INFORMATION: Synthetic

<400> SEQUENCE: 134

Gly Ala Gln Pro Gly Ala Gln Pro Gly Ala Gln Pro Gly Ala Gln Pro
1               5                   10                  15

Gly Ala Gln Pro Gly Gln Glu Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 135
<211> LENGTH: 60
<212> TYPE: PRT
<213> ORGANISM: Artificial Sequence
<220> FEATURE:
<223> OTHER INFORMATION: Synthetic

<400> SEQUENCE: 135

Gly Ala Gln Pro Gly Ala Gln Pro Gly Ala Gln Pro Gly Ala Gln Pro
1               5                   10                  15

Gly Ala Gln Pro Gly Ala Gln Pro Gly Gln Glu Pro Gly Gln Glu Pro
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 136
<211> LENGTH: 60
<212> TYPE: PRT
<213> ORGANISM: Artificial Sequence
<220> FEATURE:
<223> OTHER INFORMATION: Synthetic

<400> SEQUENCE: 136

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Glu Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 137
<211> LENGTH: 60
<212> TYPE: PRT
<213> ORGANISM: Artificial Sequence
<220> FEATURE:
<223> OTHER INFORMATION: Synthetic

<400> SEQUENCE: 137

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Gln Glu Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 138
<211> LENGTH: 60
<212> TYPE: PRT
<213> ORGANISM: Artificial Sequence
<220> FEATURE:
<223> OTHER INFORMATION: Synthetic

<400> SEQUENCE: 138

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Gln Glu Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 139
<211> LENGTH: 60
<212> TYPE: PRT
<213> ORGANISM: Artificial Sequence
<220> FEATURE:
<223> OTHER INFORMATION: Synthetic

<400> SEQUENCE: 139

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Gln Glu Pro Gly Gln Glu Pro
            35                  40                  45

Gly Gln Glu Pro Gly Gln Glu Pro Gly Gln Glu Pro
        50                  55                  60

<210> SEQ ID NO 140
<211> LENGTH: 60
<212> TYPE: PRT
<213> ORGANISM: Artificial Sequence
<220> FEATURE:
<223> OTHER INFORMATION: Synthetic

<400> SEQUENCE: 140

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Gln Glu Pro
        35                  40                  45

Gly Gln Glu Pro Gly Gln Glu Pro Gly Gln Glu Pro
    50                  55                  60

<210> SEQ ID NO 141
<211> LENGTH: 60
<212> TYPE: PRT
<213> ORGANISM: Artificial Sequence
<220> FEATURE:
<223> OTHER INFORMATION: Synthetic

<400> SEQUENCE: 141

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Gln Glu Pro Gly Gln Glu Pro
    50                  55                  60

<210> SEQ ID NO 142
<211> LENGTH: 60
<212> TYPE: PRT
<213> ORGANISM: Artificial Sequence
<220> FEATURE:
<223> OTHER INFORMATION: Synthetic

<400> SEQUENCE: 142

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Ala Gln Pro Gly Gln Glu Pro Gly Gln Glu Pro
    50                  55                  60

<210> SEQ ID NO 143
<211> LENGTH: 60
<212> TYPE: PRT
<213> ORGANISM: Artificial Sequence
<220> FEATURE:
<223> OTHER INFORMATION: Synthetic

<400> SEQUENCE: 143

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
            35                  40                  45

Gly Ala Gln Pro Gly Gln Glu Pro Gly Gln Glu Pro
        50                  55                  60

<210> SEQ ID NO 144
<211> LENGTH: 60
<212> TYPE: PRT
<213> ORGANISM: Artificial Sequence
<220> FEATURE:
<223> OTHER INFORMATION: Synthetic

<400> SEQUENCE: 144

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
            35                  40                  45

Gly Gln Glu Pro Gly Gln Glu Pro Gly Gln Glu Pro
        50                  55                  60

<210> SEQ ID NO 145
<211> LENGTH: 60
<212> TYPE: PRT
<213> ORGANISM: Artificial Sequence
<220> FEATURE:
<223> OTHER INFORMATION: Synthetic

<400> SEQUENCE: 145

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
            35                  40                  45

Gly Gln Glu Pro Gly Gln Glu Pro Gly Gln Glu Pro
        50                  55                  60

<210> SEQ ID NO 146
<211> LENGTH: 60
<212> TYPE: PRT
<213> ORGANISM: Artificial Sequence
<220> FEATURE:
<223> OTHER INFORMATION: Synthetic

<400> SEQUENCE: 146

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
            35                  40                  45

Gly Ala Gln Pro Gly Gln Glu Pro Gly Ala Gln Pro
        50                  55                  60

<210> SEQ ID NO 147
<211> LENGTH: 60
<212> TYPE: PRT

```
<213> ORGANISM: Artificial Sequence
<220> FEATURE:
<223> OTHER INFORMATION: Synthetic

<400> SEQUENCE: 147

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Gln Glu Pro
        35                  40                  45

Gly Ala Gln Pro Gly Ala Gln Pro Gly Ala Gln Pro
    50                  55                  60

<210> SEQ ID NO 148
<211> LENGTH: 60
<212> TYPE: PRT
<213> ORGANISM: Artificial Sequence
<220> FEATURE:
<223> OTHER INFORMATION: Synthetic

<400> SEQUENCE: 148

Gly Ala Gln Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 149
<211> LENGTH: 60
<212> TYPE: PRT
<213> ORGANISM: Artificial Sequence
<220> FEATURE:
<223> OTHER INFORMATION: Synthetic

<400> SEQUENCE: 149

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 150
<211> LENGTH: 60
<212> TYPE: PRT
<213> ORGANISM: Artificial Sequence
<220> FEATURE:
<223> OTHER INFORMATION: Synthetic

<400> SEQUENCE: 150

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Ala Gln Pro Gly Ala Gln Pro Gly Ala Gln Pro
```

35                  40                  45

Gly Ala Gln Pro Gly Ala Gln Pro Gly Ala Gln Pro
    50                  55                  60

<210> SEQ ID NO 151
<211> LENGTH: 60
<212> TYPE: PRT
<213> ORGANISM: Artificial Sequence
<220> FEATURE:
<223> OTHER INFORMATION: Synthetic

<400> SEQUENCE: 151

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Ala Gln Pro Gly Ala Gln Pro
        35                  40                  45

Gly Ala Gln Pro Gly Ala Gln Pro Gly Ala Gln Pro
    50                  55                  60

<210> SEQ ID NO 152
<211> LENGTH: 60
<212> TYPE: PRT
<213> ORGANISM: Artificial Sequence
<220> FEATURE:
<223> OTHER INFORMATION: Synthetic

<400> SEQUENCE: 152

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Ala Gln Pro
        35                  40                  45

Gly Ala Gln Pro Gly Ala Gln Pro Gly Ala Gln Pro
    50                  55                  60

<210> SEQ ID NO 153
<211> LENGTH: 60
<212> TYPE: PRT
<213> ORGANISM: Artificial Sequence
<220> FEATURE:
<223> OTHER INFORMATION: Synthetic

<400> SEQUENCE: 153

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Ala Gln Pro Gly Ala Gln Pro Gly Ala Gln Pro
    50                  55                  60

<210> SEQ ID NO 154
<211> LENGTH: 60
<212> TYPE: PRT
<213> ORGANISM: Artificial Sequence
<220> FEATURE:
<223> OTHER INFORMATION: Synthetic

<400> SEQUENCE: 154

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Gln Glu Pro Gly Ala Gln Pro Gly Ala Gln Pro
    50                  55                  60

<210> SEQ ID NO 155
<211> LENGTH: 60
<212> TYPE: PRT
<213> ORGANISM: Artificial Sequence
<220> FEATURE:
<223> OTHER INFORMATION: Synthetic

<400> SEQUENCE: 155

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Ala Gln Pro
    50                  55                  60

<210> SEQ ID NO 156
<211> LENGTH: 60
<212> TYPE: PRT
<213> ORGANISM: Artificial Sequence
<220> FEATURE:
<223> OTHER INFORMATION: Synthetic

<400> SEQUENCE: 156

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro Gly Gln Glu Pro Gly Gln Glu Pro
        35                  40                  45

Gly Gln Glu Pro Gly Gln Glu Pro Gly Gln Glu Pro
    50                  55                  60

<210> SEQ ID NO 157
<211> LENGTH: 40
<212> TYPE: PRT
<213> ORGANISM: Artificial Sequence
<220> FEATURE:
<223> OTHER INFORMATION: Synthetic

<400> SEQUENCE: 157

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro
        35                  40

<210> SEQ ID NO 158

```
<211> LENGTH: 40
<212> TYPE: PRT
<213> ORGANISM: Artificial Sequence
<220> FEATURE:
<223> OTHER INFORMATION: Synthetic

<400> SEQUENCE: 158

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Gln Glu Pro
            35                  40

<210> SEQ ID NO 159
<211> LENGTH: 40
<212> TYPE: PRT
<213> ORGANISM: Artificial Sequence
<220> FEATURE:
<223> OTHER INFORMATION: Synthetic

<400> SEQUENCE: 159

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
                20                  25                  30

Gly Gln Glu Pro Gly Gln Glu Pro
            35                  40

<210> SEQ ID NO 160
<211> LENGTH: 40
<212> TYPE: PRT
<213> ORGANISM: Artificial Sequence
<220> FEATURE:
<223> OTHER INFORMATION: Synthetic

<400> SEQUENCE: 160

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
                20                  25                  30

Gly Gln Glu Pro Gly Ala Gln Pro
            35                  40

<210> SEQ ID NO 161
<211> LENGTH: 40
<212> TYPE: PRT
<213> ORGANISM: Artificial Sequence
<220> FEATURE:
<223> OTHER INFORMATION: Synthetic

<400> SEQUENCE: 161

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Ala Gln Pro
                20                  25                  30

Gly Ala Gln Pro Gly Ala Gln Pro
            35                  40

<210> SEQ ID NO 162
<211> LENGTH: 40
<212> TYPE: PRT
<213> ORGANISM: Artificial Sequence
```

<220> FEATURE:
<223> OTHER INFORMATION: Synthetic

<400> SEQUENCE: 162

Gly Gln Glu Pro Gly Gln Glu Pro Gly Gln Glu Pro Gly Gln Glu Pro
1               5                   10                  15

Gly Gln Glu Pro Gly Gln Glu Pro Gly Ala Gln Pro Gly Ala Gln Pro
            20                  25                  30

Gly Ala Gln Pro Gly Ala Gln Pro
        35                  40

<210> SEQ ID NO 163
<211> LENGTH: 40
<212> TYPE: PRT
<213> ORGANISM: Artificial Sequence
<220> FEATURE:
<223> OTHER INFORMATION: Synthetic

<400> SEQUENCE: 163

Gly Gln Glu Pro Gly Gln Glu Pro Gly Gln Glu Pro Gly Gln Glu Pro
1               5                   10                  15

Gly Gln Glu Pro Gly Ala Gln Pro Gly Ala Gln Pro Gly Ala Gln Pro
            20                  25                  30

Gly Ala Gln Pro Gly Ala Gln Pro
        35                  40

<210> SEQ ID NO 164
<211> LENGTH: 40
<212> TYPE: PRT
<213> ORGANISM: Artificial Sequence
<220> FEATURE:
<223> OTHER INFORMATION: Synthetic

<400> SEQUENCE: 164

Gly Gln Glu Pro Gly Gln Glu Pro Gly Gln Glu Pro Gly Gln Glu Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro
        35                  40

<210> SEQ ID NO 165
<211> LENGTH: 40
<212> TYPE: PRT
<213> ORGANISM: Artificial Sequence
<220> FEATURE:
<223> OTHER INFORMATION: Synthetic

<400> SEQUENCE: 165

Gly Gln Glu Pro Gly Gln Glu Pro Gly Gln Glu Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro
        35                  40

<210> SEQ ID NO 166
<211> LENGTH: 40
<212> TYPE: PRT
<213> ORGANISM: Artificial Sequence
<220> FEATURE:
<223> OTHER INFORMATION: Synthetic

<400> SEQUENCE: 166

Gly Gln Glu Pro Gly Gln Glu Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro
        35                  40

<210> SEQ ID NO 167
<211> LENGTH: 40
<212> TYPE: PRT
<213> ORGANISM: Artificial Sequence
<220> FEATURE:
<223> OTHER INFORMATION: Synthetic

<400> SEQUENCE: 167

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro
        35                  40

<210> SEQ ID NO 168
<211> LENGTH: 40
<212> TYPE: PRT
<213> ORGANISM: Artificial Sequence
<220> FEATURE:
<223> OTHER INFORMATION: Synthetic

<400> SEQUENCE: 168

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Gln Glu Pro
            20                  25                  30

Gly Gln Glu Pro Gly Gln Glu Pro
        35                  40

<210> SEQ ID NO 169
<211> LENGTH: 40
<212> TYPE: PRT
<213> ORGANISM: Artificial Sequence
<220> FEATURE:
<223> OTHER INFORMATION: Synthetic

<400> SEQUENCE: 169

Gly Gln Glu Pro Gly Ala Gln Pro Gly Gln Glu Pro Gly Ala Gln Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro
        35                  40

<210> SEQ ID NO 170
<211> LENGTH: 40
<212> TYPE: PRT
<213> ORGANISM: Artificial Sequence
<220> FEATURE:
<223> OTHER INFORMATION: Synthetic

<400> SEQUENCE: 170

Gly Gln Glu Pro Gly Ala Gln Pro Gly Gln Glu Pro Gly Gln Glu Pro

```
                1               5                   10                  15
Gly Gln Glu Pro Gly Gln Glu Pro Gly Gln Glu Pro Gly Gln Glu Pro
            20                  25                  30
Gly Gln Glu Pro Gly Gln Glu Pro
        35                  40

<210> SEQ ID NO 171
<211> LENGTH: 40
<212> TYPE: PRT
<213> ORGANISM: Artificial Sequence
<220> FEATURE:
<223> OTHER INFORMATION: Synthetic

<400> SEQUENCE: 171

Gly Ala Gln Pro Gly Gln Glu Pro Gly Gln Glu Pro Gly Gln Glu Pro
1               5                   10                  15
Gly Gln Glu Pro Gly Gln Glu Pro Gly Gln Glu Pro Gly Gln Glu Pro
            20                  25                  30
Gly Gln Glu Pro Gly Gln Glu Pro
        35                  40

<210> SEQ ID NO 172
<211> LENGTH: 40
<212> TYPE: PRT
<213> ORGANISM: Artificial Sequence
<220> FEATURE:
<223> OTHER INFORMATION: Synthetic

<400> SEQUENCE: 172

Gly Ala Gln Pro Gly Ala Gln Pro Gly Gln Glu Pro Gly Gln Glu Pro
1               5                   10                  15
Gly Gln Glu Pro Gly Gln Glu Pro Gly Gln Glu Pro Gly Gln Glu Pro
            20                  25                  30
Gly Gln Glu Pro Gly Gln Glu Pro
        35                  40

<210> SEQ ID NO 173
<211> LENGTH: 40
<212> TYPE: PRT
<213> ORGANISM: Artificial Sequence
<220> FEATURE:
<223> OTHER INFORMATION: Synthetic

<400> SEQUENCE: 173

Gly Ala Gln Pro Gly Ala Gln Pro Gly Ala Gln Pro Gly Gln Glu Pro
1               5                   10                  15
Gly Gln Glu Pro Gly Gln Glu Pro Gly Gln Glu Pro Gly Gln Glu Pro
            20                  25                  30
Gly Gln Glu Pro Gly Gln Glu Pro
        35                  40

<210> SEQ ID NO 174
<211> LENGTH: 40
<212> TYPE: PRT
<213> ORGANISM: Artificial Sequence
<220> FEATURE:
<223> OTHER INFORMATION: Synthetic

<400> SEQUENCE: 174

Gly Ala Gln Pro Gly Ala Gln Pro Gly Ala Gln Pro Gly Ala Gln Pro
1               5                   10                  15
Gly Gln Glu Pro Gly Gln Glu Pro Gly Gln Glu Pro Gly Gln Glu Pro
```

```
              20                  25                  30

Gly Gln Glu Pro Gly Gln Glu Pro
        35                  40

<210> SEQ ID NO 175
<211> LENGTH: 40
<212> TYPE: PRT
<213> ORGANISM: Artificial Sequence
<220> FEATURE:
<223> OTHER INFORMATION: Synthetic

<400> SEQUENCE: 175

Gly Ala Gln Pro Gly Ala Gln Pro Gly Ala Gln Pro Gly Ala Gln Pro
1               5                   10                  15

Gly Ala Gln Pro Gly Gln Glu Pro Gly Gln Glu Pro Gly Gln Glu Pro
              20                  25                  30

Gly Gln Glu Pro Gly Gln Glu Pro
        35                  40

<210> SEQ ID NO 176
<211> LENGTH: 40
<212> TYPE: PRT
<213> ORGANISM: Artificial Sequence
<220> FEATURE:
<223> OTHER INFORMATION: Synthetic

<400> SEQUENCE: 176

Gly Ala Gln Pro Gly Ala Gln Pro Gly Ala Gln Pro Gly Ala Gln Pro
1               5                   10                  15

Gly Ala Gln Pro Gly Ala Gln Pro Gly Gln Glu Pro Gly Gln Glu Pro
              20                  25                  30

Gly Gln Glu Pro Gly Gln Glu Pro
        35                  40

<210> SEQ ID NO 177
<211> LENGTH: 40
<212> TYPE: PRT
<213> ORGANISM: Artificial Sequence
<220> FEATURE:
<223> OTHER INFORMATION: Synthetic

<400> SEQUENCE: 177

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Gln Glu Pro
              20                  25                  30

Gly Gln Glu Pro Gly Gln Glu Pro
        35                  40

<210> SEQ ID NO 178
<211> LENGTH: 40
<212> TYPE: PRT
<213> ORGANISM: Artificial Sequence
<220> FEATURE:
<223> OTHER INFORMATION: Synthetic

<400> SEQUENCE: 178

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
              20                  25                  30

Gly Gln Glu Pro Gly Gln Glu Pro
```

<210> SEQ ID NO 179
<211> LENGTH: 40
<212> TYPE: PRT
<213> ORGANISM: Artificial Sequence
<220> FEATURE:
<223> OTHER INFORMATION: Synthetic

<400> SEQUENCE: 179

Gly Ala Gln Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Ala Gln Pro
        35                  40

<210> SEQ ID NO 180
<211> LENGTH: 40
<212> TYPE: PRT
<213> ORGANISM: Artificial Sequence
<220> FEATURE:
<223> OTHER INFORMATION: Synthetic

<400> SEQUENCE: 180

Gly Ala Gln Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro
        35                  40

<210> SEQ ID NO 181
<211> LENGTH: 40
<212> TYPE: PRT
<213> ORGANISM: Artificial Sequence
<220> FEATURE:
<223> OTHER INFORMATION: Synthetic

<400> SEQUENCE: 181

Gly Ala Gln Pro Gly Ala Gln Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Ala Gln Pro
        35                  40

<210> SEQ ID NO 182
<211> LENGTH: 40
<212> TYPE: PRT
<213> ORGANISM: Artificial Sequence
<220> FEATURE:
<223> OTHER INFORMATION: Synthetic

<400> SEQUENCE: 182

Gly Ala Gln Pro Gly Ala Gln Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro
        35                  40

```
<210> SEQ ID NO 183
<211> LENGTH: 40
<212> TYPE: PRT
<213> ORGANISM: Artificial Sequence
<220> FEATURE:
<223> OTHER INFORMATION: Synthetic

<400> SEQUENCE: 183

Gly Ala Gln Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Ala Gln Pro
            20                  25                  30

Gly Ala Gln Pro Gly Ala Gln Pro
        35                  40

<210> SEQ ID NO 184
<211> LENGTH: 40
<212> TYPE: PRT
<213> ORGANISM: Artificial Sequence
<220> FEATURE:
<223> OTHER INFORMATION: Synthetic

<400> SEQUENCE: 184

Gly Ala Gln Pro Gly Ala Gln Pro Gly Ala Gln Pro Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Ala Gln Pro
        35                  40

<210> SEQ ID NO 185
<211> LENGTH: 40
<212> TYPE: PRT
<213> ORGANISM: Artificial Sequence
<220> FEATURE:
<223> OTHER INFORMATION: Synthetic

<400> SEQUENCE: 185

Gly Gln Glu Pro Gly Gln Glu Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro
        35                  40

<210> SEQ ID NO 186
<211> LENGTH: 40
<212> TYPE: PRT
<213> ORGANISM: Artificial Sequence
<220> FEATURE:
<223> OTHER INFORMATION: Synthetic

<400> SEQUENCE: 186

Gly Gln Glu Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
            20                  25                  30

Gly Ala Gln Pro Gly Gln Glu Pro
        35                  40

<210> SEQ ID NO 187
<211> LENGTH: 40
<212> TYPE: PRT
```

```
<213> ORGANISM: Artificial Sequence
<220> FEATURE:
<223> OTHER INFORMATION: Synthetic

<400> SEQUENCE: 187

Gly Gln Glu Pro Gly Gln Glu Pro Gly Gln Glu Pro Gly Gln Glu Pro
1               5                   10                  15

Gly Gln Glu Pro Gly Ala Gln Pro Gly Gln Glu Pro Gly Ala Gln Pro
                20                  25                  30

Gly Gln Glu Pro Gly Ala Gln Pro
        35                  40

<210> SEQ ID NO 188
<211> LENGTH: 40
<212> TYPE: PRT
<213> ORGANISM: Artificial Sequence
<220> FEATURE:
<223> OTHER INFORMATION: Synthetic

<400> SEQUENCE: 188

Gly Gln Glu Pro Gly Gln Glu Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Gln Glu Pro
        35                  40

<210> SEQ ID NO 189
<211> LENGTH: 40
<212> TYPE: PRT
<213> ORGANISM: Artificial Sequence
<220> FEATURE:
<223> OTHER INFORMATION: Synthetic

<400> SEQUENCE: 189

Gly Gln Glu Pro Gly Gln Glu Pro Gly Ala Gln Pro Gly Gln Glu Pro
1               5                   10                  15

Gly Ala Gln Pro Gly Gln Glu Pro Gly Ala Gln Pro Gly Gln Glu Pro
                20                  25                  30

Gly Gln Glu Pro Gly Gln Glu Pro
        35                  40

<210> SEQ ID NO 190
<211> LENGTH: 40
<212> TYPE: PRT
<213> ORGANISM: Artificial Sequence
<220> FEATURE:
<223> OTHER INFORMATION: Synthetic

<400> SEQUENCE: 190

Gly Gln Glu Pro Gly Gln Glu Pro Gly Gln Glu Pro Gly Gln Glu Pro
1               5                   10                  15

Gly Ala Gln Pro Gly Gln Glu Pro Gly Ala Gln Pro Gly Gln Glu Pro
                20                  25                  30

Gly Ala Gln Pro Gly Gln Glu Pro
        35                  40

<210> SEQ ID NO 191
<211> LENGTH: 40
<212> TYPE: PRT
<213> ORGANISM: Artificial Sequence
<220> FEATURE:
<223> OTHER INFORMATION: Synthetic
```

<400> SEQUENCE: 191

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Ala Gln Pro
            20                  25                  30

Gly Gln Glu Pro Gly Ala Gln Pro
        35                  40

<210> SEQ ID NO 192
<211> LENGTH: 40
<212> TYPE: PRT
<213> ORGANISM: Artificial Sequence
<220> FEATURE:
<223> OTHER INFORMATION: Synthetic

<400> SEQUENCE: 192

Gly Gln Glu Pro Gly Gln Glu Pro Gly Gln Glu Pro Gly Gln Glu Pro
1               5                   10                  15

Gly Ala Gln Pro Gly Gln Glu Pro Gly Ala Gln Pro Gly Gln Glu Pro
            20                  25                  30

Gly Gln Glu Pro Gly Gln Glu Pro
        35                  40

<210> SEQ ID NO 193
<211> LENGTH: 40
<212> TYPE: PRT
<213> ORGANISM: Artificial Sequence
<220> FEATURE:
<223> OTHER INFORMATION: Synthetic

<400> SEQUENCE: 193

Gly Gln Glu Pro Gly Gln Glu Pro Gly Gln Glu Pro Gly Ala Gln Pro
1               5                   10                  15

Gly Gln Glu Pro Gly Ala Gln Pro Gly Gln Glu Pro Gly Gln Glu Pro
            20                  25                  30

Gly Gln Glu Pro Gly Gln Glu Pro
        35                  40

<210> SEQ ID NO 194
<211> LENGTH: 40
<212> TYPE: PRT
<213> ORGANISM: Artificial Sequence
<220> FEATURE:
<223> OTHER INFORMATION: Synthetic

<400> SEQUENCE: 194

Gly Gln Glu Pro Gly Gln Glu Pro Gly Gln Glu Pro Gly Gln Glu Pro
1               5                   10                  15

Gly Gln Glu Pro Gly Ala Gln Pro Gly Gln Glu Pro Gly Ala Gln Pro
            20                  25                  30

Gly Gln Glu Pro Gly Gln Glu Pro
        35                  40

<210> SEQ ID NO 195
<211> LENGTH: 40
<212> TYPE: PRT
<213> ORGANISM: Artificial Sequence
<220> FEATURE:
<223> OTHER INFORMATION: Synthetic

<400> SEQUENCE: 195

```
Gly Gln Glu Pro Gly Gln Glu Pro Gly Ala Gln Pro Gly Gln Glu Pro
1               5                   10                  15
Gly Ala Gln Pro Gly Gln Glu Pro Gly Gln Glu Pro Gly Gln Glu Pro
            20                  25                  30
Gly Gln Glu Pro Gly Gln Glu Pro
        35                  40

<210> SEQ ID NO 196
<211> LENGTH: 40
<212> TYPE: PRT
<213> ORGANISM: Artificial Sequence
<220> FEATURE:
<223> OTHER INFORMATION: Synthetic

<400> SEQUENCE: 196

Gly Gln Glu Pro Gly Gln Glu Pro Gly Gln Glu Pro Gly Gln Glu Pro
1               5                   10                  15
Gly Gln Glu Pro Gly Gln Glu Pro Gly Ala Gln Pro Gly Gln Glu Pro
            20                  25                  30
Gly Ala Gln Pro Gly Gln Glu Pro
        35                  40

<210> SEQ ID NO 197
<211> LENGTH: 40
<212> TYPE: PRT
<213> ORGANISM: Artificial Sequence
<220> FEATURE:
<223> OTHER INFORMATION: Synthetic

<400> SEQUENCE: 197

Gly Gln Glu Pro Gly Ala Gln Pro Gly Gln Glu Pro Gly Gln Glu Pro
1               5                   10                  15
Gly Gln Glu Pro Gly Gln Glu Pro Gly Gln Glu Pro Gly Gln Glu Pro
            20                  25                  30
Gly Gln Glu Pro Gly Gln Glu Pro
        35                  40

<210> SEQ ID NO 198
<211> LENGTH: 80
<212> TYPE: PRT
<213> ORGANISM: Artificial Sequence
<220> FEATURE:
<223> OTHER INFORMATION: Synthetic

<400> SEQUENCE: 198

Lys Ala Gln Pro Gly Ala Gln Pro Gly Ala Gln Pro Gly Ala Gln Pro
1               5                   10                  15
Gly Ala Gln Pro Gly Ala Gln Pro Gly Ala Gln Pro Gly Ala Gln Pro
            20                  25                  30
Gly Ala Gln Pro Gly Ala Gln Pro Gly Ala Gln Pro Gly Ala Gln Pro
        35                  40                  45
Gly Gln Glu Pro Gly Gln Glu Pro Gly Gln Glu Pro Gly Gln Glu Pro
    50                  55                  60
Gly Gln Glu Pro Gly Gln Glu Pro Gly Gln Glu Pro Gly Gln Glu Pro
65                  70                  75                  80

<210> SEQ ID NO 199
<211> LENGTH: 40
<212> TYPE: PRT
<213> ORGANISM: Artificial Sequence
<220> FEATURE:
<223> OTHER INFORMATION: Synthetic
```

<400> SEQUENCE: 199

Gly Gln Glu Pro Gly Gln Glu Pro Gly Gln Glu Pro Gly Gln Glu Pro
1               5                   10                  15

Gly Gln Glu Pro Gly Ala Gln Pro Gly Gln Glu Pro Gly Gln Glu Pro
            20                  25                  30

Gly Gln Glu Pro Gly Gln Glu Pro
        35                  40

<210> SEQ ID NO 200
<211> LENGTH: 40
<212> TYPE: PRT
<213> ORGANISM: Artificial Sequence
<220> FEATURE:
<223> OTHER INFORMATION: Synthetic

<400> SEQUENCE: 200

Gly Gln Glu Pro Gly Gln Glu Pro Gly Gln Glu Pro Gly Ala Gln Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro
        35                  40

<210> SEQ ID NO 201
<211> LENGTH: 40
<212> TYPE: PRT
<213> ORGANISM: Artificial Sequence
<220> FEATURE:
<223> OTHER INFORMATION: Synthetic

<400> SEQUENCE: 201

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Ala Gln Pro
            20                  25                  30

Gly Gln Glu Pro Gly Gln Glu Pro
        35                  40

<210> SEQ ID NO 202
<211> LENGTH: 40
<212> TYPE: PRT
<213> ORGANISM: Artificial Sequence
<220> FEATURE:
<223> OTHER INFORMATION: Synthetic

<400> SEQUENCE: 202

Gly Gln Glu Pro Gly Gln Glu Pro Gly Gln Glu Pro Gly Gln Glu Pro
1               5                   10                  15

Gly Ala Gln Pro Gly Gln Glu Pro Gly Gln Glu Pro Gly Gln Glu Pro
            20                  25                  30

Gly Gln Glu Pro Gly Gln Glu Pro
        35                  40

<210> SEQ ID NO 203
<211> LENGTH: 40
<212> TYPE: PRT
<213> ORGANISM: Artificial Sequence
<220> FEATURE:
<223> OTHER INFORMATION: Synthetic

<400> SEQUENCE: 203

Gly Gln Glu Pro Gly Gln Glu Pro Gly Gln Glu Pro Gly Gln Glu Pro
1               5                   10                  15

Gly Gln Glu Pro Gly Gln Glu Pro Gly Ala Gln Pro Gly Gln Glu Pro
                20                  25                  30

Gly Gln Glu Pro Gly Gln Glu Pro
            35                  40

<210> SEQ ID NO 204
<211> LENGTH: 40
<212> TYPE: PRT
<213> ORGANISM: Artificial Sequence
<220> FEATURE:
<223> OTHER INFORMATION: Synthetic

<400> SEQUENCE: 204

Gly Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
                20                  25                  30

Gly Ala Gln Pro Gly Gln Glu Pro
            35                  40

<210> SEQ ID NO 205
<211> LENGTH: 40
<212> TYPE: PRT
<213> ORGANISM: Artificial Sequence
<220> FEATURE:
<223> OTHER INFORMATION: Synthetic

<400> SEQUENCE: 205

Gly Gln Glu Pro Gly Gln Glu Pro Gly Ala Gln Pro Gly Gln Glu Pro
1               5                   10                  15

Gly Gln Glu Pro Gly Gln Glu Pro Gly Gln Glu Pro Gly Gln Glu Pro
                20                  25                  30

Gly Gln Glu Pro Gly Gln Glu Pro
            35                  40

<210> SEQ ID NO 206
<211> LENGTH: 40
<212> TYPE: PRT
<213> ORGANISM: Artificial Sequence
<220> FEATURE:
<223> OTHER INFORMATION: Synthetic

<400> SEQUENCE: 206

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
                20                  25                  30

Gly Ala Gln Pro Gly Ala Gln Pro
            35                  40

<210> SEQ ID NO 207
<211> LENGTH: 40
<212> TYPE: PRT
<213> ORGANISM: Artificial Sequence
<220> FEATURE:
<223> OTHER INFORMATION: Synthetic

<400> SEQUENCE: 207

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Glu Gly
            20                  25                  30

Gly Ala Gln Pro Gly Gln Glu Pro
        35                  40

<210> SEQ ID NO 208
<211> LENGTH: 40
<212> TYPE: PRT
<213> ORGANISM: Artificial Sequence
<220> FEATURE:
<223> OTHER INFORMATION: Synthetic

<400> SEQUENCE: 208

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Gln Glu Pro
        35                  40

<210> SEQ ID NO 209
<211> LENGTH: 40
<212> TYPE: PRT
<213> ORGANISM: Artificial Sequence
<220> FEATURE:
<223> OTHER INFORMATION: Synthetic

<400> SEQUENCE: 209

Ser Glu Pro Ala Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

Gly Gln Glu Pro Gly Ala Gln Pro
        35                  40

<210> SEQ ID NO 210
<211> LENGTH: 24
<212> TYPE: PRT
<213> ORGANISM: Artificial Sequence
<220> FEATURE:
<223> OTHER INFORMATION: Synthetic

<400> SEQUENCE: 210

Gly Gln Glu Pro Gly Gln Glu Pro Gly Gln Glu Pro Gly Gln Glu Pro
1               5                   10                  15

Gly Gln Glu Pro Gly Gln Glu Pro
            20

<210> SEQ ID NO 211
<211> LENGTH: 12
<212> TYPE: PRT
<213> ORGANISM: Artificial Sequence
<220> FEATURE:
<223> OTHER INFORMATION: Synthetic

<400> SEQUENCE: 211

Gly Gln Glu Pro Gly Gln Glu Pro Gly Gln Glu Pro
1               5                   10

<210> SEQ ID NO 212
<211> LENGTH: 32
<212> TYPE: PRT
<213> ORGANISM: Artificial Sequence
<220> FEATURE:

<223> OTHER INFORMATION: Synthetic

<400> SEQUENCE: 212

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30

<210> SEQ ID NO 213
<211> LENGTH: 8
<212> TYPE: PRT
<213> ORGANISM: Artificial Sequence
<220> FEATURE:
<223> OTHER INFORMATION: Synthetic

<400> SEQUENCE: 213

Gly Gln Glu Pro Gly Ala Gln Pro
1               5

<210> SEQ ID NO 214
<211> LENGTH: 8
<212> TYPE: PRT
<213> ORGANISM: Artificial Sequence
<220> FEATURE:
<223> OTHER INFORMATION: Synthetic

<400> SEQUENCE: 214

Gly Ala Gln Pro Gly Ala Gln Pro
1               5

<210> SEQ ID NO 215
<211> LENGTH: 4
<212> TYPE: PRT
<213> ORGANISM: Artificial Sequence
<220> FEATURE:
<223> OTHER INFORMATION: Synthetic

<400> SEQUENCE: 215

Gly Gln Glu Pro
1

<210> SEQ ID NO 216
<211> LENGTH: 4
<212> TYPE: PRT
<213> ORGANISM: Artificial Sequence
<220> FEATURE:
<223> OTHER INFORMATION: Synthetic

<400> SEQUENCE: 216

Gly Ala Gln Pro
1

<210> SEQ ID NO 217
<211> LENGTH: 32
<212> TYPE: PRT
<213> ORGANISM: Artificial Sequence
<220> FEATURE:
<223> OTHER INFORMATION: Synthetic

<400> SEQUENCE: 217

Ser Glu Pro Ala Thr Ser Gly Ser Glu Thr Pro Gly Thr Ser Glu Ser
1               5                   10                  15
Ala Thr Pro Glu Ser Gly Pro Gly Thr Ser Thr Glu Pro Ser Glu Gly
            20                  25                  30

```
<210> SEQ ID NO 218
<211> LENGTH: 12
<212> TYPE: PRT
<213> ORGANISM: Artificial Sequence
<220> FEATURE:
<223> OTHER INFORMATION: Synthetic

<400> SEQUENCE: 218

Gly Ala Gln Pro Gly Gln Glu Pro Gly Ala Gln Pro
1               5                   10

<210> SEQ ID NO 219
<211> LENGTH: 8
<212> TYPE: PRT
<213> ORGANISM: Artificial Sequence
<220> FEATURE:
<223> OTHER INFORMATION: Synthetic

<400> SEQUENCE: 219

Gly Ala Gln Pro Gly Gln Glu Pro
1               5

<210> SEQ ID NO 220
<211> LENGTH: 4
<212> TYPE: PRT
<213> ORGANISM: Artificial Sequence
<220> FEATURE:
<223> OTHER INFORMATION: Synthetic

<400> SEQUENCE: 220

Gly Glu Gln Pro
1

<210> SEQ ID NO 221
<211> LENGTH: 4
<212> TYPE: PRT
<213> ORGANISM: Artificial Sequence
<220> FEATURE:
<223> OTHER INFORMATION: Synthetic

<400> SEQUENCE: 221

Gly Pro Gln Glu
1

<210> SEQ ID NO 222
<211> LENGTH: 4
<212> TYPE: PRT
<213> ORGANISM: Artificial Sequence
<220> FEATURE:
<223> OTHER INFORMATION: Synthetic

<400> SEQUENCE: 222

Gly Pro Glu Gln
1

<210> SEQ ID NO 223
<211> LENGTH: 4
<212> TYPE: PRT
<213> ORGANISM: Artificial Sequence
<220> FEATURE:
<223> OTHER INFORMATION: Synthetic

<400> SEQUENCE: 223

Gly Ser Glu Pro
1

<210> SEQ ID NO 224
```

```
<211> LENGTH: 4
<212> TYPE: PRT
<213> ORGANISM: Artificial Sequence
<220> FEATURE:
<223> OTHER INFORMATION: Synthetic

<400> SEQUENCE: 224

Gly Glu Ser Pro
1

<210> SEQ ID NO 225
<211> LENGTH: 4
<212> TYPE: PRT
<213> ORGANISM: Artificial Sequence
<220> FEATURE:
<223> OTHER INFORMATION: Synthetic

<400> SEQUENCE: 225

Gly Pro Ser Glu
1

<210> SEQ ID NO 226
<211> LENGTH: 4
<212> TYPE: PRT
<213> ORGANISM: Artificial Sequence
<220> FEATURE:
<223> OTHER INFORMATION: Synthetic

<400> SEQUENCE: 226

Gly Pro Glu Ser
1

<210> SEQ ID NO 227
<211> LENGTH: 4
<212> TYPE: PRT
<213> ORGANISM: Artificial Sequence
<220> FEATURE:
<223> OTHER INFORMATION: Synthetic

<400> SEQUENCE: 227

Gly Gln Ala Pro
1

<210> SEQ ID NO 228
<211> LENGTH: 4
<212> TYPE: PRT
<213> ORGANISM: Artificial Sequence
<220> FEATURE:
<223> OTHER INFORMATION: Synthetic

<400> SEQUENCE: 228

Gly Pro Ala Gln
1

<210> SEQ ID NO 229
<211> LENGTH: 4
<212> TYPE: PRT
<213> ORGANISM: Artificial Sequence
<220> FEATURE:
<223> OTHER INFORMATION: Synthetic

<400> SEQUENCE: 229

Gly Pro Gln Ala
1

<210> SEQ ID NO 230
<211> LENGTH: 4
```

```
<212> TYPE: PRT
<213> ORGANISM: Artificial Sequence
<220> FEATURE:
<223> OTHER INFORMATION: Synthetic

<400> SEQUENCE: 230

Gly Ser Gln Pro
1

<210> SEQ ID NO 231
<211> LENGTH: 4
<212> TYPE: PRT
<213> ORGANISM: Artificial Sequence
<220> FEATURE:
<223> OTHER INFORMATION: Synthetic

<400> SEQUENCE: 231

Gly Ala Ser Pro
1

<210> SEQ ID NO 232
<211> LENGTH: 4
<212> TYPE: PRT
<213> ORGANISM: Artificial Sequence
<220> FEATURE:
<223> OTHER INFORMATION: Synthetic

<400> SEQUENCE: 232

Gly Pro Ala Ser
1

<210> SEQ ID NO 233
<211> LENGTH: 4
<212> TYPE: PRT
<213> ORGANISM: Artificial Sequence
<220> FEATURE:
<223> OTHER INFORMATION: Synthetic

<400> SEQUENCE: 233

Gly Pro Ser Ala
1

<210> SEQ ID NO 234
<211> LENGTH: 4
<212> TYPE: PRT
<213> ORGANISM: Artificial Sequence
<220> FEATURE:
<223> OTHER INFORMATION: Synthetic

<400> SEQUENCE: 234

Gly Gly Gly Ser
1

<210> SEQ ID NO 235
<211> LENGTH: 4
<212> TYPE: PRT
<213> ORGANISM: Artificial Sequence
<220> FEATURE:
<223> OTHER INFORMATION: Synthetic

<400> SEQUENCE: 235

Gly Ser Gly Ser
1

<210> SEQ ID NO 236
<211> LENGTH: 5
<212> TYPE: PRT
```

```
<213> ORGANISM: Artificial Sequence
<220> FEATURE:
<223> OTHER INFORMATION: Synthetic

<400> SEQUENCE: 236

Gly Gly Gly Gly Ser
1               5

<210> SEQ ID NO 237
<211> LENGTH: 6
<212> TYPE: PRT
<213> ORGANISM: Artificial Sequence
<220> FEATURE:
<223> OTHER INFORMATION: Synthetic

<400> SEQUENCE: 237

Ser Glu Pro Ala Thr Ser
1               5

<210> SEQ ID NO 238
<211> LENGTH: 6
<212> TYPE: PRT
<213> ORGANISM: Artificial Sequence
<220> FEATURE:
<223> OTHER INFORMATION: Synthetic

<400> SEQUENCE: 238

Gly Ser Glu Thr Pro Gly
1               5

<210> SEQ ID NO 239
<211> LENGTH: 6
<212> TYPE: PRT
<213> ORGANISM: Artificial Sequence
<220> FEATURE:
<223> OTHER INFORMATION: Synthetic

<400> SEQUENCE: 239

Thr Ser Glu Ser Ala Thr
1               5

<210> SEQ ID NO 240
<211> LENGTH: 6
<212> TYPE: PRT
<213> ORGANISM: Artificial Sequence
<220> FEATURE:
<223> OTHER INFORMATION: Synthetic

<400> SEQUENCE: 240

Pro Glu Ser Gly Pro Gly
1               5

<210> SEQ ID NO 241
<211> LENGTH: 6
<212> TYPE: PRT
<213> ORGANISM: Artificial Sequence
<220> FEATURE:
<223> OTHER INFORMATION: Synthetic

<400> SEQUENCE: 241

Thr Ser Thr Glu Pro Ser
1               5

<210> SEQ ID NO 242
<211> LENGTH: 31
<212> TYPE: PRT
<213> ORGANISM: Artificial Sequence
```

```
<220> FEATURE:
<223> OTHER INFORMATION: Synthetic

<400> SEQUENCE: 242

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 243
<211> LENGTH: 31
<212> TYPE: PRT
<213> ORGANISM: Artificial Sequence
<220> FEATURE:
<223> OTHER INFORMATION: Synthetic

<400> SEQUENCE: 243

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly
            20                  25                  30

<210> SEQ ID NO 244
<211> LENGTH: 31
<212> TYPE: PRT
<213> ORGANISM: Artificial Sequence
<220> FEATURE:
<223> OTHER INFORMATION: Synthetic

<400> SEQUENCE: 244

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly
            20                  25                  30

<210> SEQ ID NO 245
<211> LENGTH: 31
<212> TYPE: PRT
<213> ORGANISM: Artificial Sequence
<220> FEATURE:
<223> OTHER INFORMATION: Synthetic

<400> SEQUENCE: 245

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Gly
            20                  25                  30

<210> SEQ ID NO 246
<211> LENGTH: 112
<212> TYPE: PRT
<213> ORGANISM: Artificial Sequence
<220> FEATURE:
<223> OTHER INFORMATION: Synthetic

<400> SEQUENCE: 246

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Leu His Ala Gln Ile Lys Thr Ser
```

```
                50                  55                  60
Leu His Arg Leu Arg Pro Asp Thr Val Pro Ala Pro Cys Cys Val Pro
 65                  70                  75                  80

Ala Ser Tyr Asn Pro Met Val Leu Ile Gln Arg Thr Asp Thr Gly Val
                 85                  90                  95

Ser Leu Gln Thr Tyr Asp Asp Leu Leu Ala Arg Asp Cys His Cys Ile
                100                 105                 110

<210> SEQ ID NO 247
<211> LENGTH: 112
<212> TYPE: PRT
<213> ORGANISM: Artificial Sequence
<220> FEATURE:
<223> OTHER INFORMATION: Synthetic

<400> SEQUENCE: 247

Ala Arg Gln Gly Asp His Cys Pro Leu Gly Pro Gly Arg Cys Cys Arg
  1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
                 35                  40                  45

Pro Ser Gln Phe Arg Ala Ala Asn Leu His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 248
<211> LENGTH: 112
<212> TYPE: PRT
<213> ORGANISM: Artificial Sequence
<220> FEATURE:
<223> OTHER INFORMATION: Synthetic

<400> SEQUENCE: 248

Ala Arg Asn Gly Asp His Cys Pro Leu Gly Pro Gly Arg Cys Cys Arg
  1               5                  10                  15

Leu His Thr Val Arg Ala Ser Leu Glu Asp Leu Gly Trp Ala Asp Trp
                 20                  25                  30

Val Leu Ser Pro Arg Glu Val Gln Val Thr Met Cys Ile Gly Ala Cys
                 35                  40                  45

Pro Ser Gln Phe Arg Ala Ala Asn Met His Ala Gln Ile Lys Thr Ser
 50                  55                  60

Leu His Arg Leu Lys Pro Asp Thr Val Pro Ala Pro Cys Cys Val Pro
 65                  70                  75                  80

Ala Ser Tyr Asn Pro Met Val Leu Ile Gln Lys Thr Asp Thr Gly Val
                 85                  90                  95

Ser Leu Gln Thr Tyr Asp Asp Leu Leu Ala Lys Asp Cys His Cys Ile
                100                 105                 110

<210> SEQ ID NO 249
<211> LENGTH: 183
<212> TYPE: PRT
<213> ORGANISM: Artificial Sequence
<220> FEATURE:
```

<223> OTHER INFORMATION: Synthetic

<400> SEQUENCE: 249

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Gln Glu Pro Gly Gln Glu Pro Gly Gln Glu Pro Gly
        35                  40                  45

Gln Glu Pro Gly Gln Glu Pro Gly Gln Glu Pro Gly Gln Glu Pro Gly
    50                  55                  60

Ala Gln Pro Gly Ala Gln Pro Ala Arg Gln Gly Asp His Cys Pro Leu
65                  70                  75                  80

Gly Pro Gly Arg Cys Cys Arg Leu His Thr Val Arg Ala Ser Leu Glu
                85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180

<210> SEQ ID NO 250
<211> LENGTH: 183
<212> TYPE: PRT
<213> ORGANISM: Artificial Sequence
<220> FEATURE:
<223> OTHER INFORMATION: Synthetic

<400> SEQUENCE: 250

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Gln Glu Pro Gly Gln Glu Pro Gly Gln Glu Pro Gly
        35                  40                  45

Gln Glu Pro Gly Gln Glu Pro Gly Gln Glu Pro Gly Gln Glu Pro Gly
    50                  55                  60

Ala Gln Pro Gly Ala Gln Pro Ala Arg Gln Gly Asp His Cys Pro Leu
65                  70                  75                  80

Gly Pro Gly Arg Cys Cys Arg Leu His Thr Val Arg Ala Ser Leu Glu
                85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180

<210> SEQ ID NO 251
<211> LENGTH: 223
<212> TYPE: PRT
<213> ORGANISM: Artificial Sequence
<220> FEATURE:
<223> OTHER INFORMATION: Synthetic

<400> SEQUENCE: 251

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 252
<211> LENGTH: 183
<212> TYPE: PRT
<213> ORGANISM: Artificial Sequence
<220> FEATURE:
<223> OTHER INFORMATION: Synthetic

<400> SEQUENCE: 252

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Gln Glu Pro Gly Gln Glu Lys Gly Gln Glu Pro Gly
            35                  40                  45

Gln Glu Pro Gly Gln Glu Pro Gly Gln Glu Pro Gly Gln Glu Pro Gly

```
            50                  55                  60

Ala Gln Pro Gly Ala Gln Pro Ala Arg Gln Gly Asp His Cys Pro Leu
 65                  70                  75                  80

Gly Pro Gly Arg Cys Cys Arg Leu His Thr Val Arg Ala Ser Leu Glu
                 85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180
```

<210> SEQ ID NO 253
<211> LENGTH: 183
<212> TYPE: PRT
<213> ORGANISM: Artificial Sequence
<220> FEATURE:
<223> OTHER INFORMATION: Synthetic

<400> SEQUENCE: 253

```
His Gly Glu Gly Thr Phe Thr Ser Asp Val Ser Ser Tyr Leu Glu Glu
  1               5                  10                  15

Gln Ala Ala Arg Glu Phe Ile Ala Trp Leu Val Arg Gly Lys Gly Gly
             20                  25                  30

Gln Glu Pro Gly Gln Glu Pro Gly Gln Glu Pro Gly Gln Glu Pro Gly
         35                  40                  45

Gln Glu Pro Gly Gln Glu Pro Gly Gln Glu Pro Gly Gln Glu Pro Gly
     50                  55                  60

Ala Gln Pro Gly Ala Gln Pro Ala Arg Gln Gly Asp His Cys Pro Leu
 65                  70                  75                  80

Gly Pro Gly Arg Cys Cys Arg Leu His Thr Val Arg Ala Ser Leu Glu
                 85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180
```

<210> SEQ ID NO 254
<211> LENGTH: 183
<212> TYPE: PRT
<213> ORGANISM: Artificial Sequence
<220> FEATURE:
<223> OTHER INFORMATION: Synthetic

<400> SEQUENCE: 254

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Gln Glu Pro Gly Gln Glu Pro Gly Gln Glu Pro Gly Gln Glu Pro Gly
        35                  40                  45

Gln Glu Pro Gly Gln Glu Pro Gly Gln Glu Pro Gly Gln Glu Pro Gly
    50                  55                  60

Ala Gln Pro Gly Ala Gln Pro Ala Arg Gln Gly Asp His Cys Pro Leu
65                  70                  75                  80

Gly Pro Gly Arg Cys Cys Arg Leu His Thr Val Arg Ala Ser Leu Glu
                85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180

<210> SEQ ID NO 255
<211> LENGTH: 183
<212> TYPE: PRT
<213> ORGANISM: Artificial Sequence
<220> FEATURE:
<223> OTHER INFORMATION: Synthetic

<400> SEQUENCE: 255

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Lys Glu Pro Gly Gln Glu Pro Gly Gln Glu Pro Gly
        35                  40                  45

Gln Glu Pro Gly Gln Glu Pro Gly Gln Glu Pro Gly Gln Glu Pro Gly
    50                  55                  60

Ala Gln Pro Gly Ala Gln Pro Ala Arg Gln Gly Asp His Cys Pro Leu
65                  70                  75                  80

Gly Pro Gly Arg Cys Cys Arg Leu His Thr Val Arg Ala Ser Leu Glu
                85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

-continued

```
Gln Arg Thr Asp Thr Gly Val Ser Leu Gln Thr Tyr Asp Asp Leu Leu
                165                 170                 175
Ala Arg Asp Cys His Cys Ile
            180

<210> SEQ ID NO 256
<211> LENGTH: 183
<212> TYPE: PRT
<213> ORGANISM: Artificial Sequence
<220> FEATURE:
<223> OTHER INFORMATION: Synthetic

<400> SEQUENCE: 256

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Gly
                20                  25                  30
Gln Glu Pro Gly Gln Glu Pro Gly Gln Glu Pro Gly Gln Lys Pro Gly
            35                  40                  45
Gln Glu Pro Gly Gln Glu Pro Gly Gln Glu Pro Gly Gln Glu Pro Gly
        50                  55                  60
Ala Gln Pro Gly Ala Gln Pro Ala Arg Gln Gly Asp His Cys Pro Leu
65                  70                  75                  80
Gly Pro Gly Arg Cys Cys Arg Leu His Thr Val Arg Ala Ser Leu Glu
                85                  90                  95
Asp Leu Gly Trp Ala Asp Trp Val Leu Ser Pro Arg Glu Val Gln Val
            100                 105                 110
Thr Met Cys Ile Gly Ala Cys Pro Ser Gln Phe Arg Ala Ala Asn Leu
        115                 120                 125
His Ala Gln Ile Lys Thr Ser Leu His Arg Leu Arg Pro Asp Thr Val
130                 135                 140
Pro Ala Pro Cys Cys Val Pro Ala Ser Tyr Asn Pro Met Val Leu Ile
145                 150                 155                 160
Gln Arg Thr Asp Thr Gly Val Ser Leu Gln Thr Tyr Asp Asp Leu Leu
                165                 170                 175
Ala Arg Asp Cys His Cys Ile
            180

<210> SEQ ID NO 257
<211> LENGTH: 175
<212> TYPE: PRT
<213> ORGANISM: Artificial Sequence
<220> FEATURE:
<223> OTHER INFORMATION: Synthetic

<400> SEQUENCE: 257

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Ser
                20                  25                  30
Glu Pro Lys Thr Ser Gly Ser Glu Thr Pro Gly Thr Ser Glu Ser Ala
            35                  40                  45
Thr Pro Glu Ser Gly Pro Gly Ser Thr Glu Pro Ser Glu Gly Ala
        50                  55                  60
Arg Gln Gly Asp His Cys Pro Leu Gly Pro Gly Arg Cys Cys Arg Leu
65                  70                  75                  80
His Thr Val Arg Ala Ser Leu Glu Asp Leu Gly Trp Ala Asp Trp Val
                85                  90                  95
```

```
Leu Ser Pro Arg Glu Val Gln Val Thr Met Cys Ile Gly Ala Cys Pro
            100                 105                 110

Ser Gln Phe Arg Ala Ala Asn Leu His Ala Gln Ile Lys Thr Ser Leu
        115                 120                 125

His Arg Leu Arg Pro Asp Thr Val Pro Ala Pro Cys Cys Val Pro Ala
    130                 135                 140

Ser Tyr Asn Pro Met Val Leu Ile Gln Arg Thr Asp Thr Gly Val Ser
145                 150                 155                 160

Leu Gln Thr Tyr Asp Asp Leu Leu Ala Arg Asp Cys His Cys Ile
            165                 170                 175

<210> SEQ ID NO 258
<211> LENGTH: 183
<212> TYPE: PRT
<213> ORGANISM: Artificial Sequence
<220> FEATURE:
<223> OTHER INFORMATION: Synthetic

<400> SEQUENCE: 258

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Lys Gly Ala Gln Pro Gly Gln Glu Pro Gly Ala Gln Pro Gly
    50                  55                  60

Gln Glu Pro Gly Gln Glu Pro Ala Arg Gln Gly Asp His Cys Pro Leu
65                  70                  75                  80

Gly Pro Gly Arg Cys Cys Arg Leu His Thr Val Arg Ala Ser Leu Glu
                85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Arg Pro Asp Thr Val
    130                 135                 140

Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180

<210> SEQ ID NO 259
<211> LENGTH: 183
<212> TYPE: PRT
<213> ORGANISM: Artificial Sequence
<220> FEATURE:
<223> OTHER INFORMATION: Synthetic

<400> SEQUENCE: 259

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Gln Glu Pro Gly Gln Glu Lys Gly Gln Glu Pro Gly
```

```
                35                  40                  45
Gln Glu Pro Gly Gln Glu Pro Gly Gln Glu Pro Gly Gln Glu Pro Gly
            50                  55                  60
Gln Glu Pro Gly Gln Glu Pro Ala Arg Gln Gly Asp His Cys Pro Leu
65                  70                  75                  80
Gly Pro Gly Arg Cys Cys Arg Leu His Thr Val Arg Ala Ser Leu Glu
                85                  90                  95
Asp Leu Gly Trp Ala Asp Trp Val Leu Ser Pro Arg Glu Val Gln Val
            100                 105                 110
Thr Met Cys Ile Gly Ala Cys Pro Ser Gln Phe Arg Ala Ala Asn Leu
        115                 120                 125
His Ala Gln Ile Lys Thr Ser Leu His Arg Leu Arg Pro Asp Thr Val
    130                 135                 140
Pro Ala Pro Cys Cys Val Pro Ala Ser Tyr Asn Pro Met Val Leu Ile
145                 150                 155                 160
Gln Arg Thr Asp Thr Gly Val Ser Leu Gln Thr Tyr Asp Asp Leu Leu
                165                 170                 175
Ala Arg Asp Cys His Cys Ile
            180

<210> SEQ ID NO 260
<211> LENGTH: 223
<212> TYPE: PRT
<213> ORGANISM: Artificial Sequence
<220> FEATURE:
<223> OTHER INFORMATION: Synthetic

<400> SEQUENCE: 260

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Lys
            20                  25                  30
Gln Glu Pro Gly Ala Gln Pro Gly Gln Glu Pro Gly Ala Gln Pro Gly
        35                  40                  45
Gln Glu Pro Gly Ala Gln Pro Gly Gln Glu Pro Gly Ala Gln Pro Gly
    50                  55                  60
Gln Glu Pro Gly Ala Gln Pro Gly Gln Glu Pro Gly Ala Gln Pro Gly
65                  70                  75                  80
Ala Gln Pro Gly Ala Gln Pro Gly Ala Gln Pro Gly Ala Gln Pro Gly
                85                  90                  95
Ala Gln Pro Gly Ala Gln Pro Gly Ala Gln Pro Gly Ala Gln Pro Ala
            100                 105                 110
Arg Gln Gly Asp His Cys Pro Leu Gly Pro Gly Arg Cys Cys Arg Leu
        115                 120                 125
His Thr Val Arg Ala Ser Leu Glu Asp Leu Gly Trp Ala Asp Trp Val
    130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Arg Pro Asp Thr Val Pro Ala Pro Cys Cys Val Pro Ala
            180                 185                 190
Ser Tyr Asn Pro Met Val Leu Ile Gln Arg Thr Asp Thr Gly Val Ser
        195                 200                 205
Leu Gln Thr Tyr Asp Asp Leu Leu Ala Arg Asp Cys His Cys Ile
```

<210> SEQ ID NO 261
<211> LENGTH: 150
<212> TYPE: PRT
<213> ORGANISM: Artificial Sequence
<220> FEATURE:
<223> OTHER INFORMATION: Synthetic

<400> SEQUENCE: 261

Ser Glu Pro Ala Thr Ser Gly Gln Glu Lys Gly Gln Glu Pro Gly Gln
1               5                   10                  15
Glu Pro Gly Gln Glu Pro Gly Gln Glu Pro Gly Gln Glu Pro Gly Ala
            20                  25                  30
Gln Pro Gly Ala Gln Pro Ala Arg Gln Gly Asp His Cys Pro Leu Gly
        35                  40                  45
Pro Gly Arg Cys Cys Arg Leu His Thr Val Arg Ala Ser Leu Glu Asp
    50                  55                  60
Leu Gly Trp Ala Asp Trp Val Leu Ser Pro Arg Glu Val Gln Val Thr
65                  70                  75                  80
Met Cys Ile Gly Ala Cys Pro Ser Gln Phe Arg Ala Ala Asn Leu His
                85                  90                  95
Ala Gln Ile Lys Thr Ser Leu His Arg Leu Arg Pro Asp Thr Val Pro
            100                 105                 110
Ala Pro Cys Cys Val Pro Ala Ser Tyr Asn Pro Met Val Leu Ile Gln
        115                 120                 125
Arg Thr Asp Thr Gly Val Ser Leu Gln Thr Tyr Asp Asp Leu Leu Ala
    130                 135                 140
Arg Asp Cys His Cys Ile
145                 150

<210> SEQ ID NO 262
<211> LENGTH: 223
<212> TYPE: PRT
<213> ORGANISM: Artificial Sequence
<220> FEATURE:
<223> OTHER INFORMATION: Synthetic

<400> SEQUENCE: 262

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Gly
            20                  25                  30
Gln Glu Pro Gly Ala Gln Pro Gly Gln Glu Lys Gly Ala Gln Pro Gly
        35                  40                  45
Gln Glu Pro Gly Ala Gln Pro Gly Gln Glu Pro Gly Ala Gln Pro Gly
    50                  55                  60
Gln Glu Pro Gly Ala Gln Pro Gly Gln Glu Pro Gly Ala Gln Pro Gly
65                  70                  75                  80
Ala Gln Pro Gly Ala Gln Pro Gly Ala Gln Pro Gly Ala Gln Pro Gly
                85                  90                  95
Ala Gln Pro Gly Ala Gln Pro Gly Ala Gln Pro Gly Ala Gln Pro Ala
            100                 105                 110
Arg Gln Gly Asp His Cys Pro Leu Gly Pro Gly Arg Cys Cys Arg Leu
        115                 120                 125
His Thr Val Arg Ala Ser Leu Glu Asp Leu Gly Trp Ala Asp Trp Val
    130                 135                 140

```
Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220
```

<210> SEQ ID NO 263
<211> LENGTH: 223
<212> TYPE: PRT
<213> ORGANISM: Artificial Sequence
<220> FEATURE:
<223> OTHER INFORMATION: Synthetic

<400> SEQUENCE: 263

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Lys Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220
```

<210> SEQ ID NO 264
<211> LENGTH: 223
<212> TYPE: PRT
<213> ORGANISM: Artificial Sequence
<220> FEATURE:
<223> OTHER INFORMATION: Synthetic

<400> SEQUENCE: 264

```
His Gly Glu Gly Thr Phe Thr Ser Asp Val Ser Ser Tyr Leu Glu Glu
1               5                   10                  15
```

Gln Ala Ala Arg Glu Phe Ile Ala Trp Leu Val Arg Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Lys Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
            210                 215                 220

<210> SEQ ID NO 265
<211> LENGTH: 223
<212> TYPE: PRT
<213> ORGANISM: Artificial Sequence
<220> FEATURE:
<223> OTHER INFORMATION: Synthetic

<400> SEQUENCE: 265

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Lys Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

```
Ser Gln Phe Arg Ala Ala Asn Leu His Ala Gln Ile Lys Thr Ser Leu
            165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
    210                 215                 220

<210> SEQ ID NO 266
<211> LENGTH: 223
<212> TYPE: PRT
<213> ORGANISM: Artificial Sequence
<220> FEATURE:
<223> OTHER INFORMATION: Synthetic

<400> SEQUENCE: 266

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
            165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
    210                 215                 220

<210> SEQ ID NO 267
<211> LENGTH: 183
<212> TYPE: PRT
<213> ORGANISM: Artificial Sequence
<220> FEATURE:
<223> OTHER INFORMATION: Synthetic

<400> SEQUENCE: 267

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
```

```
               20                  25                  30

Gln Glu Pro Gly Gln Glu Pro Gly Gln Glu Pro Gly Gln Glu Pro Gly
            35                  40                  45

Gln Glu Pro Gly Gln Glu Pro Gly Gln Glu Pro Gly Gln Glu Pro Gly
50                  55                  60

Ala Gln Pro Gly Ala Gln Pro Ala Arg Gln Gly Asp His Cys Pro Leu
65                  70                  75                  80

Gly Pro Gly Arg Cys Cys Arg Leu His Thr Val Arg Ala Ser Leu Glu
                85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
        115                 120                 125

His Ala Gln Ile Lys Thr Ser Leu His Arg Leu Lys Pro Asp Thr Val
    130                 135                 140

Pro Ala Pro Cys Cys Val Pro Ala Ser Tyr Asn Pro Met Val Leu Ile
145                 150                 155                 160

Gln Lys Thr Asp Thr Gly Val Ser Leu Gln Thr Tyr Asp Asp Leu Leu
                165                 170                 175

Ala Lys Asp Cys His Cys Ile
            180

<210> SEQ ID NO 268
<211> LENGTH: 223
<212> TYPE: PRT
<213> ORGANISM: Artificial Sequence
<220> FEATURE:
<223> OTHER INFORMATION: Synthetic

<400> SEQUENCE: 268

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
```

```
                195                 200                 205
Leu Gln Thr Tyr Asp Asp Leu Leu Ala Lys Asp Cys His Cys Ile
    210                 215                 220

<210> SEQ ID NO 269
<211> LENGTH: 167
<212> TYPE: PRT
<213> ORGANISM: Artificial Sequence
<220> FEATURE:
<223> OTHER INFORMATION: Synthetic

<400> SEQUENCE: 269

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Gln Glu Pro Gly Gln Glu Pro Gly Gln Glu Pro Gly
        35                  40                  45

Gln Glu Pro Gly Gln Glu Pro Ala Arg Gln Gly Asp His Cys Pro Leu
    50                  55                  60

Gly Pro Gly Arg Cys Cys Arg Leu His Thr Val Arg Ala Ser Leu Glu
65                  70                  75                  80

Asp Leu Gly Trp Ala Asp Trp Val Leu Ser Pro Arg Glu Val Gln Val
                85                  90                  95

Thr Met Cys Ile Gly Ala Cys Pro Ser Gln Phe Arg Ala Ala Asn Leu
            100                 105                 110

His Ala Gln Ile Lys Thr Ser Leu His Arg Leu Lys Pro Asp Thr Val
        115                 120                 125

Pro Ala Pro Cys Cys Val Pro Ala Ser Tyr Asn Pro Met Val Leu Ile
    130                 135                 140

Gln Lys Thr Asp Thr Gly Val Ser Leu Gln Thr Tyr Asp Asp Leu Leu
145                 150                 155                 160

Ala Lys Asp Cys His Cys Ile
                165

<210> SEQ ID NO 270
<211> LENGTH: 155
<212> TYPE: PRT
<213> ORGANISM: Artificial Sequence
<220> FEATURE:
<223> OTHER INFORMATION: Synthetic

<400> SEQUENCE: 270

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Gln Glu Pro Gly Gln Glu Pro Ala Arg Gln Gly Asp
        35                  40                  45

His Cys Pro Leu Gly Pro Gly Arg Cys Cys Arg Leu His Thr Val Arg
    50                  55                  60

Ala Ser Leu Glu Asp Leu Gly Trp Ala Asp Trp Val Leu Ser Pro Arg
65                  70                  75                  80

Glu Val Gln Val Thr Met Cys Ile Gly Ala Cys Pro Ser Gln Phe Arg
                85                  90                  95

Ala Ala Asn Leu His Ala Gln Ile Lys Thr Ser Leu His Arg Leu Lys
            100                 105                 110
```

```
Pro Asp Thr Val Pro Ala Pro Cys Cys Val Pro Ala Ser Tyr Asn Pro
            115                 120                 125

Met Val Leu Ile Gln Lys Thr Asp Thr Gly Val Ser Leu Gln Thr Tyr
    130                 135                 140

Asp Asp Leu Leu Ala Lys Asp Cys His Cys Ile
145                 150                 155

<210> SEQ ID NO 271
<211> LENGTH: 109
<212> TYPE: PRT
<213> ORGANISM: Artificial Sequence
<220> FEATURE:
<223> OTHER INFORMATION: Synthetic

<400> SEQUENCE: 271

Gly Asp His Cys Pro Leu Gly Pro Gly Arg Cys Cys Arg Leu His Thr
1               5                   10                  15

Val Arg Ala Ser Leu Glu Asp Leu Gly Trp Ala Asp Trp Val Leu Ser
            20                  25                  30

Pro Arg Glu Val Gln Val Thr Met Cys Ile Gly Ala Cys Pro Ser Gln
        35                  40                  45

Phe Arg Ala Ala Asn Leu His Ala Gln Ile Lys Thr Ser Leu His Arg
    50                  55                  60

Leu Lys Pro Asp Thr Val Pro Ala Pro Cys Cys Val Pro Ala Ser Tyr
65                  70                  75                  80

Asn Pro Met Val Leu Ile Gln Lys Thr Asp Thr Gly Val Ser Leu Gln
                85                  90                  95

Thr Tyr Asp Asp Leu Leu Ala Lys Asp Cys His Cys Ile
            100                 105

<210> SEQ ID NO 272

<400> SEQUENCE: 272

000

<210> SEQ ID NO 273
<211> LENGTH: 223
<212> TYPE: PRT
<213> ORGANISM: Artificial Sequence
<220> FEATURE:
<223> OTHER INFORMATION: Synthetic

<400> SEQUENCE: 273

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Gln Glu Pro Gly Gln Glu Pro Gly
65                  70                  75                  80

Gln Glu Pro Gly Gln Lys Pro Gly Gln Glu Pro Gly Gln Glu Pro Gly
                85                  90                  95

Gln Glu Pro Gly Gln Glu Pro Gly Ala Gln Pro Gly Ala Gln Pro Ala
            100                 105                 110

Arg Gln Gly Asp His Cys Pro Leu Gly Pro Gly Arg Cys Cys Arg Leu
```

```
                115                 120                 125
His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 274
<211> LENGTH: 223
<212> TYPE: PRT
<213> ORGANISM: Artificial Sequence
<220> FEATURE:
<223> OTHER INFORMATION: Synthetic

<400> SEQUENCE: 274

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Pro Gly Gln Lys Pro Gly Gln Glu Pro Gly Gln Glu Pro Gly
                85                  90                  95

Gln Glu Pro Gly Gln Glu Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 275
<211> LENGTH: 223
<212> TYPE: PRT
<213> ORGANISM: Artificial Sequence
<220> FEATURE:
<223> OTHER INFORMATION: Synthetic
```

<400> SEQUENCE: 275

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Gln Glu Pro Gly Gln Glu Pro Gly
65                  70                  75                  80

Gln Glu Lys Gly Gln Glu Pro Gly Gln Glu Pro Gly Gln Glu Pro Gly
                85                  90                  95

Gln Glu Pro Gly Gln Glu Pro Gly Ala Gln Pro Gly Ala Gln Pro Ala
                100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220
```

<210> SEQ ID NO 276
<211> LENGTH: 223
<212> TYPE: PRT
<213> ORGANISM: Artificial Sequence
<220> FEATURE:
<223> OTHER INFORMATION: Synthetic

<400> SEQUENCE: 276

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Ala Gln Pro Gly Gln Glu Pro Gly Ala Gln Pro Gly Gln Glu Pro Gly
65                  70                  75                  80

Gln Glu Lys Gly Gln Glu Pro Gly Gln Glu Pro Gly Gln Glu Pro Gly
                85                  90                  95

Gln Glu Pro Gly Gln Glu Pro Gly Ala Gln Pro Gly Ala Gln Pro Ala
                100                 105                 110

Arg Gln Gly Asp His Cys Pro Leu Gly Pro Gly Arg Cys Cys Arg Leu
            115                 120                 125
```

His Thr Val Arg Ala Ser Leu Glu Asp Leu Gly Trp Ala Asp Trp Val
130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
210                 215                 220

<210> SEQ ID NO 277
<211> LENGTH: 223
<212> TYPE: PRT
<213> ORGANISM: Artificial Sequence
<220> FEATURE:
<223> OTHER INFORMATION: Synthetic

<400> SEQUENCE: 277

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Gln Glu Pro Gly Gln Glu Pro Gly Gln Lys Pro Gly
            35                  40                  45

Gln Glu Pro Gly Gln Glu Pro Gly Gln Glu Pro Gly Gln Glu Pro Gly
50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
210                 215                 220

<210> SEQ ID NO 278
<211> LENGTH: 223
<212> TYPE: PRT
<213> ORGANISM: Artificial Sequence
<220> FEATURE:
<223> OTHER INFORMATION: Synthetic

<400> SEQUENCE: 278

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly
            20                  25                  30

Gln Glu Pro Gly Gln Glu Pro Gly Gln Glu Lys Gly Gln Glu Pro Gly
            35                  40                  45

Gln Glu Pro Gly Gln Glu Pro Gly Gln Glu Pro Gly Gln Glu Pro Gly
50                  55                  60

Ala Gln Pro Gly Ala Gln Pro Gly Ala Gln Pro Gly Ala Gln Pro Gly
65                  70                  75                  80

Ala Gln Pro Gly Ala Gln Pro Gly Ala Gln Pro Gly Ala Gln Pro Gly
            85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
            165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
210                 215                 220

<210> SEQ ID NO 279
<211> LENGTH: 183
<212> TYPE: PRT
<213> ORGANISM: Artificial Sequence
<220> FEATURE:
<223> OTHER INFORMATION: Synthetic

<400> SEQUENCE: 279

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Ser
            20                  25                  30

Glu Pro Ala Thr Ser Gly Ser Glu Thr Pro Gly Thr Lys Glu Ser Ala
            35                  40                  45

Thr Pro Glu Ser Gly Pro Gly Thr Ser Thr Glu Pro Ser Glu Gly Gly
50                  55                  60

Ala Gln Pro Gly Ala Gln Pro Ala Arg Gln Gly Asp His Cys Pro Leu
65                  70                  75                  80

Gly Pro Gly Arg Cys Cys Arg Leu His Thr Val Arg Ala Ser Leu Glu
            85                  90                  95

Asp Leu Gly Trp Ala Asp Trp Val Leu Ser Pro Arg Glu Val Gln Val
            100                 105                 110

Thr Met Cys Ile Gly Ala Cys Pro Ser Gln Phe Arg Ala Ala Asn Leu
            115                 120                 125

His Ala Gln Ile Lys Thr Ser Leu His Arg Leu Arg Pro Asp Thr Val
            130                 135                 140

```
Pro Ala Pro Cys Cys Val Pro Ala Ser Tyr Asn Pro Met Val Leu Ile
145                 150                 155                 160

Gln Arg Thr Asp Thr Gly Val Ser Leu Gln Thr Tyr Asp Asp Leu Leu
                165                 170                 175

Ala Arg Asp Cys His Cys Ile
            180
```

<210> SEQ ID NO 280
<211> LENGTH: 223
<212> TYPE: PRT
<213> ORGANISM: Artificial Sequence
<220> FEATURE:
<223> OTHER INFORMATION: Synthetic

<400> SEQUENCE: 280

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Ala Gln Pro Gly Ala Gln Pro Gly Ala Gln Pro Gly Ala Gln Pro Gly
65                  70                  75                  80

Gln Glu Pro Gly Gln Lys Pro Gly Gln Glu Pro Gly Gln Glu Pro Gly
                85                  90                  95

Gln Glu Pro Gly Gln Glu Pro Gly Gln Glu Pro Gly Gln Glu Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
210                 215                 220
```

<210> SEQ ID NO 281
<211> LENGTH: 223
<212> TYPE: PRT
<213> ORGANISM: Artificial Sequence
<220> FEATURE:
<223> OTHER INFORMATION: Synthetic

<400> SEQUENCE: 281

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
```

```
                35                   40                  45
Ala Gln Pro Gly Ala Gln Pro Gly Ala Gln Pro Gly Ala Gln Pro Gly
 50                  55                  60
Ala Gln Pro Gly Ala Gln Pro Gly Ala Gln Pro Gly Ala Gln Pro Gly
 65                  70                  75                  80
Gln Glu Lys Gly Gln Glu Pro Gly Gln Glu Pro Gly Gln Glu Pro Gly
                 85                  90                  95
Gln Glu Pro Gly Gln Glu Pro Gly Gln Glu Pro Gly Gln Glu Pro Ala
                100                 105                 110
Arg Gln Gly Asp His Cys Pro Leu Gly Pro Gly Arg Cys Cys Arg Leu
                115                 120                 125
His Thr Val Arg Ala Ser Leu Glu Asp Leu Gly Trp Ala Asp Trp Val
                130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Arg Pro Asp Thr Val Pro Ala Pro Cys Cys Val Pro Ala
                180                 185                 190
Ser Tyr Asn Pro Met Val Leu Ile Gln Arg Thr Asp Thr Gly Val Ser
                195                 200                 205
Leu Gln Thr Tyr Asp Asp Leu Leu Ala Arg Asp Cys His Cys Ile
                210                 215                 220

<210> SEQ ID NO 282
<211> LENGTH: 223
<212> TYPE: PRT
<213> ORGANISM: Artificial Sequence
<220> FEATURE:
<223> OTHER INFORMATION: Synthetic

<400> SEQUENCE: 282

His Gly Glu Gly Thr Phe Thr Ser Asp Val Ser Ser Tyr Leu Glu Glu
 1                   5                  10                  15
Gln Ala Ala Arg Glu Phe Ile Ala Trp Leu Val Arg Gly Gly Gly Gly
                 20                  25                  30
Ala Gln Pro Gly Ala Gln Pro Gly Ala Gln Pro Gly Ala Lys Pro Gly
                 35                  40                  45
Ala Gln Pro Gly Ala Gln Pro Gly Ala Gln Pro Gly Ala Gln Pro Gly
 50                  55                  60
Ala Gln Pro Gly Ala Gln Pro Gly Ala Gln Pro Gly Ala Gln Pro Gly
 65                  70                  75                  80
Gln Glu Pro Gly Gln Glu Pro Gly Gln Glu Pro Gly Gln Glu Pro Gly
                 85                  90                  95
Gln Glu Pro Gly Gln Glu Pro Gly Gln Glu Pro Gly Gln Glu Pro Ala
                100                 105                 110
Arg Gln Gly Asp His Cys Pro Leu Gly Pro Gly Arg Cys Cys Arg Leu
                115                 120                 125
His Thr Val Arg Ala Ser Leu Glu Asp Leu Gly Trp Ala Asp Trp Val
                130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Arg Pro Asp Thr Val Pro Ala Pro Cys Cys Val Pro Ala
```

```
                180                 185                 190
Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
        210                 215                 220

<210> SEQ ID NO 283
<211> LENGTH: 223
<212> TYPE: PRT
<213> ORGANISM: Artificial Sequence
<220> FEATURE:
<223> OTHER INFORMATION: Synthetic

<400> SEQUENCE: 283

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Lys Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Gln Glu Pro Gly Gln Glu Pro Gly Gln Glu Pro Gly Gln Glu Pro Gly
                85                  90                  95

Gln Glu Pro Gly Gln Glu Pro Gly Gln Glu Pro Gly Gln Glu Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 284
<211> LENGTH: 223
<212> TYPE: PRT
<213> ORGANISM: Artificial Sequence
<220> FEATURE:
<223> OTHER INFORMATION: Synthetic

<400> SEQUENCE: 284

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Gln Glu Pro Gly Ala Gln Pro Gly Gln Glu Pro Gly Ala Gln Pro Gly
        35                  40                  45
```

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
    210                 215                 220

<210> SEQ ID NO 285
<211> LENGTH: 223
<212> TYPE: PRT
<213> ORGANISM: Artificial Sequence
<220> FEATURE:
<223> OTHER INFORMATION: Synthetic

<400> SEQUENCE: 285

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Gln Glu Pro Gly Gln Glu Pro Gly
65                  70                  75                  80

Gln Glu Pro Gly Gln Glu Pro Gly Gln Glu Pro Gly Gln Glu Pro Gly
                85                  90                  95

Gln Glu Pro Gly Gln Glu Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

```
Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220
```

<210> SEQ ID NO 286
<211> LENGTH: 223
<212> TYPE: PRT
<213> ORGANISM: Artificial Sequence
<220> FEATURE:
<223> OTHER INFORMATION: Synthetic

<400> SEQUENCE: 286

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Pro Gly Gln Glu Pro Gly Gln Glu Pro Gly Gln Glu Pro Gly
                85                  90                  95

Gln Glu Pro Gly Gln Glu Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220
```

<210> SEQ ID NO 287
<211> LENGTH: 223
<212> TYPE: PRT
<213> ORGANISM: Artificial Sequence
<220> FEATURE:
<223> OTHER INFORMATION: Synthetic

<400> SEQUENCE: 287

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60
```

```
Ala Gln Pro Gly Gln Glu Pro Gly Ala Gln Pro Gly Gln Glu Pro Gly
 65                  70                  75                  80

Gln Glu Pro Gly Gln Glu Pro Gly Gln Glu Pro Gly Gln Glu Pro Gly
                 85                  90                  95

Gln Glu Pro Gly Gln Glu Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
                210                 215                 220
```

<210> SEQ ID NO 288
<211> LENGTH: 223
<212> TYPE: PRT
<213> ORGANISM: Artificial Sequence
<220> FEATURE:
<223> OTHER INFORMATION: Synthetic

<400> SEQUENCE: 288

```
His Gly Glu Gly Thr Phe Thr Ser Asp Val Ser Ser Tyr Leu Glu Glu
  1               5                  10                  15

Gln Ala Ala Arg Glu Phe Ile Ala Trp Leu Val Arg Gly Gly Gly Lys
                 20                  25                  30

Gln Glu Pro Gly Gln Glu Pro Gly Gln Glu Pro Gly Gln Glu Pro Gly
                 35                  40                  45

Gln Glu Pro Gly Gln Glu Pro Gly Gln Glu Pro Gly Gln Glu Pro Gly
 50                  55                  60

Ala Gln Pro Gly Ala Gln Pro Gly Ala Gln Pro Gly Ala Gln Pro Gly
 65                  70                  75                  80

Ala Gln Pro Gly Ala Gln Pro Gly Ala Gln Pro Gly Ala Gln Pro Gly
                 85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205
```

```
Leu Gln Thr Tyr Asp Asp Leu Leu Ala Arg Asp Cys His Cys Ile
    210                 215                 220

<210> SEQ ID NO 289
<211> LENGTH: 223
<212> TYPE: PRT
<213> ORGANISM: Artificial Sequence
<220> FEATURE:
<223> OTHER INFORMATION: Synthetic

<400> SEQUENCE: 289

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Ala Gln Pro Gly Ala Gln Pro Gly Ala Gln Pro Gly Ala Gln Pro Gly
65                  70                  75                  80

Gln Glu Pro Gly Gln Glu Pro Gly Gln Glu Pro Gly Gln Glu Pro Gly
                85                  90                  95

Gln Glu Pro Gly Gln Glu Pro Gly Gln Glu Pro Gly Gln Glu Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 290
<211> LENGTH: 112
<212> TYPE: PRT
<213> ORGANISM: Artificial Sequence
<220> FEATURE:
<223> OTHER INFORMATION: Synthetic

<400> SEQUENCE: 290

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Leu His Ala Gln Ile Lys Thr Ser
    50                  55                  60

Leu His Arg Leu Lys Pro Asp Thr Val Pro Ala Pro Cys Cys Val Pro
```

```
                65                   70                  75                  80
Ala Ser Tyr Asn Pro Met Val Leu Ile Gln Arg Thr Asp Thr Gly Val
                    85                  90                  95

Ser Leu Gln Thr Tyr Asp Asp Leu Leu Ala Arg Asp Cys His Cys Ile
                100                 105                 110

<210> SEQ ID NO 291
<211> LENGTH: 112
<212> TYPE: PRT
<213> ORGANISM: Artificial Sequence
<220> FEATURE:
<223> OTHER INFORMATION: Synthetic

<400> SEQUENCE: 291

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Leu His Ala Gln Ile Lys Thr Ser
    50                  55                  60

Leu His Arg Leu Arg Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                    85                  90                  95

Ser Leu Gln Thr Tyr Asp Asp Leu Leu Ala Lys Asp Cys His Cys Ile
                100                 105                 110

<210> SEQ ID NO 292
<211> LENGTH: 112
<212> TYPE: PRT
<213> ORGANISM: Artificial Sequence
<220> FEATURE:
<223> OTHER INFORMATION: Synthetic

<400> SEQUENCE: 292

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Leu His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                    85                  90                  95

Ser Leu Gln Thr Tyr Asp Asp Leu Leu Ala Lys Asp Cys His Cys Ile
                100                 105                 110

<210> SEQ ID NO 293
<211> LENGTH: 112
<212> TYPE: PRT
<213> ORGANISM: Artificial Sequence
<220> FEATURE:
<223> OTHER INFORMATION: Synthetic

<400> SEQUENCE: 293
```

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Arg Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 294
<211> LENGTH: 112
<212> TYPE: PRT
<213> ORGANISM: Artificial Sequence
<220> FEATURE:
<223> OTHER INFORMATION: Synthetic

<400> SEQUENCE: 294

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110

<210> SEQ ID NO 295
<211> LENGTH: 112
<212> TYPE: PRT
<213> ORGANISM: Artificial Sequence
<220> FEATURE:
<223> OTHER INFORMATION: Synthetic

<400> SEQUENCE: 295

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val

```
                    85                  90                  95

Ser Leu Gln Thr Tyr Asp Asp Leu Leu Ala Arg Asp Cys His Cys Ile
                100                 105                 110

<210> SEQ ID NO 296
<211> LENGTH: 112
<212> TYPE: PRT
<213> ORGANISM: Artificial Sequence
<220> FEATURE:
<223> OTHER INFORMATION: Synthetic

<400> SEQUENCE: 296

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Arg Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 297
<211> LENGTH: 112
<212> TYPE: PRT
<213> ORGANISM: Artificial Sequence
<220> FEATURE:
<223> OTHER INFORMATION: Synthetic

<400> SEQUENCE: 297

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
                20                  25                  30

Val Leu Ser Pro Arg Glu Val Gln Val Thr Met Cys Ile Gly Ala Cys
            35                  40                  45

Pro Ser Gln Phe Arg Ala Ala Asn Met His Ala Gln Ile Lys Thr Ser
        50                  55                  60

Leu His Arg Leu Lys Pro Asp Thr Val Pro Ala Pro Cys Cys Val Pro
65                  70                  75                  80

Ala Ser Tyr Asn Pro Met Val Leu Ile Gln Arg Thr Asp Thr Gly Val
                85                  90                  95

Ser Leu Gln Thr Tyr Asp Asp Leu Leu Ala Lys Asp Cys His Cys Ile
                100                 105                 110

<210> SEQ ID NO 298
<211> LENGTH: 40
<212> TYPE: PRT
<213> ORGANISM: Artificial Sequence
<220> FEATURE:
<223> OTHER INFORMATION: Synthetic

<400> SEQUENCE: 298

Gly Gln Glu Pro Gly Gln Glu Pro Gly Gln Glu Lys Gly Gln Glu Pro
1               5                   10                  15
```

Gly Gln Glu Pro Gly Gln Glu Pro Gly Gln Glu Pro Gly Gln Glu Pro
            20                  25                  30

Gly Ala Gln Pro Gly Ala Gln Pro
            35                  40

<210> SEQ ID NO 299
<211> LENGTH: 40
<212> TYPE: PRT
<213> ORGANISM: Artificial Sequence
<220> FEATURE:
<223> OTHER INFORMATION: Synthetic

<400> SEQUENCE: 299

Lys Gln Glu Pro Gly Gln Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro
            35                  40

<210> SEQ ID NO 300
<211> LENGTH: 40
<212> TYPE: PRT
<213> ORGANISM: Artificial Sequence
<220> FEATURE:
<223> OTHER INFORMATION: Synthetic

<400> SEQUENCE: 300

Gly Gln Glu Pro Gly Lys Glu Pro Gly Gln Glu Pro Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro
            35                  40

<210> SEQ ID NO 301
<211> LENGTH: 40
<212> TYPE: PRT
<213> ORGANISM: Artificial Sequence
<220> FEATURE:
<223> OTHER INFORMATION: Synthetic

<400> SEQUENCE: 301

Gly Gln Glu Pro Gly Gln Glu Pro Gly Gln Glu Pro Gly Gln Lys Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro
            35                  40

<210> SEQ ID NO 302
<211> LENGTH: 32
<212> TYPE: PRT
<213> ORGANISM: Artificial Sequence
<220> FEATURE:
<223> OTHER INFORMATION: Synthetic

<400> SEQUENCE: 302

Ser Glu Pro Lys Thr Ser Gly Ser Glu Thr Pro Gly Thr Ser Glu Ser
1               5                   10                  15

Ala Thr Pro Glu Ser Gly Pro Gly Thr Ser Thr Glu Pro Ser Glu Gly
            20                  25                  30

```
<210> SEQ ID NO 303
<211> LENGTH: 40
<212> TYPE: PRT
<213> ORGANISM: Artificial Sequence
<220> FEATURE:
<223> OTHER INFORMATION: Synthetic

<400> SEQUENCE: 303

Gly Gln Glu Pro Gly Ala Gln Pro Gly Gln Glu Pro Gly Ala Gln Pro
1               5                   10                  15

Gly Gln Glu Lys Gly Ala Gln Pro Gly Gln Glu Pro Gly Ala Gln Pro
            20                  25                  30

Gly Gln Glu Pro Gly Gln Glu Pro
        35                  40

<210> SEQ ID NO 304
<211> LENGTH: 40
<212> TYPE: PRT
<213> ORGANISM: Artificial Sequence
<220> FEATURE:
<223> OTHER INFORMATION: Synthetic

<400> SEQUENCE: 304

Gly Gln Glu Pro Gly Gln Glu Pro Gly Gln Glu Lys Gly Gln Glu Pro
1               5                   10                  15

Gly Gln Glu Pro Gly Gln Glu Pro Gly Gln Glu Pro Gly Gln Glu Pro
            20                  25                  30

Gly Gln Glu Pro Gly Gln Glu Pro
        35                  40

<210> SEQ ID NO 305
<211> LENGTH: 80
<212> TYPE: PRT
<213> ORGANISM: Artificial Sequence
<220> FEATURE:
<223> OTHER INFORMATION: Synthetic

<400> SEQUENCE: 305

Lys Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 306
<211> LENGTH: 38
<212> TYPE: PRT
<213> ORGANISM: Artificial Sequence
<220> FEATURE:
<223> OTHER INFORMATION: Synthetic

<400> SEQUENCE: 306

Ser Glu Pro Ala Thr Ser Gly Gln Glu Lys Gly Gln Glu Pro Gly Gln
1               5                   10                  15

Glu Pro Gly Gln Glu Pro Gly Gln Glu Pro Gly Gln Glu Pro Gly Ala
            20                  25                  30
```

Gln Pro Gly Ala Gln Pro
        35

<210> SEQ ID NO 307
<211> LENGTH: 80
<212> TYPE: PRT
<213> ORGANISM: Artificial Sequence
<220> FEATURE:
<223> OTHER INFORMATION: Synthetic

<400> SEQUENCE: 307

Gly Gln Glu Pro Gly Ala Gln Pro Gly Gln Glu Lys Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 308
<211> LENGTH: 80
<212> TYPE: PRT
<213> ORGANISM: Artificial Sequence
<220> FEATURE:
<223> OTHER INFORMATION: Synthetic

<400> SEQUENCE: 308

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Lys Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 309
<211> LENGTH: 80
<212> TYPE: PRT
<213> ORGANISM: Artificial Sequence
<220> FEATURE:
<223> OTHER INFORMATION: Synthetic

<400> SEQUENCE: 309

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Lys Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 310
<211> LENGTH: 80
<212> TYPE: PRT
<213> ORGANISM: Artificial Sequence
<220> FEATURE:
<223> OTHER INFORMATION: Synthetic

<400> SEQUENCE: 310

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Lys Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 311
<211> LENGTH: 80
<212> TYPE: PRT
<213> ORGANISM: Artificial Sequence
<220> FEATURE:
<223> OTHER INFORMATION: Synthetic

<400> SEQUENCE: 311

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Gln Glu Pro Gly Gln Glu Pro
            35                  40                  45

Gly Gln Glu Pro Gly Gln Lys Pro Gly Gln Glu Pro Gly Gln Glu Pro
    50                  55                  60

Gly Gln Glu Pro Gly Gln Glu Pro Gly Ala Gln Pro Gly Ala Gln Pro
65                  70                  75                  80

<210> SEQ ID NO 312
<211> LENGTH: 80
<212> TYPE: PRT
<213> ORGANISM: Artificial Sequence
<220> FEATURE:
<223> OTHER INFORMATION: Synthetic

<400> SEQUENCE: 312

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Gln Lys Pro Gly Gln Glu Pro Gly Gln Glu Pro
    50                  55                  60

Gly Gln Glu Pro Gly Gln Glu Pro Gly Ala Gln Pro Gly Ala Gln Pro
65                  70                  75                  80

<210> SEQ ID NO 313
<211> LENGTH: 80
<212> TYPE: PRT

```
<213> ORGANISM: Artificial Sequence
<220> FEATURE:
<223> OTHER INFORMATION: Synthetic

<400> SEQUENCE: 313

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Gln Glu Pro Gly Gln Glu Pro
            35                  40                  45

Gly Gln Glu Lys Gly Gln Glu Pro Gly Gln Glu Pro Gly Gln Glu Pro
        50                  55                  60

Gly Gln Glu Pro Gly Gln Glu Pro Gly Ala Gln Pro Gly Ala Gln Pro
65                  70                  75                  80

<210> SEQ ID NO 314
<211> LENGTH: 80
<212> TYPE: PRT
<213> ORGANISM: Artificial Sequence
<220> FEATURE:
<223> OTHER INFORMATION: Synthetic

<400> SEQUENCE: 314

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Gln Glu Pro Gly Ala Gln Pro Gly Gln Glu Pro
            35                  40                  45

Gly Gln Glu Lys Gly Gln Glu Pro Gly Gln Glu Pro Gly Gln Glu Pro
        50                  55                  60

Gly Gln Glu Pro Gly Gln Glu Pro Gly Ala Gln Pro Gly Ala Gln Pro
65                  70                  75                  80

<210> SEQ ID NO 315
<211> LENGTH: 80
<212> TYPE: PRT
<213> ORGANISM: Artificial Sequence
<220> FEATURE:
<223> OTHER INFORMATION: Synthetic

<400> SEQUENCE: 315

Gly Gln Glu Pro Gly Gln Glu Pro Gly Gln Glu Pro Gly Gln Lys Pro
1               5                   10                  15

Gly Gln Glu Pro Gly Gln Glu Pro Gly Gln Glu Pro Gly Gln Glu Pro
                20                  25                  30

Gly Ala Gln Pro Gly Ala Gln Pro Gly Ala Gln Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 316
<211> LENGTH: 80
<212> TYPE: PRT
<213> ORGANISM: Artificial Sequence
<220> FEATURE:
<223> OTHER INFORMATION: Synthetic
```

<400> SEQUENCE: 316

Gly Gln Glu Pro Gly Gln Glu Pro Gly Gln Glu Lys Gly Gln Glu Pro
1               5                   10                  15

Gly Gln Glu Pro Gly Gln Glu Pro Gly Gln Glu Pro Gly Gln Glu Pro
            20                  25                  30

Gly Ala Gln Pro Gly Ala Gln Pro Gly Ala Gln Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 317
<211> LENGTH: 40
<212> TYPE: PRT
<213> ORGANISM: Artificial Sequence
<220> FEATURE:
<223> OTHER INFORMATION: Synthetic

<400> SEQUENCE: 317

Ser Glu Pro Ala Thr Ser Gly Ser Glu Thr Pro Gly Thr Lys Glu Ser
1               5                   10                  15

Ala Thr Pro Glu Ser Gly Pro Gly Thr Ser Thr Glu Pro Ser Glu Gly
            20                  25                  30

Gly Ala Gln Pro Gly Ala Gln Pro
        35                  40

<210> SEQ ID NO 318
<211> LENGTH: 80
<212> TYPE: PRT
<213> ORGANISM: Artificial Sequence
<220> FEATURE:
<223> OTHER INFORMATION: Synthetic

<400> SEQUENCE: 318

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Gln Lys Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

<210> SEQ ID NO 319
<211> LENGTH: 80
<212> TYPE: PRT
<213> ORGANISM: Artificial Sequence
<220> FEATURE:
<223> OTHER INFORMATION: Synthetic

<400> SEQUENCE: 319

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Lys Gly Gln Glu Pro Gly Gln Glu Pro Gly Gln Glu Pro
            50                  55                  60

Gly Gln Glu Pro Gly Gln Glu Pro Gly Gln Glu Pro Gly Gln Glu Pro
65                  70                  75                  80

<210> SEQ ID NO 320
<211> LENGTH: 80
<212> TYPE: PRT
<213> ORGANISM: Artificial Sequence
<220> FEATURE:
<223> OTHER INFORMATION: Synthetic

<400> SEQUENCE: 320

Gly Ala Gln Pro Gly Ala Gln Pro Gly Ala Gln Pro Gly Ala Lys Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

<210> SEQ ID NO 321
<211> LENGTH: 80
<212> TYPE: PRT
<213> ORGANISM: Artificial Sequence
<220> FEATURE:
<223> OTHER INFORMATION: Synthetic

<400> SEQUENCE: 321

Gly Ala Gln Pro Gly Ala Gln Pro Gly Ala Gln Lys Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Gln Glu Pro Gly Gln Glu Pro Gly Gln Glu Pro
    50                  55                  60

Gly Gln Glu Pro Gly Gln Glu Pro Gly Gln Glu Pro Gly Gln Glu Pro
65                  70                  75                  80

<210> SEQ ID NO 322
<211> LENGTH: 80
<212> TYPE: PRT
<213> ORGANISM: Artificial Sequence
<220> FEATURE:
<223> OTHER INFORMATION: Synthetic

<400> SEQUENCE: 322

Lys Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

-continued

Gly Gln Glu Pro Gly Ala Gln Pro Gly Gln Glu Pro Gly Ala Gln Pro
65                  70                  75                  80

<210> SEQ ID NO 323
<211> LENGTH: 80
<212> TYPE: PRT
<213> ORGANISM: Artificial Sequence
<220> FEATURE:
<223> OTHER INFORMATION: Synthetic

<400> SEQUENCE: 323

Lys Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Ala Gln Pro Gly Ala Gln Pro Gly Gln Glu Pro Gly Gln Glu Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Ala Gln Pro Gly Ala Gln Pro
65                  70                  75                  80

<210> SEQ ID NO 324
<211> LENGTH: 80
<212> TYPE: PRT
<213> ORGANISM: Artificial Sequence
<220> FEATURE:
<223> OTHER INFORMATION: Synthetic

<400> SEQUENCE: 324

Lys Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Gln Glu Pro Gly Gln Glu Pro Gly Gln Glu Pro
        50                  55                  60

Gly Gln Glu Pro Gly Gln Glu Pro Gly Ala Gln Pro Gly Ala Gln Pro
65                  70                  75                  80

<210> SEQ ID NO 325
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa is H, imidazole-4-acetate (IA),
      imidazolepropionic acid (IPA) or absent
<220> FEATURE:
<221> NAME/KEY: misc_feature
<222> LOCATION: (2)..(2)
<223> OTHER INFORMATION: Xaa is A, G, S, V, Aib, T, I, L or absent
<220> FEATURE:
<221> NAME/KEY: misc_feature
<222> LOCATION: (16)..(16)
<223> OTHER INFORMATION: Xaa is G, or E
<220> FEATURE:
<221> NAME/KEY: misc_feature
<222> LOCATION: (20)..(20)
<223> OTHER INFORMATION: Xaa is K, R, or C
<220> FEATURE:
<221> NAME/KEY: misc_feature -continued

```
<222> LOCATION: (21)..(21)
<223> OTHER INFORMATION: Xaa is E, K, or C
<220> FEATURE:
<221> NAME/KEY: misc_feature
<222> LOCATION: (28)..(28)
<223> OTHER INFORMATION: Xaa is R, K, or C
<220> FEATURE:
<221> NAME/KEY: misc_feature
<222> LOCATION: (30)..(30)
<223> OTHER INFORMATION: Xaa is K, R, G, or C

<400> SEQUENCE: 325

Xaa Xaa Glu Gly Thr Phe Thr Ser Asp Val Ser Ser Tyr Leu Glu Xaa
1               5                   10                  15

Gln Ala Ala Xaa Xaa Phe Ile Ala Trp Leu Val Xaa Gly Xaa Gly
            20                  25                  30

<210> SEQ ID NO 326
<211> LENGTH: 203
<212> TYPE: PRT
<213> ORGANISM: Artificial Sequence
<220> FEATURE:
<223> OTHER INFORMATION: Synthetic

<400> SEQUENCE: 326

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Ala Arg Gln Gly Asp
                85                  90                  95

His Cys Pro Leu Gly Pro Gly Arg Cys Cys Arg Leu His Thr Val Arg
            100                 105                 110

Ala Ser Leu Glu Asp Leu Gly Trp Ala Asp Trp Val Leu Ser Pro Arg
        115                 120                 125

Glu Val Gln Val Thr Met Cys Ile Gly Ala Cys Pro Ser Gln Phe Arg
    130                 135                 140

Ala Ala Asn Leu His Ala Gln Ile Lys Thr Ser Leu His Arg Leu Arg
145                 150                 155                 160

Pro Asp Thr Val Pro Ala Pro Cys Cys Val Pro Ala Ser Tyr Asn Pro
                165                 170                 175

Met Val Leu Ile Gln Arg Thr Asp Thr Gly Val Ser Leu Gln Thr Tyr
            180                 185                 190

Asp Asp Leu Leu Ala Arg Asp Cys His Cys Ile
        195                 200

<210> SEQ ID NO 327
<211> LENGTH: 223
<212> TYPE: PRT
<213> ORGANISM: Artificial Sequence
<220> FEATURE:
<223> OTHER INFORMATION: Synthetic

<400> SEQUENCE: 327

His Gly Glu Gly Thr Phe Thr Ser Asp Val Ser Ser Tyr Leu Glu Glu
```

```
                1               5                   10                  15
Gln Ala Ala Lys Glu Phe Ile Ala Trp Leu Val Arg Gly Gly Gly
                20                  25                  30
Gln Glu Pro Gly Ala Gln Pro Gly Gln Glu Pro Gly Ala Gln Pro Gly
                35                  40                  45
Gln Glu Pro Gly Ala Gln Pro Gly Gln Glu Pro Gly Ala Gln Pro Gly
50                  55                  60
Gln Glu Pro Gly Ala Gln Pro Gly Gln Glu Pro Gly Ala Gln Pro Gly
65                  70                  75                  80
Ala Gln Pro Gly Ala Lys Pro Gly Ala Gln Pro Gly Ala Gln Pro Gly
                85                  90                  95
Ala Gln Pro Gly Ala Gln Pro Gly Ala Gln Pro Gly Ala Gln Pro Ala
                100                 105                 110
Arg Gln Gly Asp His Cys Pro Leu Gly Pro Gly Arg Cys Cys Arg Leu
                115                 120                 125
His Thr Val Arg Ala Ser Leu Glu Asp Leu Gly Trp Ala Asp Trp Val
                130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Arg Pro Asp Thr Val Pro Ala Pro Cys Cys Val Pro Ala
                180                 185                 190
Ser Tyr Asn Pro Met Val Leu Ile Gln Arg Thr Asp Thr Gly Val Ser
                195                 200                 205
Leu Gln Thr Tyr Asp Asp Leu Leu Ala Arg Asp Cys His Cys Ile
                210                 215                 220

<210> SEQ ID NO 328
<211> LENGTH: 223
<212> TYPE: PRT
<213> ORGANISM: Artificial Sequence
<220> FEATURE:
<223> OTHER INFORMATION: Synthetic

<400> SEQUENCE: 328

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Lys
                20                  25                  30
Gln Glu Pro Gly Ala Gln Pro Gly Gln Glu Pro Gly Ala Gln Pro Gly
                35                  40                  45
Gln Glu Pro Gly Ala Gln Pro Gly Gln Glu Pro Gly Ala Gln Pro Gly
50                  55                  60
Gln Glu Pro Gly Ala Gln Pro Gly Gln Glu Pro Gly Ala Gln Pro Gly
65                  70                  75                  80
Ala Gln Pro Gly Ala Lys Pro Gly Ala Gln Pro Gly Ala Gln Pro Gly
                85                  90                  95
Ala Gln Pro Gly Ala Gln Pro Gly Ala Gln Pro Gly Ala Gln Pro Ala
                100                 105                 110
Arg Gln Gly Asp His Cys Pro Leu Gly Pro Gly Arg Cys Cys Arg Leu
                115                 120                 125
His Thr Val Arg Ala Ser Leu Glu Asp Leu Gly Trp Ala Asp Trp Val
                130                 135                 140
Leu Ser Pro Arg Glu Val Gln Val Thr Met Cys Ile Gly Ala Cys Pro
```

-continued

```
            145                 150                 155                 160
Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
                210                 215                 220

<210> SEQ ID NO 329
<211> LENGTH: 223
<212> TYPE: PRT
<213> ORGANISM: Artificial Sequence
<220> FEATURE:
<223> OTHER INFORMATION: Synthetic

<400> SEQUENCE: 329

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Lys Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
                210                 215                 220

<210> SEQ ID NO 330
<211> LENGTH: 223
<212> TYPE: PRT
<213> ORGANISM: Artificial Sequence
<220> FEATURE:
<223> OTHER INFORMATION: Synthetic

<400> SEQUENCE: 330

His Gly Glu Gly Thr Phe Thr Ser Asp Val Ser Ser Tyr Leu Glu Glu
1               5                   10                  15
```

Gln Ala Ala Arg Glu Phe Ile Ala Trp Leu Val Arg Gly Gly Gly
            20                  25                  30

Gln Glu Pro Gly Ala Gln Pro Gly Gln Glu Pro Gly Ala Gln Pro Gly
                35                  40                  45

Gln Glu Pro Gly Ala Gln Pro Gly Gln Glu Pro Gly Ala Gln Pro Gly
 50                  55                  60

Gln Glu Pro Gly Ala Gln Lys Gly Gln Glu Pro Gly Ala Gln Pro Gly
 65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
210                 215                 220

<210> SEQ ID NO 331
<211> LENGTH: 223
<212> TYPE: PRT
<213> ORGANISM: Artificial Sequence
<220> FEATURE:
<223> OTHER INFORMATION: Synthetic

<400> SEQUENCE: 331

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly
            20                  25                  30

Ala Gln Pro Gly Gln Glu Pro Gly Ala Gln Pro Gly Gln Glu Pro Gly
                35                  40                  45

Ala Gln Pro Gly Gln Glu Pro Gly Ala Gln Pro Gly Gln Glu Pro Gly
 50                  55                  60

Ala Gln Pro Gly Gln Glu Pro Gly Ala Gln Pro Gly Gln Glu Pro Gly
 65                  70                  75                  80

Ala Gln Pro Gly Gln Glu Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
              165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 332
<211> LENGTH: 80
<212> TYPE: PRT
<213> ORGANISM: Artificial Sequence
<220> FEATURE:
<223> OTHER INFORMATION: Synthetic

<400> SEQUENCE: 332

Lys Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Lys Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 333
<211> LENGTH: 80
<212> TYPE: PRT
<213> ORGANISM: Artificial Sequence
<220> FEATURE:
<223> OTHER INFORMATION: Synthetic

<400> SEQUENCE: 333

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Lys Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 334
<211> LENGTH: 80
<212> TYPE: PRT
<213> ORGANISM: Artificial Sequence
<220> FEATURE:
<223> OTHER INFORMATION: Synthetic

<400> SEQUENCE: 334

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Lys Gly Gln Glu Pro Gly Ala Gln Pro

```
                35                  40                  45
Gly Ala Gln Pro Gly Ala Gln Pro Gly Ala Gln Pro Gly Ala Gln Pro
         50                  55                  60
Gly Ala Gln Pro Gly Ala Gln Pro Gly Ala Gln Pro Gly Ala Gln Pro
 65                  70                  75                  80

<210> SEQ ID NO 335

<400> SEQUENCE: 335

000

<210> SEQ ID NO 336
<211> LENGTH: 31
<212> TYPE: PRT
<213> ORGANISM: Artificial Sequence
<220> FEATURE:
<223> OTHER INFORMATION: Synthetic

<400> SEQUENCE: 336

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Lys Gly Gly Gly
             20                  25                  30

<210> SEQ ID NO 337
<211> LENGTH: 203
<212> TYPE: PRT
<213> ORGANISM: Artificial Sequence
<220> FEATURE:
<223> OTHER INFORMATION: Synthetic

<400> SEQUENCE: 337

His Gly Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Gly Gly Lys
             20                  25                  30

Gln Glu Pro Gly Ala Gln Pro Gly Gln Glu Pro Gly Ala Gln Pro Gly
         35                  40                  45

Gln Glu Pro Gly Ala Gln Pro Gly Gln Glu Pro Gly Ala Gln Pro Gly
         50                  55                  60

Gln Glu Pro Gly Ala Gln Pro Gly Gln Glu Pro Gly Ala Gln Pro Gly
 65                  70                  75                  80

Ala Gln Pro Gly Ala Gln Pro Gly Ala Gln Pro Ala Arg Gln Gly Asp
                 85                  90                  95

His Cys Pro Leu Gly Pro Gly Arg Cys Cys Arg Leu His Thr Val Arg
            100                 105                 110

Ala Ser Leu Glu Asp Leu Gly Trp Ala Asp Trp Val Leu Ser Pro Arg
        115                 120                 125

Glu Val Gln Val Thr Met Cys Ile Gly Ala Cys Pro Ser Gln Phe Arg
    130                 135                 140

Ala Ala Asn Leu His Ala Gln Ile Lys Thr Ser Leu His Arg Leu Arg
145                 150                 155                 160

Pro Asp Thr Val Pro Ala Pro Cys Cys Val Pro Ala Ser Tyr Asn Pro
                165                 170                 175

Met Val Leu Ile Gln Arg Thr Asp Thr Gly Val Ser Leu Gln Thr Tyr
            180                 185                 190

Asp Asp Leu Leu Ala Arg Asp Cys His Cys Ile
        195                 200
```

<210> SEQ ID NO 338
<211> LENGTH: 203
<212> TYPE: PRT
<213> ORGANISM: Artificial Sequence
<220> FEATURE:
<223> OTHER INFORMATION: Synthetic

<400> SEQUENCE: 338

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Lys Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Ala Arg Gln Gly Asp
                85                  90                  95

His Cys Pro Leu Gly Pro Gly Arg Cys Cys Arg Leu His Thr Val Arg
            100                 105                 110

Ala Ser Leu Glu Asp Leu Gly Trp Ala Asp Trp Val Leu Ser Pro Arg
        115                 120                 125

Glu Val Gln Val Thr Met Cys Ile Gly Ala Cys Pro Ser Gln Phe Arg
    130                 135                 140

Ala Ala Asn Leu His Ala Gln Ile Lys Thr Ser Leu His Arg Leu Arg
145                 150                 155                 160

Pro Asp Thr Val Pro Ala Pro Cys Cys Val Pro Ala Ser Tyr Asn Pro
                165                 170                 175

Met Val Leu Ile Gln Arg Thr Asp Thr Gly Val Ser Leu Gln Thr Tyr
            180                 185                 190

Asp Asp Leu Leu Ala Arg Asp Cys His Cys Ile
        195                 200
```

<210> SEQ ID NO 339
<211> LENGTH: 203
<212> TYPE: PRT
<213> ORGANISM: Artificial Sequence
<220> FEATURE:
<223> OTHER INFORMATION: Synthetic

<400> SEQUENCE: 339

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Lys Pro Gly Ala Gln Pro Gly Gln Glu Pro Gly Ala Gln Pro Gly
65                  70                  75                  80

Ala Gln Pro Gly Ala Gln Pro Gly Ala Gln Pro Ala Arg Gln Gly Asp
                85                  90                  95

His Cys Pro Leu Gly Pro Gly Arg Cys Cys Arg Leu His Thr Val Arg
```

```
                    100                 105                 110
Ala Ser Leu Glu Asp Leu Gly Trp Ala Asp Trp Val Leu Ser Pro Arg
                115                 120                 125

Glu Val Gln Val Thr Met Cys Ile Gly Ala Cys Pro Ser Gln Phe Arg
            130                 135                 140

Ala Ala Asn Leu His Ala Gln Ile Lys Thr Ser Leu His Arg Leu Arg
145                 150                 155                 160

Pro Asp Thr Val Pro Ala Pro Cys Cys Val Pro Ala Ser Tyr Asn Pro
                165                 170                 175

Met Val Leu Ile Gln Arg Thr Asp Thr Gly Val Ser Leu Gln Thr Tyr
            180                 185                 190

Asp Asp Leu Leu Ala Arg Asp Cys His Cys Ile
                195                 200
```

<210> SEQ ID NO 340
<211> LENGTH: 203
<212> TYPE: PRT
<213> ORGANISM: Artificial Sequence
<220> FEATURE:
<223> OTHER INFORMATION: Synthetic

<400> SEQUENCE: 340

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Lys Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Ala Arg Gln Gly Asp
                85                  90                  95

His Cys Pro Leu Gly Pro Gly Arg Cys Cys Arg Leu His Thr Val Arg
            100                 105                 110

Ala Ser Leu Glu Asp Leu Gly Trp Ala Asp Trp Val Leu Ser Pro Arg
        115                 120                 125

Glu Val Gln Val Thr Met Cys Ile Gly Ala Cys Pro Ser Gln Phe Arg
    130                 135                 140

Ala Ala Asn Leu His Ala Gln Ile Lys Thr Ser Leu His Arg Leu Arg
145                 150                 155                 160

Pro Asp Thr Val Pro Ala Pro Cys Cys Val Pro Ala Ser Tyr Asn Pro
                165                 170                 175

Met Val Leu Ile Gln Arg Thr Asp Thr Gly Val Ser Leu Gln Thr Tyr
            180                 185                 190

Asp Asp Leu Leu Ala Arg Asp Cys His Cys Ile
                195                 200
```

<210> SEQ ID NO 341
<211> LENGTH: 203
<212> TYPE: PRT
<213> ORGANISM: Artificial Sequence
<220> FEATURE:
<223> OTHER INFORMATION: Synthetic

<400> SEQUENCE: 341

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Lys Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Ala Arg Gln Gly Asp
                85                  90                  95

His Cys Pro Leu Gly Pro Gly Arg Cys Cys Arg Leu His Thr Val Arg
            100                 105                 110

Ala Ser Leu Glu Asp Leu Gly Trp Ala Asp Trp Val Leu Ser Pro Arg
            115                 120                 125

Glu Val Gln Val Thr Met Cys Ile Gly Ala Cys Pro Ser Gln Phe Arg
            130                 135                 140

Ala Ala Asn Leu His Ala Gln Ile Lys Thr Ser Leu His Arg Leu Arg
145                 150                 155                 160

Pro Asp Thr Val Pro Ala Pro Cys Cys Val Pro Ala Ser Tyr Asn Pro
                165                 170                 175

Met Val Leu Ile Gln Arg Thr Asp Thr Gly Val Ser Leu Gln Thr Tyr
            180                 185                 190

Asp Asp Leu Leu Ala Arg Asp Cys His Cys Ile
            195                 200

<210> SEQ ID NO 342
<211> LENGTH: 60
<212> TYPE: PRT
<213> ORGANISM: Artificial Sequence
<220> FEATURE:
<223> OTHER INFORMATION: Synthetic

<400> SEQUENCE: 342

Lys Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
            35                  40                  45

Gly Ala Gln Pro Gly Ala Gln Pro Gly Ala Gln Pro
        50                  55                  60

<210> SEQ ID NO 343
<211> LENGTH: 60
<212> TYPE: PRT
<213> ORGANISM: Artificial Sequence
<220> FEATURE:
<223> OTHER INFORMATION: Synthetic

<400> SEQUENCE: 343

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Lys
            20                  25                  30

Gly Gln Glu Pro Gly Ala Gln Pro Gly Gln Glu Pro Gly Ala Gln Pro
            35                  40                  45

```
Gly Ala Gln Pro Gly Ala Gln Pro Gly Ala Gln Pro
        50                  55                  60

<210> SEQ ID NO 344
<211> LENGTH: 60
<212> TYPE: PRT
<213> ORGANISM: Artificial Sequence
<220> FEATURE:
<223> OTHER INFORMATION: Synthetic

<400> SEQUENCE: 344

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Lys Pro Gly Ala Gln Pro Gly Gln Lys Pro Gly Ala Gln Pro
        35                  40                  45

Gly Ala Gln Pro Gly Ala Gln Pro Gly Ala Gln Pro
    50                  55                  60

<210> SEQ ID NO 345

<400> SEQUENCE: 345

000

<210> SEQ ID NO 346
<211> LENGTH: 60
<212> TYPE: PRT
<213> ORGANISM: Artificial Sequence
<220> FEATURE:
<223> OTHER INFORMATION: Synthetic

<400> SEQUENCE: 346

Gly Gln Glu Pro Gly Ala Gln Pro Gly Gln Glu Pro Gly Ala Lys Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro
    50                  55                  60

<210> SEQ ID NO 347
<211> LENGTH: 203
<212> TYPE: PRT
<213> ORGANISM: Artificial Sequence
<220> FEATURE:
<223> OTHER INFORMATION: Synthetic

<400> SEQUENCE: 347

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80
```

```
Ala Gln Pro Gly Ala Gln Pro Gly Ala Gln Pro Ala Arg Gln Gly Asp
                85                  90                  95

His Cys Pro Leu Gly Pro Gly Arg Cys Cys Arg Leu His Thr Val Arg
            100                 105                 110

Ala Ser Leu Glu Asp Leu Gly Trp Ala Asp Trp Val Leu Ser Pro Arg
        115                 120                 125

Glu Val Gln Val Thr Met Cys Ile Gly Ala Cys Pro Ser Gln Phe Arg
130                 135                 140

Ala Ala Asn Leu His Ala Gln Ile Lys Thr Ser Leu His Arg Leu Lys
145                 150                 155                 160

Pro Asp Thr Val Pro Ala Pro Cys Cys Val Pro Ala Ser Tyr Asn Pro
                165                 170                 175

Met Val Leu Ile Gln Lys Thr Asp Thr Gly Val Ser Leu Gln Thr Tyr
            180                 185                 190

Asp Asp Leu Leu Ala Lys Asp Cys His Cys Ile
        195                 200

<210> SEQ ID NO 348

<400> SEQUENCE: 348

000

<210> SEQ ID NO 349
<211> LENGTH: 223
<212> TYPE: PRT
<213> ORGANISM: Artificial Sequence
<220> FEATURE:
<223> OTHER INFORMATION: Synthetic

<400> SEQUENCE: 349

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
```

195                 200                 205
Leu Gln Thr Tyr Asp Asp Leu Leu Ala Arg Asp Cys His Cys Ile
    210                 215                 220

<210> SEQ ID NO 350
<211> LENGTH: 223
<212> TYPE: PRT
<213> ORGANISM: Artificial Sequence
<220> FEATURE:
<223> OTHER INFORMATION: Synthetic

<400> SEQUENCE: 350

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 351

<400> SEQUENCE: 351

000

<210> SEQ ID NO 352
<211> LENGTH: 223
<212> TYPE: PRT
<213> ORGANISM: Artificial Sequence
<220> FEATURE:
<223> OTHER INFORMATION: Synthetic

<400> SEQUENCE: 352

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 353
<211> LENGTH: 223
<212> TYPE: PRT
<213> ORGANISM: Artificial Sequence
<220> FEATURE:
<223> OTHER INFORMATION: Synthetic

<400> SEQUENCE: 353

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

```
His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Lys Asp Cys His Cys Ile
    210                 215                 220
```

<210> SEQ ID NO 354
<211> LENGTH: 223
<212> TYPE: PRT
<213> ORGANISM: Artificial Sequence
<220> FEATURE:
<223> OTHER INFORMATION: Synthetic

<400> SEQUENCE: 354

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220
```

<210> SEQ ID NO 355
<211> LENGTH: 223
<212> TYPE: PRT
<213> ORGANISM: Artificial Sequence
<220> FEATURE:
<223> OTHER INFORMATION: Synthetic

<400> SEQUENCE: 355

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
```

```
                    35                  40                  45
Gln Glu Pro Gly Ala Gln Pro Gly Gln Glu Pro Gly Ala Gln Pro Gly
         50                  55                  60
Gln Glu Pro Gly Ala Gln Pro Gly Gln Glu Pro Gly Ala Gln Pro Gly
 65                  70                  75                  80
Ala Gln Pro Gly Ala Gln Pro Gly Ala Gln Pro Gly Ala Gln Pro Gly
                 85                  90                  95
Ala Gln Pro Gly Ala Gln Pro Gly Ala Gln Pro Gly Ala Gln Pro Ala
            100                 105                 110
Arg Gln Gly Asp His Cys Pro Leu Gly Pro Gly Arg Cys Cys Arg Leu
            115                 120                 125
His Thr Val Arg Ala Ser Leu Glu Asp Leu Gly Trp Ala Asp Trp Val
            130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Lys Pro Asp Thr Val Pro Ala Pro Cys Cys Val Pro Ala
            180                 185                 190
Ser Tyr Asn Pro Met Val Leu Ile Gln Arg Thr Asp Thr Gly Val Ser
                195                 200                 205
Leu Gln Thr Tyr Asp Asp Leu Leu Ala Arg Asp Cys His Cys Ile
            210                 215                 220

<210> SEQ ID NO 356
<211> LENGTH: 223
<212> TYPE: PRT
<213> ORGANISM: Artificial Sequence
<220> FEATURE:
<223> OTHER INFORMATION: Synthetic

<400> SEQUENCE: 356

His Gly Glu Gly Thr Phe Thr Ser Asp Val Ser Ser Tyr Leu Glu Glu
  1               5                  10                  15
Gln Ala Ala Arg Glu Phe Ile Ala Trp Leu Val Arg Gly Gly Gly Gly
             20                  25                  30
Gln Glu Pro Gly Ala Gln Pro Gly Gln Glu Pro Gly Ala Gln Pro Gly
             35                  40                  45
Gln Glu Pro Gly Ala Gln Pro Gly Gln Glu Pro Gly Ala Gln Pro Gly
         50                  55                  60
Gln Glu Pro Gly Ala Gln Pro Gly Gln Glu Pro Gly Ala Gln Pro Gly
 65                  70                  75                  80
Ala Gln Pro Gly Ala Lys Pro Gly Ala Gln Pro Gly Ala Gln Pro Gly
                 85                  90                  95
Ala Gln Pro Gly Ala Gln Pro Gly Ala Gln Pro Gly Ala Gln Pro Ala
            100                 105                 110
Arg Gln Gly Asp His Cys Pro Leu Gly Pro Gly Arg Cys Cys Arg Leu
            115                 120                 125
His Thr Val Arg Ala Ser Leu Glu Asp Leu Gly Trp Ala Asp Trp Val
            130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Lys Pro Asp Thr Val Pro Ala Pro Cys Cys Val Pro Ala
```

```
            180                 185                 190
Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 357
<211> LENGTH: 223
<212> TYPE: PRT
<213> ORGANISM: Artificial Sequence
<220> FEATURE:
<223> OTHER INFORMATION: Synthetic

<400> SEQUENCE: 357

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Lys Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 358
<211> LENGTH: 112
<212> TYPE: PRT
<213> ORGANISM: Artificial Sequence
<220> FEATURE:
<223> OTHER INFORMATION: Synthetic

<400> SEQUENCE: 358

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45
```

Pro Ser Gln Phe Arg Ala Ala Asn Leu His Ala Gln Ile Lys Thr Ser
    50                  55                  60

Leu His Arg Leu Arg Pro Asp Thr Val Pro Ala Pro Cys Cys Val Pro
65                  70                  75                  80

Ala Ser Tyr Asn Pro Met Val Leu Ile Gln Lys Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 359
<211> LENGTH: 223
<212> TYPE: PRT
<213> ORGANISM: Artificial Sequence
<220> FEATURE:
<223> OTHER INFORMATION: Synthetic

<400> SEQUENCE: 359

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Lys Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 360
<211> LENGTH: 223
<212> TYPE: PRT
<213> ORGANISM: Artificial Sequence
<220> FEATURE:
<223> OTHER INFORMATION: Synthetic

<400> SEQUENCE: 360

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

```
Ala Gln Pro Gly Ala Gln Pro Gly Ala Gln Pro Gly
        35                  40                  45

Ala Gln Pro Gly Ala Gln Pro Gly Ala Gln Pro Gly
    50                  55                  60

Ala Gln Pro Gly Ala Gln Pro Gly Gln Glu Pro Gly Gln Glu Pro Gly
65                  70                  75                  80

Gln Lys Pro Gly Gln Glu Pro Gly Gln Glu Pro Gly Gln Glu Pro Gly
                85                  90                  95

Gln Glu Pro Gly Gln Glu Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
                210                 215                 220
```

<210> SEQ ID NO 361
<211> LENGTH: 223
<212> TYPE: PRT
<213> ORGANISM: Artificial Sequence
<220> FEATURE:
<223> OTHER INFORMATION: Synthetic

<400> SEQUENCE: 361

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Lys
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175
```

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
            210                 215                 220

<210> SEQ ID NO 362
<211> LENGTH: 223
<212> TYPE: PRT
<213> ORGANISM: Artificial Sequence
<220> FEATURE:
<223> OTHER INFORMATION: Synthetic

<400> SEQUENCE: 362

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Leu Val Leu Ile Gln Arg Thr Asp Thr Gly Val Ser
            195                 200                 205

Leu Gln Thr Tyr Asp Asp Leu Leu Ala Arg Asp Cys His Cys Ile
            210                 215                 220

<210> SEQ ID NO 363
<211> LENGTH: 223
<212> TYPE: PRT
<213> ORGANISM: Artificial Sequence
<220> FEATURE:
<223> OTHER INFORMATION: Synthetic

<400> SEQUENCE: 363

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Lys
            20                  25                  30

Gln Glu Pro Gly Ala Gln Pro Gly Gln Glu Pro Gly Ala Gln Pro Gly

```
            35                  40                  45
Gln Glu Pro Gly Ala Gln Pro Gly Gln Glu Pro Gly Ala Gln Pro Gly
 50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Leu Val Leu Ile Gln Arg Thr Asp Thr Gly Val Ser
                195                 200                 205

Leu Gln Thr Tyr Asp Asp Leu Leu Ala Arg Asp Cys His Cys Ile
                210                 215                 220

<210> SEQ ID NO 364
<211> LENGTH: 223
<212> TYPE: PRT
<213> ORGANISM: Artificial Sequence
<220> FEATURE:
<223> OTHER INFORMATION: Synthetic

<400> SEQUENCE: 364

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
 50                  55                  60

Gln Glu Pro Gly Ala Gln Pro Gly Gln Glu Pro Gly Ala Gln Pro Gly
65                  70                  75                  80

Ala Gln Pro Gly Ala Lys Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
```

```
                180             185             190
Ser Tyr Asn Pro Leu Val Leu Ile Gln Arg Thr Asp Thr Gly Val Ser
            195                 200                 205
Leu Gln Thr Tyr Asp Asp Leu Leu Ala Arg Asp Cys His Cys Ile
    210                 215                 220

<210> SEQ ID NO 365
<211> LENGTH: 223
<212> TYPE: PRT
<213> ORGANISM: Artificial Sequence
<220> FEATURE:
<223> OTHER INFORMATION: Synthetic

<400> SEQUENCE: 365

His Gly Glu Gly Thr Phe Thr Ser Asp Val Ser Ser Tyr Leu Glu Glu
1               5                   10                  15
Gln Ala Ala Arg Glu Phe Ile Ala Trp Leu Val Arg Gly Gly Gly Gly
            20                  25                  30
Gln Glu Pro Gly Ala Gln Pro Gly Gln Glu Pro Gly Ala Gln Pro Gly
        35                  40                  45
Gln Glu Pro Gly Ala Gln Pro Gly Gln Glu Pro Gly Ala Gln Pro Gly
    50                  55                  60
Gln Glu Pro Gly Ala Gln Pro Gly Gln Glu Pro Gly Ala Gln Pro Gly
65                  70                  75                  80
Ala Gln Lys Gly Ala Gln Pro Gly Ala Gln Pro Gly Ala Gln Pro Gly
                85                  90                  95
Ala Gln Pro Gly Ala Gln Pro Gly Ala Gln Pro Gly Ala Gln Pro Ala
            100                 105                 110
Arg Gln Gly Asp His Cys Pro Leu Gly Pro Gly Arg Cys Cys Arg Leu
        115                 120                 125
His Thr Val Arg Ala Ser Leu Glu Asp Leu Gly Trp Ala Asp Trp Val
    130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Arg Pro Asp Thr Val Pro Ala Pro Cys Cys Val Pro Ala
            180                 185                 190
Ser Tyr Asn Pro Leu Val Leu Ile Gln Arg Thr Asp Thr Gly Val Ser
        195                 200                 205
Leu Gln Thr Tyr Asp Asp Leu Leu Ala Arg Asp Cys His Cys Ile
    210                 215                 220

<210> SEQ ID NO 366
<211> LENGTH: 223
<212> TYPE: PRT
<213> ORGANISM: Artificial Sequence
<220> FEATURE:
<223> OTHER INFORMATION: Synthetic

<400> SEQUENCE: 366

His Gly Glu Gly Thr Phe Thr Ser Asp Val Ser Ser Tyr Leu Glu Glu
1               5                   10                  15
Gln Ala Ala Cys Glu Phe Ile Ala Trp Leu Val Arg Gly Gly Gly Gly
            20                  25                  30
Gln Glu Pro Gly Ala Gln Pro Gly Gln Glu Pro Gly Ala Gln Pro Gly
        35                  40                  45
```

```
Gln Glu Pro Gly Ala Gln Pro Gly Gln Glu Pro Gly Ala Gln Pro Gly
 50                  55                  60

Gln Glu Pro Gly Ala Gln Pro Gly Gln Glu Pro Gly Ala Gln Pro Gly
 65                  70                  75                  80

Ala Gln Pro Gly Ala Gln Pro Gly Ala Gln Pro Gly Ala Gln Pro Gly
                 85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
                180                 185                 190

Ser Tyr Asn Pro Met Val Leu Ile Gln Lys Thr Asp Thr Gly Val Ser
                195                 200                 205

Leu Gln Thr Tyr Asp Asp Leu Leu Ala Lys Asp Cys His Cys Ile
                210                 215                 220

<210> SEQ ID NO 367
<211> LENGTH: 223
<212> TYPE: PRT
<213> ORGANISM: Artificial Sequence
<220> FEATURE:
<223> OTHER INFORMATION: Synthetic

<400> SEQUENCE: 367

His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Arg Gly Gly Gly Cys
                 20                  25                  30

Gln Glu Pro Gly Ala Gln Pro Gly Gln Glu Pro Gly Ala Gln Pro Gly
                 35                  40                  45

Gln Glu Pro Gly Ala Gln Pro Gly Gln Glu Pro Gly Ala Gln Pro Gly
 50                  55                  60

Gln Glu Pro Gly Ala Gln Pro Gly Gln Glu Pro Gly Ala Gln Pro Gly
 65                  70                  75                  80

Ala Gln Pro Gly Ala Gln Pro Gly Ala Gln Pro Gly Ala Gln Pro Gly
                 85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
                180                 185                 190
```

Ser Tyr Asn Pro Met Val Leu Ile Gln Lys Thr Asp Thr Gly Val Ser
    195                 200                 205

Leu Gln Thr Tyr Asp Asp Leu Leu Ala Lys Asp Cys His Cys Ile
    210                 215                 220

<210> SEQ ID NO 368
<211> LENGTH: 223
<212> TYPE: PRT
<213> ORGANISM: Artificial Sequence
<220> FEATURE:
<223> OTHER INFORMATION: Synthetic

<400> SEQUENCE: 368

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Cys Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 369
<211> LENGTH: 223
<212> TYPE: PRT
<213> ORGANISM: Artificial Sequence
<220> FEATURE:
<223> OTHER INFORMATION: Synthetic

<400> SEQUENCE: 369

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Cys Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
                180                 185                 190

Ser Tyr Asn Pro Met Val Leu Ile Gln Lys Thr Asp Thr Gly Val Ser
                195                 200                 205

Leu Gln Thr Tyr Asp Asp Leu Leu Ala Lys Asp Cys His Cys Ile
                210                 215                 220

<210> SEQ ID NO 370
<211> LENGTH: 223
<212> TYPE: PRT
<213> ORGANISM: Artificial Sequence
<220> FEATURE:
<223> OTHER INFORMATION: Synthetic

<400> SEQUENCE: 370

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
                35                  40                  45

Gln Glu Pro Gly Ala Gln Pro Gly Gln Glu Pro Gly Ala Gln Pro Gly
                50                  55                  60

Gln Lys Pro Gly Ala Gln Pro Gly Gln Glu Pro Gly Ala Gln Pro Gly
65                  70                  75                  80

Gln Glu Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
                130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

```
Leu Gln Thr Tyr Asp Asp Leu Leu Ala Arg Asp Cys His Cys Ile
    210                 215                 220

<210> SEQ ID NO 371
<211> LENGTH: 223
<212> TYPE: PRT
<213> ORGANISM: Artificial Sequence
<220> FEATURE:
<223> OTHER INFORMATION: Synthetic

<400> SEQUENCE: 371

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Lys Gln Ala Pro Gly
        50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
        195                 200                 205

Leu Gln Thr Tyr Asp Asp Leu Leu Ala Arg Asp Cys His Cys Ile
    210                 215                 220

<210> SEQ ID NO 372
<211> LENGTH: 223
<212> TYPE: PRT
<213> ORGANISM: Artificial Sequence
<220> FEATURE:
<223> OTHER INFORMATION: Synthetic

<400> SEQUENCE: 372

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Lys Gln Glu Pro Gly Ala Gln Pro Gly
        50                  55                  60

Gln Glu Pro Gly Ala Gln Pro Gly Gln Glu Pro Gly Ala Gln Pro Gly
```

```
                65                  70                  75                  80
Ala Gln Pro Gly Ala Gln Pro Gly Ala Gln Pro Gly Ala Gln Pro Gly
                    85                  90                  95

Ala Gln Pro Gly Ala Gln Pro Gly Ala Gln Pro Gly Ala Gln Pro Ala
                    100                 105                 110

Arg Gln Gly Asp His Cys Pro Leu Gly Pro Gly Arg Cys Cys Arg Leu
                    115                 120                 125

His Thr Val Arg Ala Ser Leu Glu Asp Leu Gly Trp Ala Asp Trp Val
                    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                    165                 170                 175

His Arg Leu Arg Pro Asp Thr Val Pro Ala Pro Cys Cys Val Pro Ala
                    180                 185                 190

Ser Tyr Asn Pro Met Val Leu Ile Gln Arg Thr Asp Thr Gly Val Ser
                    195                 200                 205

Leu Gln Thr Tyr Asp Asp Leu Leu Ala Arg Asp Cys His Cys Ile
                    210                 215                 220

<210> SEQ ID NO 373
<211> LENGTH: 223
<212> TYPE: PRT
<213> ORGANISM: Artificial Sequence
<220> FEATURE:
<223> OTHER INFORMATION: Synthetic

<400> SEQUENCE: 373

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                    20                  25                  30

Gln Glu Pro Gly Ala Gln Pro Gly Gln Glu Pro Gly Ala Gln Pro Gly
                    35                  40                  45

Gln Glu Pro Lys Gln Ala Pro Gly Gln Glu Pro Gly Ala Gln Pro Gly
50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                    85                  90                  95

Ala Gln Pro Gly Ala Gln Pro Gly Ala Gln Pro Gly Ala Gln Pro Ala
                    100                 105                 110

Arg Gln Gly Asp His Cys Pro Leu Gly Pro Gly Arg Cys Cys Arg Leu
                    115                 120                 125

His Thr Val Arg Ala Ser Leu Glu Asp Leu Gly Trp Ala Asp Trp Val
                    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                    165                 170                 175

His Arg Leu Arg Pro Asp Thr Val Pro Ala Pro Cys Cys Val Pro Ala
                    180                 185                 190

Ser Tyr Asn Pro Met Val Leu Ile Gln Arg Thr Asp Thr Gly Val Ser
                    195                 200                 205

Leu Gln Thr Tyr Asp Asp Leu Leu Ala Arg Asp Cys His Cys Ile
```

-continued

```
                210                 215                 220

<210> SEQ ID NO 374
<211> LENGTH: 223
<212> TYPE: PRT
<213> ORGANISM: Artificial Sequence
<220> FEATURE:
<223> OTHER INFORMATION: Synthetic

<400> SEQUENCE: 374

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Cys Pro Gly Ala Gln Pro Gly Gln Glu Pro Gly Ala Gln Pro Gly
65                  70                  75                  80

Gln Glu Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 375
<211> LENGTH: 223
<212> TYPE: PRT
<213> ORGANISM: Artificial Sequence
<220> FEATURE:
<223> OTHER INFORMATION: Synthetic

<400> SEQUENCE: 375

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
        50                  55                  60

Gln Glu Pro Gly Ala Gln Pro Gly Gln Glu Pro Gly Ala Gln Pro Gly
65                  70                  75                  80
```

```
Gln Cys Pro Gly Ala Gln Pro Gly Ala Gln Pro Gly
            85                  90                  95

Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
            165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
            195                 200                 205

Leu Gln Thr Tyr Asp Asp Leu Leu Ala Lys Asp Cys His Cys Ile
            210                 215                 220
```

<210> SEQ ID NO 376
<211> LENGTH: 223
<212> TYPE: PRT
<213> ORGANISM: Artificial Sequence
<220> FEATURE:
<223> OTHER INFORMATION: Synthetic

<400> SEQUENCE: 376

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
50                  55                  60

Gln Glu Pro Gly Gln Cys Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
            85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
            165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
            195                 200                 205

Leu Gln Thr Tyr Asp Asp Leu Leu Ala Lys Asp Cys His Cys Ile
            210                 215                 220
```

<210> SEQ ID NO 377
<211> LENGTH: 223
<212> TYPE: PRT
<213> ORGANISM: Artificial Sequence
<220> FEATURE:
<223> OTHER INFORMATION: Synthetic

<400> SEQUENCE: 377

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Cys Gln Ala Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220
```

<210> SEQ ID NO 378
<211> LENGTH: 223
<212> TYPE: PRT
<213> ORGANISM: Artificial Sequence
<220> FEATURE:
<223> OTHER INFORMATION: Synthetic

<400> SEQUENCE: 378

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Gln Glu Pro Gly Ala Gln Pro Cys Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95
```

```
Gln Glu Pro Gly Ala Gln Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 379
<211> LENGTH: 223
<212> TYPE: PRT
<213> ORGANISM: Artificial Sequence
<220> FEATURE:
<223> OTHER INFORMATION: Synthetic

<400> SEQUENCE: 379

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
50                  55                  60

Gln Glu Pro Gly Gln Cys Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
            85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 380
```

<211> LENGTH: 223
<212> TYPE: PRT
<213> ORGANISM: Artificial Sequence
<220> FEATURE:
<223> OTHER INFORMATION: Synthetic

<400> SEQUENCE: 380

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Gln Cys Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220
```

<210> SEQ ID NO 381
<211> LENGTH: 223
<212> TYPE: PRT
<213> ORGANISM: Artificial Sequence
<220> FEATURE:
<223> OTHER INFORMATION: Synthetic

<400> SEQUENCE: 381

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Cys
    50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
```

```
                100                 105                 110
Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
                195                 200                 205

Leu Gln Thr Tyr Asp Asp Leu Leu Ala Lys Asp Cys His Cys Ile
            210                 215                 220

<210> SEQ ID NO 382

<400> SEQUENCE: 382

000

<210> SEQ ID NO 383
<211> LENGTH: 223
<212> TYPE: PRT
<213> ORGANISM: Artificial Sequence
<220> FEATURE:
<223> OTHER INFORMATION: Synthetic

<400> SEQUENCE: 383

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Arg Leu Ile Gln Lys Thr Asp Thr Gly Val Ser
                195                 200                 205
```

```
Leu Gln Thr Tyr Asp Asp Leu Leu Ala Lys Asp Cys His Cys Ile
    210                 215                 220
```

<210> SEQ ID NO 384
<211> LENGTH: 221
<212> TYPE: PRT
<213> ORGANISM: Artificial Sequence
<220> FEATURE:
<223> OTHER INFORMATION: Synthetic

<400> SEQUENCE: 384

```
Glu Gly Thr Phe Thr Ser Asp Val Ser Ser Tyr Leu Glu Glu Gln Ala
1               5                   10                  15

Ala Lys Glu Phe Ile Ala Trp Leu Val Arg Gly Gly Gly Gly Gln Glu
            20                  25                  30

Pro Gly Ala Gln Pro Gly Gln Glu Pro Gly Ala Gln Pro Gly Gln Glu
        35                  40                  45

Pro Gly Ala Gln Pro Gly Gln Glu Pro Gly Ala Gln Pro Gly Gln Glu
    50                  55                  60

Pro Gly Ala Gln Pro Gly Gln Glu Pro Gly Ala Gln Pro Gly Ala Gln
65                  70                  75                  80

Pro Gly Ala Gln Pro Gly Ala Gln Pro Gly Ala Gln Pro Gly Ala Gln
                85                  90                  95

Pro Gly Ala Gln Pro Gly Ala Gln Pro Gly Ala Gln Pro Ala Arg Gln
            100                 105                 110

Gly Asp His Cys Pro Leu Gly Pro Gly Arg Cys Cys Arg Leu His Thr
        115                 120                 125

Val Arg Ala Ser Leu Glu Asp Leu Gly Trp Ala Asp Trp Val Leu Ser
    130                 135                 140

Pro Arg Glu Val Gln Val Thr Met Cys Ile Gly Ala Cys Pro Ser Gln
145                 150                 155                 160

Phe Arg Ala Ala Asn Leu His Ala Gln Ile Lys Thr Ser Leu His Arg
                165                 170                 175

Leu Lys Pro Asp Thr Val Pro Ala Pro Cys Cys Val Pro Ala Ser Tyr
            180                 185                 190

Asn Pro Met Val Leu Ile Gln Lys Thr Asp Thr Gly Val Ser Leu Gln
        195                 200                 205

Thr Tyr Asp Asp Leu Leu Ala Lys Asp Cys His Cys Ile
    210                 215                 220
```

<210> SEQ ID NO 385
<211> LENGTH: 223
<212> TYPE: PRT
<213> ORGANISM: Artificial Sequence
<220> FEATURE:
<223> OTHER INFORMATION: Synthetic

<400> SEQUENCE: 385

```
His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Gln Glu Pro Gly Gln Lys Pro Gly Gln Glu Pro Gly Ala Gln Pro Gly
65                  70                  75                  80
```

```
Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
            210                 215                 220

<210> SEQ ID NO 386
<211> LENGTH: 223
<212> TYPE: PRT
<213> ORGANISM: Artificial Sequence
<220> FEATURE:
<223> OTHER INFORMATION: Synthetic

<400> SEQUENCE: 386

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Gln Glu Pro Gly Ala Gln Pro Gly
        50                  55                  60

Gln Lys Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
            210                 215                 220
```

```
<210> SEQ ID NO 387
<211> LENGTH: 147
<212> TYPE: PRT
<213> ORGANISM: Artificial Sequence
<220> FEATURE:
<223> OTHER INFORMATION: Synthetic

<400> SEQUENCE: 387

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Ala Arg Gln Gly Asp His Cys Pro Leu Gly Pro Gly Arg
        35                  40                  45

Cys Cys Arg Leu His Thr Val Arg Ala Ser Leu Glu Asp Leu Gly Trp
    50                  55                  60

Ala Asp Trp Val Leu Ser Pro Arg Glu Val Gln Val Thr Met Cys Ile
65                  70                  75                  80

Gly Ala Cys Pro Ser Gln Phe Arg Ala Ala Asn Leu His Ala Gln Ile
                85                  90                  95

Lys Thr Ser Leu His Arg Leu Lys Pro Asp Thr Val Pro Ala Pro Cys
            100                 105                 110

Cys Val Pro Ala Ser Tyr Asn Pro Met Val Leu Ile Gln Lys Thr Asp
        115                 120                 125

Thr Gly Val Ser Leu Gln Thr Tyr Asp Asp Leu Leu Ala Lys Asp Cys
    130                 135                 140

His Cys Ile
145

<210> SEQ ID NO 388
<211> LENGTH: 143
<212> TYPE: PRT
<213> ORGANISM: Artificial Sequence
<220> FEATURE:
<223> OTHER INFORMATION: Synthetic

<400> SEQUENCE: 388

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Ala
            20                  25                  30

Arg Gln Gly Asp His Cys Pro Leu Gly Pro Gly Arg Cys Cys Arg Leu
        35                  40                  45

His Thr Val Arg Ala Ser Leu Glu Asp Leu Gly Trp Ala Asp Trp Val
    50                  55                  60

Leu Ser Pro Arg Glu Val Gln Val Thr Met Cys Ile Gly Ala Cys Pro
65                  70                  75                  80

Ser Gln Phe Arg Ala Ala Asn Leu His Ala Gln Ile Lys Thr Ser Leu
                85                  90                  95

His Arg Leu Lys Pro Asp Thr Val Pro Ala Pro Cys Cys Val Pro Ala
            100                 105                 110

Ser Tyr Asn Pro Met Val Leu Ile Gln Lys Thr Asp Thr Gly Val Ser
        115                 120                 125

Leu Gln Thr Tyr Asp Asp Leu Leu Ala Lys Asp Cys His Cys Ile
    130                 135                 140
```

-continued

```
<210> SEQ ID NO 389
<211> LENGTH: 263
<212> TYPE: PRT
<213> ORGANISM: Artificial Sequence
<220> FEATURE:
<223> OTHER INFORMATION: Synthetic

<400> SEQUENCE: 389

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Gly
            100                 105                 110

Ala Gln Pro Gly Ala Gln Pro Gly Ala Gln Pro Gly Ala Gln Pro Gly
        115                 120                 125

Ala Gln Pro Gly Ala Gln Pro Gly Ala Gln Pro Gly Ala Gln Pro Gly
    130                 135                 140

Ala Gln Pro Gly Ala Gln Pro Ala Arg Gln Gly Asp His Cys Pro Leu
145                 150                 155                 160

Gly Pro Gly Arg Cys Cys Arg Leu His Thr Val Arg Ala Ser Leu Glu
                165                 170                 175

Asp Leu Gly Trp Ala Asp Trp Val Leu Ser Pro Arg Glu Val Gln Val
            180                 185                 190

Thr Met Cys Ile Gly Ala Cys Pro Ser Gln Phe Arg Ala Ala Asn Leu
        195                 200                 205

His Ala Gln Ile Lys Thr Ser Leu His Arg Leu Lys Pro Asp Thr Val
    210                 215                 220

Pro Ala Pro Cys Cys Val Pro Ala Ser Tyr Asn Pro Met Val Leu Ile
225                 230                 235                 240

Gln Lys Thr Asp Thr Gly Val Ser Leu Gln Thr Tyr Asp Asp Leu Leu
                245                 250                 255

Ala Lys Asp Cys His Cys Ile
            260

<210> SEQ ID NO 390
<211> LENGTH: 223
<212> TYPE: PRT
<213> ORGANISM: Artificial Sequence
<220> FEATURE:
<223> OTHER INFORMATION: Synthetic

<400> SEQUENCE: 390

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45
```

```
Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Lys Pro Gly Ala Gln Pro Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190

Ser Tyr Asn Pro Met Val Leu Ile Gln Arg Thr Asp Thr Gly Val Ser
                195                 200                 205

Leu Gln Thr Tyr Asp Asp Leu Leu Ala Arg Asp Cys His Cys Ile
    210                 215                 220

<210> SEQ ID NO 391
<211> LENGTH: 223
<212> TYPE: PRT
<213> ORGANISM: Artificial Sequence
<220> FEATURE:
<223> OTHER INFORMATION: Synthetic

<400> SEQUENCE: 391

His Gly Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Gly Gly Gly
                20                  25                  30

Gln Glu Pro Gly Ala Gln Pro Gly Gln Glu Pro Gly Ala Gln Pro Gly
            35                  40                  45

Gln Glu Pro Gly Ala Gln Pro Gly Gln Glu Pro Gly Ala Gln Pro Gly
    50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Lys Gly Ala Gln Pro Ala
                100                 105                 110

Arg Gln Gly Asp His Cys Pro Leu Gly Pro Gly Arg Cys Cys Arg Leu
                115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
                180                 185                 190
```

Ser Tyr Asn Pro Met Val Leu Ile Gln Arg Thr Asp Thr Gly Val Ser
            195                 200                 205

Leu Gln Thr Tyr Asp Asp Leu Leu Ala Arg Asp Cys His Cys Ile
    210                 215                 220

<210> SEQ ID NO 392
<211> LENGTH: 223
<212> TYPE: PRT
<213> ORGANISM: Artificial Sequence
<220> FEATURE:
<223> OTHER INFORMATION: Synthetic

<400> SEQUENCE: 392

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Cys
        35                  40                  45

Gln Ala Pro Gly Ala Gln Pro Gly Ala Gln Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 393
<211> LENGTH: 223
<212> TYPE: PRT
<213> ORGANISM: Artificial Sequence
<220> FEATURE:
<223> OTHER INFORMATION: Synthetic

<400> SEQUENCE: 393

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Cys Gln Ala Pro Gly Ala Gln Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 394
<211> LENGTH: 223
<212> TYPE: PRT
<213> ORGANISM: Artificial Sequence
<220> FEATURE:
<223> OTHER INFORMATION: Synthetic

<400> SEQUENCE: 394

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Cys Gln Ala Pro Gly Ala Gln Pro Gly
        50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

```
Leu Gln Thr Tyr Asp Asp Leu Leu Ala Lys Asp Cys His Cys Ile
    210                 215                 220

<210> SEQ ID NO 395
<211> LENGTH: 223
<212> TYPE: PRT
<213> ORGANISM: Artificial Sequence
<220> FEATURE:
<223> OTHER INFORMATION: Synthetic

<400> SEQUENCE: 395

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Gly Gln Glu Pro Gly Gln Cys Pro Gly
50                  55                  60

Gln Glu Pro Gly Ala Gln Pro Gly Gln Glu Pro Gly Ala Gln Pro Gly
65                  70                  75                  80

Ala Gln Pro Gly Ala Gln Pro Gly Ala Gln Pro Gly Ala Gln Pro Gly
                85                  90                  95

Ala Gln Pro Gly Ala Gln Pro Gly Ala Gln Pro Gly Ala Gln Pro Ala
                100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 396
<211> LENGTH: 223
<212> TYPE: PRT
<213> ORGANISM: Artificial Sequence
<220> FEATURE:
<223> OTHER INFORMATION: Synthetic

<400> SEQUENCE: 396

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Gln Glu Pro Gly Ala Gln Pro Gly Gln Glu Pro Gly Ala Gln Pro Gly
        35                  40                  45

Gln Glu Pro Gly Ala Gln Pro Cys Gln Glu Pro Gly Ala Gln Pro Gly
50                  55                  60

Gln Glu Pro Gly Ala Gln Pro Gly Gln Glu Pro Gly Ala Gln Pro Gly
```

```
                65                  70                  75                  80
Ala Gln Pro Gly Ala Gln Pro Gly Ala Gln Pro Gly Ala Gln Pro Gly
                    85                  90                  95

Ala Gln Pro Gly Ala Gln Pro Gly Ala Gln Pro Gly Ala Gln Pro Ala
                    100                 105                 110

Arg Gln Gly Asp His Cys Pro Leu Gly Pro Gly Arg Cys Cys Arg Leu
                    115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                    165                 170                 175

His Arg Leu Lys Pro Asp Thr Val Pro Ala Pro Cys Cys Val Pro Ala
                    180                 185                 190

Ser Tyr Asn Pro Met Val Leu Ile Gln Lys Thr Asp Thr Gly Val Ser
                    195                 200                 205

Leu Gln Thr Tyr Asp Asp Leu Leu Ala Lys Asp Cys His Cys Ile
                    210                 215                 220

<210> SEQ ID NO 397
<211> LENGTH: 223
<212> TYPE: PRT
<213> ORGANISM: Artificial Sequence
<220> FEATURE:
<223> OTHER INFORMATION: Synthetic

<400> SEQUENCE: 397

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
                    35                  40                  45

Ala Gln Pro Gly Ala Gln Pro Gly Ala Gln Pro Gly Ala Gln Pro Gly
                    50                  55                  60

Gln Glu Pro Gly Ala Gln Pro Gly Gln Glu Pro Cys Gln Ala Pro Gly
65                  70                  75                  80

Gln Glu Pro Gly Ala Gln Pro Gly Gln Glu Pro Gly Ala Gln Pro Gly
                    85                  90                  95

Gln Glu Pro Gly Ala Gln Pro Gly Gln Glu Pro Gly Ala Gln Pro Ala
                    100                 105                 110

Arg Gln Gly Asp His Cys Pro Leu Gly Pro Gly Arg Cys Cys Arg Leu
                    115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                    165                 170                 175

His Arg Leu Lys Pro Asp Thr Val Pro Ala Pro Cys Cys Val Pro Ala
                    180                 185                 190

Ser Tyr Asn Pro Met Val Leu Ile Gln Lys Thr Asp Thr Gly Val Ser
                    195                 200                 205

Leu Gln Thr Tyr Asp Asp Leu Leu Ala Lys Asp Cys His Cys Ile
```

-continued

```
              210                 215                 220
```

<210> SEQ ID NO 398
<211> LENGTH: 223
<212> TYPE: PRT
<213> ORGANISM: Artificial Sequence
<220> FEATURE:
<223> OTHER INFORMATION: Synthetic

<400> SEQUENCE: 398

```
His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Gly
    50                  55                  60

Gln Glu Pro Gly Ala Gln Pro Gly Gln Glu Pro Gly Ala Gln Pro Gly
65                  70                  75                  80

Gln Cys Pro Gly Gln Glu Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220
```

<210> SEQ ID NO 399
<211> LENGTH: 223
<212> TYPE: PRT
<213> ORGANISM: Artificial Sequence
<220> FEATURE:
<223> OTHER INFORMATION: Synthetic

<400> SEQUENCE: 399

```
His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Cys Ala Gln Pro Gly
    50                  55                  60

Gln Glu Pro Gly Ala Gln Pro Gly Gln Glu Pro Gly Gln Ala Pro Gly
65                  70                  75                  80
```

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 400
<211> LENGTH: 223
<212> TYPE: PRT
<213> ORGANISM: Artificial Sequence
<220> FEATURE:
<223> OTHER INFORMATION: Synthetic

<400> SEQUENCE: 400

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Cys
    50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
        130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Arg Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 401
<211> LENGTH: 221
<212> TYPE: PRT
<213> ORGANISM: Artificial Sequence
<220> FEATURE:
<223> OTHER INFORMATION: Synthetic

<400> SEQUENCE: 401

```
Glu Gly Thr Phe Thr Ser Asp Val Ser Ser Tyr Leu Glu Glu Gln Ala
1               5                   10                  15

Ala Lys Glu Phe Ile Ala Trp Leu Val Arg Gly Gly Gly Gly Ala Gln
            20                  25                  30

Pro Gly Ala Gln Pro Gly Ala Gln Pro Gly Ala Gln Pro Gly Ala Gln
        35                  40                  45

Pro Gly Ala Gln Pro Gly Ala Gln Pro Gly Ala Gln Pro Cys Gln Glu
    50                  55                  60

Pro Gly Ala Gln Pro Gly Gln Glu Pro Gly Ala Gln Pro Gly Gln Glu
65                  70                  75                  80

Pro Gly Ala Gln Pro Gly Gln Glu Pro Gly Ala Gln Pro Gly Gln Glu
                85                  90                  95

Pro Gly Ala Gln Pro Gly Gln Glu Pro Gly Ala Gln Pro Ala Arg Gln
                100                 105                 110

Gly Asp His Cys Pro Leu Gly Pro Gly Arg Cys Cys Arg Leu His Thr
            115                 120                 125

Val Arg Ala Ser Leu Glu Asp Leu Gly Trp Ala Asp Trp Val Leu Ser
        130                 135                 140

Pro Arg Glu Val Gln Val Thr Met Cys Ile Gly Ala Cys Pro Ser Gln
145                 150                 155                 160

Phe Arg Ala Ala Asn Leu His Ala Gln Ile Lys Thr Ser Leu His Arg
                165                 170                 175

Leu Lys Pro Asp Thr Val Pro Ala Pro Cys Cys Val Pro Ala Ser Tyr
                180                 185                 190

Asn Pro Met Val Leu Ile Gln Lys Thr Asp Thr Gly Val Ser Leu Gln
            195                 200                 205

Thr Tyr Asp Asp Leu Leu Ala Lys Asp Cys His Cys Ile
        210                 215                 220
```

<210> SEQ ID NO 402
<211> LENGTH: 224
<212> TYPE: PRT
<213> ORGANISM: Artificial Sequence
<220> FEATURE:
<223> OTHER INFORMATION: Synthetic

<400> SEQUENCE: 402

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
            20                  25                  30

Ala Gln Pro Gly Ala Gln Pro Gly Ala Gln Pro Gly Ala Gln Pro Gly
        35                  40                  45

Ala Gln Pro Gly Ala Gln Pro Gly Ala Gln Pro Gly Ala Gln Pro Cys
    50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95
```

Gln Glu Pro Gly Ala Gln Pro Gly Gln Glu Pro Gly Ala Gln Pro Gly
                100                 105                 110

Ala Gln Pro Gly Asp His Cys Pro Leu Gly Pro Gly Arg Cys Cys Arg
                115                 120                 125

Leu His Thr Val Arg Ala Ser Leu Glu Asp Leu Gly Trp Ala Asp Trp
                130                 135                 140

Val Leu Ser Pro Arg Glu Val Gln Val Thr Met Cys Ile Gly Ala Cys
145                 150                 155                 160

Pro Ser Gln Phe Arg Ala Ala Asn Leu His Ala Gln Ile Lys Thr Ser
                165                 170                 175

Leu His Arg Leu Lys Pro Asp Thr Val Pro Ala Pro Cys Cys Val Pro
                180                 185                 190

Ala Ser Tyr Asn Pro Met Val Leu Ile Gln Lys Thr Asp Thr Gly Val
                195                 200                 205

Ser Leu Gln Thr Tyr Asp Asp Leu Leu Ala Lys Asp Cys His Cys Ile
                210                 215                 220

<210> SEQ ID NO 403
<211> LENGTH: 224
<212> TYPE: PRT
<213> ORGANISM: Artificial Sequence
<220> FEATURE:
<223> OTHER INFORMATION: Synthetic

<400> SEQUENCE: 403

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
                35                  40                  45

Ala Gln Pro Gly Ala Gln Pro Gly Ala Gln Pro Gly Ala Gln Pro Gly
            50                  55                  60

Gln Glu Pro Gly Gln Cys Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Gly
                100                 105                 110

Ala Gln Pro Gly Asp His Cys Pro Leu Gly Pro Gly Arg Cys Cys Arg
                115                 120                 125

Leu His Thr Val Arg Ala Ser Leu Glu Asp Leu Gly Trp Ala Asp Trp
                130                 135                 140

Val Leu Ser Pro Arg Glu Val Gln Val Thr Met Cys Ile Gly Ala Cys
145                 150                 155                 160

Pro Ser Gln Phe Arg Ala Ala Asn Leu His Ala Gln Ile Lys Thr Ser
                165                 170                 175

Leu His Arg Leu Lys Pro Asp Thr Val Pro Ala Pro Cys Cys Val Pro
                180                 185                 190

Ala Ser Tyr Asn Pro Met Val Leu Ile Gln Lys Thr Asp Thr Gly Val
                195                 200                 205

Ser Leu Gln Thr Tyr Asp Asp Leu Leu Ala Lys Asp Cys His Cys Ile
                210                 215                 220

<210> SEQ ID NO 404

```
<211> LENGTH: 223
<212> TYPE: PRT
<213> ORGANISM: Artificial Sequence
<220> FEATURE:
<223> OTHER INFORMATION: Synthetic

<400> SEQUENCE: 404

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Cys
        50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220

<210> SEQ ID NO 405
<211> LENGTH: 223
<212> TYPE: PRT
<213> ORGANISM: Artificial Sequence
<220> FEATURE:
<223> OTHER INFORMATION: Synthetic

<400> SEQUENCE: 405

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Gln Glu Pro Gly Gln Cys Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
```

```
              100                 105                 110
Arg Gln Gly Asp His Cys Pro Leu Gly Pro Gly Arg Cys Cys Arg Leu
            115                 120                 125
His Thr Val Arg Ala Ser Leu Glu Asp Leu Gly Trp Ala Asp Trp Val
            130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Lys Pro Asp Thr Val Pro Ala Pro Cys Cys Val Pro Ala
            180                 185                 190
Ser Tyr Asn Pro Met Val Leu Ile Gln Lys Thr Asp Thr Gly Val Ser
            195                 200                 205
Leu Gln Thr Tyr Asp Asp Leu Leu Ala Lys Asp Cys His Cys Ile
            210                 215                 220

<210> SEQ ID NO 406
<211> LENGTH: 223
<212> TYPE: PRT
<213> ORGANISM: Artificial Sequence
<220> FEATURE:
<223> OTHER INFORMATION: Synthetic

<400> SEQUENCE: 406

His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Arg Gly Gly Gly Gly
            20                  25                  30
Ala Gln Pro Gly Ala Gln Pro Gly Ala Gln Pro Gly Ala Gln Pro Gly
            35                  40                  45
Ala Gln Pro Gly Ala Gln Pro Gly Ala Gln Pro Gly Ala Gln Pro Gly
            50                  55                  60
Gln Glu Pro Gly Gln Cys Pro Gly Gln Glu Pro Gly Ala Gln Pro Gly
65                  70                  75                  80
Gln Glu Pro Gly Ala Gln Pro Gly Gln Glu Pro Gly Ala Gln Pro Gly
            85                  90                  95
Gln Glu Pro Gly Ala Gln Pro Gly Gln Glu Pro Gly Ala Gln Pro Ala
            100                 105                 110
Arg Gln Gly Asp His Cys Pro Leu Gly Pro Gly Arg Cys Cys Arg Leu
            115                 120                 125
His Thr Val Arg Ala Ser Leu Glu Asp Leu Gly Trp Ala Asp Trp Val
            130                 135                 140
Leu Ser Pro Arg Glu Val Gln Val Thr Met Cys Ile Gly Ala Cys Pro
145                 150                 155                 160
Ser Gln Phe Arg Ala Ala Asn Leu His Ala Gln Ile Lys Thr Ser Leu
                165                 170                 175
His Arg Leu Lys Pro Asp Thr Val Pro Ala Pro Cys Cys Val Pro Ala
            180                 185                 190
Ser Tyr Asn Pro Met Arg Leu Ile Gln Lys Thr Asp Thr Gly Val Ser
            195                 200                 205
Leu Gln Thr Tyr Asp Asp Leu Leu Ala Lys Asp Cys His Cys Ile
            210                 215                 220

<210> SEQ ID NO 407
<211> LENGTH: 221
<212> TYPE: PRT
```

<213> ORGANISM: Artificial Sequence
<220> FEATURE:
<223> OTHER INFORMATION: Synthetic

<400> SEQUENCE: 407

```
Glu Gly Thr Phe Thr Ser Asp Val Ser Ser Tyr Leu Glu Gln Ala
1               5                   10                  15
Ala Lys Glu Phe Ile Ala Trp Leu Val Arg Gly Gly Gly Gly Ala Gln
            20                  25                  30
Pro Gly Ala Gln Pro Gly Ala Gln Pro Gly Ala Gln Pro Gly Ala Gln
        35                  40                  45
Pro Gly Ala Gln Pro Gly Ala Gln Pro Gly Ala Gln Pro Gly Gln Glu
50                  55                  60
Pro Gly Gln Cys Pro Gly Gln Glu Pro Gly Ala Gln Pro Gly Gln Glu
65                  70                  75                  80
Pro Gly Ala Gln Pro Gly Gln Glu Pro Gly Ala Gln Pro Gly Gln Glu
                85                  90                  95
Pro Gly Ala Gln Pro Gly Gln Glu Pro Gly Ala Gln Pro Ala Arg Gln
                100                 105                 110
Gly Asp His Cys Pro Leu Gly Pro Gly Arg Cys Cys Arg Leu His Thr
            115                 120                 125
Val Arg Ala Ser Leu Glu Asp Leu Gly Trp Ala Asp Trp Val Leu Ser
    130                 135                 140
Pro Arg Glu Val Gln Val Thr Met Cys Ile Gly Ala Cys Pro Ser Gln
145                 150                 155                 160
Phe Arg Ala Ala Asn Leu His Ala Gln Ile Lys Thr Ser Leu His Arg
                165                 170                 175
Leu Lys Pro Asp Thr Val Pro Ala Pro Cys Cys Val Pro Ala Ser Tyr
            180                 185                 190
Asn Pro Met Val Leu Ile Gln Lys Thr Asp Thr Gly Val Ser Leu Gln
        195                 200                 205
Thr Tyr Asp Asp Leu Leu Ala Lys Asp Cys His Cys Ile
    210                 215                 220
```

<210> SEQ ID NO 408
<211> LENGTH: 315
<212> TYPE: PRT
<213> ORGANISM: Artificial Sequence
<220> FEATURE:
<223> OTHER INFORMATION: Synthetic

<400> SEQUENCE: 408

```
His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Arg Gly Gly Gly Gly
            20                  25                  30
Ala Gln Pro Gly Ala Gln Pro Gly Ala Gln Pro Gly Ala Gln Pro Gly
        35                  40                  45
Ala Gln Pro Gly Ala Gln Pro Gly Ala Gln Pro Gly Ala Gln Pro Gly
50                  55                  60
Ala Gln Pro Gly Ala Gln Pro Gly Ala Gln Pro Gly Ala Gln Pro Gly
65                  70                  75                  80
Gln Glu Pro Gly Ala Gln Pro Gly Gln Glu Pro Gly Ala Gln Pro Gly
                85                  90                  95
Gln Glu Pro Gly Ala Gln Pro Gly Gln Glu Pro Gly Ala Gln Pro Gly
                100                 105                 110
```

```
Gln Glu Pro Gly Ala Gln Pro Gly Gln Pro Gly Ala Gln Pro Gly
        115                 120                 125

Ala Gln Pro Gly Ala Gln Pro Gly Ala Gln Pro Gly Ala Gln Pro Gly
130                 135                 140

Ala Gln Pro Gly Ala Gln Pro Gly Ala Gln Pro Gly Ala Gln Pro Gly
145                 150                 155                 160

Ala Gln Pro Gly Ala Gln Pro Gly Ala Gln Pro Gly Ala Gln Pro Gly
                165                 170                 175

Ala Gln Pro Gly Ala Gln Pro Gly Ala Gln Pro Gly Ala Gln Pro Gly
            180                 185                 190

Ala Gln Pro Gly Ala Gln Pro Gly Ala Gln Pro Ala Arg Gln Gly Asp
        195                 200                 205

His Cys Pro Leu Gly Pro Gly Arg Cys Cys Arg Leu His Thr Val Arg
    210                 215                 220

Ala Ser Leu Glu Asp Leu Gly Trp Ala Asp Trp Val Leu Ser Pro Arg
225                 230                 235                 240

Glu Val Gln Val Thr Met Cys Ile Gly Ala Cys Pro Ser Gln Phe Arg
                245                 250                 255

Ala Ala Asn Leu His Ala Gln Ile Lys Thr Ser Leu His Arg Leu Lys
            260                 265                 270

Pro Asp Thr Val Pro Ala Pro Cys Cys Val Pro Ala Ser Tyr Asn Pro
        275                 280                 285

Met Val Leu Ile Gln Lys Thr Asp Thr Gly Val Ser Leu Gln Thr Tyr
    290                 295                 300

Asp Asp Leu Leu Ala Lys Asp Cys His Cys Ile
305                 310                 315

<210> SEQ ID NO 409
<211> LENGTH: 80
<212> TYPE: PRT
<213> ORGANISM: Artificial Sequence
<220> FEATURE:
<223> OTHER INFORMATION: Synthetic

<400> SEQUENCE: 409

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Ala Lys Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 410
<211> LENGTH: 80
<212> TYPE: PRT
<213> ORGANISM: Artificial Sequence
<220> FEATURE:
<223> OTHER INFORMATION: Synthetic

<400> SEQUENCE: 410

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30
```

Gly Ala Gln Pro Gly Ala Gln Pro Gly Gln Glu Pro Gly Gln Glu Pro
          35                  40                  45

Gly Gln Lys Pro Gly Gln Glu Pro Gly Gln Glu Pro Gly Gln Glu Pro
        50                  55                  60

Gly Gln Glu Pro Gly Gln Glu Pro Gly Ala Gln Pro Gly Ala Gln Pro
65                  70                  75                  80

<210> SEQ ID NO 411
<211> LENGTH: 80
<212> TYPE: PRT
<213> ORGANISM: Artificial Sequence
<220> FEATURE:
<223> OTHER INFORMATION: Synthetic

<400> SEQUENCE: 411

Cys Gln Glu Pro Gly Ala Gln Pro Gly Gln Glu Pro Gly Ala Gln Pro
1               5                  10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
          35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 412
<211> LENGTH: 80
<212> TYPE: PRT
<213> ORGANISM: Artificial Sequence
<220> FEATURE:
<223> OTHER INFORMATION: Synthetic

<400> SEQUENCE: 412

Gly Gln Glu Pro Gly Ala Gln Pro Gly Gln Glu Pro Gly Ala Gln Pro
1               5                  10                  15

Gly Gln Glu Pro Gly Ala Gln Pro Gly Gln Glu Pro Gly Ala Gln Pro
                20                  25                  30

Gly Gln Glu Pro Gly Ala Gln Pro Gly Gln Glu Pro Gly Ala Gln Pro
          35                  40                  45

Gly Ala Gln Pro Gly Ala Cys Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 413
<211> LENGTH: 80
<212> TYPE: PRT
<213> ORGANISM: Artificial Sequence
<220> FEATURE:
<223> OTHER INFORMATION: Synthetic

<400> SEQUENCE: 413

Gly Gln Glu Pro Gly Ala Gln Pro Gly Gln Glu Pro Gly Ala Gln Pro
1               5                  10                  15

Gly Gln Glu Pro Gly Ala Gln Pro Gly Gln Glu Pro Gly Ala Gln Pro
                20                  25                  30

Gly Gln Glu Pro Gly Ala Gln Pro Cys Gln Glu Pro Gly Ala Gln Pro
          35                  40                  45

Gly Ala Gln Pro Gly Ala Gln Pro Gly Ala Gln Pro Gly Ala Gln Pro
            50                  55                  60

Gly Ala Gln Pro Gly Ala Gln Pro Gly Ala Gln Pro Gly Ala Gln Pro
65                  70                  75                  80

<210> SEQ ID NO 414
<211> LENGTH: 80
<212> TYPE: PRT
<213> ORGANISM: Artificial Sequence
<220> FEATURE:
<223> OTHER INFORMATION: Synthetic

<400> SEQUENCE: 414

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Lys Pro Gly Ala Gln Pro Gly Gln Glu Pro Gly Ala Gln Pro
            35                  40                  45

Gly Gln Glu Pro Gly Ala Gln Pro Gly Ala Gln Pro Gly Ala Gln Pro
            50                  55                  60

Gly Ala Gln Pro Gly Ala Gln Pro Gly Ala Gln Pro Gly Ala Gln Pro
65                  70                  75                  80

<210> SEQ ID NO 415
<211> LENGTH: 80
<212> TYPE: PRT
<213> ORGANISM: Artificial Sequence
<220> FEATURE:
<223> OTHER INFORMATION: Synthetic

<400> SEQUENCE: 415

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Lys Gln Ala Pro
                20                  25                  30

Gly Gln Glu Pro Gly Ala Gln Pro Gly Gln Glu Pro Gly Ala Gln Pro
            35                  40                  45

Gly Ala Gln Pro Gly Ala Gln Pro Gly Ala Gln Pro Gly Ala Gln Pro
            50                  55                  60

Gly Ala Gln Pro Gly Ala Gln Pro Gly Ala Gln Pro Gly Ala Gln Pro
65                  70                  75                  80

<210> SEQ ID NO 416
<211> LENGTH: 80
<212> TYPE: PRT
<213> ORGANISM: Artificial Sequence
<220> FEATURE:
<223> OTHER INFORMATION: Synthetic

<400> SEQUENCE: 416

Gly Gln Glu Pro Gly Ala Gln Pro Gly Gln Glu Pro Gly Ala Gln Pro
1               5                   10                  15

Gly Gln Glu Pro Gly Ala Gln Pro Lys Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Ala Gln Pro Gly Ala Gln Pro Gly Ala Gln Pro Gly Ala Gln Pro
            50                  55                  60

Gly Ala Gln Pro Gly Ala Gln Pro Gly Ala Gln Pro Gly Ala Gln Pro

| 65 | 70 | 75 | 80 |

<210> SEQ ID NO 417
<211> LENGTH: 80
<212> TYPE: PRT
<213> ORGANISM: Artificial Sequence
<220> FEATURE:
<223> OTHER INFORMATION: Synthetic

<400> SEQUENCE: 417

| Gly | Gln | Glu | Pro | Gly | Ala | Gln | Pro | Gly | Gln | Glu | Pro | Gly | Ala | Gln | Pro |
| 1 | | | | 5 | | | | | 10 | | | | | 15 | |

| Gly | Gln | Glu | Pro | Lys | Gln | Ala | Pro | Gly | Gln | Glu | Pro | Gly | Ala | Gln | Pro |
| | | 20 | | | | | 25 | | | | | 30 | | | |

| Gly | Gln | Glu | Pro | Gly | Ala | Gln | Pro | Gly | Gln | Glu | Pro | Gly | Ala | Gln | Pro |
| | | | 35 | | | | | 40 | | | | | 45 | | |

| Gly | Ala | Gln | Pro | Gly | Ala | Gln | Pro | Gly | Ala | Gln | Pro | Gly | Ala | Gln | Pro |
| | 50 | | | | | 55 | | | | | 60 | | | | |

| Gly | Ala | Gln | Pro | Gly | Ala | Gln | Pro | Gly | Ala | Gln | Pro | Gly | Ala | Gln | Pro |
| 65 | | | | 70 | | | | | 75 | | | | | 80 | |

<210> SEQ ID NO 418
<211> LENGTH: 80
<212> TYPE: PRT
<213> ORGANISM: Artificial Sequence
<220> FEATURE:
<223> OTHER INFORMATION: Synthetic

<400> SEQUENCE: 418

| Gly | Gln | Glu | Pro | Gly | Ala | Gln | Pro | Gly | Gln | Glu | Pro | Gly | Ala | Gln | Pro |
| 1 | | | | 5 | | | | | 10 | | | | | 15 | |

| Gly | Gln | Glu | Pro | Gly | Ala | Gln | Pro | Gly | Gln | Glu | Pro | Gly | Ala | Gln | Pro |
| | | 20 | | | | | 25 | | | | | 30 | | | |

| Gly | Gln | Cys | Pro | Gly | Ala | Gln | Pro | Gly | Gln | Glu | Pro | Gly | Ala | Gln | Pro |
| | | | 35 | | | | | 40 | | | | | 45 | | |

| Gly | Gln | Glu | Pro | Gly | Ala | Gln | Pro | Gly | Ala | Gln | Pro | Gly | Ala | Gln | Pro |
| | 50 | | | | | 55 | | | | | 60 | | | | |

| Gly | Ala | Gln | Pro | Gly | Ala | Gln | Pro | Gly | Ala | Gln | Pro | Gly | Ala | Gln | Pro |
| 65 | | | | 70 | | | | | 75 | | | | | 80 | |

<210> SEQ ID NO 419
<211> LENGTH: 80
<212> TYPE: PRT
<213> ORGANISM: Artificial Sequence
<220> FEATURE:
<223> OTHER INFORMATION: Synthetic

<400> SEQUENCE: 419

| Gly | Gln | Glu | Pro | Gly | Ala | Gln | Pro | Gly | Gln | Glu | Pro | Gly | Ala | Gln | Pro |
| 1 | | | | 5 | | | | | 10 | | | | | 15 | |

| Gly | Gln | Glu | Pro | Gly | Ala | Gln | Pro | Gly | Gln | Glu | Pro | Gly | Ala | Gln | Pro |
| | | 20 | | | | | 25 | | | | | 30 | | | |

| Gly | Gln | Glu | Pro | Gly | Ala | Gln | Pro | Gly | Gln | Glu | Pro | Gly | Ala | Gln | Pro |
| | | | 35 | | | | | 40 | | | | | 45 | | |

| Gly | Gln | Cys | Pro | Gly | Ala | Gln | Pro | Gly | Ala | Gln | Pro | Gly | Ala | Gln | Pro |
| | 50 | | | | | 55 | | | | | 60 | | | | |

| Gly | Ala | Gln | Pro | Gly | Ala | Gln | Pro | Gly | Ala | Gln | Pro | Gly | Ala | Gln | Pro |
| 65 | | | | 70 | | | | | 75 | | | | | 80 | |

<210> SEQ ID NO 420

<211> LENGTH: 80
<212> TYPE: PRT
<213> ORGANISM: Artificial Sequence
<220> FEATURE:
<223> OTHER INFORMATION: Synthetic

<400> SEQUENCE: 420

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Gln Cys Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 421
<211> LENGTH: 80
<212> TYPE: PRT
<213> ORGANISM: Artificial Sequence
<220> FEATURE:
<223> OTHER INFORMATION: Synthetic

<400> SEQUENCE: 421

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Cys Gln Ala Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 422
<211> LENGTH: 80
<212> TYPE: PRT
<213> ORGANISM: Artificial Sequence
<220> FEATURE:
<223> OTHER INFORMATION: Synthetic

<400> SEQUENCE: 422

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Ala Gln Pro Cys Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 423
<211> LENGTH: 80
<212> TYPE: PRT
<213> ORGANISM: Artificial Sequence
<220> FEATURE:

<223> OTHER INFORMATION: Synthetic

<400> SEQUENCE: 423

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Cys Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 424
<211> LENGTH: 80
<212> TYPE: PRT
<213> ORGANISM: Artificial Sequence
<220> FEATURE:
<223> OTHER INFORMATION: Synthetic

<400> SEQUENCE: 424

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Cys Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 425
<211> LENGTH: 80
<212> TYPE: PRT
<213> ORGANISM: Artificial Sequence
<220> FEATURE:
<223> OTHER INFORMATION: Synthetic

<400> SEQUENCE: 425

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Cys Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 426
<211> LENGTH: 80
<212> TYPE: PRT
<213> ORGANISM: Artificial Sequence
<220> FEATURE:
<223> OTHER INFORMATION: Synthetic

<400> SEQUENCE: 426

-continued

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Lys Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 427
<211> LENGTH: 80
<212> TYPE: PRT
<213> ORGANISM: Artificial Sequence
<220> FEATURE:
<223> OTHER INFORMATION: Synthetic

<400> SEQUENCE: 427

Gly Ala Gln Pro Gly Ala Gln Pro Gly Ala Gln Pro Gly Ala Gln Pro
1               5                   10                  15

Gly Ala Gln Pro Gly Ala Gln Pro Gly Gln Glu Pro Gly Ala Gln Pro
            20                  25                  30

Gly Gln Lys Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 428
<211> LENGTH: 80
<212> TYPE: PRT
<213> ORGANISM: Artificial Sequence
<220> FEATURE:
<223> OTHER INFORMATION: Synthetic

<400> SEQUENCE: 428

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Lys Pro Gly Ala Gln Pro Gly Ala Gln Pro
65                  70                  75                  80

<210> SEQ ID NO 429
<211> LENGTH: 80
<212> TYPE: PRT
<213> ORGANISM: Artificial Sequence
<220> FEATURE:
<223> OTHER INFORMATION: Synthetic

<400> SEQUENCE: 429

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro

```
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Lys Gly Ala Gln Pro
65                  70                  75                  80

<210> SEQ ID NO 430
<211> LENGTH: 80
<212> TYPE: PRT
<213> ORGANISM: Artificial Sequence
<220> FEATURE:
<223> OTHER INFORMATION: Synthetic

<400> SEQUENCE: 430

Gly Ala Gln Pro Gly Ala Gln Pro Gly Ala Gln Pro Gly Ala Gln Pro
1               5                   10                  15

Cys Gln Ala Pro Gly Ala Gln Pro Gly Ala Gln Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 431
<211> LENGTH: 80
<212> TYPE: PRT
<213> ORGANISM: Artificial Sequence
<220> FEATURE:
<223> OTHER INFORMATION: Synthetic

<400> SEQUENCE: 431

Gly Ala Gln Pro Gly Ala Gln Pro Gly Ala Gln Pro Gly Ala Gln Pro
1               5                   10                  15

Gly Ala Gln Pro Cys Gln Ala Pro Gly Ala Gln Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 432
<211> LENGTH: 80
<212> TYPE: PRT
<213> ORGANISM: Artificial Sequence
<220> FEATURE:
<223> OTHER INFORMATION: Synthetic

<400> SEQUENCE: 432

Gly Ala Gln Pro Gly Ala Gln Pro Gly Ala Gln Pro Gly Ala Gln Pro
1               5                   10                  15

Gly Ala Gln Pro Gly Ala Gln Pro Cys Gln Ala Pro Gly Ala Gln Pro
            20                  25                  30

Gly Gln Glu Pro Gly Ala Gln Pro Gly Gln Glu Pro Gly Ala Gln Pro
        35                  40                  45
```

Gly Gln Glu Pro Gly Ala Gln Pro Gly Gln Glu Pro Gly Ala Gln Pro
            50                  55                  60

Gly Gln Glu Pro Gly Ala Gln Pro Gly Gln Glu Pro Gly Ala Gln Pro
65                  70                  75                  80

<210> SEQ ID NO 433
<211> LENGTH: 80
<212> TYPE: PRT
<213> ORGANISM: Artificial Sequence
<220> FEATURE:
<223> OTHER INFORMATION: Synthetic

<400> SEQUENCE: 433

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Gln Cys Pro
                20                  25                  30

Gly Gln Glu Pro Gly Ala Gln Pro Gly Gln Glu Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 434
<211> LENGTH: 80
<212> TYPE: PRT
<213> ORGANISM: Artificial Sequence
<220> FEATURE:
<223> OTHER INFORMATION: Synthetic

<400> SEQUENCE: 434

Gly Gln Glu Pro Gly Ala Gln Pro Gly Gln Glu Pro Gly Ala Gln Pro
1               5                   10                  15

Gly Gln Glu Pro Gly Ala Gln Pro Cys Gln Glu Pro Gly Ala Gln Pro
                20                  25                  30

Gly Gln Glu Pro Gly Ala Gln Pro Gly Gln Glu Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 435
<211> LENGTH: 80
<212> TYPE: PRT
<213> ORGANISM: Artificial Sequence
<220> FEATURE:
<223> OTHER INFORMATION: Synthetic

<400> SEQUENCE: 435

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Ala Gln Pro Gly Gln Glu Pro Cys Gln Ala Pro
            35                  40                  45

Gly Gln Glu Pro Gly Ala Gln Pro Gly Gln Glu Pro Gly Ala Gln Pro
        50                  55                  60

Gly Gln Glu Pro Gly Ala Gln Pro Gly Gln Glu Pro Gly Ala Gln Pro
65                  70                  75                  80

<210> SEQ ID NO 436
<211> LENGTH: 80
<212> TYPE: PRT
<213> ORGANISM: Artificial Sequence
<220> FEATURE:
<223> OTHER INFORMATION: Synthetic

<400> SEQUENCE: 436

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Cys Pro Gly Gln Glu Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 437
<211> LENGTH: 80
<212> TYPE: PRT
<213> ORGANISM: Artificial Sequence
<220> FEATURE:
<223> OTHER INFORMATION: Synthetic

<400> SEQUENCE: 437

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Cys Ala Gln Pro
            20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 438
<211> LENGTH: 80
<212> TYPE: PRT
<213> ORGANISM: Artificial Sequence
<220> FEATURE:
<223> OTHER INFORMATION: Synthetic

<400> SEQUENCE: 438

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Cys Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

```
<210> SEQ ID NO 439
<211> LENGTH: 80
<212> TYPE: PRT
<213> ORGANISM: Artificial Sequence
<220> FEATURE:
<223> OTHER INFORMATION: Synthetic

<400> SEQUENCE: 439

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Cys Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 440
<211> LENGTH: 84
<212> TYPE: PRT
<213> ORGANISM: Artificial Sequence
<220> FEATURE:
<223> OTHER INFORMATION: Synthetic

<400> SEQUENCE: 440

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Cys Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

Gly Ala Gln Pro

<210> SEQ ID NO 441
<211> LENGTH: 84
<212> TYPE: PRT
<213> ORGANISM: Artificial Sequence
<220> FEATURE:
<223> OTHER INFORMATION: Synthetic

<400> SEQUENCE: 441

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Cys Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

Gly Ala Gln Pro
```

```
<210> SEQ ID NO 442
<211> LENGTH: 80
<212> TYPE: PRT
<213> ORGANISM: Artificial Sequence
<220> FEATURE:
<223> OTHER INFORMATION: Synthetic

<400> SEQUENCE: 442

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Cys Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 443
<211> LENGTH: 80
<212> TYPE: PRT
<213> ORGANISM: Artificial Sequence
<220> FEATURE:
<223> OTHER INFORMATION: Synthetic

<400> SEQUENCE: 443

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Cys Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 444
<211> LENGTH: 80
<212> TYPE: PRT
<213> ORGANISM: Artificial Sequence
<220> FEATURE:
<223> OTHER INFORMATION: Synthetic

<400> SEQUENCE: 444

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Cys Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 445
<211> LENGTH: 80
<212> TYPE: PRT
<213> ORGANISM: Artificial Sequence
```

```
<220> FEATURE:
<223> OTHER INFORMATION: Synthetic

<400> SEQUENCE: 445

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Cys Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

<210> SEQ ID NO 446
<211> LENGTH: 172
<212> TYPE: PRT
<213> ORGANISM: Artificial Sequence
<220> FEATURE:
<223> OTHER INFORMATION: Synthetic

<400> SEQUENCE: 446

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

Gly Gln Glu Pro Gly Ala Gln Pro Cys Gln Glu Pro Gly Ala Gln Pro
                85                  90                  95

Gly Ala Gln Pro Gly Ala Gln Pro Gly Ala Gln Pro Gly Ala Gln Pro
            100                 105                 110

Gly Ala Gln Pro Gly Ala Gln Pro Gly Ala Gln Pro Gly Ala Gln Pro
        115                 120                 125

Gly Ala Gln Pro Gly Ala Gln Pro Gly Ala Gln Pro Gly Ala Gln Pro
    130                 135                 140

Gly Ala Gln Pro Gly Ala Gln Pro Gly Ala Gln Pro Gly Ala Gln Pro
145                 150                 155                 160

Gly Ala Gln Pro Gly Ala Gln Pro Gly Ala Gln Pro
                165                 170

<210> SEQ ID NO 447
<211> LENGTH: 80
<212> TYPE: PRT
<213> ORGANISM: Artificial Sequence
<220> FEATURE:
<223> OTHER INFORMATION: Synthetic

<400> SEQUENCE: 447

Gly Ala Gln Pro Cys Gln Ala Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30
```

Gly Gln Glu Pro Gly Ala Gln Pro Gly Gln Glu Pro Gly Ala Gln Pro
            35                  40                  45

Gly Gln Glu Pro Gly Ala Gln Pro Gly Gln Glu Pro Gly Ala Gln Pro
50                  55                  60

Gly Gln Glu Pro Gly Ala Gln Pro Gly Gln Glu Pro Gly Ala Gln Pro
65                  70                  75                  80

<210> SEQ ID NO 448
<211> LENGTH: 31
<212> TYPE: PRT
<213> ORGANISM: Artificial Sequence
<220> FEATURE:
<223> OTHER INFORMATION: Synthetic

<400> SEQUENCE: 448

His Gly Glu Gly Thr Phe Thr Ser Asp Val Ser Ser Tyr Leu Glu Glu
1               5                   10                  15

Gln Ala Ala Cys Glu Phe Ile Ala Trp Leu Val Arg Gly Gly Gly
            20                  25                  30

<210> SEQ ID NO 449

<400> SEQUENCE: 449

000

<210> SEQ ID NO 450
<211> LENGTH: 29
<212> TYPE: PRT
<213> ORGANISM: Artificial Sequence
<220> FEATURE:
<223> OTHER INFORMATION: Synthetic

<400> SEQUENCE: 450

Glu Gly Thr Phe Thr Ser Asp Val Ser Ser Tyr Leu Glu Glu Gln Ala
1               5                   10                  15

Ala Lys Glu Phe Ile Ala Trp Leu Val Arg Gly Gly Gly
            20                  25

<210> SEQ ID NO 451
<211> LENGTH: 112
<212> TYPE: PRT
<213> ORGANISM: Artificial Sequence
<220> FEATURE:
<223> OTHER INFORMATION: Synthetic

<400> SEQUENCE: 451

Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Leu His Ala Gln Ile Lys Thr Ser
    50                  55                  60

Leu His Arg Leu Arg Pro Asp Thr Val Pro Ala Pro Cys Cys Val Pro
65                  70                  75                  80

Ala Ser Tyr Asn Pro Leu Val Leu Ile Gln Arg Thr Asp Thr Gly Val
                85                  90                  95

Ser Leu Gln Thr Tyr Asp Asp Leu Leu Ala Arg Asp Cys His Cys Ile
            100                 105                 110

<210> SEQ ID NO 452
<211> LENGTH: 112
<212> TYPE: PRT
<213> ORGANISM: Artificial Sequence
<220> FEATURE:
<223> OTHER INFORMATION: Synthetic

<400> SEQUENCE: 452

```
Ala Arg Gln Gly Asp His Cys Pro Leu Gly Pro Gly Arg Cys Cys Arg
1               5                   10                  15

Leu His Thr Val Arg Ala Ser Leu Glu Asp Leu Gly Trp Ala Asp Trp
            20                  25                  30

Val Leu Ser Pro Arg Glu Val Gln Val Thr Met Cys Ile Gly Ala Cys
        35                  40                  45

Pro Ser Gln Phe Arg Ala Ala Asn Leu His Ala Gln Ile Lys Thr Ser
    50                  55                  60

Leu His Arg Leu Lys Pro Asp Thr Val Pro Ala Pro Cys Cys Val Pro
65                  70                  75                  80

Ala Ser Tyr Asn Pro Met Arg Leu Ile Gln Lys Thr Asp Thr Gly Val
                85                  90                  95

Ser Leu Gln Thr Tyr Asp Asp Leu Leu Ala Lys Asp Cys His Cys Ile
            100                 105                 110
```

<210> SEQ ID NO 453
<211> LENGTH: 8
<212> TYPE: PRT
<213> ORGANISM: Artificial Sequence
<220> FEATURE:
<223> OTHER INFORMATION: Synthetic

<400> SEQUENCE: 453

```
Gly Gln Glu Pro Gly Gln Ala Pro
1               5
```

<210> SEQ ID NO 454
<211> LENGTH: 80
<212> TYPE: PRT
<213> ORGANISM: Artificial Sequence
<220> FEATURE:
<223> OTHER INFORMATION: Synthetic

<400> SEQUENCE: 454

```
Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Ala Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80
```

<210> SEQ ID NO 455
<211> LENGTH: 80
<212> TYPE: PRT
<213> ORGANISM: Artificial Sequence
<220> FEATURE:
<223> OTHER INFORMATION: Synthetic

<400> SEQUENCE: 455

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
                20                  25                  30

Gly Gln Glu Pro Gly Gln Ala Pro Gly Gln Glu Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 456
<211> LENGTH: 80
<212> TYPE: PRT
<213> ORGANISM: Artificial Sequence
<220> FEATURE:
<223> OTHER INFORMATION: Synthetic

<400> SEQUENCE: 456

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Gln Ala Pro Gly Gln Glu Pro Gly Ala Gln Pro
            35                  40                  45

Gly Gln Glu Pro Gly Ala Gln Pro Gly Gln Glu Pro Gly Ala Gln Pro
        50                  55                  60

Gly Gln Glu Pro Gly Ala Gln Pro Gly Gln Glu Pro Gly Ala Gln Pro
65                  70                  75                  80

<210> SEQ ID NO 457
<211> LENGTH: 80
<212> TYPE: PRT
<213> ORGANISM: Artificial Sequence
<220> FEATURE:
<223> OTHER INFORMATION: Synthetic

<400> SEQUENCE: 457

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Gln Ala Pro
                20                  25                  30

Gly Gln Glu Pro Gly Ala Gln Pro Gly Gln Glu Pro Gly Ala Gln Pro
            35                  40                  45

Gly Ala Gln Pro Gly Ala Gln Pro Gly Ala Gln Pro Gly Ala Gln Pro
        50                  55                  60

Gly Ala Gln Pro Gly Ala Gln Pro Gly Ala Gln Pro Gly Ala Gln Pro
65                  70                  75                  80

<210> SEQ ID NO 458
<211> LENGTH: 84
<212> TYPE: PRT
<213> ORGANISM: Artificial Sequence
<220> FEATURE:
<223> OTHER INFORMATION: Synthetic

<400> SEQUENCE: 458

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro 20                  25                  30

Gly Gln Glu Pro Gly Ala Gln Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

Gly Ala Gln Pro

<210> SEQ ID NO 459
<211> LENGTH: 84
<212> TYPE: PRT
<213> ORGANISM: Artificial Sequence
<220> FEATURE:
<223> OTHER INFORMATION: Synthetic

<400> SEQUENCE: 459

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Ala Pro Gly Gln Glu Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

Gly Ala Gln Pro

<210> SEQ ID NO 460
<211> LENGTH: 4
<212> TYPE: PRT
<213> ORGANISM: Artificial Sequence
<220> FEATURE:
<223> OTHER INFORMATION: Synthetic

<400> SEQUENCE: 460

Gly Gln Glu Pro
1

<210> SEQ ID NO 461
<211> LENGTH: 120
<212> TYPE: PRT
<213> ORGANISM: Artificial Sequence
<220> FEATURE:
<223> OTHER INFORMATION: Synthetic

<400> SEQUENCE: 461

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Ala Gln Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

Gly Ala Gln Pro Gly Ala Gln Pro Gly Ala Gln Pro Gly Ala Gln Pro

```
                     85                  90                  95

Gly Ala Gln Pro Gly Ala Gln Pro Gly Ala Gln Pro Gly Ala Gln Pro
            100                 105                 110

Gly Ala Gln Pro Gly Ala Gln Pro
        115                 120

<210> SEQ ID NO 462
<211> LENGTH: 172
<212> TYPE: PRT
<213> ORGANISM: Artificial Sequence
<220> FEATURE:
<223> OTHER INFORMATION: Synthetic

<400> SEQUENCE: 462

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Ala Gln Pro Gly Ala Gln Pro Gly Ala Gln Pro Gly Ala Gln Pro
        35                  40                  45

Gly Gln Glu Pro Gly Ala Gln Pro Gly Gln Glu Pro Gly Ala Gln Pro
    50                  55                  60

Gly Gln Glu Pro Gly Ala Gln Pro Gly Gln Glu Pro Gly Ala Gln Pro
65                  70                  75                  80

Gly Gln Glu Pro Gly Ala Gln Pro Cys Gln Glu Pro Gly Ala Gln Pro
                85                  90                  95

Gly Ala Gln Pro Gly Ala Gln Pro Gly Ala Gln Pro Gly Ala Gln Pro
            100                 105                 110

Gly Ala Gln Pro Gly Ala Gln Pro Gly Ala Gln Pro Gly Ala Gln Pro
        115                 120                 125

Gly Ala Gln Pro Gly Ala Gln Pro Gly Ala Gln Pro Gly Ala Gln Pro
    130                 135                 140

Gly Ala Gln Pro Gly Ala Gln Pro Gly Ala Gln Pro Gly Ala Gln Pro
145                 150                 155                 160

Gly Ala Gln Pro Gly Ala Gln Pro Gly Ala Gln Pro
                165                 170

<210> SEQ ID NO 463
<211> LENGTH: 80
<212> TYPE: PRT
<213> ORGANISM: Artificial Sequence
<220> FEATURE:
<223> OTHER INFORMATION: Synthetic

<400> SEQUENCE: 463

Gly Gln Glu Pro Gly Ala Gln Pro Gly Gln Glu Pro Gly Ala Gln Pro
1               5                   10                  15

Gly Gln Glu Pro Gly Ala Gln Pro Gly Gln Glu Pro Gly Ala Gln Pro
            20                  25                  30

Gly Gln Glu Pro Gly Gln Ala Pro Gly Gln Glu Pro Gly Ala Gln Pro
        35                  40                  45

Gly Ala Gln Pro Gly Ala Gln Pro Gly Ala Gln Pro Gly Ala Gln Pro
    50                  55                  60

Gly Ala Gln Pro Gly Ala Gln Pro Gly Ala Gln Pro Gly Ala Gln Pro
65                  70                  75                  80

<210> SEQ ID NO 464
<211> LENGTH: 80
```

<212> TYPE: PRT
<213> ORGANISM: Artificial Sequence
<220> FEATURE:
<223> OTHER INFORMATION: Synthetic

<400> SEQUENCE: 464

Gly Ala Gln Pro Gly Ala Gln Pro Gly Ala Gln Pro Gly Ala Gln Pro
1               5                   10                  15
Gly Gln Ala Pro Gly Ala Gln Pro Gly Ala Gln Pro Gly Ala Gln Pro
            20                  25                  30
Gly Gln Glu Pro Gly Ala Gln Pro Gly Gln Glu Pro Gly Ala Gln Pro
        35                  40                  45
Gly Gln Glu Pro Gly Ala Gln Pro Gly Gln Glu Pro Gly Ala Gln Pro
    50                  55                  60
Gly Gln Glu Pro Gly Ala Gln Pro Gly Gln Glu Pro Gly Ala Gln Pro
65                  70                  75                  80

<210> SEQ ID NO 465
<211> LENGTH: 80
<212> TYPE: PRT
<213> ORGANISM: Artificial Sequence
<220> FEATURE:
<223> OTHER INFORMATION: Synthetic

<400> SEQUENCE: 465

Gly Ala Gln Pro Gly Ala Gln Pro Gly Ala Gln Pro Gly Ala Gln Pro
1               5                   10                  15
Gly Ala Gln Pro Gly Gln Ala Pro Gly Ala Gln Pro Gly Ala Gln Pro
            20                  25                  30
Gly Gln Glu Pro Gly Ala Gln Pro Gly Gln Glu Pro Gly Ala Gln Pro
        35                  40                  45
Gly Gln Glu Pro Gly Ala Gln Pro Gly Gln Glu Pro Gly Ala Gln Pro
    50                  55                  60
Gly Gln Glu Pro Gly Ala Gln Pro Gly Gln Glu Pro Gly Ala Gln Pro
65                  70                  75                  80

<210> SEQ ID NO 466
<211> LENGTH: 80
<212> TYPE: PRT
<213> ORGANISM: Artificial Sequence
<220> FEATURE:
<223> OTHER INFORMATION: Synthetic

<400> SEQUENCE: 466

Gly Ala Gln Pro Gly Ala Gln Pro Gly Ala Gln Pro Gly Ala Gln Pro
1               5                   10                  15
Gly Ala Gln Pro Gly Ala Gln Pro Gly Gln Ala Pro Gly Ala Gln Pro
            20                  25                  30
Gly Gln Glu Pro Gly Ala Gln Pro Gly Gln Glu Pro Gly Ala Gln Pro
        35                  40                  45
Gly Gln Glu Pro Gly Ala Gln Pro Gly Gln Glu Pro Gly Ala Gln Pro
    50                  55                  60
Gly Gln Glu Pro Gly Ala Gln Pro Gly Gln Glu Pro Gly Ala Gln Pro
65                  70                  75                  80

<210> SEQ ID NO 467
<211> LENGTH: 80
<212> TYPE: PRT
<213> ORGANISM: Artificial Sequence
<220> FEATURE:
<223> OTHER INFORMATION: Synthetic

<400> SEQUENCE: 467

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Ala Gln Pro Gly Gln Glu Pro Gly Gln Ala Pro
        35                  40                  45

Gly Gln Glu Pro Gly Gln Ala Pro Gly Gln Glu Pro Gly Gln Ala Pro
    50                  55                  60

Gly Gln Glu Pro Gly Gln Ala Pro Gly Gln Glu Pro Gly Gln Ala Pro
65                  70                  75                  80

<210> SEQ ID NO 468
<211> LENGTH: 80
<212> TYPE: PRT
<213> ORGANISM: Artificial Sequence
<220> FEATURE:
<223> OTHER INFORMATION: Synthetic

<400> SEQUENCE: 468

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Ala Gln Pro Gly Gln Glu Pro Gly Ala Gln Pro
        35                  40                  45

Gly Gln Ala Pro Gly Gln Glu Pro Gly Gln Glu Pro Gly Gln Ala Pro
    50                  55                  60

Gly Gln Glu Pro Gly Gln Ala Pro Gly Gln Glu Pro Gly Gln Ala Pro
65                  70                  75                  80

<210> SEQ ID NO 469
<211> LENGTH: 80
<212> TYPE: PRT
<213> ORGANISM: Artificial Sequence
<220> FEATURE:
<223> OTHER INFORMATION: Synthetic

<400> SEQUENCE: 469

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
            20                  25                  30

Gly Gln Glu Pro Gly Gln Ala Pro Gly Gln Glu Pro Gly Gln Ala Pro
        35                  40                  45

Gly Gln Glu Pro Gly Gln Ala Pro Gly Gln Glu Pro Gly Gln Ala Pro
    50                  55                  60

Gly Gln Glu Pro Gly Gln Ala Pro Gly Gln Glu Pro Gly Gln Ala Pro
65                  70                  75                  80

<210> SEQ ID NO 470
<211> LENGTH: 80
<212> TYPE: PRT
<213> ORGANISM: Artificial Sequence
<220> FEATURE:
<223> OTHER INFORMATION: Synthetic

<400> SEQUENCE: 470

Gly Ala Gln Pro Gly Gln Ala Pro Gly Ala Gln Pro Gly Ala Gln Pro

```
                 1               5                  10                  15
Gly Ala Gln Pro Gly Ala Gln Pro Gly Ala Gln Pro Gly Ala Gln Pro
                20                  25                  30
Gly Gln Glu Pro Gly Ala Gln Pro Gly Gln Glu Pro Gly Ala Gln Pro
                35                  40                  45
Gly Gln Glu Pro Gly Ala Gln Pro Gly Gln Glu Pro Gly Ala Gln Pro
             50                  55                  60
Gly Gln Glu Pro Gly Ala Gln Pro Gly Gln Glu Pro Gly Ala Gln Pro
 65                  70                  75                  80

<210> SEQ ID NO 471
<211> LENGTH: 80
<212> TYPE: PRT
<213> ORGANISM: Artificial Sequence
<220> FEATURE:
<223> OTHER INFORMATION: Synthetic

<400> SEQUENCE: 471

Gly Ala Gln Pro Gly Ala Gln Pro Gly Ala Gln Pro Gly Ala Gln Pro
 1               5                  10                  15
Gly Ala Gln Pro Gly Ala Gln Pro Gly Ala Gln Pro Gly Ala Gln Pro
                20                  25                  30
Gly Gln Glu Pro Gly Ala Gln Pro Gly Gln Glu Pro Gly Ala Gln Pro
                35                  40                  45
Gly Gln Glu Pro Gly Ala Gln Pro Gly Gln Glu Pro Gly Ala Gln Pro
             50                  55                  60
Gly Gln Glu Pro Gly Ala Gln Pro Gly Gln Glu Pro Gly Gln Ala Pro
 65                  70                  75                  80

<210> SEQ ID NO 472
<211> LENGTH: 223
<212> TYPE: PRT
<213> ORGANISM: Artificial Sequence
<220> FEATURE:
<223> OTHER INFORMATION: Synthetic

<400> SEQUENCE: 472

His Gly Glu Gly Thr Phe Thr Ser Asp Val Ser Ser Tyr Leu Glu Glu
 1               5                  10                  15
Gln Ala Ala Lys Glu Phe Ile Ala Trp Leu Val Arg Gly Gly Gly Gly
                20                  25                  30
Ala Gln Pro Cys Gln Ala Pro Gly Ala Gln Pro Gly Ala Gln Pro Gly
                35                  40                  45
Ala Gln Pro Gly Ala Gln Pro Gly Ala Gln Pro Gly Ala Gln Pro Gly
             50                  55                  60
Gln Glu Pro Gly Ala Gln Pro Gly Gln Glu Pro Gly Ala Gln Pro Gly
 65                  70                  75                  80
Gln Glu Pro Gly Ala Gln Pro Gly Gln Glu Pro Gly Ala Gln Pro Gly
                85                  90                  95
Gln Glu Pro Gly Ala Gln Pro Gly Gln Glu Pro Gly Ala Gln Pro Ala
                100                 105                 110
Arg Gln Gly Asp His Cys Pro Leu Gly Pro Gly Arg Cys Cys Arg Leu
             115                 120                 125
His Thr Val Arg Ala Ser Leu Glu Asp Leu Gly Trp Ala Asp Trp Val
             130                 135                 140
Leu Ser Pro Arg Glu Val Gln Val Thr Met Cys Ile Gly Ala Cys Pro
 145                 150                 155                 160
```

```
Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220
```

<210> SEQ ID NO 473
<211> LENGTH: 223
<212> TYPE: PRT
<213> ORGANISM: Artificial Sequence
<220> FEATURE:
<223> OTHER INFORMATION: Synthetic

<400> SEQUENCE: 473

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
        50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Gln Cys Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
        195                 200                 205

Leu Gln Thr Tyr Asp Asp Leu Leu Ala Lys Asp Cys His Cys Ile
    210                 215                 220
```

<210> SEQ ID NO 474

<400> SEQUENCE: 474

000

<210> SEQ ID NO 475
<211> LENGTH: 80
<212> TYPE: PRT
<213> ORGANISM: Artificial Sequence
<220> FEATURE:
<223> OTHER INFORMATION: Synthetic

```
<400> SEQUENCE: 475

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Ala Gln Pro Gly Gln Glu Pro Gly Ala Gln Pro
        50                  55                  60

Gly Gln Glu Pro Gly Ala Gln Pro Gly Gln Glu Pro Gly Gln Cys Pro
65                  70                  75                  80

<210> SEQ ID NO 476
<211> LENGTH: 8
<212> TYPE: PRT
<213> ORGANISM: Artificial Sequence
<220> FEATURE:
<223> OTHER INFORMATION: Synthetic

<400> SEQUENCE: 476

Gly Gln Ala Pro Gly Gln Glu Pro
1               5

<210> SEQ ID NO 477
<211> LENGTH: 223
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: X is Aib

<400> SEQUENCE: 477

His Xaa Glu Gly Thr Phe Thr Ser Asp Val Ser Ser Tyr Leu Glu Glu
1               5                   10                  15

Gln Ala Ala Lys Glu Phe Ile Ala Trp Leu Val Arg Gly Gly Gly Gly
                20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Cys
        50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
        115                 120                 125

His Thr Val Arg Ala Ser Leu Glu Asp Leu Gly Trp Ala Asp Trp Val
    130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Arg Pro Asp Thr Val Pro Ala Pro Cys Cys Val Pro Ala
            180                 185                 190
```

```
Ser Tyr Asn Pro Met Val Leu Ile Gln Arg Thr Asp Thr Gly Val Ser
        195                 200                 205
Leu Gln Thr Tyr Asp Asp Leu Leu Ala Arg Asp Cys His Cys Ile
    210                 215                 220

<210> SEQ ID NO 478
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: X is Aib

<400> SEQUENCE: 478

His Xaa Glu Gly Thr Phe Thr Ser Asp Val Ser Ser Tyr Leu Glu Glu
1               5                   10                  15
Gln Ala Ala Lys Glu Phe Ile Ala Trp Leu Val Arg Gly Gly Gly
            20                  25                  30

<210> SEQ ID NO 479
<211> LENGTH: 112
<212> TYPE: PRT
<213> ORGANISM: Artificial Sequence
<220> FEATURE:
<223> OTHER INFORMATION: Synthetic

<400> SEQUENCE: 479

Ala Arg Asn Gly Asp His Cys Pro Leu Gly Pro Gly Arg Cys Cys Arg
1               5                   10                  15
Leu His Thr Val Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Asn Leu His Ala Gln Ile Lys Thr Ser
    50                  55                  60
Leu His Arg Leu Lys Pro Asp Thr Val Pro Ala Pro Cys Cys Val Pro
65                  70                  75                  80
Ala Ser Tyr Asn Pro Met Val Leu Ile Gln Lys Thr Asp Thr Gly Val
                85                  90                  95
Ser Leu Gln Thr Tyr Asp Asp Leu Leu Ala Lys Asp Cys His Cys Ile
            100                 105                 110

<210> SEQ ID NO 480
<211> LENGTH: 112
<212> TYPE: PRT
<213> ORGANISM: Artificial Sequence
<220> FEATURE:
<223> OTHER INFORMATION: Synthetic

<400> SEQUENCE: 480

Ala Arg Asn Gly Asp His Cys Pro Leu Gly Pro Gly Arg Cys Cys Arg
1               5                   10                  15
Leu His Thr Val Arg Ala Ser Leu Glu Asp Leu Gly Trp Ala Asp Trp
            20                  25                  30
Val Leu Ser Pro Arg Glu Val Gln Val Thr Met Cys Ile Gly Ala Cys
        35                  40                  45
Pro Ser Gln Phe Arg Ala Ala Asn Leu His Ala Gln Ile Lys Thr Ser
    50                  55                  60
```

```
Leu His Arg Leu Arg Pro Asp Thr Val Pro Ala Pro Cys Cys Val Pro
 65                  70                  75                  80

Ala Ser Tyr Asn Pro Met Val Leu Ile Gln Arg Thr Asp Thr Gly Val
                 85                  90                  95

Ser Leu Gln Thr Tyr Asp Asp Leu Leu Ala Arg Asp Cys His Cys Ile
            100                 105                 110
```

<210> SEQ ID NO 481
<211> LENGTH: 223
<212> TYPE: PRT
<213> ORGANISM: Artificial Sequence
<220> FEATURE:
<223> OTHER INFORMATION: Synthetic

<400> SEQUENCE: 481

```
His Gly Glu Gly Thr Phe Thr Ser Asp Val Ser Ser Tyr Leu Glu Glu
 1               5                  10                  15

Gln Ala Ala Lys Glu Phe Ile Ala Trp Leu Val Arg Gly Gly Gly Gly
                 20                  25                  30

Ala Gln Pro Gly Ala Gln Pro Gly Ala Gln Pro Gly Ala Gln Pro Gly
            35                  40                  45

Ala Gln Pro Gly Ala Gln Pro Gly Ala Gln Pro Gly Ala Gln Pro Gly
         50                  55                  60

Gln Glu Pro Gly Ala Gln Pro Gly Gln Glu Pro Gly Ala Gln Pro Gly
 65                  70                  75                  80

Gln Glu Pro Gly Ala Gln Pro Gly Gln Glu Pro Gly Ala Gln Pro Gly
                 85                  90                  95

Gln Glu Pro Gly Ala Gln Pro Cys Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
         130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
         195                 200                 205

Leu Gln Thr Tyr Asp Asp Leu Leu Ala Lys Asp Cys His Cys Ile
     210                 215                 220
```

<210> SEQ ID NO 482
<211> LENGTH: 223
<212> TYPE: PRT
<213> ORGANISM: Artificial Sequence
<220> FEATURE:
<223> OTHER INFORMATION: Synthetic

<400> SEQUENCE: 482

```
His Gly Glu Gly Thr Phe Thr Ser Asp Val Ser Ser Tyr Leu Glu Glu
 1               5                  10                  15

Gln Ala Ala Cys Glu Phe Ile Ala Trp Leu Val Arg Gly Gly Gly Gly
                 20                  25                  30

Ala Gln Pro Gly Ala Gln Pro Gly Ala Gln Pro Gly Ala Gln Pro Gly
```

```
                    35                  40                  45
Ala Gln Pro Gly Ala Gln Pro Gly Ala Gln Pro Gly Ala Gln Pro Gly
            50                  55                  60

Gln Glu Pro Gly Ala Gln Pro Gly Gln Glu Pro Gly Ala Gln Pro Gly
65                  70                  75                  80

Gln Glu Pro Gly Ala Gln Pro Gly Gln Glu Pro Gly Ala Gln Pro Gly
                85                  90                  95

Gln Glu Pro Gly Ala Gln Pro Gly Gln Glu Pro Gly Ala Gln Pro Ala
            100                 105                 110

Arg Gln Gly Asp His Cys Pro Leu Gly Pro Gly Arg Cys Cys Arg Leu
            115                 120                 125

His Thr Val Arg Ala Ser Leu Glu Asp Leu Gly Trp Ala Asp Trp Val
            130                 135                 140

Leu Ser Pro Arg Glu Val Gln Val Thr Met Cys Ile Gly Ala Cys Pro
145                 150                 155                 160

Ser Gln Phe Arg Ala Ala Asn Leu His Ala Gln Ile Lys Thr Ser Leu
                165                 170                 175

His Arg Leu Lys Pro Asp Thr Val Pro Ala Pro Cys Cys Val Pro Ala
            180                 185                 190

Ser Tyr Asn Pro Met Val Leu Ile Gln Lys Thr Asp Thr Gly Val Ser
                195                 200                 205

Leu Gln Thr Tyr Asp Asp Leu Leu Ala Lys Asp Cys His Cys Ile
            210                 215                 220

<210> SEQ ID NO 483
<211> LENGTH: 80
<212> TYPE: PRT
<213> ORGANISM: Artificial Sequence
<220> FEATURE:
<223> OTHER INFORMATION: Synthetic

<400> SEQUENCE: 483

Gly Ala Gln Pro Gly Ala Gln Pro Gly Ala Gln Pro Gly Ala Gln Pro
1               5                   10                  15

Gly Ala Gln Pro Gly Ala Gln Pro Gly Ala Gln Pro Gly Ala Gln Pro
                20                  25                  30

Gly Gln Glu Pro Gly Ala Gln Pro Gly Gln Glu Pro Gly Ala Gln Pro
            35                  40                  45

Gly Gln Glu Pro Gly Ala Gln Pro Gly Gln Glu Pro Gly Ala Gln Pro
        50                  55                  60

Gly Gln Glu Pro Gly Ala Gln Pro Cys Gln Glu Pro Gly Ala Gln Pro
65                  70                  75                  80
```

FUSION PROTEINS OF GLP-1 AND GDF15 AND CONJUGATES THEREOF

SEQUENCE LISTING

A copy of the Sequence Listing is submitted with the specification electronically via EFS-Web as an ASCII formatted sequence listing with a file name of "074585-8001_SL_20210922-hxr_ST25", a creation date of Sep. 22, 2021, and a size of about 442 Kb. The sequence listing contained this ASCII formatted document is part of the specification and is herein incorporated by reference in its entirety.

FIELD OF THE INVENTION

The present invention relates to fusion proteins, pharmaceutical compositions thereof, and methods of using such to prevent and/or treat diseases.

BACKGROUND

Major biologically active fragment of Glucagon-Like Peptide-1 (GLP-1) is a 30 or 31 amino acid peptide fragment (amino acid 7-36 or 7-37 of GLP-1) deriving from the posttranslational processing of the proglucagon peptide. The initial GLP-1 product GLP-1 stimulates insulin synthesis and secretion and has been shown to prevent hyperglycemia in diabetics, especially type 2 diabetes. However, endogenous GLP-1 only has a half-life of approximately 2 minutes, which results in fasting plasma levels of GLP-1 of only 0-15 pmol/L.

Growth differentiation factor 15 (GDF15), also named as Macrophage inhibitory cytokine-1 or MIC-1, is a member of the transforming growth factor beta superfamily. The function of GDF15 is not fully understood. Existing studies show that GDF15 may have a role in regulating inflammatory pathways, participating in regulating apoptosis, cell repair and cell growth, which are biological processes observed in cardiovascular and neoplastic disorders. Other studies show that GDF15 possesses therapeutic utility in metabolic disorders such as obesity.

Metabolic disorders are commonly associated with insulin resistance, visceral adiposity, atherogenic dyslipidemia, etc., which pose major and escalating public health and clinical challenge worldwide. However, existing treatment for metabolic diseases faces problems such as short half-life and/or low efficacy.

Therefore, there is a need for an improved therapeutic solution for treating metabolic diseases.

SUMMARY OF THE INVENTION

Provided herein are fusion proteins and the conjugates thereof, and pharmaceutical compositions and methods of use for treating/preventing metabolic disorders.

In a first aspect, the present disclosure provides a fusion polypeptide comprising: a) a first polypeptide fragment comprising a Glucagon-like peptide-1 (GLP-1) receptor agonist; and b) a second polypeptide fragment comprising a GDNF receptor alpha like (GFRAL) receptor agonist; wherein the first polypeptide fragment and the second polypeptide fragment are linked to one another directly or via a linker.

In certain embodiments, the first polypeptide fragment comprises GLP-1 and/or the second polypeptide fragment comprises GDF15.

In certain embodiments, the GLP-1 comprises an amino acid sequence having at least 70% sequence identity to SEQ ID NO: 242 while retaining substantial biological activity of SEQ ID NO: 242, and/or the GDF15 comprises an amino acid sequence having at least 90% sequence identity to SEQ ID NO: 248 while retaining substantial biological activity of SEQ ID NO: 248.

In certain embodiments, the GLP-1 comprises no more than 9, 8, 7, 6, 5, 4 substitutions relative to SEQ ID NO: 242 while retaining substantial biological activity of SEQ ID NO: 242, and/or the GDF15 comprises no more than 10, 9, 8, 7, 6, 5, 4, 3, 2 substitutions relative to SEQ ID NO: 248 while retaining substantial biological activity of SEQ ID NO: 248.

In certain embodiments, the GLP-1 comprises one or more mutations at a position selected from the group consisting of: A8, G22, K34, R36, and H7, or any combination thereof, relative to SEQ ID NO: 242.

In certain embodiments, the GLP-1 comprises or consists of one or more substitutions selected from the group consisting of: H7IA, H7IPA, A8G, A8Aib, K34R, G22E, and R36G, or any combination thereof.

In certain embodiments, the GDF15 comprises one or more mutations at a position selected from the group consisting of: A1, R2, N3, H6, P11, H18, T19, V20, R21, A30, M43, A47, R53, A54, M57, H66, R67, L68, A75, A81, P85, M86, Q90, T92, and L105, or any combination thereof.

In certain embodiments, the one or more mutations in GDF15 comprises:
1) mutation of N3 selected from the group consisting of: N3Q, N3S, N3E, N3A, N3T, N3P, N3G, N3V, N3H, N3Y and deletion of N3; and/or
2) substitution of M57 selected from the group consisting of: M57A, M57E and M57L; and/or
3) substitution of M86L or M86A.

In certain embodiments, the one or more mutations in GDF15 are selected from the group consisting of: R2S, R2A, R2E, N3S, N3E, N3A, N3T, N3P, N3G, N3V, N3H, N3Y, N3Q, H6D, P11E, H18E, H18Q, T19S, V20L, R21E, A30E, M43L, M43E, A47E, R53E, A54E, M57A, M57E, M57L, H66E, R67E, L68E, A75E, A81E, P85E, M86F, M86A, M86L, Q90E, T92E, L105E, deletion of N3, and deletion of N-terminal 1-3 residues, or any combination thereof.

In certain embodiments, the fusion polypeptide comprises from N terminus to C terminus, the GLP-1, the linker and the GDF15.

In certain embodiments, the linker comprises a polypeptide linker.

In certain embodiments, the polypeptide linker has a length of 4-172 amino acid residues (e.g. at least 4, 12, 24, 40, 50, 60, 70, 80, 90, 100, 110, or 120 amino acid resides) or more.

In certain embodiments, the polypeptide linker comprises at least one acidic amino acid residue.

In certain embodiments, the at least one acidic amino acid residue comprises Aspartic acid or glutamic acid.

In certain embodiments, the polypeptide linker comprises one or more repeats of a repeating sequence.

In certain embodiments, the repeating sequence consists of no more than 4, 5 or 6 types of amino acid residues selected from the group consisting of: G, Q, A, E, P, and S.

In certain embodiments, the repeating sequence comprises Q.

In certain embodiments, the repeating sequence consists of G, Q, A, E, and P.

In certain embodiments, the repeating sequence consists of a sequence selected from the group consisting of: SEQ ID NO: 213 (GQEPGAQP), SEQ ID NO: 214 (GAQPGAQP), SEQ ID NO: 215 (GQEP), SEQ ID NO: 216 (GAQP), SEQ ID NO: 217 (SEPATSGSETPGTSESATPESGPGTSTEPSEG), SEQ ID NO: 218 (GAQPGQEPGAQP), SEQ ID NO: 219 (GAQPGQEP), SEQ ID NO: 220 (GEQP), SEQ ID NO: 221 (GPQE), SEQ ID NO: 222 (GPEQ), SEQ ID NO: 223 (GSEP), SEQ ID NO: 224 (GESP), SEQ ID NO: 225 (GPSE), SEQ ID NO: 226 (GPES), SEQ ID NO: 227 (GQAP), SEQ ID NO: 228 (GPAQ), SEQ ID NO: 229 (GPQA), SEQ ID NO: 230 (GSQP), SEQ ID NO: 231 (GASP), SEQ ID NO: 232 (GPAS), SEQ ID NO: 233 (GPSA), SEQ ID NO: 234 (GGGS), SEQ ID NO: 235 (GSGS), SEQ ID NO: 236 (GGGGS), SEQ ID NO: 453 (GQEPGQAP), SEQ ID NO: 476: (GQAPGQEP) and GS.

In certain embodiments, the polypeptide linker comprises (Repeat1)r(Repeat2)s(Repeat3)x(Repeat4)y, wherein: Repeat1, Repeat2, Repeat3 and Repeat4 are linked via a peptide bond or via one or more amino acid residues, Repeat1, Repeat2, Repeat3 and Repeat4 independently, comprise or consist of a sequence selected from the group consisting of SEQ ID NO: 213 (GQEPGAQP), SEQ ID NO: 214 (GAQPGAQP), SEQ ID NO: 215 (GQEP), SEQ ID NO: 216 (GAQP), SEQ ID NO: 217 (SEPATSGSETPGTSESATPESGPGTSTEPSEG), SEQ ID NO: 218 (GAQPGQEPGAQP), SEQ ID NO: 219 (GAQPGQEP), SEQ ID NO: 220 (GEQP), SEQ ID NO: 221 (GPQE), SEQ ID NO: 222 (GPEQ), SEQ ID NO: 223 (GSEP), SEQ ID NO: 224 (GESP), SEQ ID NO: 225 (GPSE), SEQ ID NO: 226 (GPES), SEQ ID NO: 227 (GQAP), SEQ ID NO: 228 (GPAQ), SEQ ID NO: 229 (GPQA), SEQ ID NO: 230 (GSQP), SEQ ID NO: 231 (GASP), SEQ ID NO: 232 (GPAS), SEQ ID NO: 233 (GPSA), SEQ ID NO: 234 (GGGS), SEQ ID NO: 235 (GSGS), SEQ ID NO: 236 (GGGGS), SEQ ID NO: 453 (GQEPGQAP), SEQ ID NO: 476: (GQAPGQEP) and GS, and r, s, x and y are independently an integer selected from 0 to 30, provided that r, s, x and y are not 0 at the same time.

In certain embodiments, x and y are 0, r, and s are independently an integer selected from 1 to 30, and Repeat1 and Repeat2 are a combination selected from the group consisting of:
Repeat1 comprises or consists of a sequence of SEQ ID NO: 213, Repeat2 comprises or consists of a sequence of SEQ ID NO: 216;
Repeat1 comprises or consists of a sequence of SEQ ID NO: 215, Repeat2 comprises or consists of a sequence of SEQ ID NO: 216;
Repeat1 comprises or consists of a sequence of SEQ ID NO: 216, Repeat2 comprises or consists of a sequence of SEQ ID NO: 215;
Repeat1 comprises or consists of a sequence of SEQ ID NO: 216, Repeat2 comprises or consists of a sequence of SEQ ID NO: 213;
Repeat1 comprises or consists of a sequence of SEQ ID NO: 218, Repeat2 comprises or consists of a sequence of SEQ ID NO: 216;
Repeat1 comprises or consists of a sequence of SEQ ID NO: 217, Repeat2 comprises or consists of a sequence of SEQ ID NO: 216;
Repeat1 comprises or consists of a sequence of SEQ ID NO: 216, Repeat2 comprises or consists of a sequence of SEQ ID NO: 453; and
Repeat1 comprises or consists of a sequence of SEQ ID NO: 217, Repeat2 comprises or consists of a sequence of SEQ ID NO: 215.

In certain embodiments, r, x and y are 0, s is an integer selected from 1 to 30, and Repeat1 comprises or consists of a sequence of SEQ ID NO: 213.

In certain embodiments, y is 0, r, s and x are independently an integer selected from 1 to 30, and Repeat1, Repeat2 and Repeat3 are a combination selected from the group consisting of:
Repeat1 comprises or consists of a sequence of SEQ ID NO: 216, Repeat2 comprises or consists of a sequence of SEQ ID NO: 218; and Repeat3 comprises or consists of a sequence of SEQ ID NO: 216;
Repeat1 comprises or consists of a sequence of SEQ ID NO: 216, Repeat2 comprises or consists of a sequence of SEQ ID NO: 215; and Repeat3 comprises or consists of a sequence of SEQ ID NO: 216;
Repeat1 comprises or consists of a sequence of SEQ ID NO: 217, Repeat2 comprises or consists of a sequence of SEQ ID NO: 215; Repeat3 comprises or consists of a sequence of SEQ ID NO: 216;
Repeat1 comprises or consists of a sequence of SEQ ID NO: 217, Repeat2 comprises or consists of a sequence of SEQ ID NO: 216; Repeat3 comprises or consists of a sequence of SEQ ID NO: 215;
Repeat1 comprises or consists of a sequence of SEQ ID NO: 213, Repeat2 comprises or consists of a sequence of SEQ ID NO: 227; Repeat3 comprises or consists of a sequence of SEQ ID NO: 216,
Repeat1 comprises or consists of a sequence of SEQ ID NO: 216, Repeat2 comprises or consists of a sequence of SEQ ID NO: 453; Repeat3 comprises or consists of a sequence of SEQ ID NO: 213,
Repeat1 comprises or consists of a sequence of SEQ ID NO: 216, Repeat2 comprises or consists of a sequence of SEQ ID NO: 213; Repeat3 comprises or consists of a sequence of SEQ ID NO: 216, and
Repeat1 comprises or consists of a sequence of SEQ ID NO: 216, Repeat2 comprises or consists of a sequence of SEQ ID NO: 213; Repeat3 comprises or consists of a sequence of SEQ ID NO: 453.

In certain embodiments, r, s, x and y are independently an integer selected from 1 to 30, and Repeat1, Repeat2, Repeat 3 and Repeat 4 are a combination selected from the group consisting of:
Repeat1 comprises or consists of a sequence of SEQ ID NO: 216, Repeat2 comprises or consists of a sequence of SEQ ID NO: 219; Repeat3 comprises or consists of a sequence of SEQ ID NO: 215, and Repeat4 comprises or consists of a sequence of SEQ ID NO: 216;
Repeat1 comprises or consists of a sequence of SEQ ID NO: 213, Repeat2 comprises or consists of a sequence of SEQ ID NO: 453; Repeat3 comprises or consists of a sequence of SEQ ID NO: 213, and Repeat4 comprises or consists of a sequence of SEQ ID NO: 216,
Repeat1 comprises or consists of a sequence of SEQ ID NO: 216, Repeat2 comprises or consists of a sequence of SEQ ID NO: 453; Repeat3 comprises or consists of a sequence of SEQ ID NO: 213, and Repeat4 comprises or consists of a sequence of SEQ ID NO: 216,
Repeat1 comprises or consists of a sequence of SEQ ID NO: 216, Repeat2 comprises or consists of a sequence of SEQ ID NO: 227; Repeat3 comprises or consists of a sequence of SEQ ID NO: 216, and Repeat4 comprises or consists of a sequence of SEQ ID NO: 213, and
Repeat1 comprises or consists of a sequence of SEQ ID NO: 216, Repeat2 comprises or consists of a sequence of SEQ ID NO: 213; Repeat3 comprises or consists of a sequence of SEQ ID NO: 476, and Repeat4 comprises or consists of a sequence of SEQ ID NO: 453.

In certain embodiments, the polypeptide linker comprises an amino acid sequence selected from the group consisting of: a) SEQ ID NOs: 1-59, 61-88, 90-197, 199-212, and 454-471, or a variant thereof; b) SEQ ID NOs: 1-59, 61-88, 90-93, 454-459, and 463-471, or a variant thereof; c) SEQ ID NOs: 94-156, or a variant thereof; d) SEQ ID NOs: 210-212, and 460-462, or a variant thereof, or e) SEQ ID NOs: 157-197, and 199-209, or a variant thereof.

In certain embodiments, the fusion polypeptide comprises up to two conjugatable residue.

In certain embodiments, the fusion polypeptide comprises a first conjugatable residue which is present in one of the GLP-1, the GDF15, and the polypeptide linker.

In certain embodiments, the fusion polypeptide comprises a second conjugatable residue which is present in one of the GLP-1, the GDF15, and the polypeptide linker.

In certain embodiments, the fusion polypeptide comprises a first conjugatable residue and a second conjugatable residue, wherein:
1) both conjugatable residues are present in the linker,
2) both conjugatable residues are present in the GLP-1,
3) both conjugatable residues are present in the GDF15,
4) the first conjugatable residue is present in the GLP-1 and the second conjugatable residue is present in the linker,
5) the first conjugatable residue is present in the GDF15 and the second conjugatable residue is present in the linker, or
6) the first conjugatable residue is present in the GLP-1 and the second conjugatable residue is present in the GDF15.

In certain embodiments, the GLP-1 comprises up to two conjugatable residues or up to one conjugatable residue.

In certain embodiments, the conjugatable residue(s) in the GLP-1 comprises or consists of lysine.

In certain embodiments, the conjugatable residue(s) in the GLP-1 comprises or consists of K26 and/or K34.

In certain embodiments, the GLP-1 further comprises substitution of K26 and/or K34 to a non-conjugatable residue.

In certain embodiments, the GLP-1 comprises substitution of K26 and/or K34 to a residue selected from the group consisting of Arginine (R), Glutamine (Q), Alanine (A), Glycine (G), Histidine (H), Serine (S), and Threonine (T).

In certain embodiments, the substitution of K26 is selected from K26R and K26Q, and/or the substitution at K34 is selected from K34R and K34Q.

In certain embodiments, the conjugatable residue(s) in the GLP-1 comprises an introduced residue, optionally by substitution of a non-conjugatable residue to a conjugatable residue, or by insertion of a conjugatable residue.

In certain embodiments, the conjugatable residue(s) in the GLP-1 comprises or consists of lysine and is introduced by a substitution selected from the group consisting of: E27K, and R36K relative to SEQ ID NO: 242.

In certain embodiments, the conjugatable residue(s) in the GLP-1 comprises or consists of cysteine or a non-natural amino acid.

In certain embodiments, the conjugatable residue(s) in the GLP-1 comprises or consists of cysteine and is introduced by a substitution at a position selected from the group consisting of: K26C, K34C, E27C and R36C, relative to SEQ ID NO: 242.

In certain embodiments, the GLP-1 comprises no conjugatable residue.

In certain embodiments, the GLP-1 comprises an amino acid sequence of $X_7X_8$EGTFTSDVSSYLE$X_{22}$QAA$X_{26}X_{27}$FIAWLV$X_{34}$GX$_{36}$G (SEQ ID NO: 325), wherein: the $X_7$ is H, imidazole-4-acetate (IA), imidazolepropionic acid (IPA); the $X_8$ is A, G, S, V, Aib, T, I, or L; the $X_{22}$ is G, or E; the $X_{26}$ is K, R, or C; the $X_{27}$ is E, K, or C; the $X_{34}$ is R, K, or C, and the $X_{36}$ is K, R, G, or C.

In certain embodiments, the $X_7$ is H, $X_8$ is G, the $X_{22}$ is E; the $X_{26}$ is K, R or C; the $X_{27}$ is E; the $X_{34}$ is K or R, and the $X_{36}$ is K, or G.

In certain embodiments, the GLP-1 comprises an amino acid sequence selected from the group consisting of: SEQ ID NO: 242, SEQ ID NO: 243, SEQ ID NO: 244, SEQ ID NO: 245, SEQ ID NO: 336, SEQ ID NO: 448 and SEQ ID NO: 478.

In certain embodiments, the GDF15 comprises no conjugatable residue.

In certain embodiments, the conjugatable residue comprises or consists of lysine.

In certain embodiments, the GDF15 comprises or consists substitutions of K91 and K107, relative to SEQ ID NO: 248.

In certain embodiments, the GDF15 comprises substitutions at K91, and K107, to a non-conjugatable residue optionally selected from the group consisting of Arginine (R), Glutamine (Q), Alanine (A), Glycine (G), Histidine (H), Serine (S), and Threonine (T).

In certain embodiments, the GDF15 further comprises substitutions at K62 and/or K69.

In certain embodiments, the GDF15 comprises K62 and/or K69.

In certain embodiments, the GDF15 comprises up to two or up to one conjugatable residue.

In certain embodiments, the conjugatable residue in GDF15 comprises K91, K107, or an introduced conjugatable residue selected from the group consisting of lysine, cysteine and non-natural amino acid. In certain embodiments, the GDF15 comprises an amino acid sequence of SEQ ID NO: 291 or SEQ ID NO: 358.

In certain embodiments, the fusion polypeptide comprises or consisting of an amino acid sequence selected from the group consisting of SEQ ID NOs: 349 and 350.

In certain embodiments, the GDF15 comprises or consists of combination of substitutions selected from the group consisting of: 1) N3Q, M57L, K69R, K107R, and K91R; 2) N3Q, K69R, K107R, and K91R; 3) K69R, K107R, and K91R; 4) N3Q, M57L, K107R, and K91R; 5) N3Q, K107R, and K91R; 6) K107R, and K91R; 7) K62R, K69R, K107R, and K91R, N3Q, and M57L; 8) K62R, K69R, K107R, K91R, and N3Q; 9) K62R, K69R, K107R, and K91R, and 10) N3Q, M57L, K69R, and K91R, 11) del 1-3 and M57L, 12) N3Q, M57L, M86L, K69R, K107R, K91R, 13) N3Q and M57L, 14) M57L, and 15) M57L, K69R, K107R, K91R.

In certain embodiments, the GDF15 comprises an amino acid sequence selected from the group consisting of: SEQ ID NO: 246, SEQ ID NO: 247, SEQ ID NO: 248, SEQ ID NOs: 290-297, SEQ ID NO: 358, SEQ ID NO: 271, and SEQ ID NO: 451, SEQ ID NO: 479 and SEQ ID NO: 480.

In certain embodiments, the polypeptide linker comprises a first conjugatable residue, and optionally, a second conjugatable residue.

In certain embodiments, the first conjugatable residue and/or the second conjugatable residue in the polypeptide linker is/are at least 2 amino acid residue away from the most N-terminal residue of the GDF15.

In certain embodiments, the first conjugatable residue and/or the second conjugatable residue is/are at least 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61. 62, 63, 64, 65, 66, 67, 68, 69. 70, 71, 72, 73, 74, 75, or 76 amino acid residue away (inclusive of the conjugatable residue) from the most N-terminal residue of the GDF15, and optionally the first conjugatable residue and/or the second conjugatable residue is/are in the polypeptide linker.

In certain embodiments, the polypeptide linker comprises or consists of an amino acid sequence selected from the group consisting of SEQ ID NOs: 1-59, 61-88, 90-93, 454-459, and 463-471, except for one or two substitution to the conjugatable residue at a position ranging from the $1^{st}$ to the $78^{th}$, $1^{st}$ to the $72^{nd}$, $1^{st}$ to the $60^{th}$, $1^{st}$ to the $50^{th}$, $1^{st}$ to the $40^{th}$, $1^{st}$ to the $38^{th}$, $1^{st}$ to the $32^{nd}$, $1^{st}$ to the $24^{th}$, $1^{st}$ to the $16^{th}$, $4^{th}$ to the $72^{nd}$, $4^{th}$ to the $60^{th}$, $4^{th}$ to the $50^{th}$, $4^{th}$ to the $40^{th}$, $4^{th}$ to the $38^{th}$, $4^{th}$ to the $32^{nd}$, $4^{th}$ to the $24^{th}$, $4^{th}$ to the $16^{th}$, $16^{th}$ to the $72^{nd}$, $16^{th}$ to the $60^{th}$, $16^{th}$ to the $50^{th}$, $16^{th}$ to the $40^{th}$, $16^{th}$ to the $38^{th}$, $16^{th}$ to the $32^{nd}$, $16^{th}$ to the $24^{th}$, $24^{th}$ to the $72^{nd}$, $24^{th}$ to the $60^{th}$, $24^{th}$ to the $50^{th}$, $24^{th}$ to the $40^{th}$, $24^{th}$ to the $38^{th}$, $24^{th}$ to the $32^{nd}$, the $5^{th}$ to the $73^{rd}$, the $17^{th}$ to the $73^{rd}$, the $25^{th}$ to the $73^{rd}$, the $33^{rd}$ to the $73^{rd}$, the $39^{th}$ to the $73^{rd}$, the $41^{st}$ to the $73^{rd}$, the $51^{st}$ to the $73^{rd}$, the $5^{th}$ to the $51^{st}$, the $17^{th}$ to the $51^{st}$, the $25^{th}$ to the $51^{st}$, the $33^{rd}$ to the $51^{st}$, the $39^{th}$ to the $51^{st}$, the $41^{st}$ to the $51^{st}$, the $5^{th}$ to the $41^{st}$, the $17^{th}$ to the $41^{st}$, the $25^{th}$ to the $41^{st}$, the $33^{rd}$ to the $41^{st}$, the $39^{th}$ to the $41^{st}$, the $5^{th}$ to the $39^{th}$, the $17^{th}$ to the $39^{th}$, the $25^{th}$ to the $39^{th}$, the $33^{rd}$ to the $39^{th}$, the $5^{th}$ to the $33^{rd}$, the $17^{th}$ to the $33^{rd}$, the $25^{th}$ to the $33^{rd}$, the $5^{th}$ to the $25^{th}$, the $17^{th}$ to the $25^{th}$, or the $5^{th}$ to the $17^{th}$ residue in the amino acid sequence.

In certain embodiments, the polypeptide linker comprises or consists of an amino acid sequence selected from the group consisting of: SEQ ID NOs: 94-156, except for one or two substitution to the conjugatable residue at a position ranging from the $1^{st}$ to the $58^{th}$, $1^{st}$ to the $52^{nd}$, $1^{st}$ to the $45^{th}$, $1^{st}$ to the $40^{th}$, $1^{st}$ to the $30^{th}$, $1^{st}$ to the $25^{th}$, or $1^{st}$ to the $20^{th}$ residue in the amino acid sequence.

In certain embodiments, the polypeptide linker comprises or consists of an amino acid sequence selected from the group consisting of: SEQ ID NOs: 157-197 and 199-209, except for one or two substitutions to the conjugatable residue at a position ranging from the $1^{st}$ to the $38^{th}$, $1^{st}$ to the $32^{nd}$, $1^{st}$ to the $30^{th}$, $1^{st}$ to the $25^{th}$, or $1^{st}$ to the $20^{th}$ residue in the amino acid sequence.

In certain embodiments, the polypeptide linker comprises or consists of an amino acid sequence selected from the group consisting of: SEQ ID NOs: 210-212, 460-462, and 458-459, except for one or two substitution to the conjugatable residue at a position at least 2, 5, 6, 7, 8, 9, 10, 11, 12, 13, 14, 15, 16, 17, 18, 19, 20, 21, 22, 23, 24, 25, 26, 27, or 28, 29, or 30 amino acid residues away from the most N-terminal residue of the GDF15.

In certain embodiments, the conjugatable residue in the polypeptide linker comprises lysine, cysteine, or a non-natural amino acid.

In certain embodiments, the polypeptide linker comprises or consists of an amino acid sequence selected from the group consisting of: SEQ ID NOs: 298-324, 60, 89, 198, 332, 333, 334, 342-346, 409-447, 475 and 483, or a variant thereof in which the lysine residue in the polypeptide linker is substituted with a cysteine residue or a non-natural amino acid, or in which the cysteine residue in the polypeptide linker is substituted with a lysine residue or a non-natural amino acid.

In certain embodiments, the conjugatable residue in the polypeptide linker comprises lysine, and the polypeptide linker comprises or consists of an amino acid sequence selected from the group consisting of: SEQ ID NOs: 298-324, 60, 89, 198, 332, 333, 334, 342-346, 409-410, 414-417, and 426-429.

In certain embodiments, the GDF15 comprises an amino acid sequence selected from the group consisting of: SEQ ID NO: 246, SEQ ID NOs: 290-293, 295-297, SEQ ID NO: 358, SEQ ID NO: 451, SEQ ID NO: 479 and SEQ ID NO: 480, and/or the GLP-1 comprises an amino acid sequence selected from the group consisting of: SEQ ID NO: 243, SEQ ID NO: 244, SEQ ID NO: 245, SEQ ID NO: 448 and SEQ ID NO: 478.

In certain embodiments, the fusion polypeptide comprises an amino acid sequence selected from the group consisting of: SEQ ID NOs: 252, 254-260, 262-265, 273-289, 327-330, 337-341, 354, 356-357, 359-361, 363-365, 370-373, and 385-386, 390-391.

In certain embodiments, the conjugatable residue in the polypeptide linker comprises cysteine, and the polypeptide linker comprises or consists of an amino acid sequence selected from the group consisting of: SEQ ID NOs: 411-413, 418-425, 430-447 475, and 483.

In certain embodiments, the GDF15 comprises an amino acid sequence selected from the group consisting of: SEQ ID NO: 247, SEQ ID NO: 248, SEQ ID NO: 294, and SEQ ID NO: 271, and/or the GLP-1 comprises an amino acid sequence selected from the group consisting of: SEQ ID NO: 242, SEQ ID NO: 243, SEQ ID NO: 244, SEQ ID NO: 245, SEQ ID NO: 336, SEQ ID NO: 448 and SEQ ID NO: 478.

In certain embodiments, the fusion polypeptide comprises an amino acid sequence selected from the group consisting of: SEQ ID NOs: 367-369, 374-381, 392-400, 402-408, 472-473, 477, 481 and 482.

In certain embodiments, the polypeptide linker comprises no conjugatable residue.

In certain embodiments, the polypeptide linker comprises an amino acid sequence selected from the group consisting of SEQ ID NOs: 5, 9, 33, 51, 58, 64, 18, 91, 157, 158, 159, 116, 210, 211 and 461.

In certain embodiments, fusion polypeptide comprises an amino acid sequence comprising or consisting of: SEQ ID NOs: 249, 266-270, 347, 383 and 387.

In certain embodiments, the fusion polypeptide comprises up to one conjugatable residue for acylation, and comprises an amino acid sequence selected from the group consisting of: SEQ ID NOs: 249, 251-260, 262-265, 273-289, 326, 329-331, 337-341, 349, 350, 354-357, 359-365, 370-373, 385-386, and 390-391.

In certain embodiments, the fusion polypeptide comprises up to one conjugatable residue for alkylation, and comprises an amino acid sequence selected from the group consisting of: SEQ ID NOs: 366-369, 374-381, 392-408, 472-473, 477, 481 and 482.

In certain embodiments, the fusion polypeptide comprises up to two conjugatable residues, and comprises an amino acid sequence selected from the group consisting of: SEQ ID NOs: 327-328, 352-353, and 361.

In certain embodiments, the GLP-1 comprises an amino acid sequence of SEQ ID NO: 243 or SEQ ID NO: 336, the GDF15 comprises an amino acid sequence of SEQ ID NO: 247, and a polypeptide linker.

In certain embodiments, the fusion polypeptide comprises an amino acid sequence selected from the group consisting of: SEQ ID NOs: 249, 266, 267, 268, 269, 270, 347, 251, 260, 263-265, 273, 277, 329-330, 359, 369, 374, 376-381, and 392-408.

In a second aspect, the present disclosure provides a polypeptide complex comprising a dimer of the fusion polypeptide of the first aspect of the present disclosure.

In certain embodiments, the polypeptide complex is a homo-dimer.

In certain embodiments, the dimer is associated with a disulfide bond.

In certain embodiments, the disulfide bond is formed between the second polypeptide fragments comprising the GDF15.

In a third aspect, the present disclosure provides a polynucleotide encoding the fusion polypeptide of the first aspect of the present disclosure or the polypeptide complex of the second aspect of the present disclosure.

In a fourth aspect, the present disclosure provides a vector comprising the polynucleotide of the third aspect of the present disclosure.

In a fifth aspect, the present disclosure provides a host cell comprising the vector of the fourth aspect of the present disclosure.

In certain embodiments, the host cell is a prokaryotic cell or eukaryotic cell.

In a sixth aspect, the present disclosure provides a method of producing the polypeptide complex of the second aspect of the present disclosure, comprising culturing the host cell of the fifth aspect of the present disclosure under a condition that allows expression of the polynucleotide of the third aspect of the present disclosure.

In certain embodiments, the host cell is prokaryotic cell or a eukaryotic cell.

In certain embodiments, the polypeptide complex is expressed as inclusion bodies.

In certain embodiments, the method further comprises renaturing the polypeptide complex from the inclusion bodies.

In a seventh aspect, the present disclosure provides a conjugate comprising the fusion polypeptide of the first aspect and at least one clearance-reducing moiety (CRM), wherein the at least one CRM is conjugated to at least one conjugatable residue on the fusion polypeptide.

In certain embodiments, the fusion polypeptides comprises two or no more than two conjugatable residues, each of which is conjugated to a CRM.

In an eighth aspect, the present disclosure provides a conjugate comprising the polypeptide complex of the second aspect and at least two clearance-reducing moieties (CRMs), wherein the at least two CRM are conjugated respectively to one of the conjugatable residues on the polypeptide complex.

In certain embodiments, the polypeptide complex comprises four and no more than four conjugatable residues, each of which is conjugated to a CRM.

In certain embodiments, the CRM comprises a plasma protein-binding moiety, a polymer, Fc, HSA (albumin), Xten sequence, or PAS sequence.

In certain embodiments, the CRM comprises an albumin-binding moiety.

In certain embodiments, the albumin-binding moiety comprises a structure of: *-A-B-C-D-E, wherein A, B, C, D and E are interconnected via amide bonds, and the * end of A is connected to a reactive group of the conjugatable residue on the polypeptide complex, and wherein:

A is selected from a bond,

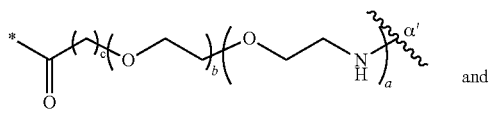 and

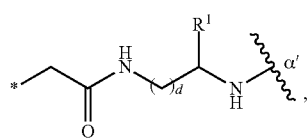

a, b, c and d are independently an integer from 0 to 4, $R^1$ is hydrogen or —COOH;

B is selected from a bond,

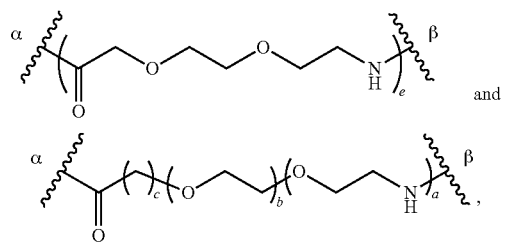

e is an integer from 1 to 4, wherein position α is linked to the position α',

C is a bond or

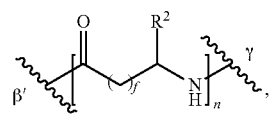

$R^2$ is —CH$_2$SO$_3$H or —COOH, f is an integer from 1 to 4, n is an integer from 1 to 25, wherein when B is not bond, then position β' is linked to position β, or when B is bond, then position β' is linked to position α';

D is selected from a bond,

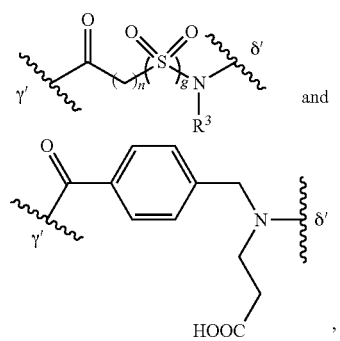

g and h are independently 0 or 1, and $R^3$ is H or —CH$_2$COOH, wherein:

when B is not a bond and C is a bond, then position γ' is linked to position β;

when C is not a bond, then position γ' is linked to position γ; and when B is a bond and C is a bond, then position γ' is linked to position α'; E is an acidic group having a formula:

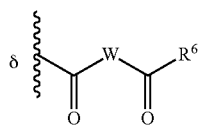 (I)

wherein W represents —(CR$^4$R$^5$)$_l$—,

R$^4$ and R$^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide, R$^6$ is selected from hydroxyl or NR$^7$R$^8$;

R$^7$ and R$^8$ are independently selected from the group consisting of hydrogen, alkyl, hydroxyl, and

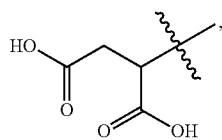 [SMILES: *C(CC(=O)O)C(=O)O]

and l is an integer from 10 to 20, and wherein:
when D is not a bond, then position δ is linked to position δ',
when C is not a bond and D is a bond, then position δ is linked to position γ,
when B is not a bond, C is a bond and D is a bond, then position δ is linked to position β,
when A is not a bond, and all of B, C, and D are bond, then position δ is linked to position α'.

In certain embodiments, wherein the CRM is conjugated to a lysine residue, optionally the lysine residue is in the polypeptide linker or in the GLP-1 or in the GDF15.

In certain embodiments, A is a bond.

In certain embodiments, A is a bond, and B is a bond or

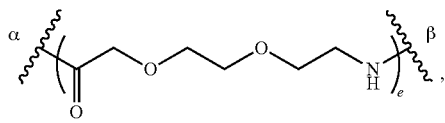

wherein e is 1, 2 or 3.

In certain embodiments, A is a bond, B is

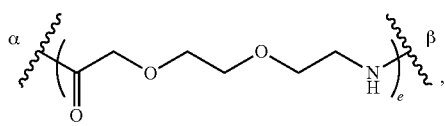

and C is

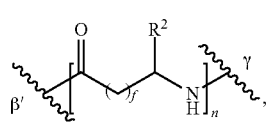

wherein e is 1, 2 or 3, f is 1, 2, or 3, and n is 1 or 2, wherein position β' is linked to position β. In certain embodiments, D is a bond, and E is an acidic group having a formula:

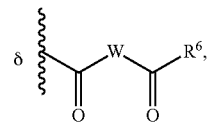

wherein position δ is linked to position γ. In certain embodiments, R$^2$ is —COOH, and R$^6$ is hydroxyl. In certain embodiments, W represents —(CR$^4$R$^5$)$_l$—, R$^4$ and R$^5$ are independently hydrogen, l is an integer from 10 to 20.

In certain embodiments, A is a bond, B is a bond, and C is a bond.

In certain embodiments, A is a bond, B is a bond, and C is

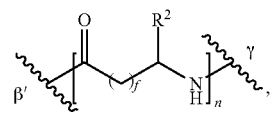

wherein f is 1, 2, or 3, and n is 1 or 2, and the position β' is linked to position β.

In certain embodiments, A is

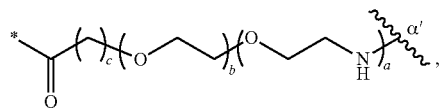

wherein a is 1, 2 or 3, b is 1, 2 or 3, and c is 1 or 2.

In certain embodiments, A is

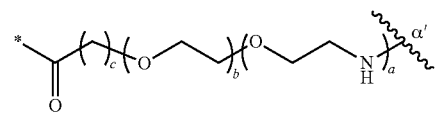

and B is

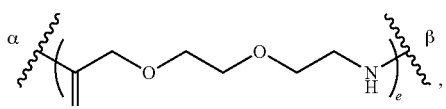

wherein a is 1, 2 or 3, b is 1, 2 or 3, c is 1 or 2, and e is 1, 2 or 3, wherein position α is linked to the position α'.

In certain embodiments, A is

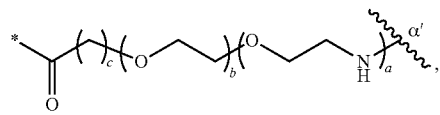

B is

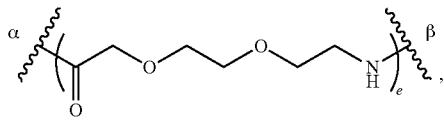

wherein position α is linked to the position α', and C is

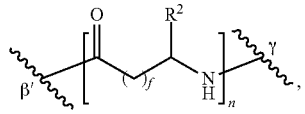

wherein a is 1, 2 or 3, b is 1, 2 or 3, c is 1 or 2, e is 1, 2 or 3, f is 1, 2, or 3, and n is 1 or 2, wherein position β' is linked to position β.

In certain embodiments, A is

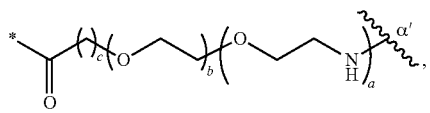

B is

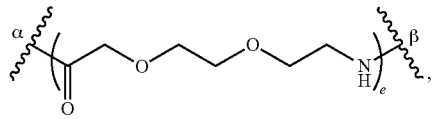

wherein position α is linked to the position α', and C is bond, wherein a is 1, 2 or 3, b is 1, 2 or 3, c is 1 or 2, and e is 1, 2 or 3.

In certain embodiments, A is

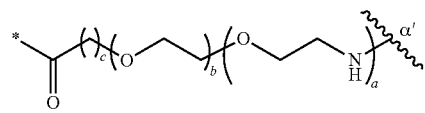

and B is a bond, wherein a is 1, 2 or 3, b is 1, 2 or 3, and c is 1 or 2.

In certain embodiments, A is

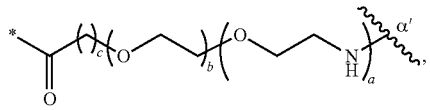

B is a bond, and C is

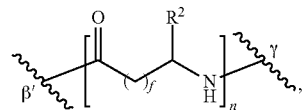

wherein a is 1, 2 or 3, b is 1, 2 or 3, c is 1 or 2, f is 1, 2, or 3, and n is 1 or 2, wherein position β' is linked to position α'.

In certain embodiments, A is

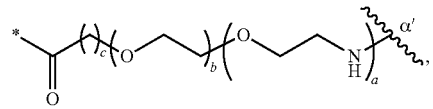

B is a bond, and C is a bond, wherein a is 1, 2 or 3, b is 1, 2 or 3, and c is 1 or 2.

In certain embodiments, D is a bond.

In certain embodiments, A is

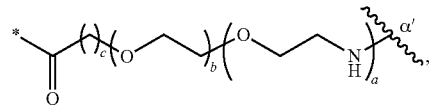

B is

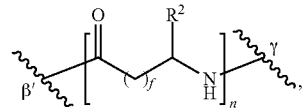

wherein position α is linked to the position α', C is

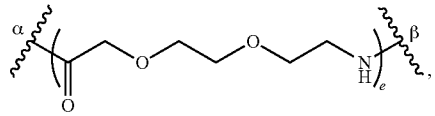

wherein position β' is linked to position β, and D is a bond, wherein a is 1, 2 or 3, b is 1, 2 or 3, c is 1 or 2, e is 1, 2 or 3, f is 1, 2, or 3, and n is 1 or 2.

In certain embodiments, D is

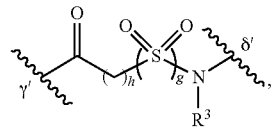

wherein g is 0 or 1, and h is 0 or 1.

In certain embodiments, A is

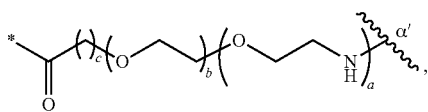

B is a bond or

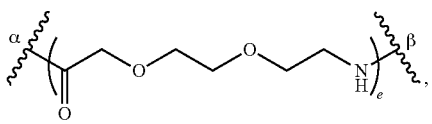

wherein when B is not a bond, position α is linked to the position α', C is a bond, and D is

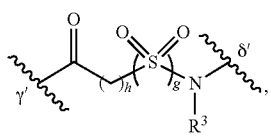

wherein a is 1, 2 or 3, b is 1, 2 or 3, c is 1 or 2, e is 1, 2 or 3, g is 0 or 1, and h is 0 or 1, wherein when B is not a bond, then position γ' is linked to position β, or when B is a bond, then position γ' is linked to position α'.

In certain embodiments, D is

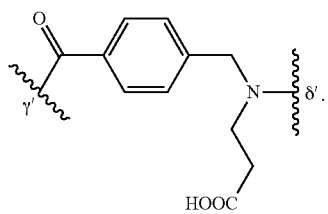 [SMILES: *C(=O)c1ccc(CN(*)CCC(=O)O)cc1]

In certain embodiments, A is

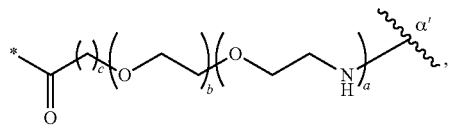

B is

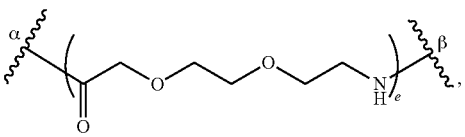

wherein position α is linked to the position α', C is a bond or

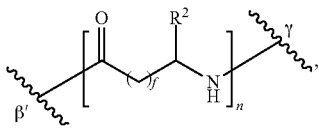

wherein when C is not a bond, then position β' is linked to position β; and D is

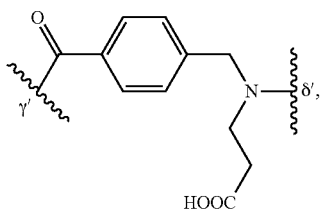

wherein a is 1, 2 or 3, b is 1, 2 or 3, c is 1 or 2, e is 1, 2 or 3, f is 1, 2, or 3, and n is 1 or 2, wherein when C is not a bond, then position γ' is linked to position γ, or when C is a bond, then position γ' is linked to position β.

In certain embodiments, the CRM comprises the structure of below formula:

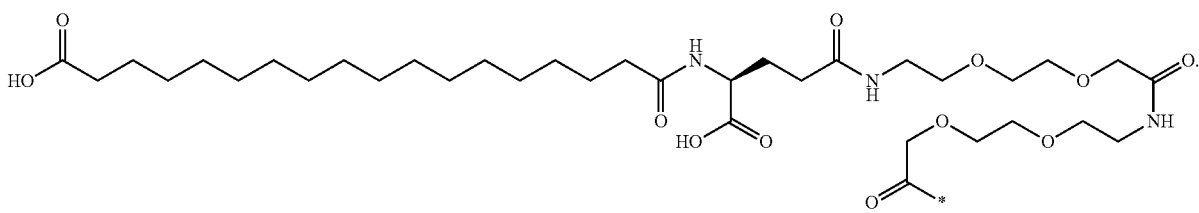 [SMILES: *C(=O)COCCOCCNC(=O)COCCOCCNC(=O)CC[C@H](NC(=O)CCCCCCCCCCCCCCCCC(=O)O)C(=O)O]

In certain embodiments, the CRM is conjugated to a cysteine residue, optionally the cysteine residue is in the polypeptide linker or in the GLP-1 or in the GDF15.

In certain embodiments, A is

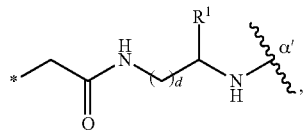

and B is

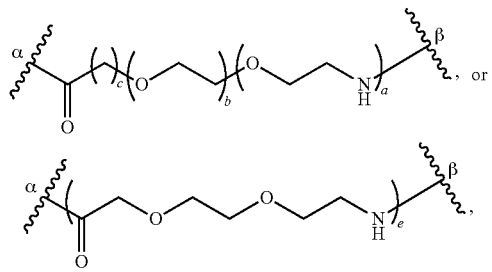

wherein position α is linked to the position α', wherein a is 1, 2 or 3, b is 1, 2 or 3, c is 1 or 2, d is 1, 2, or 3, e is 1, 2 or 3, $R^1$ is hydrogen or —COOH.

In certain embodiments, A is

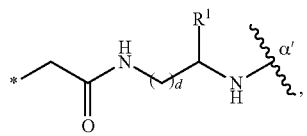

B is

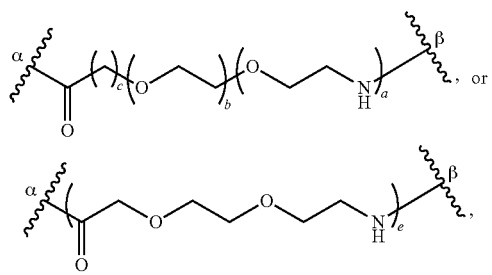

wherein position α is linked to the position α', and C is

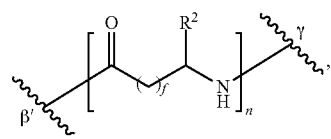

wherein β' is linked to position β, wherein a is 1, 2 or 3, b is 1, 2 or 3, c is 1 or 2, d is 1, 2, or 3, f is 1, 2, or 3, and n is 1 or 2. In certain embodiments, D is a bond, and E is an acidic group having a formula:

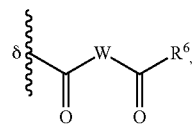

wherein position δ is linked to position γ. In certain embodiments, $R^2$ is —COOH, and $R^6$ is hydroxyl. In certain embodiments, W represents —$(CR^4R^5)_l$—, $R^4$ and $R^5$ are independently hydrogen, l is an integer from 10 to 20.

In certain embodiments, A is

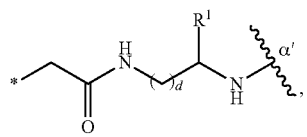

B is

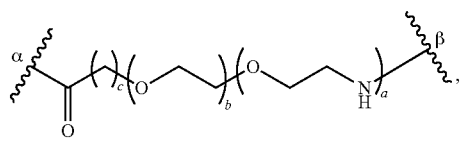

wherein position α is linked to the position α', C is

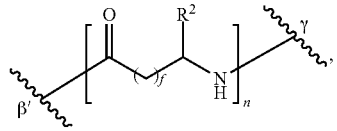

wherein position β' is linked to position β, and D is a bond, wherein a is 1, 2 or 3, b is 1, 2 or 3, c is 1 or 2, d is 1, 2, or 3, f is 1, 2, or 3, and n is 1 or 2.

In certain embodiments, A is

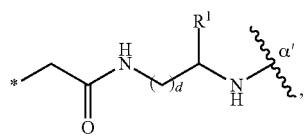

and B is

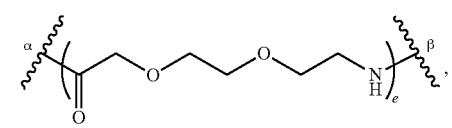

wherein d is 1, 2, or 3, and e is 1, 2 or 3, wherein position α is linked to the position α'.

In certain embodiments, A is

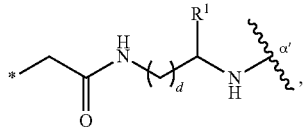

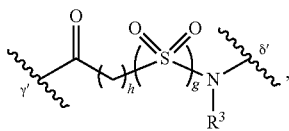

wherein position γ' is linked to position β, wherein d is 1, 2, or 3, e is 1, 2 or 3, g is 0 or 1, and h is 0 or 1.

In certain embodiments, the CRM comprises the structure of below formula:

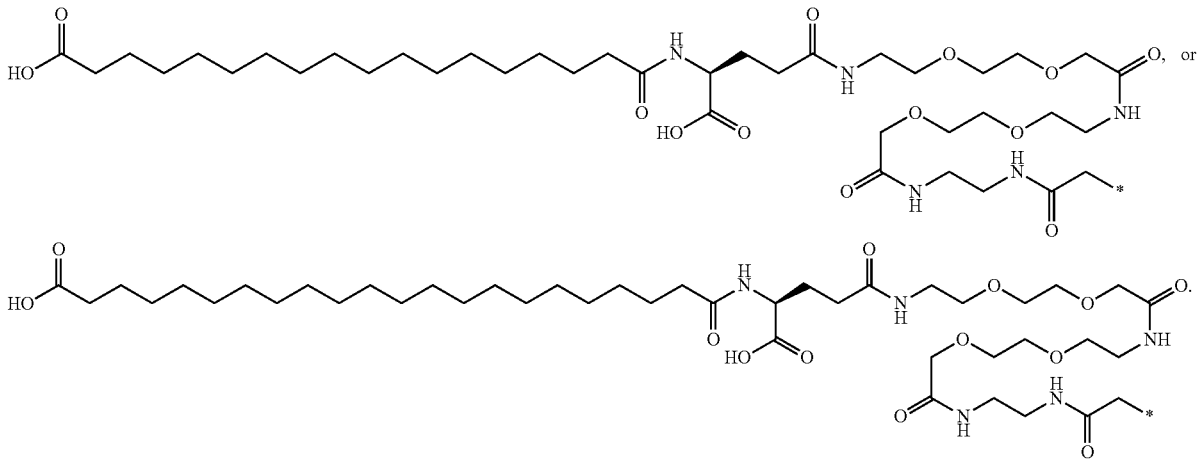

B is

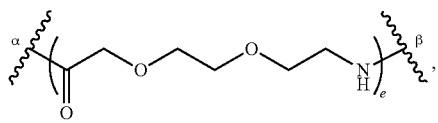

wherein position α is linked to the position α', and C is a bond, wherein d is 1, 2, or 3, and e is 1, 2 or 3.

In certain embodiments, A is

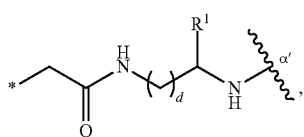

B is

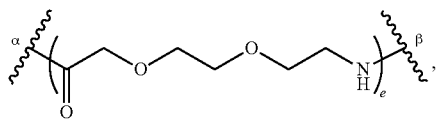

wherein position α is linked to the position α', C is a bond, and D is

In a ninth aspect, the present disclosure provides a pharmaceutical composition comprising the fusion polypeptide according to the first aspect, the polypeptide complex according to the second aspect, or the conjugate according to the seventh or eighth aspect, and a pharmaceutically acceptable salt.

In a tenth aspect, the present disclosure provides a method of producing the conjugate of the seventh or eighth aspect, comprising conjugating a clearance-reducing moiety to the fusion polypeptide of the first aspect or the polypeptide complex of the second aspect.

In a eleventh aspect, the present disclosure provides a method of preventing or treating a metabolic disorder in a subject in need thereof, comprising administering a therapeutically effective amount of the fusion polypeptide of the first aspect, the polypeptide complex of the second aspect, or the conjugate of the seventh or eighth aspect.

In certain embodiments, the metabolic disorder is diabetes, obesity, non-alcoholic steatohepatitis (NASH), cardiovascular disorders like dyslipidemia, atherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

Throughout the present disclosure, the articles "a," "an," and "the" are used herein to refer to one or to more than one (i.e., to at least one) of the grammatical object of the article. By way of example, "a fusion polypeptide" means one fusion polypeptide or more than one fusion polypeptides.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Similarly, ranges delimited by "at least" are understood to include the lower value provided and all higher numbers.

As used herein, "about" is understood to include within three standard deviations of the mean or within standard ranges of tolerance in the specific art. In certain embodiments, about is understood a variation of no more than 0.5.

The articles "a" and "an" are used herein to refer to one or more than one (i.e. to at least one) of the grammatical object of the article. By way of example, "an element" means one element or more than one element.

The term "including" is used herein to mean, and is used interchangeably with, the phrase "including but not limited to". Similarly, "such as" is used herein to mean, and is used interchangeably, with the phrase "such as but not limited to".

The term "or" is used inclusively herein to mean, and is used interchangeably with, the term "and/or," unless context clearly indicates otherwise.

BRIEF DESCRIPTION OF THE FIGURES

FIGS. 1A and 1B show body weight loss upon protein treatments from Day1 to Day15. FIG. 1C shows body weight loss on Day 15. Compared to Vehicle control: *, $p<0.05$; ***, $p<0.001$; ns, non-statistically significant; Compared to Semaglutide (JP51144): #, $p<0.05$; ###, $p<0.001$; unlabeled, non-statistically significant. FIGS. 1D and 1E show cumulative food intake with protein treatments from Day1 to Day15. FIG. 1F shows cumulative food intake on Day15. Vehicle: 1.42 mg/mL disodium phosphate dihydrate, 14 mg/mL propylene glycol pH7.4. Data are expressed as mean values and standard error (SEM) for FIGS. 1A, 1B and 1C. n=5 for each treatment group. For FIGS. 1D, 1E and 1F, a pooled food intake was measured for each treatment group.

FIG. 4A shows body weight loss upon protein treatments from Day1 to Day15. FIG. 4B shows body weight loss on Day 15. Compared to Vehicle control: *, $p<0.001$; ns, non-statistically significant; Compared to Semaglutide (JP51144): $$$, $p<0.001$. FIG. 4C shows cumulative food intake with protein treatments from Day1 to Day15. FIG. 4D shows glucose level on Day0, 7 and 14. Compared to Vehicle control: *, $p<0.001$. Data are expressed as mean values and standard error (SEM) for FIGS. 4A, 4B and 4D. n=5 for each treatment group. For FIG. 4C, a pooled food intake was measured for each treatment group.

FIGS. 5A and 5B show body weight loss upon protein treatments from Day1 to Day15. FIG. 5C shows body weight loss on Day 15. Compared to Vehicle control: *, $p<0.001$; , $p<0.01$; *, $p<0.05$; ns, non-statistically significant; FIGS. 5D and 5E show cumulative food intake with protein treatments from Day1 to Day15. FIG. 5F shows glucose level on Day 15. Compared to Vehicle control: *, $p<0.001$, $p<0.01$; *, $p<0.05$; ns, non-statistically significant. Data are expressed as mean values and standard error (SEM) for FIGS. 5A, 5B, 5C and 5F. n=5 for each treatment group. For FIGS. 5D and 5E, a pooled food intake was measured for each treatment group.

FIG. 6A shows body weight loss upon protein treatments. FIG. 6B shows cumulative food intake with protein treatments. FIG. 6C shows fasting glucose change upon treatment. FIGS. 6D and 6E show body weight change with dose titrations of MLC089 and MLC093 at 3, 10 and 30 nmol/kg. Data are expressed as mean values and standard error (SEM) for FIGS. 6A, 6C, 6D and 6E. n=5 for each treatment group. For FIG. 6B, a pooled food intake was measured for each treatment group.

FIG. 7A shows body weight loss upon protein treatments from Day1 to Day11. FIG. 7B shows cumulative food intake with protein treatments. Data are expressed as mean values and standard error (SEM) for FIG. 7A. n=5 for each treatment group. For FIG. 7B, a pooled food intake was measured for each treatment group.

FIG. 8A shows body weight loss upon protein treatments. FIG. 8B shows cumulative food intake with protein treatments. FIG. 8C shows fasting glucose level. FIGS. 8D-8F show body weight loss upon dose titrations of fusion protein conjugates. FIG. 8G shows plasma triglyceride concentrations in the terminal plasma on Day 15. 8H shows plasma ALT concentrations in the terminal plasma on Day 15. FIG. 8I shows liver triglyceride levels on Day 15. Data are expressed as mean values and standard error (SEM) for FIGS. 8A and 8C-I. n=5 for each treatment group. For FIG. 8B, a pooled food intake was measured for each treatment group.

FIG. 9A shows body weight loss upon protein treatments. FIG. 9B shows cumulative food intake with protein treatments. FIG. 9C shows fasting glucose change upon treatment. FIG. 9D shows plasma triglyceride concentrations in the terminal plasma on Day 22. FIG. 9E shows plasma cholesterol concentrations in the terminal plasma on Day 22. FIG. 9F shows plasma insulin concentrations in the terminal plasma on Day 22. FIG. 9G shows liver triglyceride levels on Day 22. Data are expressed as mean values and standard error (SEM) for FIGS. 9A and 9C-G. n=5 for each treatment group. For FIG. 9B, a pooled food intake was measured for each treatment group.

FIG. 10A shows body weight loss upon protein treatments. FIG. 10B shows cumulative food intake with protein treatment.

FIGS. 11A-11H show all the sequences disclosed in the present disclosure.

DETAILED DESCRIPTION

Figure 1A:
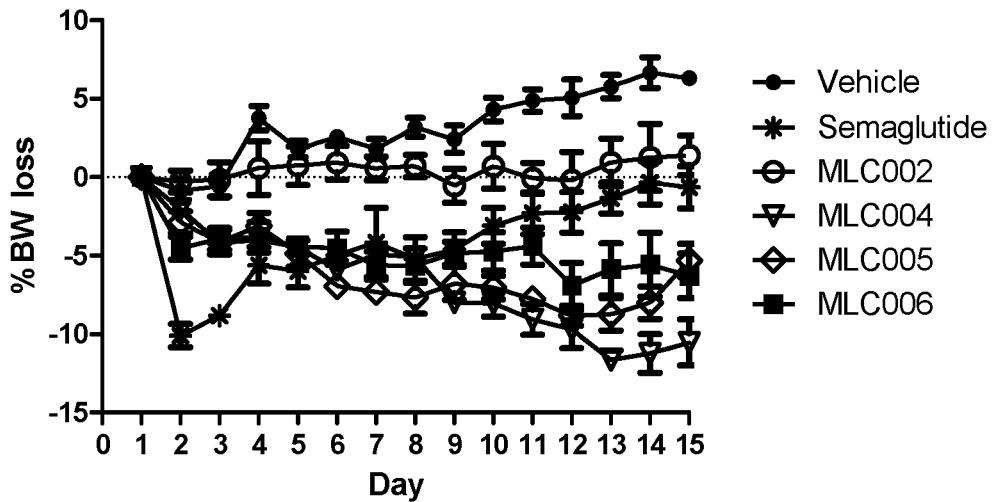
FIGS. 1A-1F show In vivo activities of fusion proteins. To evaluate the body weight and food intake effects of the fusion proteins, 10 week old male C57BL/6J mice were dosed everyday subcutaneously with 15 nmol/kg protein for 14 days. Food intake and body weight were measured daily.
Figure 1B:
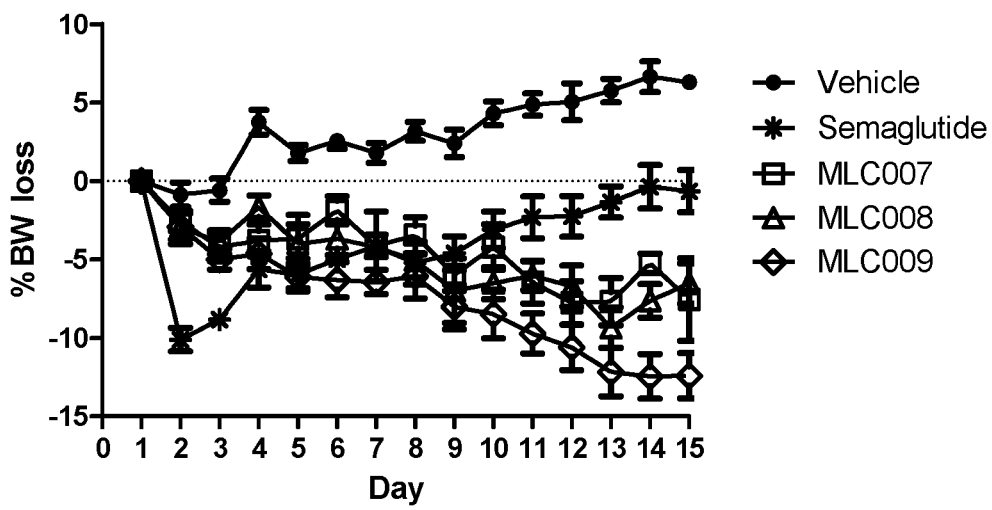
Figure 1C:
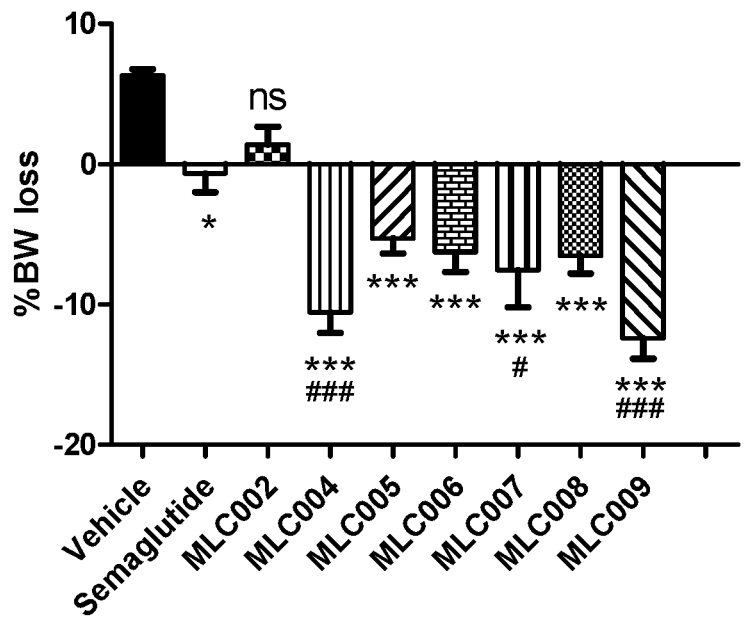
Figure 1D:
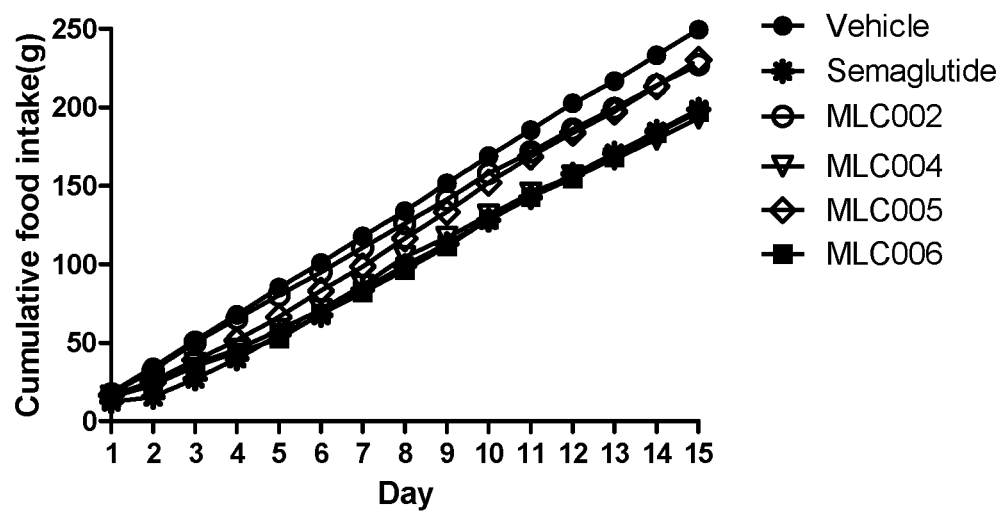
Figure 1E:
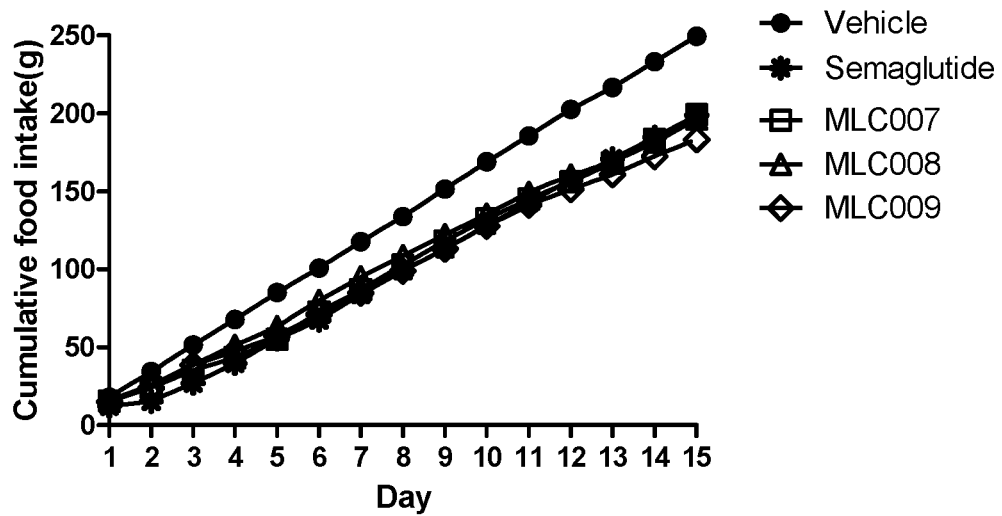
Figure 1F:
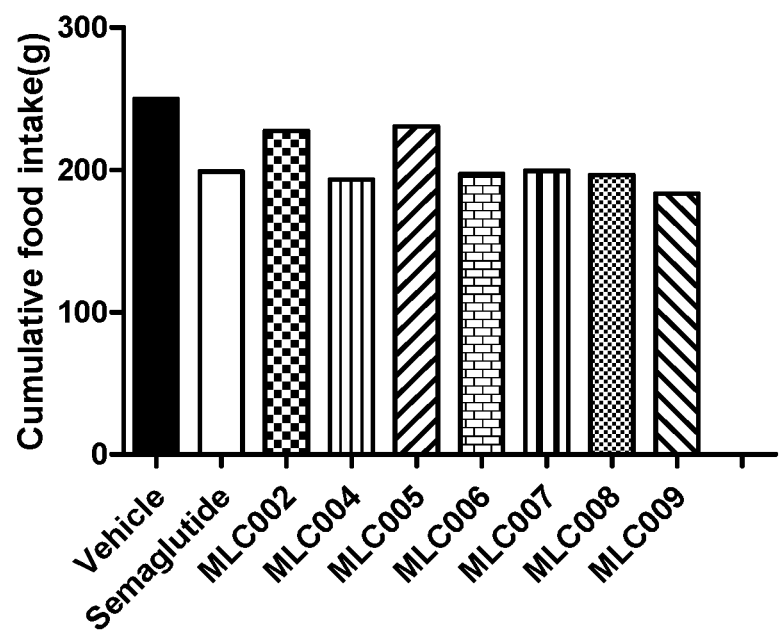

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein, including publications, patents and patent applications are incorporated herein by reference in their entirety.

Definitions

"Percent (%) sequence identity" is defined as the percentage of amino acid (or nucleic acid) residues in a candidate sequence that are identical to the amino acid (or nucleic acid) residues in a reference sequence, after aligning the sequences and, if necessary, introducing gaps, to achieve the maximum number of identical amino acids (or nucleic acids). In other words, percent (%) sequence identity of an amino acid sequence (or nucleic acid sequence) can be calculated by dividing the number of amino acid residues (or bases) that are identical relative to the reference sequence to which it is being compared by the total number of the amino acid residues (or bases) in the candidate sequence or in the reference sequence, whichever is shorter. Conservative substitution of the amino acid residues is not considered as identical residues. Alignment for purposes of determining percent amino acid (or nucleic acid) sequence identity can be achieved, for example, using publicly available tools such as BLASTN, BLASTp (available on the website of U.S. National Center for Biotechnology Information (NCBI), see also, Altschul S. F. et al, J. Mol. Biol., 215:403-410 (1990); Stephen F. et al, Nucleic Acids Res., 25:3389-3402 (1997)), ClustalW2 (available on the website of European Bioinformatics Institute, see also, Higgins D. G. et al, Methods in Enzymology, 266:383-402 (1996); Larkin M. A. et al, Bioinformatics (Oxford, England), 23(21): 2947-8 (2007)), and ALIGN or Megalign (DNASTAR) software. Those skilled in the art may use the default parameters provided by the tool, or may customize the parameters as appropriate for the alignment, such as for example, by selecting a suitable algorithm.

A "conservative substitution" with reference to amino acid sequence refers to replacing an amino acid residue with a different amino acid residue having a side chain with similar physiochemical properties. For example, conservative substitutions can be made among amino acid residues with hydrophobic side chains (e.g. Met, Ala, Val, Leu, and Ile), among residues with neutral hydrophilic side chains (e.g. Cys, Ser, Thr, Asn and Gin), among residues with acidic side chains (e.g. Asp, Glu), among amino acids with basic side chains (e.g. His, Lys, and Arg), or among residues with aromatic side chains (e.g. Trp, Tyr, and Phe). As known in the art, conservative substitution usually does not cause significant change in the protein conformational structure, and therefore could retain the biological activity of a protein.

The term "functional form" as used herein, refers to different forms (such as variants, fragments, fusions, derivatives and mimetics) of the parent molecule, which, despite of having difference in amino acid sequences or in chemical structures, still retains substantial biological activity of the parent molecule. The expression "retain substantial biological activity", as used herein, means exhibiting at least part of (for example, no less than about 20%, 30%, 40%, 50%, 60%, 70%, 80%, or 90%) or all of the biological activity of the parent molecule. A functional form of a parent polypeptide may include both naturally-occurring variant forms and non-naturally occurring forms such as those obtained by recombinant methods or chemical synthesis. The functional forms may contain non-natural amino acid residues.

The term "variant" as used herein refers to a polypeptide having at least 70% sequence identity to the parent polypeptide. A variant may differ from the parent peptide by one or more amino acid residues. For example, a variant may have substitutions, additions, deletions, insertions, or truncations of one or more amino acid residue of the parent polypeptide.

The term "fragment" as used herein refers to partial sequence of the parent polypeptide of any length. A fragment can still retain at least partial function of the parent polypeptide.

The term "derivative" as used herein refers to a chemically modified polypeptide or fusion polypeptide, in which one or more well-defined number of substituent groups have been covalently attached to one or more specific amino acid residues of the polypeptide or fusion polypeptide. Exemplary chemical modification can be, e.g. alkylation, acylation, esterification, amidation, phosphorylation, glycosylation, labeling, methylation of one or more amino acids, or conjugation with one or more moieties.

The term "mimetics" as used herein refers to molecular structures that serve as substitutes for amino acids, peptides, polypeptides, or fusion polypeptide. For example, amino acid mimetics, as used herein, can be synthetic structures (either known or yet unknown), which may or may not be an amino acid, but retain the functional features of the parent amino acids while the structure of the amino acid mimetic is different from the structure of the parent amino acid. Examples include a methacryloyl or acryloyl derivative of an amide, β-, γ-, δ-imino acids (such as piperidine-4-carboxylic acid) and the like.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasm ids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating. A vector can be an expression vector or a cloning vector. The present disclosure provides vectors (e.g., expression vectors) containing the nucleic acid sequence provided herein encoding the fusion polypeptide, at least one promoter (e.g., SV40, CMV, EF-1α) operably linked to the nucleic acid sequence, and at least one selection marker. Examples of vectors include, but are not limited to, retrovirus (including lentivirus), adenovirus, adeno-associated virus, herpesvirus (e.g., herpes simplex virus), poxvirus, baculovirus, papillomavirus, papovavirus (e.g., SV40), lambda phage, and M13 phage, plasmid pcDNA3.3, pMD18-T, pOptivec, pCMV, pEGFP, pIRES, pQD-Hyg-GSeu, pALTER, pBAD, pcDNA, pCaI, pL, pET, pGEMEX, pGEX, pCI, pEGFT, pSV2, pFUSE, pVITRO, pVIVO, pMAL, pMONO, pSELECT, pUNO, pDUO, Psg5L, pBABE, pWPXL, pBI, p15TV-L, pPro18, pTD, pRS10, pLexA, pACT2.2, pCMV-SCRIPT®, pCDM8, pCDNA1.1/amp, pcDNA3.1, pRc/RSV, PCR 2.1, pEF-1, pFB, pSG5, pXT1, pCDEF3, pSVSPORT, pEF-Bos etc.

The phrase "host cell" as used herein refers to a cell into which an exogenous polynucleotide and/or a vector has been introduced.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

The term "subject" or "individual" or "animal" or "patient" as used herein refers to human or non-human animal, including a mammal or a primate, in need of diagnosis, prognosis, amelioration, prevention and/or treatment of a disease or disorder. Mammalian subjects include humans, domestic animals, farm animals, and zoo, sports, or pet animals such as dogs, cats, guinea pigs, rabbits, rats, mice, horses, swine, cows, bears, and so on.

Fusion Polypeptides

Provided herein are fusion proteins or fusion polypeptides, and the conjugates thereof.

In one aspect, the present disclosure provides a fusion polypeptide comprising: a) a first polypeptide fragment comprising a Glucagon-like peptide-1 (GLP-1) receptor agonist; and b) a second polypeptide fragment comprising a glial cell line-derived neurotrophic factor (GDNF) receptor alpha like (GFRAL receptor) agonist; wherein the first polypeptide fragment and the second polypeptide fragment are linked to one another directly or via a linker.

The term "fusion" or "fused" when used with respect to amino acid sequences (e.g. peptide, polypeptide or protein) refers to combination of two or more amino acid sequences, for example by chemical bonding or recombinant means, into a single amino acid sequence which does not exist naturally. A fusion amino acid sequence may be produced by genetic recombination of two encoding polynucleotide sequences, and can be expressed by a method of introducing a construct containing the recombinant polynucleotides into a host cell.

The term "protein" and "polypeptide" are used interchangeably herein and refer a polymer of amino acid residues linked by covalent bonds such as peptide bonds. A protein or polypeptide as provided herein can comprise naturally occurring or non-natural amino acid residues, or both. Polypeptides and proteins provided herein can comprise any suitable length of amino acid residues, for example, from at least 5, 10, 20, 30, 40, 50, 60, 70, 80, 90, 100, 200, 300, 400, 500, 600, 700, 800, 900, 1000, or more amino acid residues in length.

The term "naturally occurring" amino acid residue, as used herein, refers to an amino acid residue found in native proteins or peptides, all in their D and L stereoisomers if their structure allows such stereoisomeric forms. Examples of naturally occurring amino acid residues include, but are not limited to, 20 standard amino acids, including, glycine (Gly or G), alanine (Ala or A), valine (Val or V), leucine (Leu or L), isoleucine (Ile or I), serine (Ser or S), cysteine (Cys or C), threonine (Thr or T), methionine (Met or M), proline (Pro or P), phenylalanine (Phe or F), tyrosine (Tyr or Y), tryptophan (Trp or W), histidine (His or H), lysine (Lys or K), arginine (Arg or R), aspartate (Asp or D), glutamate (Glu or E), asparagine (Asn or N), and glutamine (Gln or Q), and their natural analogs, such as canavanine, pyrrolysine (PYL), selenocysteine, pyrroline-carboxy-lysine (PCL), Sarcosine, beta-Alanine, phosphoserine, γ-carboxyglutamate, and ornithine. Examples of naturally occurring amino acid residues in their D stereoisomer include, for example, D-aspartate, D-Serine, D-Cysteine, D-Alanine, D-glutamate and so on.

An "amino acid analog" is a compound that has the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs can have modified R groups {e.g., norleucine) or modified peptide backbones, but will retain the same basic chemical structure as a naturally occurring amino acid.

A "non-natural" amino acid residue, as used herein, refers to any amino acid residues that are not found in nature, including without limitation, a modified amino acid residue, and/or an amino acid mimetic, which is not one of the known naturally occurring amino acids, yet functions in a manner similar to the naturally occurring amino acids. Modified amino acid or a mimetic can be generated by addition of a chemical entity such as a carbohydrate group, a phosphate group, a farnesyl group, an isofarnesyl group, a fatty acid group, a linker for conjugation, functionalization, or other modification, etc. A non-natural amino acid can also refer to an amino acid manufactured by chemical synthesis. Exemplary non-natural amino acids include, but not limited to, 2-Aminoisobutyric acid (Aib), imidazole-4-acetate (IA), imidazolepropionic acid (IPA), a-aminobutyric acid (Abu), tert-butylglycine (TIe), b-alanine, 3-aminomethyl benzoic acid, anthranilic acid, des-amino-histidine (abbreviated DesaminoHis, alternative name imidazopropionic acid, abbreviated Impr), the beta analogues of amino acids such as β-alanine, 2-amino-histidine, β-hydroxy-histidine, homohistidine, Nα-acetyl-histidine, α-fluoro-methyl-histidine, α-methyl-histidine, α,α-dimethyl-glutamic acid, m-CF3-phenylalanine, α,β-diaminopropionic acid (abbreviated Dap), 3-pyridylalanine, 2-pyridylalanine or 4-pyridylalanine, (1-aminocyclopropyl)carboxylic acid, (1-aminocyclobutyl)-carboxylic acid, (1-aminocyclopentyl)carboxylic acid, (1-aminocyclohexyl)carboxylic acid, (1-aminocycloheptyl)carboxylic acid, and (1-aminocyclooctyl)carboxylic acid.

Introduction of non-natural amino acids into a fusion polypeptide, polypeptide fragment, and/or polypeptide complex may be realized by the technology described in Wang et al., Science 292:498-500, 2001; Deiters et al., J Am Chem Soc 125:1 1782-1 1783, 2003; Wang and Schultz, Science 301:964-967, 2003; Zhang et al., Science 303:371-373, 2004 or in U.S. Pat. No. 7,083,970. Briefly, some of these expression systems involve site-directed mutagenesis to introduce a stop codon, such as an amber (UAG), ochre (UAA), and opal (UGA) codons) into the open reading frame encoding a fusion polypeptide of the present disclosure. Other codons, such as a four-base codon (e.g. AGGA, AGGU, CGGU, CGCU, CGAU, CCCU, CUCU, CUAU, and GGGU), a five-base codon, a six-base codon, etc. can also be introduced into the expression systems for non-natural amino acids. Such expression vectors are then introduced into a host that can utilize a tRNA specific for the introduced stop codon or other codons and carried with the non-natural amino acid of choice.

The term "Glucagon-like peptide-1 (GLP-1) receptor" (also referred to as GLP1R) is a receptor protein found on beta cells on the pancreas and on neurons of the brain, comprising one extracellular domain and one transmembrane domain. The extracellular domain can bind to the C-terminal helix of GLP-1, and the transmembrane domain can bind to the N-terminal regions of GLP-1. The GLP-1 receptor is involved in the control of blood sugar level by enhancing insulin secretion. When expressed in the brain, the GLP-1 receptor can also be involved in the control of appetite.

The term "Glucagon-like peptide-1 (GLP-1) receptor agonist" or "GLP-1 receptor agonist" as used herein refers to a molecule which is capable of binding to and activating the GLP-1 receptor. A GLP-1 receptor agonist may elicit a magnitude of GLP-1 receptor response that is similar to or partial of a natural ligand.

A GLP-1 receptor agonist can include both a natural ligand of the receptor and an artificially designed or modified molecules that exhibits agonist activity comparable to or no less than 30%, 40% or 50% of that of the natural ligand. In certain embodiments, the GLP-1 receptor agonist comprises GLP-1, glucagon, Oxyntomodulin, exendin-4, exenatide, beinaglutide, efpeglenatide, langlenatide, semaglutide, Taspoglutide, Pegapamodutide, liraglutide, albiglutide, dulaglutide, or lixisenatide.

In certain embodiments, the GLP-1 receptor agonist comprises GLP-1.

The term "Glucagon-like peptide-1" or "GLP-1" as used herein is intended to broadly encompasses native GLP-1 peptide and all its functional forms such as its functional variants, fragments, fusions, derivatives and mimetics.

The term "native GLP-1 peptide" as used herein refers to the native human Glucagon-Like Peptide-1 (GLP-1 (7-37)), the sequence of which is set forth in SEQ ID NO: 242. As used herein, when referring to a particular amino acid residue in SEQ ID NO: 242 (i.e. GLP-1 (7-37)), the numbering of the GLP-1 (1-37) is followed. In other words, SEQ ID NO: 242 corresponds to GLP-1 (7-37), and therefore the $1^{st}$ residue (which is Histidine (H)) in SEQ ID NO: 242 is referred to as 7H, meaning that it corresponds to the $7^{th}$ residue in GLP (1-37); and the $31^{st}$ residue (which is Glycine (G)) in SEQ ID NO: 242 is referred to as 37G, meaning corresponds to the $37^{th}$ residue in GLP (1-37).

A functional form of the native GLP-1 peptide is capable of activating the GLP-1 receptor at a level comparable to, or no less than about 20% (or no less than 30%, 40%, 50%, 60%, 70%, 80%, 90%) of, that of the native GLP-1 peptide. Activation of the GLP-1 receptor typically initiates signal transduction pathway resulting in insulinotropic action or other physiological effects as is known in the art. Many functional forms of native GLP-1 peptide are known in the art, for example, without limitation, liraglutide, semaglutide, dulaglutide, albiglutide, and those disclosed in WO2000055203A1, WO 98/08871, WO 2006/097537, the disclosure of which is incorporated herein to its entirety.

In certain embodiments, the GLP-1 provided herein comprises an amino acid sequence having at least 70% (e.g. at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%) sequence identity to SEQ ID NO: 242 while retaining substantial biological activity of SEQ ID NO: 242.

In certain embodiments, the GLP-1 comprises no more than 9, 8, 7, 6, 5, 4, 3, or 2 substitutions relative to SEQ ID NO: 242 while retaining substantial biological activity of SEQ ID NO: 242. In certain embodiments, the GLP-1 comprises at least 2, 3, 4, 5, 6, 7, 8, or 9 substitutions relative to SEQ ID NO: 242 while retaining substantial biological activity of SEQ ID NO: 242.

One of ordinary skill in the art will appreciate that various amino acid substitutions, e.g., conservative amino acid substitutions, may be made in the sequence of any of the polypeptide fragment described herein, without necessarily decreasing its activity. Examples of amino acid substitutions include substituting an L-amino acid for its corresponding D-amino acid, substituting cysteine for homocysteine or other non-natural amino acids having a thiol-containing side chain, substituting a lysine for homolysine, diaminobutyric acid, diaminopropionic acid, ornithine or other non-natural amino acids having an amino containing side chain, or substituting an alanine for norvaline or the like.

Various substitutions have been introduced to native GLP-1 peptide, and have been shown to be capable of retaining or even improving its biological activities. In certain embodiments, the GLP-1 comprises one or more mutations at a position selected from the group consisting of: A8, G22, K34, R36, and H7, and or any combination thereof. For example, it is believed that substitution at A8 is useful to prevent DPP4 enzymatic cleavage at the residue, substitution at G22 is desirable to improve activity and solubility, and substitution at R36 is useful to reduce immunogenicity. Examples of substitutions at these positions include, without limitation, H7IA, H71IPA, A8G, A8S, A8V, A8Aib, A8T, A8I, A8L, G22E, K34R, R36G, as well as the substitutions described in U.S. Pat. No. 8,273,854, which are incorporated herein by its entirety. In certain embodiments, the one or more substitutions comprises a conservative substitution. As used herein, the numbering of the residues in GLP-1 is referred to with reference to the 31 amino-acid sequence set forth in SEQ ID NO: 242, which is also known as GLP-1 (7-37), where residue 7 is Histidine (H7, i.e. the first residue in SEQ ID NO: 242) and residue 37 is Glycine (G37, i.e. the last residue in SEQ ID NO: 242).

In certain embodiments, the GLP-1 comprises a substitution of A8 which is selected from the group consisting of: A8G, A8S, A8V, A8Aib, A8T, and A8L. In certain embodiments, the GLP-1 comprises a substitution of G22E. In certain embodiments, the GLP-1 comprises a substitution of R36G. In certain embodiments, the GLP-1 comprises a substitution of H7 which is H7IA or H7IPA. In certain embodiments, the GLP-1 comprises a substitution of K34 which is K34R.

In certain embodiments, the GLP-1 comprises or consists of one or more substitutions at a position selected from the group consisting of: H7, A8, G22, K34, and R36, or any combination thereof. In certain embodiments, the GLP-1 comprises or consists of one or more substitutions at a position selected from the group consisting of: H7IA, H7IPA, A8G, A8Aib, K34R, G22E, and R36G, or any combination thereof.

The term "GDNF receptor alpha like (GFRAL) receptor" or "GFRAL receptor" or "glial cell line-derived neurotrophic factor receptor alpha like (GFRAL) receptor" refers to a receptor for GDF15 to recognize and bind so as to initiate a signal transduction as described in WO/2017/121865, the disclosure of which is incorporated herein to its entirety.

The term "GDNF receptor alpha like (GFRAL) receptor agonist" or "GFRAL receptor agonist" as used herein refers to a molecule which is capable of binding to and activating the GFRAL receptor. A GFRAL receptor agonist may elicit a magnitude of GFRAL receptor response that is similar to or partial of a natural ligand.

A GFRAL receptor agonist can include both a natural ligand of the receptor and an artificially designed or modified molecules that exhibits agonist activity comparable to or no less than 30%, 40% or 50% of that of the natural ligand. In certain embodiments, the GFRAL receptor agonist include, without limitation, GDF15, those disclosed in WO 2017/109706, WO 2013/148117, WO 2014/120619, WO 2012/138919, WO 2013/1 13008, WO 2015/017710, the disclosure of which are incorporated herein to their entirety.

In certain embodiments, the GFRAL receptor agonist comprises GDF15.

The term "Growth Differentiation Factor 15" or "GDF15" as used herein is intended to broadly encompasses the mature domain of the native GDF15 peptide, its homodimer, and all its functional forms such as its functional variants, fragments, fusions, derivatives and mimetics. The full length native GDF15 peptide consists of 308 amino acid residues (NCI Ref. Seq. NP_004855.2), with amino acids 1-29 being a signal peptide, amino acids 30-196 being a pro-domain, and amino acids 197-308 being a mature domain of 112 amino acids. The GDF15 provided in the present disclosure can be the 112 amino acid mature domain of the full length native GDF15, or functional variants, fragments, fusions, derivatives or mimetics thereof.

The mature GDF15 peptide contains nine cysteine residues that form four intrachain disulfide bonds and one interchain disulfide bond that gives rise to a covalently linked homodimer. In other words, biologically active GDF15 is a homodimer of the mature peptide covalently linked by one interchain disulfide bond. The term "GDF15" as used herein also includes multimer, more particularly dimer of the protein.

A functional form of the mature domain of the native GDF15 polypeptide is capable of activating the GFRAL receptor at a level comparable to, or no less than about 20% (or no less than 30%, 40%, 50%, 60%, 70%, 80%, 90%) of, that of the mature domain of the native GDF15 polypeptide. Activation of the GFRAL receptor can lead to biological activities such as, for example, the ability to lower blood glucose, insulin, triglyceride, or cholesterol levels; the ability to reduce body weight; or the ability to improve glucose tolerance, lipid tolerance, or insulin sensitivity; the ability to lower urine glucose and protein excretion. Many functional forms of the mature domain of the native GDF15 polypeptide are known in the art, for example, without limitation, those disclosed in WO 2015/197446, WO2017/121865, WO2017/109706, WO2017/109706, WO2013/148117, WO2014/120619 (definition to the diseases), WO2012/138919, WO2013/113008, WO2015/017710, disclosure of which are incorporated herein by their entirety.

In certain embodiments, the GDF15 provided herein comprises an amino acid sequence having at least 90% sequence identity to SEQ ID NO: 248 while retaining substantial biological activity of SEQ ID NO: 248.

In certain embodiments, the GDF15 comprises no more than 10, 9, 8, 7, 6, 5, 4, 3, 2 substitutions relative to SEQ ID NO: 248 while retaining substantial biological activity of SEQ ID NO: 248. In certain embodiments, the GDF15 comprises at least 2, 3, 4, 5, 6, 7, 8, 9 or 10 substitutions relative to SEQ ID NO: 248 while retaining substantial biological activity of SEQ ID NO: 248.

In certain embodiments, the fusion polypeptide comprises, from N terminus to C terminus, GLP-1, a linker and GDF15. In certain embodiments, the fusion polypeptide is a single chain polypeptide. A single chain polypeptide can still have intrachain bonds within the molecule but does not include complexes formed by one or more interchain bonds.

In certain embodiments, the GDF15 comprises one or more mutations at a position selected from the group consisting of: A1, R2, N3, H6, P11, H18, T19, V20, R21, A30, M43, A47, R53, A54, M57, H66, R67, L68, A75, A81, P85, M86, Q90, T92, and L105, or any combination thereof. For example, it is believed that substitution at N3 is useful to prevent deamidation and substitution at M57 is useful to reduce oxidation. In certain embodiments, the one or more additional substitutions in GDF15 is at a position of N3 and/or M57. In certain embodiments, the one or more mutations comprise a conservative substitution. As used herein, the numbering of the residues in GDF15 is referred to with reference to the 112 amino acid monomer sequence as set forth in SEQ ID NO: 248, where residue 1 is Alanine (A1) and residue 112 is Isoleucine (I112).

In certain embodiments, the GDF15 comprises a mutation of N3 which is selected from the group consisting of: N3Q, N3S, N3E, N3A, N3T, N3P, N3G, N3V, N3H, N3Y, and deletion of N3. In certain embodiments, the GDF15 comprises a substitution of M57 which is M57A, M57E or M57L. In certain embodiments, the GDF15 comprises a substitution of R2 which is R2S, R2A, or R2E.

In certain embodiments, the one or more mutations in GDF15 are selected from the group consisting of: R2S, R2A, R2E, N3S, N3E, N3A, N3T, N3P, N3G, N3V, N3H, N3Y, N3Q, H6D, P11E, H18E, H18Q, T19S, V20L, R21E, A30E, M43L, M43E, A47E, R53E, A54E, M57A, M57E, M57L, H66E, R67E, L68E, A75E, A81E, P85E, M86F, M86A, M86L, Q90E, T92E, L105E, deletion of N3, deletion of N-terminal 1-3 residues (i.e. A1R2N3), or any combination thereof. More suitable mutations that can be made to GDF15 without significantly reducing its biological activity are described in WO2012138919, WO2013148117, WO2014120619, WO2016018931, WO2017202936, and WO2018215525, disclosure of which is incorporated herein by their entirety.

In certain embodiments, the first polypeptide fragment provided herein comprises GLP-1, and/or the second polypeptide fragment provided herein comprises GDF15. In certain embodiments, the fusion polypeptide comprises, from N terminus to C terminus, GLP-1 operably linked to GDF15.

In certain embodiments, the GLP-1 is linked the GDF15 directly or via a linker. In certain embodiments, the linker comprises a polypeptide linker.

In certain embodiments, the fusion polypeptide comprises, from N terminus to C terminus, GLP-1 linked to GDF15, either directly or via a linker. In certain embodiments, the GLP-1 is N-terminal of the GDF15. In other words, the N-terminus of the GDF15 is linked to the C-terminus of the GLP-1, either directly or via a linker.

In certain embodiments, the fusion polypeptide comprises, from N terminus to C terminus, the first polypeptide fragment (e.g. the GLP-1 receptor agonist) linked to the second polypeptide fragment (e.g. the GFAR1 receptor agonist), either directly or via a linker. A direct linkage can be, for example, a covalent bond such as a peptide bond.

The term "linker" as used herein can be any suitable bifunctional moiety capable of reacting with at least two entities to be linked, thereby bonding the entities to form one molecule or maintaining association of the entities in sufficiently close proximity. The linker can be integrated in the resulting linked molecule or structure, with or without its reacted functional groups. In certain embodiments, the linker separates the GLP-1 receptor agonist and the GFAR1 receptor agonist, without substantial interference to the respective biological activities of the receptor agonists. Suitable linkers can be, for example without limitation, polypeptide linkers and non-peptide linkers, such as bifunctional chemical moieties, or polymers such as PEG.

In certain embodiments, the linker comprises a polypeptide linker. The polypeptide linker can be made up of amino acid residues linked together by peptide bonds. The polypeptide linker can further comprise one or more non-natural amino acids.

In certain embodiments, the polypeptide linker comprises at least 1, 4, 5, 10, 12, 20, 24, 30, 40, 50, 60, 70, 80, 90, 100, 110, 120, 130, 140, 150 or 172 amino acid residues, or more. In certain embodiments, the polypeptide linker has a length of from 1 to 200 (1-200), 1-180, 1-170, 1-160, 1-150, 1-140, 1-130, 1-120, 1-110, 1-100, 1-90, 1-80, 1-70, 1-60, 1-50, 1-40, 40-200, 40-180, 40-170, 40-160, 40-150, 40-140, 40-130, 40-120, 40-110, 40-100, 40-90, or 40-80 amino acid residues. Without wishing to be bound by any theory, it is believed that a suitable length of the polypeptide linker can further improve the biological activity or stability or pharmacokinetic parameters of the linked polypeptide molecule.

Any suitable polypeptide linkers can be used. For example, the polypeptide linker may comprise or consist of amino acid residues selected from the amino acids glycine, serine, alanine, methionine, asparagine, glutamine, cysteine and lysine. In some embodiments, the polypeptide linker can be made up of a majority of amino acids that are sterically unhindered, such as glycine and alanine. In some embodiments, linkers are polyglycines, polyalanines, combinations of glycine and alanine (such as poly(Gly-Ala)), or combinations of glycine and serine (such as poly(Gly-Ser)).

In certain embodiments, the polypeptide linker comprises at least one acidic amino acid residue. Acidic amino acid residue refers to an amino acid residue having an acidic side chain that contains a carboxylic acid group with a pKa between 3.5 and 4.5. Exemplary acidic amino acid residues include, but not limited to, aspartic acid and glutamic acid. In certain embodiments, the at least one acidic amino acid residue comprises aspartic acid or glutamic acid.

In certain embodiments, the polypeptide linker comprises or consists of one or more repeats of a repeating sequence. In certain embodiments, the polypeptide linker comprises or consists of 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 repeats of a repeating sequence, or within any numerical range defined by any two numbers listed above.

In certain embodiments, the repeating sequence comprises or consists of no more than 4, 5 or 6 types of amino acid residues selected from the group consisting of: G, Q, A, E, P, T and S. In certain embodiments, the repeating sequence comprises or consists of no more than 4, 5 or 6 types of amino acid residues selected from the group consisting of: G, Q, A, E, P, and S. In certain embodiments, the repeating sequence comprises Q. In certain embodiments, the repeating sequence consists of Q and no more than 3, 4 or 5 types of amino acid residues selected from the group consisting of: G, A, E, P, and S.

In certain embodiments, the repeating sequence consists of G, Q, A, E, and P.

In certain embodiments, the repeating sequence comprises or consists of a sequence selected from the group consisting of: SEQ ID NOs: 213-236, SEQ ID NOs: 453 and 476, and GS.

In certain embodiments, the polypeptide linker comprises or consists of more than one repeating sequence. For example, the polypeptide linker comprises or consists of 2, 3, or 4 different repeating sequences. In certain embodiments, the polypeptide linker comprises or consists of sequential or tandem repeats of the different repeating sequences.

In certain embodiments, the polypeptide linker comprises or consists of (Repeat1)r(Repeat2)s(Repeat3)x(Repeat4)y, wherein:
Repeat1, Repeat2, Repeat3 and Repeat4 are linked via a peptide bond or via one or more amino acid residues;
Repeat1, Repeat2, Repeat3 and Repeat4 independently, comprise or consist of a sequence selected from the group consisting of: SEQ ID NOs: 213-236 and GS, and
r, s, x and y are independently an integer selected from 0 to 30 (e.g. from 0-29, 0-28, 0-27, 0-26, 0-25, 0-24, 0-23, 0-22, 0-21, 0-20, 0-19, 0-18, 0-17, 0-16, 0-15, 0-14, 0-13, 0-12, 0-11, 0-10, 0-9, 0-8, 0-7, 0-6, 0-5, 0-4, 0-3, 0-2, or 0-1), provided that r, s, x and y are not 0 at the same time.

In certain embodiments, x and y are 0, r, and s are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 and Repeat2 are a combination selected from the group consisting of:
1) Repeat1 comprises or consists of a sequence of SEQ ID NO: 213, and Repeat2 comprises or consists of a sequence of SEQ ID NO: 216;
2) Repeat1 comprises or consists of a sequence of SEQ ID NO: 215, and Repeat2 comprises or consists of a sequence of SEQ ID NO: 216;
3) Repeat1 comprises or consists of a sequence of SEQ ID NO: 216, and Repeat2 comprises or consists of a sequence of SEQ ID NO: 215;

4) Repeat1 comprises or consists of a sequence of SEQ ID NO: 216, and Repeat2 comprises or consists of a sequence of SEQ ID NO: 213;
5) Repeat1 comprises or consists of a sequence of SEQ ID NO: 218, and Repeat2 comprises or consists of a sequence of SEQ ID NO: 216;
6) Repeat1 comprises or consists of a sequence of SEQ ID NO: 217, and Repeat2 comprises or consists of a sequence of SEQ ID NO: 216;
7) Repeat1 comprises or consists of a sequence of SEQ ID NO: 216, Repeat2 comprises or consists of a sequence of SEQ ID NO: 453 and
8) Repeat1 comprises or consists of a sequence of SEQ ID NO: 217, and Repeat2 comprises or consists of a sequence of SEQ ID NO: 215.

In certain embodiments, r, x and y are 0, s is an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1 comprises or consists of a sequence of SEQ ID NO: 213.

In certain embodiments, y is 0, r, s and x are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1, Repeat2 and Repeat3 are a combination selected from the group consisting of:
1) Repeat1 comprises or consists of a sequence of SEQ ID NO: 216, Repeat2 comprises or consists of a sequence of SEQ ID NO: 218; and Repeat3 comprises or consists of a sequence of SEQ ID NO: 216;
2) Repeat1 comprises or consists of a sequence of SEQ ID NO: 216, Repeat2 comprises or consists of a sequence of SEQ ID NO: 215; and Repeat3 comprises or consists of a sequence of SEQ ID NO: 216;
3) Repeat1 comprises or consists of a sequence of SEQ ID NO: 217, Repeat2 comprises or consists of a sequence of SEQ ID NO: 215; and Repeat3 comprises or consists of a sequence of SEQ ID NO: 216;
4) Repeat1 comprises or consists of a sequence of SEQ ID NO: 217, Repeat2 comprises or consists of a sequence of SEQ ID NO: 216; and Repeat3 comprises or consists of a sequence of SEQ ID NO: 215;
5) Repeat1 comprises or consists of a sequence of SEQ ID NO: 213, Repeat2 comprises or consists of a sequence of SEQ ID NO: 227; Repeat3 comprises or consists of a sequence of SEQ ID NO: 216,
6) Repeat1 comprises or consists of a sequence of SEQ ID NO: 216, Repeat2 comprises or consists of a sequence of SEQ ID NO: 453; Repeat3 comprises or consists of a sequence of SEQ ID NO: 213,
7) Repeat1 comprises or consists of a sequence of SEQ ID NO: 216, Repeat2 comprises or consists of a sequence of SEQ ID NO: 213; Repeat3 comprises or consists of a sequence of SEQ ID NO: 216, and
8) Repeat1 comprises or consists of a sequence of SEQ ID NO: 216, Repeat2 comprises or consists of a sequence of SEQ ID NO: 213; Repeat3 comprises or consists of a sequence of SEQ ID NO: 453.

In certain embodiments, r, s, x and y are independently an integer selected from 1 to 30 (e.g. from 1-29, 1-28, 1-27, 1-26, 1-25, 1-24, 1-23, 1-22, 1-21, 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, or 1-2), and Repeat1, Repeat2, Repeat 3 and Repeat 4 are a combination selected from the group consisting of:

1) Repeat1 comprises or consists of a sequence of SEQ ID NO: 216, Repeat2 comprises or consists of a sequence of SEQ ID NO: 219; Repeat3 comprises or consists of a sequence of SEQ ID NO: 215, and Repeat4 comprises or consists of a sequence of SEQ ID NO: 216,
2) Repeat1 comprises or consists of a sequence of SEQ ID NO: 213, Repeat2 comprises or consists of a sequence of SEQ ID NO: 453; Repeat3 comprises or consists of a sequence of SEQ ID NO: 213, and Repeat4 comprises or consists of a sequence of SEQ ID NO: 216,
3) Repeat1 comprises or consists of a sequence of SEQ ID NO: 216, Repeat2 comprises or consists of a sequence of SEQ ID NO: 453; Repeat3 comprises or consists of a sequence of SEQ ID NO: 213, and Repeat4 comprises or consists of a sequence of SEQ ID NO: 216,
4) Repeat1 comprises or consists of a sequence of SEQ ID NO: 216, Repeat2 comprises or consists of a sequence of SEQ ID NO: 227; Repeat3 comprises or consists of a sequence of SEQ ID NO: 216, and Repeat4 comprises or consists of a sequence of SEQ ID NO: 213, and
5) Repeat1 comprises or consists of a sequence of SEQ ID NO: 216, Repeat2 comprises or consists of a sequence of SEQ ID NO: 213; Repeat3 comprises or consists of a sequence of SEQ ID NO: 476, and Repeat4 comprises or consists of a sequence of SEQ ID NO: 453.

In certain embodiments, the polypeptide linker comprises an amino acid sequence selected from the group consisting of: a) SEQ ID NOs: 1-59, 61-88, 90-197, 199-212, and 454-471, or a variant thereof; b) SEQ ID NOs: 1-59, 61-88, 90-93, 454-459, and 463-471, or a variant thereof; c) SEQ ID NOs: 94-156, or a variant thereof; d) SEQ ID NOs: 210-212, and 460-462, or a variant thereof, or e) SEQ ID NOs: 157-197, and 199-209, or a variant thereof.

In certain embodiments, the polypeptide linker comprises or consists of an amino acid sequence selected from the group consisting of: SEQ ID NOs: 298-324, 60, 89, 198, 332, 333, 334, 342-346, 409-447, 475 and 483.

In certain embodiments, the conjugatable residue in the polypeptide linker comprises lysine. In such embodiments, the polypeptide linker comprises or consists of an amino acid sequence selected from the group consisting of: SEQ ID NOs: 298-324, 60, 89, 198, 332-334, 342-346, 409-410, 414-417, and 426-429. In such embodiments, the GDF15 comprises an amino acid sequence selected from the group consisting of: SEQ ID NO: 246, SEQ ID NOs: 290-293, 295-297, SEQ ID NO: 358, SEQ ID NO: 451, SEQ ID NO: 479 and SEQ ID NO: 480, and/or the GLP-1 comprises an amino acid sequence selected from the group consisting of: SEQ ID NO: 243, SEQ ID NO: 244, SEQ ID NO: 245, SEQ ID NO: 448 and SEQ ID NO: 478.

In certain embodiments, the conjugatable residue in the polypeptide linker comprises cysteine. In such embodiments, the polypeptide linker comprises or consists of an amino acid sequence selected from the group consisting of: SEQ ID NOs: 411-413, 418-425, 430-447 and 475. In such embodiments, the GDF15 comprises an amino acid sequence selected from the group consisting of: SEQ ID NO: 247, SEQ ID NO: 248, SEQ ID NO: 294, and SEQ ID NO: 271, and/or the GLP-1 comprises an amino acid sequence selected from the group consisting of: SEQ ID NO: 242, SEQ ID NO: 243, SEQ ID NO: 244, SEQ ID NO: 245, SEQ ID NO: 336, SEQ ID NO: 448 and SEQ ID NO: 478.

In certain embodiments, the fusion polypeptide comprises an amino acid sequence of SEQ ID NOs: 249, 266, 267, 268, 269, 270, 347, 251, 260, 263-265, 273, 277, 329-330, 359, 369, 374, 376-381, and 392-408.

Conjugatable Residues

In certain embodiments, the fusion polypeptide comprises at least one or up to one conjugatable residue. In certain embodiments, the fusion polypeptide comprises at least two or up to two conjugatable residues. The term "up to" with respect to a certain number, in intended to mean any integer equal to or below that number, including zero. For example, up to 2 means 0, 1, and 2; up to 1 means 0, and 1. In certain embodiments, the conjugatable residue is lysine residue or cysteine residue.

In certain embodiments, the fusion polypeptide provided herein can be conjugated with another molecule. Such molecule can be conjugated at the conjugatable residue in the fusion polypeptide. In certain embodiments, the number and/or position of the conjugatable residue in the fusion polypeptide can be designed, to provide for specific and/or effective conjugation, for example.

The term "conjugatable residue" as used herein, refers to an amino acid residue at a particular position within the fusion polypeptide, which residue not only has a functional group capable of being chemically or enzymatically conjugated to a chemical moiety, but its position in the fusion polypeptide allows it to be prone to such conjugation in a conjugating reaction for that particular functional group. "Conjugation" as used herein refers to a reaction that joins two molecules together to form one physical entity. For example, a covalent bond linking the two molecules can be formed in conjugation.

A skilled person would understand that, whether a residue is conjugatable residue would depend on the given conjugating reaction, and/or the functional group to be conjugated. If the functional group to be conjugated is an amino group and/or the conjugation reaction is specific or selective for an amino group, then a cysteine residue (i.e. having no functional amino group in its side chain) would not be a conjugatable group regardless of its position in the polypeptide, whereas a lysine residue at a particular position could be. Similarly, if the function group to be conjugated is a thiol group and/or the conjugation reaction is specific or selective for a thiol group, then lysine (i.e. having no functional thiol group in its side chain) would not be the conjugatable residue regardless of its position, whereas an unpaired cysteine residue that does not form a disulfide bond (whether intrachain bond or interchain bond), could be a conjugatable residue.

In certain embodiments, the fusion polypeptide has a conjugatable residue for a conjugation reaction specific or selective for an amino group or amine (for example, an acylation reaction). In certain embodiments, the fusion polypeptide has a conjugatable residue for a conjugation reaction specific or selective for thiol group (for example, an alkylation reaction, or a reaction for disulfide bond formation).

The expression "prone to conjugation" as used herein is intended to mean that, the residue at a particular position in the fusion polypeptide is sufficiently accessible for conjugation, to the extent that when the fusion polypeptide is subject to a given conjugation reaction, no less than 30% of that residue at that particular position is conjugated. For example, a residue may contain the functional group to be conjugated, but it is at a position that is not sufficiently accessible (for example, not sufficiently exposed on the polypeptide) in the conjugation reaction, and therefore would not be sufficiently conjugated in the conjugation reaction. Such residues which are not prone to conjugation are not considered as conjugatable residues in the present disclosure.

A conjugatable residue can be a natural amino acid residue, a non-natural amino acid residue, modified amino acid residue or an amino acid mimetic. Examples of conjugatable residues include, without limitation, lysine, cysteine, or a non-natural amino acid residue.

In certain embodiments, the fusion polypeptide comprises a first conjugatable residue. In certain embodiments, the first conjugatable residue is present in one of the GLP-1, the GDF15, and the polypeptide linker. In certain embodiments, the first conjugatable residue is present in the GLP-1 or the polypeptide linker.

In certain embodiments, the fusion polypeptide further comprises a second conjugatable residue. In certain embodiments, the second conjugatable residue is present in the GLP-1, GDF15 or the linker.

In certain embodiments, the fusion polypeptide comprises a first conjugatable residue and a second conjugatable residue, wherein: 1) both conjugatable residues are present in the linker, 2) both conjugatable residues are present in the GLP-1, 3) both conjugatable residues are present in the GDF15, 4) the first conjugatable residue is present in the GLP-1 and the second conjugatable residue is present in the linker, 5) the first conjugatable residue is present in the GDF15 and the second conjugatable residue is present in the linker, or 6) the first conjugatable residue is present in the GLP-1 and the second conjugatable residue is present in the GDF15.

In certain embodiments, at least one of the conjugatable residues is a naturally occurring residue found in the native GLP-1 sequence, or a naturally occurring residue found in the native GDF15 sequence. In certain embodiments, such a naturally occurring residue is a naturally occurring lysine residue.

In certain embodiments, when the native GLP-1 or native GDF15 mature domain has more than one naturally occurring conjugatable residue, one or more of such naturally occurring conjugatable residue can be removed for example by mutation. For example, native GLP-1 has two naturally occurring lysine residues, and native GDF15 has four naturally occurring lysine residues, and at least some of them, or all of them can be mutated, without significantly reducing the biological activity of the fusion polypeptide.

In certain embodiments, at least one of the conjugatable residues is an introduced residue, for example, by substitution of a non-conjugatable residue to a conjugatable residue, or by insertion of a conjugatable residue. The term "non-conjugatable residue" refers to an amino acid residue in the fusion polypeptide that is not a conjugatable residue for a given functional group to be conjugated and/or for the given conjugation reaction. For example, when lysine is the conjugatable residue, any amino acid residue can be considered as a non-conjugatable residue if it does not contain an amino group and/or does not react in the conjugation reaction specific or selective for an amino group.

Conjugatable Residues in GLP-1

In certain embodiments, the GLP-1 comprises one or two conjugatable residue. In certain embodiments, the GLP-1 comprises up to one conjugatable residue or up to two conjugatable residues.

In certain embodiments, the conjugatable residue(s) in GLP-1 comprises or consists of lysine. The native GLP-1 peptide (GLP-1 (7-37)), as set forth in SEQ ID NO: 242, has two lysine (K) residues, namely K26 and K34. Throughout the specification, when K residue is present in GLP-1, the position of K is identified in reference to the amino acid sequence of GLP-1 (1-37). For example, K26 indicates that the 26$^{th}$ position in reference to the amino acid sequence of GLP-1 (1-37) (which corresponds to the 20$^{th}$ position in reference to the amino acid sequence of GLP-1 (7-37), i.e. SEQ ID NO: 242) is K. Similarly, K34 indicates that the 34$^{th}$ position in reference to the amino acid sequence of GLP-1 (1-37) (which corresponds to the 28$^{th}$ position in reference to the amino acid sequence of GLP-1 (7-37), i.e. SEQ ID NO: 242) is K. In certain embodiments, the conjugatable residue(s) in the GLP-1 is a naturally occurring residue found in the native GLP-1 peptide, for example, K26 or K34.

In certain embodiments, the GLP-1 comprises substitution of both lysine residues or substitution of only one lysine residue. In certain embodiments, the GLP-1 comprises one or two substitutions at K26 and/or K34. In certain embodiments, the GLP-1 comprises substitution of K26 and/or K34 to a non-conjugatable residue. In certain embodiments, for lysine conjugation reaction, the non-conjugatable residue is optionally selected from the group consisting of Arginine (R), Glutamine (Q), Alanine (A), Glycine (G), Histidine (H), Serine (S), and Threonine (T).

In certain embodiments, the GLP-1 comprises substitution of K26 which is selected from the group consisting of K26R, K26Q, K26A, K26G, K26H, K26S, and K26T. In certain embodiments, the GLP-1 comprises, or further comprises, substitution of K34 which selected from the group consisting of K34R, K34Q, K34A, K34G, K34H, K34S, and K34T. In certain embodiments, the substitution of K26 is selected from K26R and K26Q, and/or the substitution at K34 is selected from K34R and K34Q. In certain embodiments, the GLP-1 comprises K26R, and/or K34R, relative to SEQ ID NO: 242.

In certain embodiments, the conjugatable residue(s) in the GLP-1 comprises an introduced residue, for example, by substitution of a non-conjugatable residue to a conjugatable residue, or by insertion of a conjugatable residue (for example at the N terminus or C terminus of the GLP-1 or within the GLP-1 sequence). Any non-conjugatable residue in GLP-1 can be substituted with a conjugatable residue, as long as such substitution does not substantially diminish the biological activity of the GLP-1 or the fusion polypeptide. In certain embodiments, the conjugatable residue(s) in the GLP-1 comprises or consists of lysine and is introduced by a substitution at E27 or R36 in the GLP-1. In certain embodiments, the conjugatable residue in the GLP-1 is introduced by a substitution selected from the group consisting of: E27K, and R36K, relative to SEQ ID NO: 242.

In certain embodiments, the GLP-1 comprises one or two conjugatable residues selected from the group consisting of K26, E27K, and R36K. In certain embodiments, the GLP-1 comprises two conjugatable residues comprising 1) K26 and E27K; 2) K26 and R36K, or 3) E27K, and R36K.

In certain embodiments, the conjugatable residue in the GLP-1 comprises a cysteine residue. In certain embodiments, the conjugatable residue in the GLP-1 is a non-natural amino acid residue (NNAA). Non-natural amino acid can contain a variety of functional groups or reactive groups, which can provide for additional functions and/or reactivity. Particular non-natural amino acids that are beneficial for purpose of conjugating moieties to the fusion polypeptides of the present disclosure include those with a side chain having azide, alkyne, alkene, cycloalkyne or halide.

In certain embodiments, the cysteine residue or the NNAA in the GLP-1 is introduced by a substitution at the position selected from the group consisting of: K26, K34, E27 and R36, relative to SEQ ID NO: 242. In certain embodiments, the cysteine residue or the NNAA in the GLP-1 is introduced by a substitution at the position selected from the group consisting of: K26, E27 and R36, relative to SEQ ID NO: 242. In certain embodiments, the conjugatable residue in the GLP-1 comprises or consists of cysteine and is introduced by a substitution at a position selected from the group consisting of: K26C, K34C, E27C and R36C, relative to SEQ ID NO: 242.

In certain embodiments, the GLP-1 comprises no conjugatable residue. In certain embodiments, the GLP-1 comprises no lysine, no cysteine, and/or no non-natural amino acid residue.

In certain embodiments, the GLP-1 comprises or consists of one or more substitutions selected from the group consisting of A8G, A8Aib, K34R, G22E, and R36G. In certain embodiments, the GLP-1 comprises or consists of one or more substitutions selected from the group consisting of A8G, A8Aib, K26R, K34R, G22E, and R36G. In certain embodiments, the GLP-1 comprises or consists of one or more substitutions selected from the group consisting of: H7IA, H7IPA, A8G, A8Aib, K26R, K34R, G22E, and R36K.

In certain embodiments, the GLP-1 comprises an amino acid sequence of $X_7X_8EGTFTSDVSSYLEX_{22}QAAX_{26}X_{27}FIAWLVX_{34}GX_{36}G$ (SEQ ID NO: 325), wherein: the $X_7$ is H, imidazole-4-acetate (IA), or imidazolepropionic acid (IPA); $X_8$ is A, G, S, V, Aib, T, I, or L; the $X_{22}$ is G, or E; the $X_{26}$ is K, R, or C; the $X_{27}$ is E, K, or C; the $X_{34}$ is R, K, or C, and the $X_{36}$ is K, R, G, or C.

In certain embodiments, the $X_7$ is H, the $X_8$ is G, the $X_{22}$ is E; the $X_{26}$ is K, R or C; the $X_{27}$ is E; the $X_{34}$ is K or R, and the $X_{36}$ is K, or G.

In certain embodiments, the GLP-1 comprises an amino acid sequence selected from the group consisting of: SEQ ID NO: 242 (wild-type), SEQ ID NO: 243 (A8G/K34R/G22E/R36G GLP-1(7-37)), SEQ ID NO: 244 (A8G/K26R/K34R/G22E/R36G GLP-1(7-37)), SEQ ID NO: 245 (A8G/K26R/K34R/G22E/R36K GLP-1(7-37)) and SEQ ID NO: 336 (A8G/G22E/R36G GLP-1(7-37)), SEQ ID NO: 448 (8G, 26C, 34R, 22E, 36G), and SEQ ID NO: 478 (8Aib, 34R, 22E, 36G).

Conjugatable Residues in GDF15

In certain embodiments, the GDF15 comprises no conjugatable residue. In certain embodiments, the conjugatable residue in GDF15 has been removed, by e.g. substitution of a conjugatable residue with a non-conjugatable residue or deletion of the conjugatable residue or any other means that prevents the side chain of the conjugatable residue from reacting in a given conjugation reaction.

In certain embodiments, the conjugatable residue comprises or consists of lysine. The native GDF15 polypeptide, as set forth in SEQ ID NO: 248, has four lysine (K) residues, namely K62, K69, K91, and K107.

Without wishing to be bound by any theory, but it is believed that K62, and optionally K69, is/are not a conjugatable residue in the GDF15. While K62 contains amino group which can be conjugated in an amino group conjugation reaction, K62 is not prone to conjugation, as demonstrated by very low or even undetectable level of conjugation. Similarly, K69 may also be potentially considered as a non-conjugatable residue for amino group conjugation reaction, as it is insufficiently conjugated in the conjugation reaction. Accordingly, the GDF15 having no lysine residues except K62, or except K62 and K69, are considered as comprising no conjugatable residue for amino group conjugation reaction.

In certain embodiments, the GDF15 comprises substitutions of K91 and K107, relative to SEQ ID NO: 248. In certain embodiments, the GDF15 comprises substitutions at K91 and/or K107, to a non-conjugatable residue. K91 and K107 may be substituted to the same or different non-conjugatable residues. In certain embodiments, the GDF15 further comprises substitutions at K62 and/or K69.

In certain embodiments, all four lysine residues are substituted except K62. That is, K69, K91, K107 are substituted to one or more non-conjugatable residues, but K62 remains in the GDF15. In certain embodiments, all four lysine residues except K62 and K69 are substituted. That is, both K91 and K107 are substituted to one or more non-conjugatable residues, but K62 and K69 remain in the GDF15.

In certain embodiments, the GDF15 comprises substitutions at one or more positions selected from the group consisting of: K69, K91, K107, and K62. In certain embodiments, the GDF15 comprises substitution of K69, K91, K107, K62, or any combination thereof, to a non-conjugatable residue, optionally selected from the group consisting of Arginine (R), Glutamine (Q), Alanine (A), Glycine (G), Histidine (H), Serine (S), and Threonine (T). In certain embodiments, the GDF15 comprises substitution of K69 which is selected from the group consisting of K69R, K69Q, K69A, K69G, K69H, K69S, K69T, and K69E. In certain embodiments, the GDF15 comprises substitution of K91 which is selected from the group consisting of K91R, K91Q, K91A, K91G, K91H, K91S, and K91T. In certain embodiments, the GDF15 comprises substitution of K107 which is selected from the group consisting of K107R, K107Q, K107A, K107G, K107H, K107S, K107T and K107E. In certain embodiments, the GDF15 comprises substitution of K62 which is selected from the group consisting of K62R, K62Q, K62A, K62G, K62H, K62S, and K62T.

In certain embodiments, the GDF15 comprises substitution of K69 which is selected from K69R, K69E and K69Q, and/or the substitution at K91 is selected from K91R and K91Q, and/or the substitution at K107 is selected from K107R, K107E and K107Q, and/or the substitution at K62 is selected from K62R and K62Q. In certain embodiments, the GDF15 comprises substitution of K69R, K91R, and K107R. In certain embodiments, the GDF15 comprises substitution of K91R, and K107R.

In certain embodiments, the GDF15 comprises K62. In certain embodiments, the GDF15 further comprises K69.

In certain embodiments, the GDF15 comprises or consists of one or more substitutions at a position selected from the group consisting of: N3, M57, M86, K69, K107, and K91, or any combination thereof. In certain embodiments, the GDF15 comprises or consists of one or more substitutions at a position selected from the group consisting of: N3, M57, M86, K69, K107, K91, and K62, or any combination thereof. In certain embodiments, the GDF15 comprises or consists of one or more substitutions selected from the group consisting of: N3Q, M57L, M86L, K69R, K107R, and K91R, or any combination thereof.

In certain embodiments, the GDF15 comprises one or two conjugatable residue. In certain embodiments, the GDF15 comprises up to one conjugatable residue or up to two conjugatable residues. Such an conjugatable residue in the GDF15 can be a naturally occurring residue found in the native GDF15, or a residue introduced by substitution of a non-conjugatable residue with a conjugatable residue, or by insertion of a conjugatable residue (for example at the N terminus or C terminus of the GDF15 or within the GDF15 sequence).

In certain embodiments, the conjugatable residue in GDF15 comprises or consists of cysteine. To avoid any doubt, none of the 9 cysteine residues in the native GDF15 are considered as conjugatable residues defined herein, because the 9 cysteine residues in the native GDF15 are not available for conjugation due to the formation of the four intrachain disulfide bonds and one interchain disulfide bond. In other words, if the conjugatable residue is cysteine, then the native GDF15 would be considered as having no conjugatable residues.

In certain embodiments, the conjugatable residue in GDF15 comprises K91, or K107, or an introduced conjugatable residue selected from the group consisting of lysine, cysteine and non-natural amino acid. In certain embodiments, the GDF15 comprises an amino acid sequence of SEQ ID NO: 291 or SEQ ID NO: 358.

In certain embodiments, when the introduced conjugatable residue is cysteine or NNAA, it can also be introduced at a position selected from the group consisting of K107, and K91. Such introduced conjugatable residue can be introduced to a position that does not significantly reduce the biological activity of GDF15, for example, at a position selected from the group consisting of: H6, P11, H18, T19, V20, R21, A30, M43, A47, R53, A54, M57, H66, R67, L68, A75, A81, P85, M86, Q90, T92, and L105.

In certain embodiments, the GDF15 comprises or consists of combination of substitutions selected from the group consisting of: 1) N3Q, K69R, and K91R; 2) N3Q, and K91R; 3) N3Q and M57L; 4) N3Q, M57L, K69R, and K91R; 5) N3Q, M57L, and K91R; and 6) N3Q; and 7) N3Q, M57L, K69R, and K91R, 8) del 1-3 and M57L, 9) N3Q, M57L, M86L, K69R, K107R, K91R, and 10) N3Q, M57L.

In certain embodiments, the GDF15 comprises or consists of combination of substitutions selected from the group consisting of: 1) N3Q, M57L, K69R, K107R, and K91R; 2) N3Q, K69R, K107R, and K91R; 3) K69R, K107R, and K91R; 4) N3Q, M57L, K107R, and K91R; 5) N3Q, K107R, and K91R; 6) K107R, and K91R; 7) K62R, K69R, K107R, K91R, N3Q, and M57L; 8) K62R, K69R, K107R, K91R, and N3Q; 9) K62R, K69R, K107R, K91R and 10) N3Q, M57L, K69R, and K91R, 11) del 1-3 and M57L, 12) N3Q, M57L, M86L, K69R, K107R, K91R, 13) N3Q, M57L, 14) M57L, and 15) M57L, K69R, K107R, K91R.

In certain embodiments, the GDF15 provided herein comprises or consists of an amino acid sequence selected from the group consisting of: SEQ ID NO: 246, SEQ ID NO: 247, SEQ ID NO: 248, SEQ ID NOs: 290-297, SEQ ID NO: 358, SEQ ID NO: 271, and SEQ ID NO: 451, SEQ ID NO: 479 and SEQ ID NO: 480.

Conjugatable Residues in the Linker

In certain embodiments, the polypeptide linker further comprises a first conjugatable residue, and optionally, a second conjugatable residue. The first conjugatable residue and/or the second conjugatable residue can be introduced to the linker sequence by substitution or insertion. In certain embodiments, a non-conjugatable amino acid residue in the polypeptide linker is substituted with a conjugatable residue. In certain embodiments, a conjugatable residue is inserted into the polypeptide linker. For example, the conjugatable residue can be inserted within one repeat of the repeating sequences, between two repeats of the repeating sequences, or inserted at the N terminal or C terminal of the polypeptide linker.

In certain embodiments, the polypeptide linker comprises up to one or up to two conjugatable residues. In certain embodiments, the polypeptide linker has 1, or 2 conjugatable residues.

In certain embodiments, the conjugatable residue is introduced at any suitable position in the polypeptide linker. In certain embodiments, the first conjugatable residue and/or the second conjugatable residue is/are introduced in the polypeptide linker at a position such that the conjugatable residue is at least 2 amino acid residue away from the N-terminal residue of the GDF15. In certain embodiments, the first conjugatable residue and/or the second conjugatable residue is/are at least 2, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 64, 66, 68, 70, 72, 73, 74, 75 or 76 amino acid residue away from the most N-terminal residue of the GDF15.

In certain embodiments, the C terminus of the linker is directly fused to the N terminus of the GDF15. In certain embodiments, the conjugatable residue is introduced at any position which is at least 2 amino acid residue away from the C-terminus of the polypeptide linker.

In certain embodiments, the polypeptide linker has a length of at least or around 80 amino acid residues. In certain embodiments, the polypeptide linker comprises or consists of an amino acid sequence selected from the group consisting of SEQ ID NOs: 1-59 and 61-88 and 90-93, 454-459, and 463-471, except for one or two substitutions with a conjugatable residue at a position ranging from the $1^{st}$ to the $78^{th}$, from the $1^{st}$ to the $72^{nd}$, from the $1^{st}$ to the $60^{th}$, from the $1^{st}$ to the $50^{th}$, from the $1^{st}$ to the $40^{th}$, from the $1^{st}$ to the $38^{th}$, from the $1^{st}$ to the $32^{nd}$, from the $1^{st}$ to the $30^{th}$, from the $1^{st}$ to the $24^{th}$, from the $1^{st}$ to the $20^{th}$, from $1^{st}$ to the $16^{th}$, from $4^{th}$ to the $60^{th}$, from $4^{th}$ to the $50^{th}$, from $4^{th}$ to the $40^{th}$, from $4^{th}$ to the $38^{th}$, from $4^{th}$ to the $32^{nd}$, from $4^{th}$ to the $24^{th}$, from $4^{th}$ to the $16^{th}$, from $16^{th}$ to the $72^{nd}$, from $16^{th}$ to the $60^{th}$, from $16^{th}$ to the $50^{th}$, from $16^{th}$ to the $40^{th}$, from $16^{th}$ to the $38^{th}$, from $16^{th}$ to the $32^{nd}$, from $16^{th}$ to the $24^{th}$, from $24^{th}$ to the $72^{nd}$, from $24^{th}$ to the $60^{th}$, from $24^{th}$ to the $50^{th}$, from $24^{th}$ to the $40^{th}$, from $24^{th}$ to the $38^{th}$, from $24^{th}$ to the $32^{nd}$, from the $20^{th}$ to the $60^{th}$, from the $30^{th}$ to the $60^{th}$, from the $35^{th}$ to the $50^{th}$, from the $30^{th}$ to the $45^{th}$, from the $25^{th}$ to the $55^{th}$, from the $30^{th}$ to the $50^{th}$, from the $32^{th}$ to the $47^{th}$, from the $35^{th}$ to the $45^{th}$, from the $36^{th}$ to the $44^{th}$, from the $37^{th}$ to the $43^{rd}$, from the $38^{th}$ to the $42^{th}$, from the $39^{th}$ to the $41^{th}$, or the $40^{th}$ residue in the amino acid sequence of the polypeptide linker, with the N terminal residue in the polypeptide linker being the $1^{st}$ residue. In certain embodiments, the conjugatable residue is introduced to a position ranging from the $5^{th}$ to the $73^{rd}$, the $17^{th}$ to the $73^{rd}$, the $25^{th}$ to the $73^{rd}$, the $33^{rd}$ to the $73^{rd}$, the $39^{th}$ to the $73^{rd}$, the $41^{st}$ to the $73^{rd}$, the $51^{st}$ to the $73^{rd}$, the $5^{th}$ to the $51^{st}$, the $17^{th}$ to the $51^{st}$, the $25^{th}$ to the $51^{st}$, the $33^{rd}$ to the $51^{st}$, the $39^{th}$ to the $51^{st}$, the $41^{st}$ to the $51^{st}$, the $5^{th}$ to the $41^{st}$, the $17^{th}$ to the $41^{st}$, the $25^{th}$ to the $41^{st}$, the $33^{rd}$ to the $41^{st}$, the $39^{th}$ to the $41^{st}$, the $5^{th}$ to the $39^{th}$, the $17^{th}$ to the $39^{th}$, the $25^{th}$ to the $39^{th}$, the $33^{rd}$ to the $39^{th}$, the $5^{th}$ to the $33^{rd}$, the $17^{th}$ to the $33^{rd}$, the $25^{th}$ to the $33^{rd}$, the $5^{th}$ to the $25^{th}$, the $17^{th}$ to the $25^{th}$, or the $5^{th}$ to the $17^{th}$ residues in the amino acid sequence of the linker, with the N terminal residue in the polypeptide linker being the $1^{st}$ residue. In certain embodiments, the conjugatable residue is introduced to the $1^{st}$, $5^{th}$, $12^{th}$, $15^{th}$, $17^{th}$, $20^{th}$, $21^{st}$, $25^{th}$, $29^{th}$, $31^{st}$, $32^{nd}$, $33^{rd}$, $35^{th}$, $36^{th}$, $37^{th}$, $39^{th}$, $41^{st}$, $43^{rd}$, $45^{th}$, $51^{st}$, $52^{nd}$, $55^{th}$, 58th, $60^{th}$, $71^{st}$, $76^{th}$, residue of the polypeptide linker. In certain embodiments, the conjugatable residue in the polypeptide linker comprises lysine, cysteine, or a non-natural amino acid.

In certain embodiments, the polypeptide linker comprises two conjugatable residues, in which the first and the second conjugatable residue are introduced to a respective position independently selected from the $1^{st}$ to the 78th, from the $1^{st}$ to the $60^{th}$, from the $1^{st}$ to the $50^{th}$, from the $1^{st}$ to the $40^{th}$, from the $1^{st}$ to the $30^{th}$, from the $1^{st}$ to the $20^{th}$, from the $20^{th}$ to the $60^{th}$, from the $30^{th}$ to the $60^{th}$, from the $35^{th}$ to the $50^{th}$, from the $30^{th}$ to the $45^{th}$, from the $25^{th}$ to the $55^{th}$, from the $30^{th}$ to the $50^{th}$, from the $32^{th}$ to the $47^{th}$, from the $35^{th}$ to the $45^{th}$, from the $36^{th}$ to the $44^{th}$, from the $37^{th}$ to the $43^{th}$, from the $38^{th}$ to the $42^{th}$, from the $39^{th}$ to the $41^{th}$, or the $40^{th}$ residue in the amino acid sequence of the polypeptide linker (e.g. selected from the group consisting of the $1^{st}$, $5^{th}$, $12^{th}$, $15^{th}$, $17^{th}$, $20^{th}$, $21^{st}$, $25^{th}$, $29^{th}$, $31^{st}$, $32^{nd}$, $33^{rd}$, $35^{th}$, $36^{th}$, $37^{th}$, $39^{th}$, $41^{st}$, $43^{rd}$, $45^{th}$, $51^{st}$, $52^{nd}$, $55^{th}$, 58th, $60^{th}$, $71^{st}$, $76^{th}$ residue). In certain embodiments, polypeptide linker comprises two conjugatable residues, in which the first conjugatable residue is introduced to the $1^{st}$ residue and the second conjugatable residue is introduced to the 58th residue of the polypeptide linker. In certain embodiments, the conjugatable residue in the polypeptide linker comprises lysine, cysteine, or a non-natural amino acid. In certain embodiments, the polypeptide linker comprises a sequence set forth in SEQ ID NO: 332.

In certain embodiments, the polypeptide linker has a length of at least or around 60 amino acid residues. In certain embodiments, the polypeptide linker comprises or consists of an amino acid sequence selected from the group consisting of: SEQ ID NOs: 94-156, except for one or two substitutions with the conjugatable residue at a position ranging from the $1^{st}$ to the 58th, from $1^{st}$ to the $52^{nd}$, from the $1^{st}$ to the $50^{th}$, from $1^{st}$ to the $45^{th}$, from the $1^{st}$ to the $40^{th}$, from the $1^{st}$ to the $30^{th}$, from $1^{st}$ to the $25^{th}$, from the $1^{st}$ to the $20^{th}$, from the $20^{th}$ to the $58^{th}$, from the $35^{th}$ to the $50^{th}$, from the $20^{th}$ to the $45^{th}$, from the $25^{th}$ to the $45^{th}$, or from the $20^{th}$ to the $30^{th}$ residue in the amino acid sequence of the linker, with the N terminal residue in the polypeptide linker being the $1^{st}$ residue. In certain embodiments, the conjugatable residue is introduced to the $1^{st}$, $5^{th}$, $12^{th}$, $15^{th}$, $17^{th}$, $20^{th}$, $21^{st}$, $25^{th}$, $29^{th}$, $31^{st}$, $32^{nd}$, $33^{rd}$, $35^{th}$, $36^{th}$, $37^{th}$, $39^{th}$, $41^{st}$, $43^{rd}$, $45^{th}$, $51^{st}$, $52^{nd}$, $55^{th}$, and $58^{th}$ residue of the polypeptide linker. In certain embodiments, the polypeptide linker comprises two conjugatable residues, in which the first and the second conjugatable residue are introduced to a respective position independently selected from the $1^{st}$ to the 58th residue in the amino acid sequence of the polypeptide linker (e.g. selected from the group consisting of the $1^{st}$, $5^{th}$, $12^{th}$, $15^{th}$, $17^{th}$, $20^{th}$, $25^{th}$, $29^{th}$, $31^{st}$, $32^{nd}$, $33^{rd}$, $35^{th}$, $36^{th}$, $37^{th}$, $39^{th}$, $41^{st}$, $43^{rd}$, $45^{th}$, $51^{st}$, $52^{nd}$, $55^{th}$, $58^{th}$ residue). In certain embodiments, the conjugatable residue in the polypeptide linker comprises lysine, cysteine, or a non-natural amino acid.

In certain embodiments, the polypeptide linker has a length of at least or around 40 amino acid residues. In certain embodiments, the polypeptide linker comprises or consists of an amino acid sequence selected from the group consisting of: SEQ ID NOs: 157-197 and 199-209, except for a substitution with the conjugatable residue at a position ranging from the $1^{st}$ to the $38^{th}$, from $1^{st}$ to the $32^{nd}$, from the $1^{st}$ to the $30^{th}$, from $1^{st}$ to the $25^{th}$, from the $1^{st}$ to the $20^{th}$, from the $10^{th}$ to the $30^{th}$, or from the $10^{th}$ to the $20^{th}$ residue in the amino acid sequence of the linker, with the N terminal residue in the polypeptide linker being the $1^{st}$ residue. In certain embodiments, the conjugatable residue is introduced to the $1^{st}$, $6^{th}$, $10^{th}$, $12^{th}$, $14^{th}$, or $15^{th}$ residue of the polypeptide linker.

In certain embodiments, the polypeptide linker comprises two conjugatable residues, in which the first and the second conjugatable residue are introduced to a respective position independently selected from the $1^{st}$ to the 38th, from the $1^{st}$ to the 30th, from the 1st to the 20th, from the 10th to the 30th, or from the 10th to the 20th residue in the amino acid sequence of the polypeptide linker (e.g. selected from the group consisting of the 1st, 6th, 10th, 12th, 14th, or 15th residue). In certain embodiments, the conjugatable residue in the polypeptide linker comprises lysine, cysteine, or a non-natural amino acid.

In certain embodiments, the polypeptide linker comprises or consists of an amino acid sequence selected from the group consisting of: SEQ ID NOs: 210-212, and 460-462, except for one or two substitutions to the conjugatable residue at a position at least 2, 5, 6, 7, 8, 9, 10, 11, 12, 13, 14, 15, 16, 17, 18, 19, 20, 21, 22, 23, 24, 25, 26, 27, 28, 29, or 30 amino acid residues away from the most N-terminal residue of the GDF15. In certain embodiments, the conjugatable residue in the polypeptide linker comprises lysine, cysteine, or a non-natural amino acid.

In certain embodiments, the polypeptide linker comprises or consists of an amino acid sequence selected from the group consisting of: SEQ ID NOs: 298-324, 60, 89, 198, 332, 333, 334, 342-346, 409-447, 475 and 483, or a variant thereof in which the lysine residue in the polypeptide linker is substituted with a cysteine residue or a non-natural amino acid, or in which the cysteine residue in the polypeptide linker is substituted with a lysine residue or a non-natural amino acid.

In such embodiments, the polypeptide linker comprises a substitution with a conjugatable residue which is lysine. In certain embodiments, the conjugatable residue in the polypeptide linker comprises lysine. In such embodiments, the polypeptide linker comprises or consists of an amino acid sequence selected from the group consisting of: SEQ ID NOs: 298-324, 60, 89, 198, 332, 333, 334, 342-346, 409-410, 414-417, and 426-429. In such embodiments, the GDF15 comprises an amino acid sequence selected from the group consisting of: SEQ ID NO: 246, SEQ ID NOs: 290-293, 295-297, SEQ ID NO: 358, SEQ ID NO: 451, SEQ ID NO: 479 and SEQ ID NO: 480 and/or the GLP-1 comprises an amino acid sequence selected from the group consisting of: SEQ ID NO: 243, SEQ ID NO: 244, SEQ ID NO: 245, SEQ ID NO: 448 and SEQ ID NO: 478. In such embodiments, the fusion polypeptide comprises an amino acid sequence selected from the group consisting of: SEQ ID NOs: 252, 254-260, 262-265, 273-289, 327-330, 337-341, 354, 356-357, 359-361, 363-365, 370-373, and 385-386, 390-391.

Alternatively, the polypeptide linker comprises a substitution with a conjugatable residue which is cysteine, or a non-natural amino acid residue. In certain embodiments, the conjugatable residue in the polypeptide linker comprises cysteine. In such embodiments, the polypeptide linker comprises or consists of an amino acid sequence selected from the group consisting of: SEQ ID NOs: 411-413, 418-425, 430-447, 475 and 483. In such embodiments, the GDF15 comprises an amino acid sequence selected from the group consisting of: SEQ ID NO: 247, SEQ ID NO: 248, SEQ ID NO: 294, and SEQ ID NO: 271, and/or the GLP-1 comprises an amino acid sequence selected from the group consisting of: SEQ ID NO: 242, SEQ ID NO: 243, SEQ ID NO: 244, SEQ ID NO: 245, SEQ ID NO: 336, SEQ ID NO: 448 and SEQ ID NO: 478. In such embodiments, the fusion polypeptide comprises an amino acid sequence selected from the group consisting of: SEQ ID NOs: 367-369, 374-381, 392-400, 402-408, 472-473, 477, 481 and 482. In certain embodiments, the polypeptide linker comprising at least one conjugatable residue comprises or consists of an amino acid sequence selected from the group consisting of: SEQ ID NOs: 298-324, 60, 89, 198, 332, 333, 334, 342-346, 409-447, 475 and 483, or a variant thereof in which the lysine residue in the polypeptide linker is substituted with a cysteine residue or a non-natural amino acid, or in which the cysteine residue in the polypeptide linker is substituted with a lysine residue or a non-natural amino acid.

In certain embodiments, the polypeptide linker has no conjugatable residue. In such embodiments, the polypeptide linker comprises an amino acid sequence selected from the group consisting of SEQ ID NOs: 5, 9, 33, 51, 58, 64, 18, 91, 157, 158, 159, 116, 210, 211 and 461. In such embodiments, the fusion polypeptide comprises an amino acid sequence comprising or consisting of: SEQ ID NOs: 249, 266-270, 347, 383 and 387.

In certain embodiments, the fusion polypeptide comprises up to one conjugatable residue for acylation. In such embodiments, the one conjugatable residue is in the GLP-1, in the polypeptide linker, or in the GDF15.

In certain embodiments, the fusion polypeptide comprises up to one conjugatable residue for acylation. In such embodiments, the fusion polypeptide comprises an amino acid sequence selected from the group consisting of: SEQ ID NOs: 249, 251-260, 262-265, 273-289, 326, 329-331, 337-341, 349, 350, 354-357, 359-365, 370-373, 385-386, and 390-391.

In certain embodiments, the fusion polypeptide comprises up to one conjugatable residue for alkylation. In such embodiments, the fusion polypeptide comprises up to one conjugatable residue for alkylation, and comprises an amino acid sequence selected from the group consisting of: SEQ ID NOs: 366-369, 374-381, 392-408, 472-473 and 477.

In certain embodiments, the fusion polypeptide comprises up to two conjugatable residues. In such embodiments, the two conjugatable residues can be both in the polypeptide linker. For example, such a polypeptide linker may comprise an amino acid sequence selected from the group consisting of: SEQ ID NOs: 327-328, 352-353 and 361. In certain other embodiments, the first of the two conjugatable residues can be in the GLP-1 and the second can be in the polypeptide linker. In certain embodiments, the first conjugatable residue in the GLP-1 is selected from the group consisting of: K26, K34, E27K, and R36K, relative to SEQ ID NO: 242, and the second conjugatable residue is at the 1st, 12th, 15th, 41st, 52nd, 58th, or 60th residue of the polypeptide linker having a length of 80 amino acid residues (e.g. those having a sequence of any of SEQ ID NOs: 1-59 and 61-88 and 90-93), or the 1st, 12th, 15th, 32nd 38th and 40th residue of the polypeptide linker having a length of 60 amino acid residues (e.g. those having a sequence of any of SEQ ID NOs: 94-156) or at the 1st, 6th, 10th, 12th, 14th, 15th or 20th residue of the polypeptide linker having a length of 40 amino acid residues (e.g. those having a sequence of any of SEQ ID NOs: 157-197 and 199-209).

In certain embodiments, the fusion polypeptide provided herein comprise an amino acid sequence selected from the group consisting of: SEQ ID NOs: 249, 266, 267, 268, 269, 270, 347, 251, 260, 263-265, 273, 277, 329-330, 359, 369, 374, 376-381, and 392-408.

Table 1 below shows the SEQ ID NOs of the exemplary fusion polypeptide sequences, and the SEQ ID NOs for the GLP-1, linker and GDF15 sequences contained in the fusion polypeptides provided herein. Table 1 below also shows the mutations in the GLP-1 and in the GDF15, as well as the repeating sequences and number of repeats in the linker sequences.

TABLE 1

Exemplary fusion polypeptide sequences

| SEQ ID NO | Mutations in GLP-1** | Linker | Mutations in GDF154 |
|---|---|---|---|
| 249 | 8G, 34R, 22E, 36G (SEQ ID NO: 243) | (GQEP)8(GAQP)2 (SEQ ID NO: 157) | N3Q, M57L, Triple-R* (SEQ ID NO: 246) |
| 251 | 8G, 34R, 22E, 36G (SEQ ID NO: 243) | (GQEPGAQP)6(GAQP)8 (SEQ ID NO: 5) | N3Q, M57L, Triple-R* (SEQ ID NO: 246) |
| 252 | 8G, 26R, 34R, 22E, 36G (SEQ ID NO: 244) | (GQEP)2GQEK(GQEP)5(GAQP)2 (SEQ ID NO: 298) | N3Q, M57L, Triple-R* (SEQ ID NO: 246) |
| 253 | 8G, 26R, 34R, 22E, 36K (SEQ ID NO: 245) | (GQEP)8(GAQP)2 (SEQ ID NO: 157) | N3Q, M57L, Triple-R* (SEQ ID NO: 246) |
| 254 | 8G, 26R, 34R, 22E, 36G (SEQ ID NO: 244) | KQEP(GQEP)7(GAQP)2 (SEQ ID NO: 299) | N3Q, M57L, Triple-R* (SEQ ID NO: 246) |
| 255 | 8G, 26R, 34R, 22E, 36G (SEQ ID NO: 244) | GQEPGKEP(GQEP)6(GAQP)2 (SEQ ID NO: 300) | N3Q, M57L, Triple-R* (SEQ ID NO: 246) |
| 256 | 8G, 26R, 34R, 22E, 36G (SEQ ID NO: 244) | (GQEP)3GQKP(GQEP)4(GAQP)2 (SEQ ID NO: 301) | N3Q, M57L, Triple-R* (SEQ ID NO: 246) |
| 257 | 8G, 26R, 34R, 22E, 36G (SEQ ID NO: 244) | SEPKTSGSETPGTSESATPESGPGTSTEPSEG (SEQ ID NO: 302) | N3Q, M57L, Triple-R* (SEQ ID NO: 246) |
| 258 | 8G, 26R, 34R, 22E, 36G (SEQ ID NO: 244) | (GQEPGAQP)2(GQEKGAQP)(GQEPGAQP)(GQEP)2 (SEQ ID NO: 303) | N3Q, M57L, Triple-R* (SEQ ID NO: 246) |
| 259 | 8G, 26R, 34R, 22E, 36G (SEQ ID NO: 244) | (GQEP)2GQEK(GQEP)7 (SEQ ID NO: 304) | N3Q, M57L, Triple-R* (SEQ ID NO: 246) |
| 260 | 8G, 26R, 34R, 22E, 36G (SEQ ID NO: 244) | KQEPGAQP(GQEPGAQP)5(GAQP)8 (SEQ ID NO: 305) | N3Q, M57L, Triple-R* (SEQ ID NO: 246) |
| 262 | 8G, 26R, 34R, 22E, 36G (SEQ ID NO: 244) | GQEPGAQPGQEKGAQP(GQEPGAQP)4(GAQP)8 (SEQ ID NO: 307) | N3Q, M57L, Triple-R* (SEQ ID NO: 246) |
| 263 | 8G, 26R, 34R, 22E, 36G (SEQ ID NO: 244) | (GQEPGAQP)6(GAQK)(GAQP)7 (SEQ ID NO: 308) | N3Q, M57L, Triple-R* (SEQ ID NO: 246) |
| 264 | 8G, 26R, 34R, 22E, 36G (SEQ ID NO: 244) | (GQEPGAQP)6(GAQP)(GAKP)(GAQP)6 (SEQ ID NO: 309) | N3Q, M57L, Triple-R* (SEQ ID NO: 246) |
| 265 | 8G, 26R, 34R, 22E, 36G (SEQ ID NO: 244) | (GQEPGAQP)6(GQEKGAQP)(GQEPGAQP)3 (SEQ ID NO: 310) | N3Q, M57L, Triple-R* (SEQ ID NO: 246) |

TABLE 1 -continued

Exemplary fusion polypeptide sequences

| SEQ ID NO | Mutations in GLP-1** | Linker | Mutations in GDF154 |
|---|---|---|---|
| 267 | 8G, 34R, 22E, 36G (SEQ ID NO: 243) | (GQEP)8(GAQP)2 (SEQ ID NO: 157) | N3Q, M57L (SEQ ID NO: 247) |
| 268 | 8G, 34R, 22E, 36G (SEQ ID NO: 243) | (GQEPGAQP)6(GAQP)8 (SEQ ID NO: 5) | N3Q, M57L (SEQ ID NO: 247) |
| 269 | 8G, 34R, 22E, 36G (SEQ ID NO: 243) | (GQEP)6 (SEQ ID NO: 210) | N3Q, M57L (SEQ ID NO: 247) |
| 270 | 8G, 34R, 22E, 36G (SEQ ID NO: 243) | (GQEP)3 (SEQ ID NO: 211) | N3Q, M57L (SEQ ID NO: 247) |
| 273 | 8G, 26R, 34R, 22E, 36G (SEQ ID NO: 244) | (GAQP)10(GQEP)3GQKP(GQEP)4(GAQP)2 (SEQ ID NO: 311) | N3Q, M57L, Triple-R* (SEQ ID NO: 246) |
| 274 | 8G, 26R, 34R, 22E, 36G (SEQ ID NO: 244) | (GAQP)7(GAQPGQEP)3GQKP(GQEP)4(GAQP)2 (SEQ ID NO: 312) | N3Q, M57L, Triple-R* (SEQ ID NO: 246) |
| 275 | 8G, 26R, 34R, 22E, 36G (SEQ ID NO: 244) | (GAQP)10(GQEP)2GQEK(GQEP)5(GAQP)2 (SEQ ID NO: 313) | N3Q, M57L, Triple-R* (SEQ ID NO: 246) |
| 276 | 8G, 26R, 34R, 22E, 36G (SEQ ID NO: 244) | (GAQP)8(GAQPGQEP)2GQEK(GQEP)5(GAQP)2 (SEQ ID NO: 314) | N3Q, M57L, Triple-R* (SEQ ID NO: 246) |
| 277 | 8G, 26R, 34R, 22E, 36G (SEQ ID NO: 244) | (GQEP)3GQKP(GQEP)4(GAQP)12 (SEQ ID NO: 315) | N3Q, M57L, Triple-R* (SEQ ID NO: 246) |
| 278 | 8G, 26R, 34R, 22E, 36G (SEQ ID NO: 244) | (GQEP)2GQEK(GQEP)5(GAQP)12 (SEQ ID NO: 316) | N3Q, M57L, Triple-R* (SEQ ID NO: 246) |
| 279 | 8G, 26R, 34R, 22E, 36G (SEQ ID NO: 244) | SEPATSGSETPGTKESATPESGPGTSTEPSEG(GAQP)2 (SEQ ID NO: 317) | N3Q, M57L, Triple-R* (SEQ ID NO: 246) |
| 280 | 8G, 26R, 34R, 22E, 36G (SEQ ID NO: 244) | (GAQP)12GQEPGQKP(GQEP)6 (SEQ ID NO: 318) | N3Q, M57L, Triple-R* (SEQ ID NO: 246) |
| 281 | 8G, 26R, 34R, 22E, 36G (SEQ ID NO: 244) | (GAQP)12GQEK(GQEP)7 (SEQ ID NO: 319) | N3Q, M57L, Triple-R* (SEQ ID NO: 246) |
| 282 | 8G, 26R, 34R, 22E, 36G (SEQ ID NO: 244) | (GAQP)3GAKP(GAQP)8(GQEP)8 (SEQ ID NO: 320) | N3Q, M57L, Triple-R* (SEQ ID NO: 246) |
| 283 | 8G, 26R, 34R, 22E, 36G (SEQ ID NO: 244) | (GAQP)2GAQK(GAQP)9(GQEP)8 (SEQ ID NO: 321) | N3Q, M57L, Triple-R* (SEQ ID NO: 246) |

TABLE 1 -continued

Exemplary fusion polypeptide sequences

| SEQ ID NO | Mutations in GLP-1** | Linker | Mutations in GDF154 |
|---|---|---|---|
| 284 | 8G, 26R, 34R, 22E, 36G (SEQ ID NO: 244) | KQEPGAQP(GQEPGAQP)9 (SEQ ID NO: 322) | N3Q, M57L, Triple-R* (SEQ ID NO: 246) |
| 285 | 8G, 26R, 34R, 22E, 36G (SEQ ID NO: 244) | KAQP(GAQP)9(GQEP)8(GAQP)2 (SEQ ID NO: 323) | N3Q, M57L, Triple-R* (SEQ ID NO: 246) |
| 286 | 8G, 26R, 34R, 22E, 36G (SEQ ID NO: 244) | KAQP(GAQP)6(GAQPGQEP)3(GQEP)5(GAQP)2 (SEQ ID NO: 324) | N3Q, M57L, Triple-R* (SEQ ID NO: 246) |
| 287 | 8G, 26R, 34R, 22E, 36G (SEQ ID NO: 244) | KAQP(GAQP)7(GAQPGQEP)2(GQEP)6(GAQP)2 (SEQ ID NO: 89) | N3Q, M57L, Triple-R* (SEQ ID NO: 246) |
| 288 | 8G, 26R, 34R, 22E, 36G (SEQ ID NO: 244) | KQEP(GQEP)7(GAQP)12 (SEQ ID NO: 60) | N3Q, M57L, Triple-R* (SEQ ID NO: 246) |
| 289 | 8G, 26R, 34R, 22E, 36G (SEQ ID NO: 244) | KAQP(GAQP)11(GQEP)8 (SEQ ID NO: 198) | N3Q, M57L, Triple-R* (SEQ ID NO: 246) |
| 326 | 8G, 34R, 22E, 36G (SEQ ID NO: 243) | (GQEPGAQP)6(GAQP)3 (SEQ ID NO: 116) | N3Q, M57L, Triple-R* (SEQ ID NO:246) |
| 327 | 8G, 34R, 22E, 36G (SEQ ID NO: 243) | (GQEPGAQP)6(GAQP)(GAKP)(GAQP)6 (SEQ ID NO: 309) | N3Q, M57L, Triple-R* (SEQ ID NO: 246) |
| 328 | 8G, 26R, 34R, 22E, 36G (SEQ ID NO: 244) | KQEP(GQEPGAQP)5(GAQP)(GAKP)(GAQP)6 (SEQ ID NO: 332) | N3Q, M57L, Triple-R* (SEQ ID NO: 246) |
| 329 | 8G, 26R, 34R, 22E, 36G (SEQ ID NO: 244) | (GQEPGAQP)6(GAQP)2(GAQK)(GAQP)5 (SEQ ID NO: 333) | N3Q, M57L, Triple-R* (SEQ ID NO: 246) |
| 330 | 8G, 26R, 34R, 22E, 36G (SEQ ID NO: 244) | (GQEPGAQP)4(GQEPGAQK)(GQEPGAQP)(GAQP)8 (SEQ ID NO: 334) | N3Q, M57L, Triple-R* (SEQ ID NO: 246) |
| 331 | 8G, 34R, 22E, 36G (SEQ ID NO: 243) | (GAQPGQEP)7(GAQP)6 (SEQ ID NO: 91) | N3Q, M57L, Triple-R* (SEQ ID NO: 246) |
| 337 | 8G, 26R, 34R, 22E, 36G (SEQ ID NO: 244) | (KQEPGAQP)(GQEPGAQP)5(GAQP)3 (SEQ ID NO: 342) | N3Q, M57L, Triple-R* (SEQ ID NO: 246) |
| 338 | 8G, 26R, 34R, 22E, 36G (SEQ ID NO: 244) | (GQEPGAQP)3(GQEPGAQK)(GQEPGAQP)2(GAQP)3 (SEQ ID NO: 343) | N3Q, M57L, Triple-R* (SEQ ID NO: 246) |
| 339 | 8G, 26R, 34R, 22E, 36G (SEQ ID NO: 244) | (GQEPGAQP)3(GQEPGAQP)(GQKPGAQP)2 (GAQP)3 (SEQ ID NO: 344) | N3Q, M57L, Triple-R* (SEQ ID NO: 246) |

TABLE 1 -continued

Exemplary fusion polypeptide sequences

| SEQ ID NO | Mutations in GLP-1** | Linker | Mutations in GDF154 |
|---|---|---|---|
| 340 | 8G, 26R, 34R, 22E, 36G (SEQ ID NO: 244) | (GQEPGAQP)(GQEKGAQP)(GQEPGAQP)4 (GAQP)3 (SEQ ID NO: 345) | N3Q, M57L, Triple-R* (SEQ ID NO: 246) |
| 341 | 8G, 26R, 34R, 22E, 36G (SEQ ID NO: 244) | (GQEPGAQP)(GQEPGAKP)(GQEPGAQP)4(GAQP)3 (SEQ ID NO: 346) | N3Q, M57L, Triple-R* (SEQ ID NO: 246) |
| 347 | 8G, 34R, 22E, 36G (SEQ ID NO: 243) | (GQEPGAQP)6(GAQP)3 (SEQ ID NO: 116) | N3Q, M57L (SEQ ID NO: 247) |
| 349 | 8G, 26R, 34R, 22E, 36G (SEQ ID NO: 244) | (GQEPGAQP)6(GAQP)8 (SEQ ID NO: 5) | N3Q, M57L, K69R, K107R (SEQ ID NO: 358) |
| 350 | 8G, 26R, 34R, 22E, 36G (SEQ ID NO: 244) | (GQEPGAQP)6(GAQP)8 (SEQ ID NO: 5) | N3Q, M57L, K69R, K91R (SEQ ID NO: 291) |
| 352 | 8G, 34R, 22E, 36G (SEQ ID NO: 243) | (GQEPGAQP)6(GAQP)8 (SEQ ID NO: 5) | N3Q, M57L, K69R, K107R (SEQ ID NO: 358) |
| 353 | 8G, 34R, 22E, 36G (SEQ ID NO: 243) | (GQEPGAQP)6(GAQP)8 (SEQ ID NO: 5) | N3Q, M57L, K69R, K91R (SEQ ID NO: 291) |
| 354 | 8G, 26R, 34R, 22E, 36G (SEQ ID NO: 244) | KQEPGAQP(GQEPGAQP)5(GAQP)8 (SEQ ID NO: 305) | N3Q, M57L, K91R, K107R (SEQ ID NO: 290) |
| 355 | 8G, 34R, 22E, 36G (SEQ ID NO: 243) | (GQEPGAQP)6(GAQP)8 (SEQ ID NO: 5) | N3Q, M57L, K91R, K107R (SEQ ID NO: 290) |
| 356 | 8G, 26R, 34R, 22E, 36G (SEQ ID NO: 244) | (GQEPGAQP)6(GAQP)(GAKP)(GAQP)6 (SEQ ID NO: 309) | N3Q, M57L, K91R, K107R (SEQ ID NO: 290) |
| 357 | 8G, 26R, 34R, 22E, 36G (SEQ ID NO: 244) | (GQEPGAQP)6(GQEKGAQP)(GQEPGAQP)3 (SEQ ID NO: 310) | N3Q, M57L, K91R, K107R (SEQ ID NO: 290) |
| 359 | 8G, 26R, 34R, 22E, 36G (SEQ ID NO: 244) | (GQEPGAQP)6(GAKP)(GAQP)7 (SEQ ID NO: 409) | N3Q, M57L, Triple-R* (SEQ ID NO: 246) |
| 360 | 8G, 26R, 34R, 22E, 36G (SEQ ID NO: 244) | (GAQP)10(GQEP)2GQKP(GQEP)5(GAQP)2 (SEQ ID NO: 410) | N3Q, M57L, Triple-R* (SEQ ID NO: 246) |
| 361 | 8G, 34R, 22E, 36G (SEQ ID NO: 243) | KQEPGAQP(GQEPGAQP)5(GAQP)8 (SEQ ID NO: 305) | N3Q, M57L, Triple-R* (SEQ ID NO: 246) |
| 362 | 8G, 34R, 22E, 36G (SEQ ID NO: 243) | (GQEPGAQP)6(GAQP)8 (SEQ ID NO: 5) | N3Q, M57L, M86L, Triple-R* (SEQ ID NO: 452) |

TABLE 1 -continued

Exemplary fusion polypeptide sequences

| SEQ ID NO | Mutations in GLP-1** | Linker | Mutations in GDF154 |
|---|---|---|---|
| 363 | 8G, 26R, 34R, 22E, 36G (SEQ ID NO: 244) | KQEPGAQP(GQEPGAQP)5(GAQP)8 (SEQ ID NO: 305) | N3Q, M57L, M86L, Triple-R* (SEQ ID NO: 452) |
| 364 | 8G, 26R, 34R, 22E, 36G (SEQ ID NO: 244) | (GQEPGAQP)6(GAQP)(GAKP)(GAQP)6 (SEQ ID NO: 309) | N3Q, M57L, M86L, Triple-R* (SEQ ID NO: 452) |
| 365 | 8G, 26R, 34R, 22E, 36G (SEQ ID NO: 244) | (GQEPGAQP)6(GAQK)(GAQP)7 (SEQ ID NO: 308) | N3Q, M57L, M86L, Triple-R* (SEQ ID NO: 452) |
| 366 | 8G, 26O, 34R, 22E, 36G (SEQ ID NO: 448) | (GQEPGAQP)6(GAQP)8 (SEQ ID NO: 5) | N3Q, M57L (SEQ ID NO: 247) |
| 367 | 8G, 34R, 22E, 36G (SEQ ID NO: 243) | CQEPGAQP(GQEPGAQP)5(GAQP)8 (SEQ ID NO: 411) | N3Q, M57L (SEQ ID NO: 247) |
| 368 | 8G, 34R, 22E, 36G (SEQ ID NO: 243) | (GQEPGAQP)6(GAQP)(GACP)(GAQP)6 (SEQ ID NO: 412) | N3Q, M57L (SEQ ID NO: 247) |
| 369 | 8G, 34R, 22E, 36G (SEQ ID NO: 243) | (GQEPGAQP)5(CQEPGAQP)(GAQP)8 (SEQ ID NO: 413) | N3Q, M57L (SEQ ID NO: 247) |
| 370 | 8G, 26R, 34R, 22E, 36G (SEQ ID NO: 244) | (GQEPGAQP)4(GQKPGAQP)(GQEPGAQP)2(GAQP)6 (SEQ ID NO: 414) | N3Q, M57L, Triple-R* (SEQ ID NO: 246) |
| 371 | 8G, 26R, 34R, 22E, 36G (SEQ ID NO: 244) | (GQEPGAQP)3(GQEPKQAP)(GQEPGAQP)2(GAQP)8 (SEQ ID NO: 415) | N3Q, M57L, Triple-R* (SEQ ID NO: 246) |
| 372 | 8G, 26R, 34R, 22E, 36G (SEQ ID NO: 244) | (GQEPGAQP)3(KQEPGAQP)(GQEPGAQP)2(GAQP)8 (SEQ ID NO: 416) | N3Q, M57L, Triple-R* (SEQ ID NO: 246) |
| 373 | 8G, 26R, 34R, 22E, 36G (SEQ ID NO: 244) | (GQEPGAQP)2(GQEPKQAP)(GQEPGAQP)3 (GAQP)8 (SEQ ID NO: 417) | N3Q, M57L, Triple-R* (SEQ ID NO: 246) |
| 374 | 8G, 34R, 22E, 36G (SEQ ID NO: 243) | (GQEPGAQP)4(GQCPGAQP)(GQEPGAQP)2(GAQP)6 (SEQ ID NO: 418) | N3Q, M57L (SEQ ID NO: 247) |
| 375 | 8G, 34R, 22E, 36G (SEQ ID NO: 243) | (GQEPGAQP)6(GQCP)(GAQP)7 (SEQ ID NO: 419) | N3Q, M57L (SEQ ID NO: 247) |
| 376 | 8G, 34R, 22E, 36G (SEQ ID NO: 243) | (GQEPGAQP)4(GQEPGQCP)(GQEPGAQP)(GAQP)8 (SEQ ID NO: 420) | N3Q, M57L (SEQ ID NO: 247) |
| 377 | 8G, 34R, 22E, 36G (SEQ ID NO: 243) | (GQEPGAQP)4(GQEPCQAP)(GQEPGAQP)(GAQP)8 (SEQ ID NO: 421) | N3Q, M57L (SEQ ID NO: 247) |

TABLE 1 -continued

Exemplary fusion polypeptide sequences

| SEQ ID NO | Mutations in GLP-1** | Linker | Mutations in GDF154 |
|---|---|---|---|
| 378 | 8G, 34R, 22E, 36G (SEQ ID NO: 243) | (GAQP)8(GQEPGAQP)(CQEPGAQP)(GQEPGAQP)4 (SEQ ID NO: 422) | N3Q, M57L (SEQ ID NO: 247) |
| 379 | 8G, 34R, 22E, 36G (SEQ ID NO: 243) | (GAQP)8(GQEPGQCP)(GQEPGAQP)5 (SEQ ID NO: 423) | N3Q, M57L (SEQ ID NO: 247) |
| 380 | 8G, 34R, 22E, 36G (SEQ ID NO: 243) | (GAQP)8(GQCPGAQP)(GQEPGAQP)5 (SEQ ID NO: 424) | N3Q, M57L (SEQ ID NO: 247) |
| 381 | 8G, 34R, 22E, 36G (SEQ ID NO: 243) | (GAQP)8(CQEPGAQP)(GQEPGAQP)5 (SEQ ID NO: 425) | N3Q, M57L (SEQ ID NO: 247) |
| 385 | 8G, 34R, 22E, 36G (SEQ ID NO: 243) | (GAQP)8(GQEPGQKP)(GQEPGAQP)(GQEPGAQP)4 (SEQ ID NO: 426) | N3Q, M57L, Triple-R* (SEQ ID NO: 246) |
| 386 | 8G, 34R, 22E, 36G (SEQ ID NO: 243) | (GAQP)6(GQEPGAQP)(GQKPGAQP)(GQEPGAQP)(GQEPGAQP)4 (SEQ ID NO: 427) | N3Q, M57L, Triple-R* (SEQ ID NO: 246) |
| 387 | 8G, 34R, 22E, 36G (SEQ ID NO: 243) | (GQEP) (SEQ ID NO: 215) | N3Q, M57L (SEQ ID NO: 247) |
| 388 | 8G, 34R, 22E, 36G (SEQ ID NO: 243) | / | N3Q, M57L (SEQ ID NO: 247) |
| 389 | 8G, 34R, 22E, 36G (SEQ ID NO: 243) | (GQEPGAQP)6(GAQP)18 (SEQ ID NO: 461) | N3Q, M57L (SEQ ID NO: 247) |
| 390 | 8G, 26R, 34R, 22E, 36G (SEQ ID NO: 244) | (GQEPGAQP)6(GAQP)5(GAKP)(GAQP)2 (SEQ ID NO: 428) | N3Q, M57L, Triple-R* (SEQ ID NO: 246) |
| 391 | 8G, 26R, 34R, 22E, 36G (SEQ ID NO: 244) | (GQEPGAQP)6(GAQP)6(GAQK)(GAQP) (SEQ ID NO: 429) | N3Q, M57L, Triple-R* (SEQ ID NO: 246) |
| 392 | 8G, 34R, 22E, 36G (SEQ ID NO: 243) | (GAQP)4(CQAP)(GAQP)3(GQEPGAQP)6 (SEQ ID NO: 430) | N3Q, M57L (SEQ ID NO: 247) |
| 393 | 8G, 34R, 22E, 36G (SEQ ID NO: 243) | (GAQP)5(CQAP)(GAQP)2(GQEPGAQP)6 (SEQ ID NO: 431) | N3Q, M57L (SEQ ID NO: 247) |
| 394 | 8G, 34R, 22E, 36G (SEQ ID NO: 243) | (GAQP)6(CQAP)(GAQP)(GQEPGAQP)6 (SEQ ID NO: 432) | N3Q, M57L (SEQ ID NO: 247) |
| 395 | 8G, 34R, 22E, 36G (SEQ ID NO: 243) | (GQEPGAQP)3(GQEPGQCP)(GQEPGAQP)2(GAQP)8 (SEQ ID NO: 433) | N3Q, M57L (SEQ ID NO: 247) |

TABLE 1 -continued

Exemplary fusion polypeptide sequences

| SEQ ID NO | Mutations in GLP-1** | Linker | Mutations in GDF154 |
|---|---|---|---|
| 396 | 8G, 34R, 22E, 36G (SEQ ID NO: 243) | (GQEPGAQP)3(CQEPGAQP)(GQEPGAQP)2(GAQP)8 (SEQ ID NO: 434) | N3Q, M57L (SEQ ID NO: 247) |
| 397 | 8G, 34R, 22E, 36G (SEQ ID NO: 243) | (GAQP)8(GQEPGAQP)(GQEPCQAP)(GQEPCQAP)4 (SEQ ID NO: 435) | N3Q, M57L (SEQ ID NO: 247) |
| 398 | 8G, 34R, 22E, 36G (SEQ ID NO: 243) | (GAQP)8(GQEPGAQP)2(GQCPGQEP)(GQEPCQAP)3 (SEQ ID NO: 436) | N3Q, M57L (SEQ ID NO: 247) |
| 399 | 8G, 34R, 22E, 36G (SEQ ID NO: 243) | (GAQP)7(CAQP)(GQEPCQAP)6 (SEQ ID NO: 437) | N3Q, M57L (SEQ ID NO: 247) |
| 402 | 8G, 34R, 22E, 36G (SEQ ID NO: 243) | (GAQP)8(CQEPGAQP)(GQEPGAQP)5(GAQP) (SEQ ID NO: 440) | del 1-3##, M57L (SEQ ID NO: 271) |
| 403 | 8G, 34R, 22E, 36G (SEQ ID NO: 243) | (GAQP)8(GQEPGQCP)(GQEPGAQP)5(GAQP) (SEQ ID NO: 441) | del 1-3##, M57L (SEQ ID NO: 271) |
| 404 | 8G, 22E, 36G (SEQ ID NO: 336) | (GAQP)8(CQEPGAQP)(GQEPGAQP)5 (SEQ ID NO: 442) | N3Q, M57L (SEQ ID NO: 247) |
| 405 | 8G, 22E, 36G (SEQ ID NO: 336) | (GAQP)8(GQEPGQCP)(GQEPGAQP)5 (SEQ ID NO: 443) | N3Q, M57L (SEQ ID NO: 247) |
| 408 | 8G, 34R, 22E, 36G (SEQ ID NO: 243) | (GAQP)12(GQEPGAQP)5(CQEPGAQP)(GAQP)19 (SEQ ID NO: 446) | N3Q, M57L (SEQ ID NO: 247) |
| 472 | 8G, 34R, 22E, 36G (SEQ ID NO: 243) | (GAQP)(CQAP)(GAQP)6(GQEPGAQP)6 (SEQ ID NO: 447) | N3Q, M57L (SEQ ID NO: 247) |
| 473 | 8G, 34R, 22E, 36G (SEQ ID NO: 243) | (GAQP)8(GQEPGAQP)5(GQEPGQCP) (SEQ ID NO: 475) | N3Q, M57L (SEQ ID NO: 247) |
| 477 | 8Aib, 34R, 22E, 36G (SEQ ID NO: 278) | (GAQP)8(CQEPGAQP)(GQEPGAQP)5(GAQP) (SEQ ID NO: 440) | N3Q, M57L, Triple-R* (SEQ ID NO: 246) |
| 481 | 8G, 34R, 22E, 36G (SEQ ID NO: 243) | (GAQP)8(GQEPGAQP)5(CQEPGAQP) (SEQ ID NO: 483) | N3Q, M57L (SEQ ID NO: 247) |
| 482 | 8G, 34R, 22E, 26C, 36G (SEQ ID NO: 448) | (GAQP)8(GQEPGAQP)6 (SEQ ID NO: 44) | N3Q, M57L (SEQ ID NO: 247) |

**: Mutations in GLP-1 means mutations relative to SEQ ID NO: 242, wherein the first residue is 7H, and the last residue is 37G;
: Mutations in GDF15 means mutations relative to SEQ ID NO: 248, wherein the first residue is A1, and the last residue is I112;
*: Triple-R refers to K69R, K107R, and K91R
: del 1-3 in GDF15 means deletion of the first three amino acids from the N-terminus relative to SEQ ID NO: 248;

Polypeptide Complex

In another aspect, the present disclosure provides a polypeptide complex comprising a dimer of the fusion polypeptide provided herein.

The term "polypeptide complex(es)" as used herein, means a complex comprises two or more fusion polypeptides, polypeptides or polypeptide fragments held together by covalent interactions (e.g. disulfide bond between cysteines) or non-covalent interactions. A polypeptide complex can be generated naturally or synthetically. The two or more fusion polypeptides, polypeptides or polypeptide fragments in the polypeptide complex may be the same or different. In certain embodiments, the polypeptide complex is a homodimer.

In certain embodiments, the dimer is associated with a disulfide bond.

In certain embodiments, the disulfide bond is formed between the second polypeptide fragments comprising the GDF15.

Method of Preparation

The present disclosure provides isolated nucleic acids or polynucleotides that encode the fusion polypeptide provided herein or the polypeptide complex provided herein.

The term "nucleic acid" or "polynucleotide" as used herein refers to deoxyribonucleic acids (DNA) or ribonucleic acids (RNA) and polymers thereof in either single- or double-stranded form. Unless specifically limited, the term encompasses polynucleotides containing known analogues of natural nucleotides that have similar binding properties as the reference nucleic acid and are metabolized in a manner similar to naturally occurring nucleotides. Unless otherwise indicated, a particular polynucleotide sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (see Batzer et al., Nucleic Acid Res. 19:5081 (1991); Ohtsuka et al., J. Biol. Chem. 260: 2605-2608 (1985); and Rossolini et al., Mol. Cell. Probes 8:91-98 (1994)).

The nucleic acids or polynucleotides encoding the fusion polypeptide provided herein or the polypeptide complex provided herein can be constructed using recombinant techniques. To this end, DNA encoding the GLP-1 receptor agonist (such as GLP-1) and DNA encoding the GFARL agonist (such as GFD 15) fusion polypeptide or the polypeptide complex can be obtained and operably linked to allow transcription and expression in a host cell to produce the fusion polypeptide. If needed, polynucleotide sequences encoding for one or more linkers are also operably linked to allow expression of the desired product.

The encoding polynucleotide sequences can be further operably linked to one or more regulatory sequences, optionally in an expression vector, such that the expression or production of the fusion polypeptides or polypeptide complexes is feasible and under proper control.

The encoding polynucleotide sequence(s) can be inserted into a vector for further cloning (amplification of the DNA) or for expression, using recombinant techniques known in the art. Many vectors are available. The vector components generally include, but are not limited to, one or more of the following: a signal sequence, an origin of replication, one or more marker genes, an enhancer element, a promoter (e.g. prokaryotic promoters such as T7, T7lac, Sp6, araBAD, trp, lac, tac, pLm, A3, lac, Ipp, npr, pac, syn, trc and T3, or eukaryotic promoters such as SV40, CMV, and EF-1α), and a transcription termination sequence.

Vectors and Host Cells

In another aspect, the present disclosure provides a vector comprising the polynucleotide of provided herein.

Vectors comprising the polynucleotide sequence(s) provided herein can be introduced to a host cell for cloning or gene expression. The phrase "host cell" as used herein refers to a cell into which an exogenous polynucleotide and/or a vector has been introduced. In other embodiments, the vectors are extra-chromosomal. The host cells can be isolated if desired. In certain embodiments, the host cell is a prokaryotic cell or eukaryotic cell.

Suitable host cells for cloning or expressing the DNA in the vectors herein are mainly prokaryotes. Suitable prokaryotes for this purpose include eubacteria, such as Gram-negative or Gram-positive organisms, for example, Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as Bacilli such as *B. subtilis* and *B. licheniformis*, *Pseudomonas* such as *P. aeruginosa*, and *Streptomyces*. In some embodiments, host cells are eukaryotes, such as yeast and mammalian cells (e.g., immortalized mammalian cells).

A vector comprising the polynucleotide sequence(s) provided herein can be introduced into a host cell using any suitable method known to a skilled person in the art, e.g., transformation, transfection or transduction. In one example, the polynucleotide sequence encoding the GLP-1/GDF15 fusion polypeptide can be subcloned into an expression vector, which is expressed as inclusion bodies in the host cells. The vector can be a viral vector, and any suitable viral vector can be used in this capacity.

In another aspect, the present disclosure provides a host cell comprising the vector provided herein. The host cell is prokaryotic cell or a eukaryotic cell. Host cells transformed with the above-described expression or cloning vectors can be cultured in conventional nutrient media modified as appropriate for inducing promoters, selecting transformants, or amplifying the cloning vectors.

In another aspect, the present disclosure provides a method of producing the polypeptide complex provided herein, comprising culturing the host cell provided herein under a condition that allows expression of the polynucleotide provided herein.

For production of the fusion polypeptide or polypeptide complex provided herein, the host cells transformed with the expression vector may be cultured in a variety of media. Commercially available bacteria growth media such as Terrific Broth, LB Broth, LB Agar, M9 minimal media, MagiaMedia Medium, and ImMedia Medium (ThermoFisher) are suitable for culturing the bacterial host cells. Commercially available media such as Ham's F10 (Sigma), Minimal Essential Medium (MEM), (Sigma), RPMI-1640 (Sigma), and Dulbecco's Modified Eagle's Medium (DMEM), Sigma) are suitable for culturing the eukaryotic host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source.

Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In one aspect, the present disclosure provides a method of expressing the fusion polypeptide and/or polypeptide complex provided herein, comprising culturing the host cell provided herein under the condition at which the fusion polypeptide and/or the polypeptide complex is expressed.

In certain embodiments, the polypeptide complex is expressed as inclusion bodies. In certain embodiments, the method further comprises renaturing the polypeptide complex from the inclusion bodies.

When using recombinant techniques, the fusion polypeptide and the polypeptide complex provided herein can be produced intracellularly, in the periplasmic space, or directly secreted into the medium. If the product is produced intracellularly, as a first step, the particulate debris, either host cells or lysed fragments, is removed, for example, by centrifugation or ultrafiltration. Carter et al., Bio/Technology 10:163-167 (1992) describe a procedure for isolating proteins which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the product is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In certain embodiments, the method further comprises isolating the fusion polypeptide and/or polypeptide complex.

The fusion polypeptide and the polypeptide complex provided herein prepared from the cells can be purified using, for example, hydroxylapatite chromatography, gel electrophoresis, dialysis, DEAE-cellulose ion exchange chromatography, ammonium sulfate precipitation, salting out, and affinity chromatography.

Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the protein to be recovered.

Conjugates

In another aspect, the present disclosure provides a conjugate comprising the fusion polypeptide provided herein and at least one clearance-reducing moiety (CRM), wherein the at least one CRM is conjugated to the at least one conjugatable residue in the fusion polypeptide.

In certain embodiments, the fusion polypeptide comprises two and no more than two conjugatable residues, each of which is conjugated to a CRM.

In another aspect, the present disclosure provides a conjugate comprising the polypeptide complex provided herein and at least two clearance-reducing moieties (CRMs), wherein the at least two CRM are conjugated respectively to one of the conjugatable residues on the polypeptide complex. In such embodiments, the polypeptide complex comprises a dimer of the fusion polypeptide, and each monomer has one conjugatable residue to which the CRM is conjugated.

In certain embodiments, the polypeptide complex provided herein comprises four and no more than four conjugatable residues, each of which is conjugated to a CRM. In such embodiments, the polypeptide complex comprises a dimer of the fusion polypeptide, and each monomer comprises two conjugatable residues, each of which is conjugated to a CRM.

The term "conjugate" as used herein refers to a compound as a result of two or more molecules joined together to form one physical entity. For example, the conjugate of the present disclosure means a compound as a result of the fusion polypeptide or polypeptide complex and one or more clearance-modifying moieties joined together. The molecules may attach together by covalent, non-covalent bonds, linkers, chemical modification, or protein fusion or by any means known to one skilled in the art. Preferably, the molecules may attach together by covalent bonds. The joining may be permanent or reversible. In some embodiments, certain cleavable or non-cleavable linkers may be included.

The term "clearance-modifying moiety" or "CRM" as used herein refers to moiety that can alter one or more pharmacokinetic (PK) properties (for example, to increase the half-life in vivo). Examples of CRMs can include, without limitation, polyethylene glycol (PEG), glucuronic acid or other sugar based linkers, polar, positively or negatively charged groups that can increase the rates of hydrolysis of a succinimidyl ring and reduce or minimize the rate of reverse Michael reaction, therefore reduce or minimize the rate of loss of drug and the linker group from the antibody or antibody fragments to other thiol-containing proteins and small molecules.

In certain embodiments, the CRM comprises a plasma protein-binding moiety, a polymer, Fc, human serum albumin (HSA) and functional fragments thereof, Xten sequence, or PAS sequence. In certain embodiments, the Xten sequence is an extended recombinant polypeptide sequence with an amino acid sequence described in WO2007103515, WO2009023270, WO2010091122, WO2011123813, WO2013130683, WO2017146979, WO2011084808, WO2013040093, WO2013122617, WO2014011819, WO2013184216, WO2014164568, WO2015023891, WO2016077505 and WO2017040344, disclosures of which have been incorporated by their entirety. In certain embodiments, the term "PAS", which can also be used interchangeable with the term "APS", refers to an amino acid repeats consisting of Ala, Ser, and Pro residues, as described in U.S. Pat. No. 8,563,521B2, disclosure of which has been incorporated by its entirety.

In certain embodiments, the CRM comprises an albumin-binding moiety. The term "albumin-binding moiety" refers to any functional moiety that is capable of binding albumin (e.g. human serum albumin) or any functional fragment thereof with sufficient specificity, preferably non-covalently. The albumin-binding moiety attached to a therapeutic fusion polypeptide, polypeptide, or polypeptide complex typically has an affinity below 10 μM to human serum albumin and preferably below 1 pM. The albumin-binding moiety can include, without limitation, an albumin-binding domain, an albumin-binding sequences from synthetic peptides, and an albumin-binding chemical moiety. For example, the albumin-binding moiety is selected from an albumin-binding domain from streptococcal protein G, an albumin-binding domain from *Peptostreptococcus magnus* protein PAB, an albumin-binding peptide having the core sequence DICL-PRWGCLW (SEQ ID NO: 335). A number of small peptides which are albumin binding moieties have been described in J. Biol Chem. 277, 38 (2002) 35035-35043. For another example, the albumin-binding moiety is selected from linear and branched lipohophillic moieties containing 4-40 carbon atoms, compounds with a cyclopentanophenanthrene skeleton etc. For example, the albumin-binding moiety is a group of the formula $CH_3$—$(CH_2)_v$CO—NHCH(COOH)—$(CH_2)_2$CO—, wherein v is an integer of from 10 to 24.

In certain embodiments, the albumin-binding moiety comprises a structure of: *-A-B-C-D-E, wherein A, B, C, D and E are interconnected via amide bonds, and the * end of A is connected to a reactive group of the conjugatable residue on the polypeptide complex, and wherein:

A is selected from a bond,

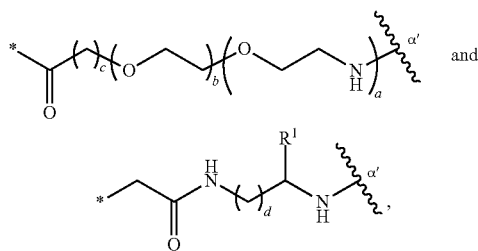

and a, b, c and d are independently an integer from 0 to 4, $R^1$ is hydrogen or —COOH;

B is selected from a bond,

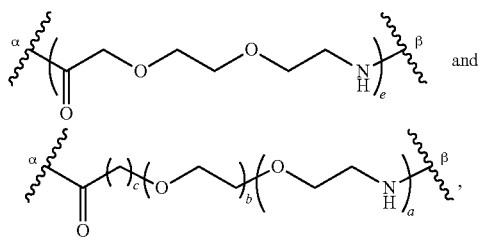

e is an integer from 1 to 4, wherein position α is linked to the position α',

C is a bond or

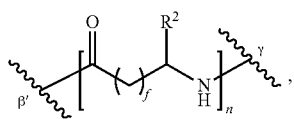

$R^2$ is —$CH_2SO_3H$ or —COOH, f is an integer from 1 to 4, n is an integer from 1 to 25;

D is selected from a bond,

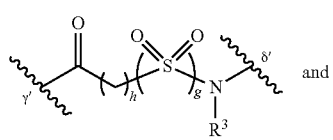

and

-continued

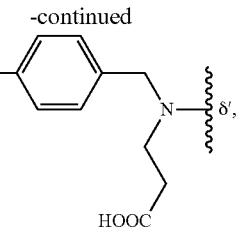

g and h are independently 0 or 1, and $R^3$ is H or —$CH_2COOH$, wherein:
when B is not a bond and C is a bond, then position γ' is linked to position β;
when C is not a bond, then position γ' is linked to position γ; and
when B is a bond and C is a bond, then position γ' is linked to position α';

E is an acidic group having a formula:

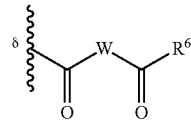

(I)

wherein W represents —$(CR^4R^5)_l$—,
$R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide,
$R^6$ is selected from hydroxyl or $NR^7R^8$;
$R^7$ and $R^8$ are independently selected from the group consisting of hydrogen, alkyl, hydroxyl, and

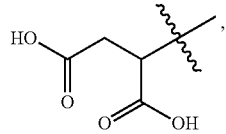 [SMILES: *C(CC(=O)O)C(=O)O]

and l is an integer from 10 to 20, and wherein:
when D is not a bond, then position δ is linked to position δ',
when C is not a bond and D is a bond, then position δ is linked to position γ,
when B is not a bond, C is a bond and D is a bond, then position δ is linked to position β,
when A is not a bond, and all of B, C, and D are bond, then position δ is linked to position α'.

In certain embodiments, the CRM is conjugated to a lysine residue, optionally the lysine residue is in the polypeptide linker or in the GLP-1 or in the GDF15.

In certain embodiments, A is a bond.

In certain embodiments, A is a bond, and B is a bond or

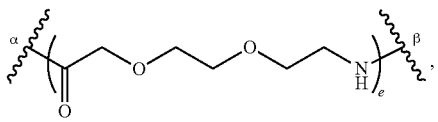

wherein e is 1, 2 or 3.

In certain embodiments, A is a bond, B is

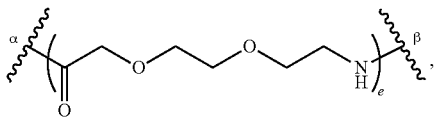

and C is

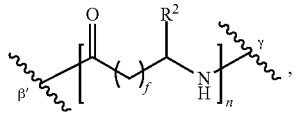

wherein e is 1, 2 or 3, f is 1, 2, or 3, and n is 1 or 2, wherein position β' is linked to position β. In certain embodiments, D is a bond, and E is an acidic group having a formula:

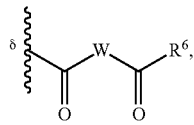

wherein position δ is linked to position γ. In certain embodiments, $R^2$ is —COOH, and $R^6$ is hydroxyl. In certain embodiments, W represents —$(CR^4R^5)_l$—, $R^4$ and $R^5$ are independently hydrogen, l is an integer from 10 to 20.

In certain embodiments, A is a bond, B is a bond, and C is a bond.

In certain embodiments, A is a bond, B is a bond, and C is

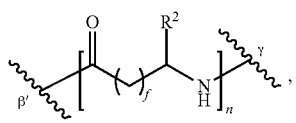

wherein f is 1, 2, or 3, and n is 1 or 2.

In certain embodiments, A is

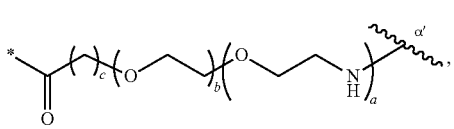

wherein a is 1, 2 or 3, b is 1, 2 or 3, and c is 1 or 2.

In certain embodiments, A is

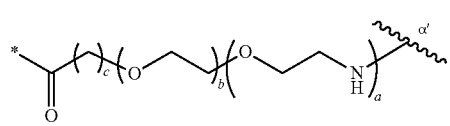

and B is

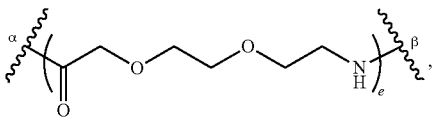

wherein a is 1, 2 or 3, b is 1, 2 or 3, c is 1 or 2, and e is 1, 2 or 3, wherein position α is linked to the position α'.

In certain embodiments, A is

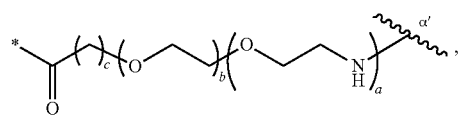

B is

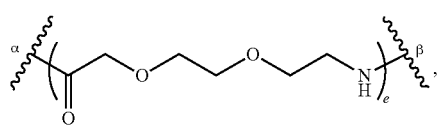

wherein position α is linked to the position α', and C is

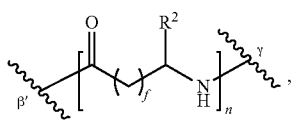

wherein a is 1, 2 or 3, b is 1, 2 or 3, c is 1 or 2, e is 1, 2 or 3, f is 1, 2, or 3, and n is 1 or 2, wherein position β' is linked to position β.

In certain embodiments, A is

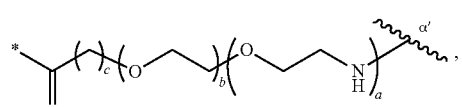

B is

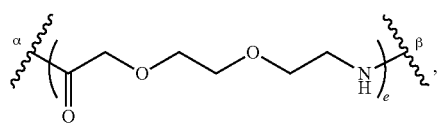

wherein position α is linked to the position α', and C is bond, wherein a is 1, 2 or 3, b is 1, 2 or 3, c is 1 or 2, and e is 1, 2 or 3.

In certain embodiments, A is

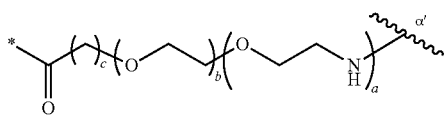

and B is a bond, wherein a is 1, 2 or 3, b is 1, 2 or 3, and c is 1 or 2.

In certain embodiments, A is

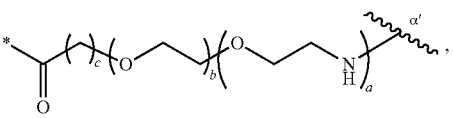

B is a bond, and C is

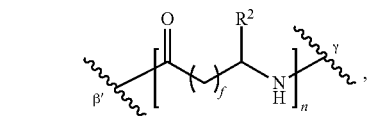

wherein a is 1, 2 or 3, b is 1, 2 or 3, c is 1 or 2, f is 1, 2, or 3, and n is 1 or 2, wherein position β' is linked to position α'.

In certain embodiments, A is

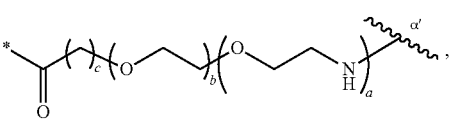

B is a bond, and C is a bond, wherein a is 1, 2 or 3, b is 1, 2 or 3, and c is 1 or 2.

In certain embodiments, D is a bond.

In certain embodiments, A is

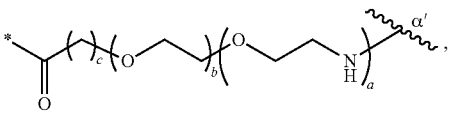

B is

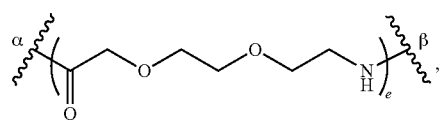

wherein position α is linked to the position α', C is

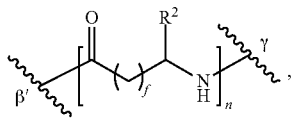

wherein position β' is linked to position β, and D is a bond, wherein a is 1, 2 or 3, b is 1, 2 or 3, c is 1 or 2, e is 1, 2 or 3, f is 1, 2, or 3, and n is 1 or 2.

In certain embodiments, D is

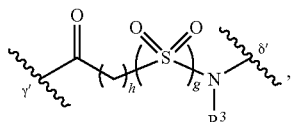

wherein g is 0 or 1, and h is 0 or 1.

In certain embodiments, A is

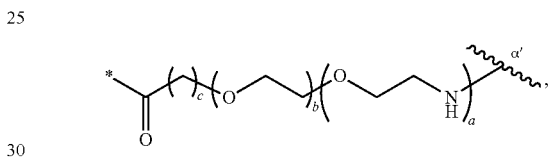

B is

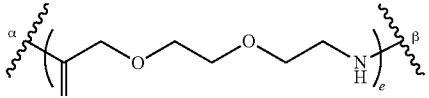

or a bond, wherein when B is not a bond, position α is linked to the position α', C is a bond, and D is

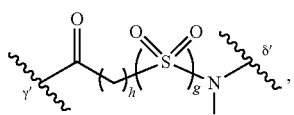

wherein a is 1, 2 or 3, b is 1, 2 or 3, c is 1 or 2, e is 1, 2 or 3, g is 0 or 1, and h is 0 or 1, wherein when B is not a bond, then position γ' is linked to position β, or when B is a bond, then position γ' is linked to position α'.

In certain embodiments, D is

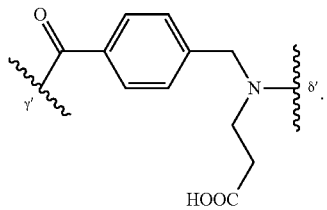 [SMILES: *C(=O)c1ccc(CN(*)CCC(=O)O)cc1]

In certain embodiments, A is

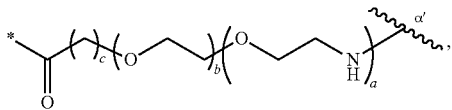

B is

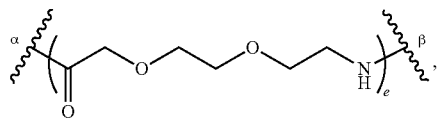

wherein position α is linked to the position α', C is a bond or

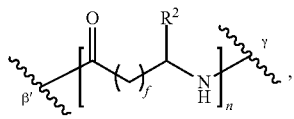

wherein when C is not a bond, then position β' is linked to position β; and D is

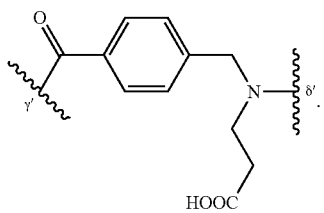

wherein a is 1, 2 or 3, b is 1, 2 or 3, c is 1 or 2, e is 1, 2 or 3, f is 1, 2, or 3, and n is 1 or 2, wherein when C is not a bond, then position γ' is linked to position γ, or when C is a bond, then position γ' is linked to position β.

In such embodiments, the CRM comprises the structure of below formula (also referred to as —HOOC—(CH2)16-CO-gGlu-2XADO, where 2XADO means two consecutive ADO moieties, and ADO is short for 8-amino-3,6-dioxaoctanoic acid):

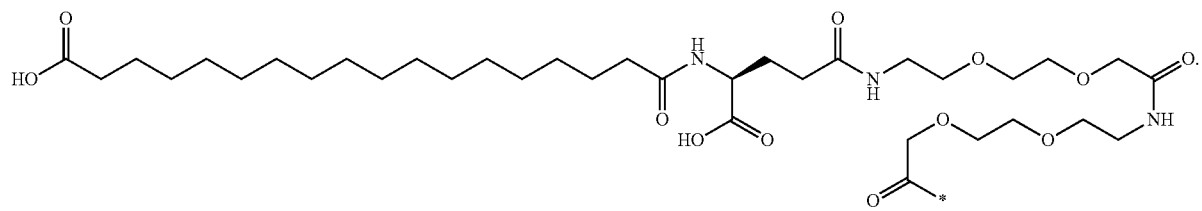 [SMILES: *C(=O)COCCOCCNC(=O)COCCOCCNC(=O)CC[C@H](NC(=O)CCCCCCCCCCCCCCCCC(=O)O)C(=O)O]

In certain embodiments, the CRM is conjugated to a cysteine residue, optionally the cysteine residue is in the polypeptide linker or in the GLP-1 or in the GDF15.

In certain embodiments, A is

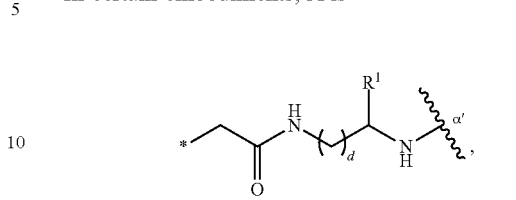

and B is

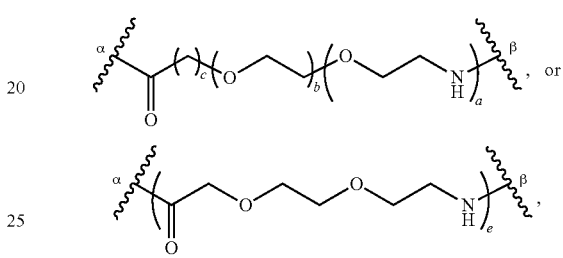

wherein position α is linked to the position α', wherein a is 1, 2 or 3, b is 1, 2 or 3, c is 1 or 2, d is 1, 2, or 3, e is 1, 2 or 3, $R^1$ is hydrogen or —COOH.

In certain embodiments, A is

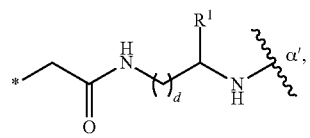

B is

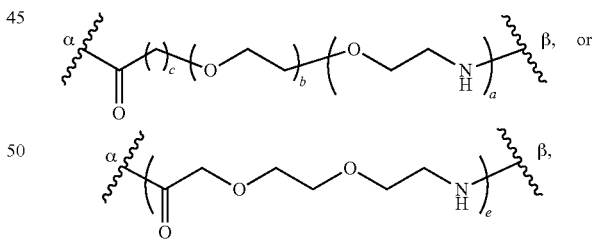

wherein position α is linked to the position α', and C is

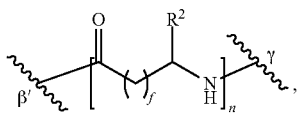

wherein β' is linked to position β, wherein a is 1, 2 or 3, b is 1, 2 or 3, c is 1 or 2, d is 1, 2, or 3, f is 1, 2, or 3, and n is 1 or 2. In certain embodiments, D is a bond, and E is an acidic group having a formula:

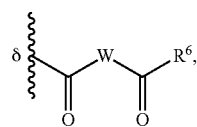

wherein position δ is linked to position γ. In certain embodiments, R2 is —COOH, and R6 is hydroxyl. In certain embodiments, W represents —(CR4R5)l-, R4 and R5 are independently hydrogen, l is an integer from 10 to 20.

In certain embodiments, A is

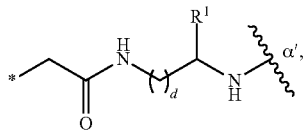

B is

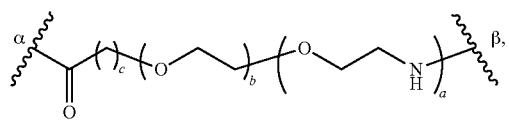

wherein position α is linked to the position α', C is

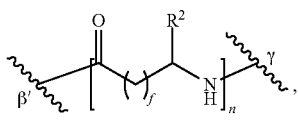

wherein position β' is linked to position β, and D is a bond, wherein a is 1, 2 or 3, b is 1, 2 or 3, c is 1 or 2, d is 1, 2, or 3, f is 1, 2, or 3, and n is 1 or 2.

In certain embodiments, A is

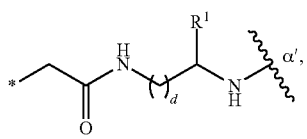

and B is

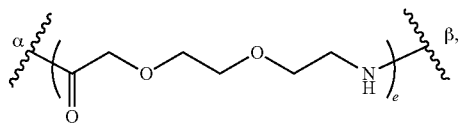

wherein d is 1, 2, or 3, and e is 1, 2 or 3, wherein position α is linked to the position α'.

In certain embodiments, A is

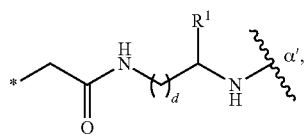

B is

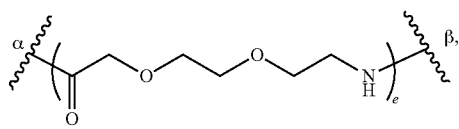

wherein position α is linked to the position α', and C is a bond, wherein d is 1, 2, or 3, and e is 1, 2 or 3.

In certain embodiments, A is

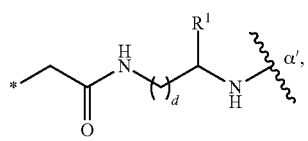

B is

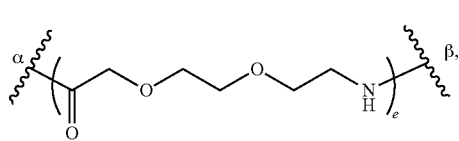

wherein position α is linked to the position α', C is a bond, and D is

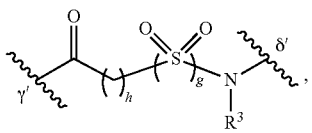

wherein position γ' is linked to position β, wherein d is 1, 2, or 3, e is 1, 2 or 3, g is 0 or 1, and h is 0 or 1.

In such embodiments, the CRM comprises the structure of below formula:

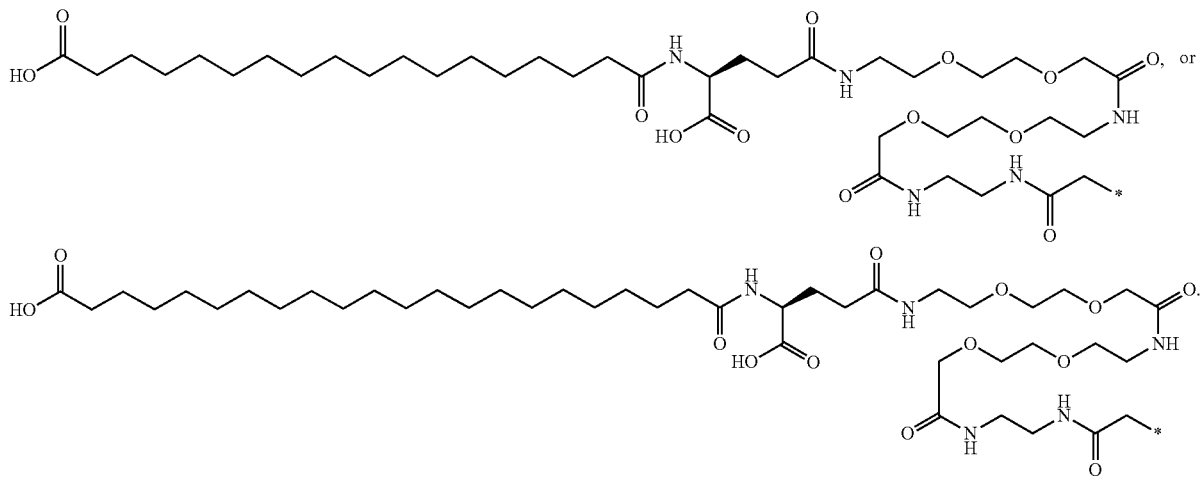

Exemplary fusion polypeptide conjugates via lysine residue are shown in Table 2 below

TABLE 2

Exemplary fusion polypeptide conjugates

| Molecule Code (MLC) | Fusion polypeptide SEQ ID NO | Conjugation residue | Moiety |
|---|---|---|---|
| 002 | 249 | 26K of GLP-1; (20K of fusion polypeptide) | Moiety A** |
| 004 | 251 | 26K of GLP-1; (20K of fusion polypeptide) | Moiety A** |
| 005 | 252 | 12K of Linker; (43K of fusion polypeptide) | Moiety A** |
| 006 | 253 | 36K of GLP-1; (30K of fusion polypeptide) | Moiety A** |
| 007 | 254 | 1K of Linker; (32K of fusion polypeptide) | Moiety A** |
| 008 | 255 | 6K of Linker; (37K of fusion polypeptide) | Moiety A** |
| 009 | 256 | 15K of Linker; (46K of fusion polypeptide) | Moiety A** |
| 010 | 257 | 4K of Linker; (35K of fusion polypeptide) | Moiety A** |
| 011 | 258 | 20K of Linker; (51K of fusion polypeptide) | Moiety A** |
| 012 | 259 | 12K of Linker; (43K of fusion polypeptide) | Moiety A** |
| 013 | 260 | 1K of Linker; (32K of fusion polypeptide) | Moiety A** |
| 015 | 262 | 12K of Linker; (43K of fusion polypeptide) | Moiety A** |
| 016 | 263 | 52K of Linker; (83K of fusion polypeptide) | Moiety A** |
| 017 | 264 | 55K of Linker; (86K of fusion polypeptide) | Moiety A** |
| 018 | 265 | 52K of Linker; (83K of fusion polypeptide) | Moiety A** |
| 026 | 273 | 55K of Linker; (86K of fusion polypeptide) | Moiety A** |
| 027 | 274 | 55K of Linker; (86K of fusion polypeptide) | Moiety A** |
| 028 | 275 | 52K of Linker; (83K of fusion polypeptide) | Moiety A** |
| 029 | 276 | 52K of Linker; (83K of fusion polypeptide) | Moiety A** |
| 030 | 277 | 15K of Linker; (46K of fusion polypeptide) | Moiety A** |
| 031 | 278 | 12K of Linker; (43K of fusion polypeptide) | Moiety A** |

TABLE 2-continued

Exemplary fusion polypeptide conjugates

| Molecule Code (MLC) | Fusion polypeptide SEQ ID NO | Conjugation residue | Moiety |
|---|---|---|---|
| 032 | 279 | 14K of Linker; (45K of fusion polypeptide) | Moiety A** |
| 033 | 280 | 55K of Linker; (86K of fusion polypeptide) | Moiety A** |
| 034 | 281 | 52K of Linker; (83K of fusion polypeptide) | Moiety A** |
| 035 | 282 | 15K of Linker; (46K of fusion polypeptide) | Moiety A** |
| 036 | 283 | 12K of Linker; (43K of fusion polypeptide) | Moiety A** |
| 037 | 284 | 1K of Linker; (32K of fusion polypeptide) | Moiety A** |
| 038 | 285 | 1K of Linker; (32K of fusion polypeptide) | Moiety A** |
| 039 | 286 | 1K of Linker; (32K of fusion polypeptide) | Moiety A** |
| 040 | 287 | 1K of Linker; (32K of fusion polypeptide) | Moiety A** |
| 041 | 288 | 1K of Linker; (32K of fusion polypeptide) | Moiety A** |
| 042 | 289 | 1K of Linker; (32K of fusion polypeptide) | Moiety A** |
| 043 | 326 | 26K of GLP-1; (20K of fusion polypeptide) | Moiety A** |
| 044 | 327 | 26K of GLP-1 and of 55K of Linker; (20K and 86K of fusion polypeptide) | Moiety A** |
| 045 | 328 | 1K and 55K of Linker; (32K and 86K of fusion polypeptide) | Moiety A** |
| 046 | 329 | 60K of linker; (91K of fusion polypeptide) | Moiety A** |
| 047 | 330 | 40K of linker; (71K of fusion polypeptide) | Moiety A** |
| 048 | 331 | 26K of GLP-1; (20K of fusion polypeptide) | Moiety A** |
| 049 | 337 | 1K of linker (32K of fusion polypeptide) | Moiety A** |
| 050 | 338 | 32K of linker (63K of fusion polypeptide) | Moiety A** |
| 051 | 339 | 35K of linker (66K of fusion polypeptide) | Moiety A** |
| 052 | 340 | 12K of linker (43K of fusion polypeptide) | Moiety A** |
| 053 | 341 | 15K of linker (46K of fusion polypeptide) | Moiety A** |
| 055 | 349 | GDF15 91K (202K of fusion polypeptide) | Moiety A** |
| 056 | 350 | GDF15 107K (218K of fusion polypeptide) | Moiety A** |
| 058 | 352 | GLP1 26K and GDF15 91K (20K and 202K of fusion polypeptide) | Moiety A** |
| 059 | 353 | GLP1 26K and GDF15 107K (20K and 218K of fusion polypeptide) | Moiety A** |
| 060 | 354 | 1K of linker (32K of fusion polypeptide) | Moiety A** |
| 061 | 355 | 26K of GLP-1 (20K of fusion polypeptide) | Moiety A** |
| 062 | 356 | 55K of linker (86K of fusion polypeptide) | Moiety A** |
| 063 | 357 | 52K of linker (83K of fusion polypeptide) | Moiety A** |
| 064 | 359 | 51K of Linker; (82K of fusion polypeptide) | Moiety A** |
| 065 | 360 | 51K of Linker; (82K of fusion polypeptide) | Moiety A** |
| 066 | 361 | 26K of GLP1 and 1K of Linker; (20K and 32K of fusion polypeptide) | Moiety A** |
| 067 | 362 | 26K of GLP-1 (20K of fusion polypeptide) | Moiety A** |
| 068 | 363 | 1K of Linker; (32K of fusion polypeptide) | Moiety A** |
| 069 | 364 | 55K of Linker; (86K of fusion polypeptide) | Moiety A** |
| 070 | 365 | 52K of Linker; (83K of fusion polypeptide) | Moiety A** |

TABLE 2-continued

Exemplary fusion polypeptide conjugates

| Molecule Code (MLC) | Fusion polypeptide SEQ ID NO | Conjugation residue | Moiety |
|---|---|---|---|
| 071 | 366 | 26C of GLP-1 (20C of fusion polypeptide) | Moiety B*** |
| 072 | 367 | 1C of Linker; (32C of fusion polypeptide) | Moiety B*** |
| 073 | 368 | 55C of Linker; (86C of fusion polypeptide) | Moiety B*** |
| 074 | 369 | 41C of Linker; (72C of fusion polypeptide) | Moiety B*** |
| 075 | 369 | 41C of Linker; (72C of fusion polypeptide) | Moiety C&& |
| 076 | 370 | 35K of Linker; (66K of fusion polypeptide) | Moiety A** |
| 077 | 371 | 29K of Linker; (60K of fusion polypeptide) | Moiety A** |
| 078 | 372 | 25K of Linker; (56K of fusion polypeptide) | Moiety A** |
| 079 | 373 | 21K of Linker; (52K of fusion polypeptide) | Moiety A** |
| 080 | 374 | 35C of Linker; (66C of fusion polypeptide) | Moiety B*** |
| 081 | 374 | 35C of Linker; (66C of fusion polypeptide) | Moiety C&& |
| 082 | 375 | 51C of Linker; (82C of fusion polypeptide) | Moiety B*** |
| 083 | 376 | 39C of Linker; (70C of fusion polypeptide) | Moiety B*** |
| 084 | 376 | 39C of Linker; (70C of fusion polypeptide) | Moiety C&& |
| 085 | 377 | 37C of Linker; (68C of fusion polypeptide) | Moiety B*** |
| 086 | 377 | 37C of Linker; (68C of fusion polypeptide) | Moiety C&& |
| 087 | 378 | 41C of Linker; (72C of fusion polypeptide) | Moiety B*** |
| 088 | 378 | 41C of Linker; (72C of fusion polypeptide) | Moiety C&& |
| 089 | 379 | 39C of Linker; (70C of fusion polypeptide) | Moiety B*** |
| 090 | 379 | 39C of Linker; (70C of fusion polypeptide) | Moiety C&& |
| 091 | 380 | 35C of Linker; (66C of fusion polypeptide) | Moiety B*** |
| 092 | 380 | 35C of Linker; (66C of fusion polypeptide) | Moiety C&& |
| 093 | 381 | 33C of Linker; (64C of fusion polypeptide) | Moiety B*** |
| 094 | 381 | 33C of Linker; (64C of fusion polypeptide) | Moiety C&& |
| 098 | 385 | 39K of Linker; (70K of fusion polypeptide) | Moiety A** |
| 099 | 386 | 35K of Linker; (66K of fusion polypeptide) | Moiety A** |
| 103 | 390 | 71K of Linker; (102K of fusion polypeptide) | Moiety A** |
| 104 | 391 | 76K of Linker; (107K of fusion polypeptide) | Moiety A** |
| 105 | 392 | 17C of Linker; (48C of fusion polypeptide) | Moiety B*** |
| 106 | 393 | 21C of Linker; (52C of fusion polypeptide) | Moiety B*** |
| 107 | 394 | 25C of Linker; (56C of fusion polypeptide) | Moiety B*** |
| 108 | 395 | 31C of Linker; (62C of fusion polypeptide) | Moiety B*** |
| 109 | 396 | 25C of Linker; (56C of fusion polypeptide) | Moiety B*** |
| 110 | 397 | 45C of Linker; (76C of fusion polypeptide) | Moiety B*** |
| 111 | 398 | 51C of Linker; (82C of fusion polypeptide) | Moiety B*** |
| 112 | 399 | 29C of Linker; (60C of fusion polypeptide) | Moiety B*** |
| 115 | 402 | 33C of Linker; (64C of fusion polypeptide) | Moiety B*** |

TABLE 2-continued

Exemplary fusion polypeptide conjugates

| Molecule Code (MLC) | Fusion polypeptide SEQ ID NO | Conjugation residue | Moiety |
|---|---|---|---|
| 116 | 403 | 39C of Linker; (70C of fusion polypeptide) | Moiety B*** |
| 117 | 404 | 33C of Linker; (64C of fusion polypeptide) | Moiety B*** |
| 118 | 405 | 39C of Linker; (70C of fusion polypeptide) | Moiety B*** |
| 121 | 408 | 89C of Linker; (120C of fusion polypeptide) | Moiety B*** |
| 122 | 472 | 5C of Linker; (36C of fusion polypeptide) | Moiety B*** |
| 123 | 473 | 79C of Linker; (110C of fusion polypeptide) | Moiety B*** |
| 125 | 477 | 33C of Linker; (64C of fusion polypeptide) | Moiety B*** |
| 126 | 481 | 73C of Linker (104C of fusion polypeptide) | Moiety B*** |
| 127 | 482 | 26C of GLP-1 (20C of fusion polypeptide) | Moiety B*** |

**Moiety A referts to HOOC—(CH2)16-CO-gGlu-2XADO or

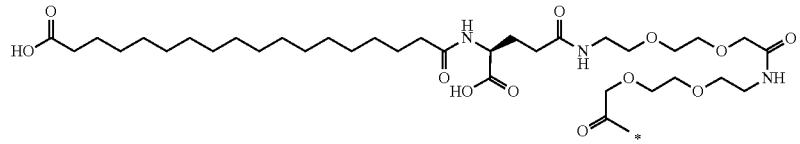 [SMILES: CC(=O)COCCOCCNC(=O)COCCOCCNC(=O)CC[C@H](NC(=O)CCCCCCCCCCCCCCCCC(=O)O)C(=O)O]

***Moiety B refers to HOOC—(CH2)16-CO-gGlu-2XADO-EDA-CO—CH2, or the following structure

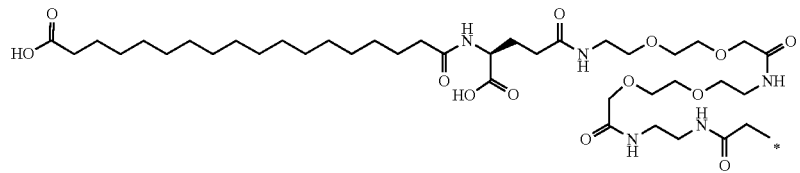

&&Moiety C refers to HOOC—(CH2)20-CO-gGlu-2XADO-EDA-CO—CH2, or the following structure:

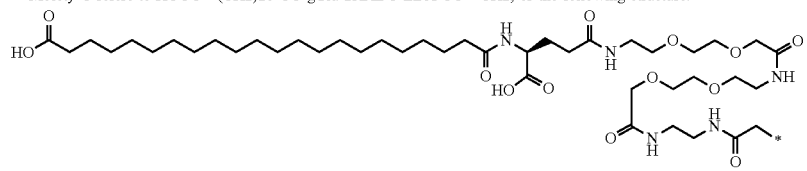

In certain embodiments, the conjugate provided herein comprises a polypeptide complex comprising a dimer of the fusion polypeptide comprising an amino acid sequence selected from a sequence shown in SEQ ID NOs: 249, 251-260, 262-265, 273-289, 326 and 329-331, 337-341, 349, 350, 354-357, 359-360, 362-381, 385-386, 390-400, 402-405, 407-408, 472, 473, and 477, and two CRMs each of which is attached to one of the conjugatable lysine residue in the fusion polypeptide.

In certain embodiments, the conjugate provided herein comprises a dimer of the fusion polypeptide comprising an amino acid sequence selected from a group consisting of: SEQ ID NOs: 249, 251, 253, 326, 331, 355, 362, 366, and two CRMs each of which is attached to the lysine or cysteine residue in the GLP-1 of the fusion polypeptide. In certain embodiments, each of the CRMs is conjugated to K26 in the GLP-1 of the fusion polypeptide. In certain embodiments, each of the CRMs is conjugated to K36 in the GLP-1 of the fusion polypeptide. In certain embodiments, each of the CRMs is conjugated to C26, or C36 in the GLP-1 of the fusion polypeptide.

In certain embodiments, the conjugate provided herein comprises a dimer of the fusion polypeptide comprising an amino acid sequence selected from a group consisting of: SEQ ID NOs: 252, 254-260, 262-265, 273-289, and 329-330, 337-341, 354, 356-357, 359-360, 363-365, 367-381, 385-386, 390-400, 402-405, 407-408, 472-473, and 477, and two CRMs each of which is attached to the conjugatable lysine or cysteine residue in the polypeptide linker of the fusion polypeptide. In certain embodiments, the polypeptide linker comprises an amino acid sequence selected from a group consisting of: SEQ ID NOs: 60, 89, 198, 298-324 and 332-334, 342-346, 305, 309-310, 305, 308, 309, 409-438, 440-443, 445-447, 475, and 458. In certain embodiments, the lysine in the polypeptide linkers can be substituted with a cysteine or a non-natural amino acid, and the CRM is conjugated to such cysteine or non-natural amino acid.

In certain embodiments, the conjugate provided herein comprises a dimer of a fusion polypeptide comprising an amino acid sequence of SEQ ID NO: N, and two CRMs each of which is covalently attached to the $m^{th}$ residue (which is lysine, i.e. Km) counting in a direction from N terminus to C terminus in the respective fusion polypeptide monomer, with one CRM attached to one residue, wherein:

1) N is 249, m is 20, and Km is K20 (such a conjugate molecule is also referred to as 002);

2) N is 251, m is 20, and Km is K20 (such a conjugate molecule is also referred to as 004);
3) N is 252, m is 43, and Km is K43 (such a conjugate molecule is also referred to as 005);
4) N is 253, m is 30, and Km is K30 (such a conjugate molecule is also referred to as 006);
5) N is 254, m is 32, and Km is K32 (such a conjugate molecule is also referred to as 007);
6) N is 255, m is 37, and Km is K37 (such a conjugate molecule is also referred to as 008);
7) N is 256, m is 46, and Km is K46 (such a conjugate molecule is also referred to as 009);
8) N is 257, m is 35, and Km is K35 (such a conjugate molecule is also referred to as 010);
9) N is 258, m is 51, and Km is K51 (such a conjugate molecule is also referred to as 011);
10) N is 259, m is 43, and Km is K43 (such a conjugate molecule is also referred to as 012);
11) N is 260, m is 32, and Km is K32 (such a conjugate molecule is also referred to as 013);
12) N is 262, m is 43, and Km is K43 (such a conjugate molecule is also referred to as 015);
13) N is 263, m is 83, and Km is K83 (such a conjugate molecule is also referred to as 016);
14) N is 264, m is 86, and Km is K86 (such a conjugate molecule is also referred to as 017);
15) N is 265, m is 83, and Km is K83 (such a conjugate molecule is also referred to as 018);
16) N is 273, m is 86, and Km is K86 (such a conjugate molecule is also referred to as 026);
17) N is 274, m is 86, and Km is K86 (such a conjugate molecule is also referred to as 027);
18) N is 275, m is 83, and Km is K83 (such a conjugate molecule is also referred to as 028);
19) N is 276, m is 83, and Km is K83 (such a conjugate molecule is also referred to as 029);
20) N is 277, m is 46, and Km is K46 (such a conjugate molecule is also referred to as 030);
21) N is 278, m is 43, and Km is K43 (such a conjugate molecule is also referred to as 031);
22) N is 279, m is 45, and Km is K45 (such a conjugate molecule is also referred to as 032);
23) N is 280, m is 86, and Km is K86 (such a conjugate molecule is also referred to as 033);
24) N is 281, m is 83, and Km is K83 (such a conjugate molecule is also referred to as 034);
25) N is 282, m is 46, and Km is K46 (such a conjugate molecule is also referred to as 035);
26) N is 283, m is 43, and Km is K43 (such a conjugate molecule is also referred to as 036);
27) N is 284, m is 32, and Km is K32 (such a conjugate molecule is also referred to as 037);
28) N is 285, m is 32, and Km is K32 (such a conjugate molecule is also referred to as 038);
29) N is 286, m is 32, and Km is K32 (such a conjugate molecule is also referred to as 039);
30) N is 287, m is 32, and Km is K32 (such a conjugate molecule is also referred to as 040);
31) N is 288, m is 32, and Km is K32 (such a conjugate molecule is also referred to as 041);
32) N is 289, m is 32, and Km is K32 (such a conjugate molecule is also referred to as 042);
33) N is 326, m is 20, and Km is K20 (such a conjugate molecule is also referred to as 043);
34) N is 329, m is 91, and Km is K91 (such a conjugate molecule is also referred to as 046);
35) N is 330, m is 71, and Km is K71 (such a conjugate molecule is also referred to as 047);
36) N is 331, m is 20, and Km is K20 (such a conjugate molecule is also referred to as 048);
37) N is 337, m is 32, and Km is K32 (such a conjugate molecule is also referred to as 049);
38) N is 338, m is 63, and Km is K63 (such a conjugate molecule is also referred to as 050);
39) N is 339, m is 66, and Km is K66 (such a conjugate molecule is also referred to as 051);
40) N is 340, m is 43, and Km is K43 (such a conjugate molecule is also referred to as 052);
41) N is 341, m is 46, and Km is K46 (such a conjugate molecule is also referred to as 053);
42) N is 349, m is 202, and Km is K202 (such a conjugate molecule is also referred to as 055); or
43) N is 350, m is 218, and Km is K218 (such a conjugate molecule is also referred to as 056);
44) N is 354, m is 32, and Km is K32 (such a conjugate molecule is also referred to as 060);
45) N is 355, m is 20, and Km is K20 (such a conjugate molecule is also referred to as 061);
46) N is 356, m is 86, and Km is K86 (such a conjugate molecule is also referred to as 062);
47) N is 357, m is 83, and Km is K83 (such a conjugate molecule is also referred to as 063);
48) N is 359, m is 82, and Km is K82 (such a conjugate molecule is also referred to as 064);
49) N is 360, m is 82, and Km is K82 (such a conjugate molecule is also referred to as 065);
50) N is 362, m is 20, and Km is K20 (such a conjugate molecule is also referred to as 067);
51) N is 363, m is 32, and Km is K32 (such a conjugate molecule is also referred to as 068);
52) N is 364, m is 86, and Km is K86 (such a conjugate molecule is also referred to as 069);
53) N is 365, m is 52, and Km is K52 (such a conjugate molecule is also referred to as 070);
54) N is 370, m is 66, and Km is K66 (such a conjugate molecule is also referred to as 076);
55) N is 371, m is 60, and Km is K60 (such a conjugate molecule is also referred to as 077);
56) N is 372, m is 56, and Km is K56 (such a conjugate molecule is also referred to as 078);
57) N is 373, m is 52, and Km is K52 (such a conjugate molecule is also referred to as 079);
58) N is 385, m is 70, and Km is K70 (such a conjugate molecule is also referred to as 098);
59) N is 386, m is 66, and Km is K66 (such a conjugate molecule is also referred to as 099);
60) N is 390, m is 102, and Km is K102 (such a conjugate molecule is also referred to as 103); or
61) N is 391, m is 107, and Km is K107 (such a conjugate molecule is also referred to as 104).

In certain embodiments, the CRM comprises the structure of —HOOC—(CH2)16-CO-gGlu-2XADO.

In certain embodiments, the conjugate provided herein comprises a dimer of a fusion polypeptide comprising an amino acid sequence of SEQ ID NO: Y, and two CRMs each of which is covalently attached to the $z^{th}$ residue (which is cysteine, i.e. Cz) counting in a direction from N terminus to C terminus in the respective fusion polypeptide monomer, with one CRM attached to one residue, wherein:
1) Y is 366, z is 20, and Cz is C20 (such a conjugate molecule is also referred to as 071);
2) Y is 367, z is 32, and Cz is C32 (such a conjugate molecule is also referred to as 072);

3) Y is 368, z is 86, and Cz is C86 (such a conjugate molecule is also referred to as 073);
4) Y is 369, z is 72, and Cz is C72 (such a conjugate molecule is also referred to as 074 or 075, depending on the CRM);
5) Y is 374, z is 66, and Cz is C66 (such a conjugate molecule is also referred to as 080 or 081, depending on the CRM);
6) Y is 375, z is 82, and Cz is C82 (such a conjugate molecule is also referred to as 082);
7) Y is 376, z is 70, and Cz is C70 (such a conjugate molecule is also referred to as 083 or 084, depending on the CRM);
8) Y is 377, z is 68, and Cz is C68 (such a conjugate molecule is also referred to as 085 or 086, depending on the CRM);
9) Y is 378, z is 72, and Cz is C72 (such a conjugate molecule is also referred to as 087 or 088, depending on the CRM);
10) Y is 379, z is 70, and Cz is C70 (such a conjugate molecule is also referred to as 089 or 090, depending on the CRM);
11) Y is 380, z is 66, and Cz is C66 (such a conjugate molecule is also referred to as 091 or 092, depending on the CRM);
12) Y is 381, z is 64, and Cz is C64 (such a conjugate molecule is also referred to as 093 or 094, depending on the CRM);
13) Y is 392, z is 48, and Cz is C48 (such a conjugate molecule is also referred to as 105);
14) Y is 393, z is 52, and Cz is C52 (such a conjugate molecule is also referred to as 106);
15) Y is 394, z is 56, and Cz is C56 (such a conjugate molecule is also referred to as 107);
16) Y is 395, z is 62, and Cz is C62 (such a conjugate molecule is also referred to as 108);
17) Y is 396, z is 56, and Cz is C56 (such a conjugate molecule is also referred to as 109);
18) Y is 397, z is 76, and Cz is C76 (such a conjugate molecule is also referred to as 110);
19) Y is 398, z is 82, and Cz is C82 (such a conjugate molecule is also referred to as 111);
20) Y is 399, z is 60, and Cz is C60 (such a conjugate molecule is also referred to as 112);
21) Y is 402, z is 64, and Cz is C64 (such a conjugate molecule is also referred to as 115);
22) Y is 403, z is 70, and Cz is C70 (such a conjugate molecule is also referred to as 116);
23) Y is 404, z is 64, and Cz is C64 (such a conjugate molecule is also referred to as 117);
24) Y is 405, z is 70, and Cz is C70 (such a conjugate molecule is also referred to as 118);
25) Y is 408, z is 120, and Cz is C120 (such a conjugate molecule is also referred to as 121);
26) Y is 472, z is 36, and Cz is C36 (such a conjugate molecule is also referred to as 122);
27) Y is 473, z is 110, and Cz is C110 (such a conjugate molecule is also referred to as 123), or
28) Y is 477, z is 64, and Cz is C64 (such a conjugate molecule is also referred to as 125).

In certain embodiments, the CRM comprises the structure of HOOC—(CH2)16-CO-gGlu-2XADO-EDA-CO—CH2, or HOOC—(CH2)20-CO-gGlu-2XADO-EDA-CO—CH2.

In certain embodiments, the conjugate provided herein comprises a dimer of a fusion polypeptide comprising an amino acid sequence of SEQ ID NO: X, and four CRMs each of which is covalently attached respectively to the $p^{th}$ or the $q^{th}$ residue (both of which are lysine, i.e. Kp or Kq) counting in a direction from N terminus to C terminus in the respective fusion polypeptide monomer, with one CRM attached to one residue, wherein:
1) X is 327, p is 20, Kp is K20, q is 86, Kq is K86 (such a conjugate molecule is also referred to as 044);
2) X is 328, p is 32, Kp is K32, q is 86, Kq is K86 (such a conjugate molecule is also referred to as 045);
3) X is 352, p is 20, Kp is K20, q is 202, Kq is K202 (such a conjugate molecule is also referred to as 058);
4) X is 353, p is 20, Kp is K20, q is 218, Kq is K218 (such a conjugate molecule is also referred to as 059); or
5) X is 361, p is 20, Kp is K20, q is 32, Kq is K32 (such a conjugate molecule is also referred to as 066).

In certain embodiments, the CRM comprises the structure of HOOC—(CH2)16-CO-gGlu-2XADO.

In certain embodiments, the CRM is conjugated to a non-natural amino acid residue in the fusion polypeptide. In certain embodiments, the CRM is conjugated to a non-natural amino acid residue in the polypeptide linker or in the GLP-1 or in the GDF15.

In another aspect, the present disclosure provides a method of producing the conjugate provided herein, comprising conjugating a clearance-reducing moiety to the fusion polypeptide provided herein or the polypeptide complex provided herein.

CRMs may be linked to the fusion polypeptide or the polypeptide complex by covalent binding, affinity binding, intercalation, coordinate binding, complexation, association, blending, or addition, among other methods.

In certain embodiments, the fusion polypeptide or the polypeptide complex may be linked to a CRM directly, or indirectly for example through another moiety or through a coupling agent.

The fusion polypeptide or the polypeptide complex can be conjugated at, for example, the lysine residue, the cysteine residue, or the non-natural amino acid by a suitable conjugation reaction.

For example, the fusion polypeptide or the polypeptide complex having a conjugatable residue such as lysine may be reacted with an amino-reactive agent. In certain embodiments, the CRM is conjugated to the conjugatable lysine residue via an acyl group in an acylation reaction. Exemplary methods of acylation reaction is described in, for example, WO2009083549 and WO2010029159, the content of which is incorporated herein to its entirety. The CRM to be conjugated in an acylation reaction may contain a carboxylic acid group, an α,ω-fatty diacid residue, an activated ester, or an activated N-hydroxy imide ester, among others. Examples of activated esters include, O-succinimide reagents like N-hydroxysuccinimidyl (NHS) or sulfo-NHS esters and imido ester compounds like Traut's reagent, which can react with the ε-amino group of a conjugatable lysine residue to form amide or amidine bonds. Additional examples of suitable amino-reactive agent include, O-acylisourea, N-hydroxy trialzole esters, anhydride, phenyl active esters, P-hydroxamic active esters, acylimidazoles, acylbenzotriazoles, acyl azides, acid hylides, phophonium salts, aminium/uronium salts.

For another example, the fusion polypeptide or the polypeptide complex having a conjugatable residue such as cysteine may be linked to a thiol-reactive agent. In certain embodiments, the CRM is conjugated to the conjugatable cysteine residue in an alkylation reaction. In certain embodiments, the CRM is conjugated to the conjugatable cysteine residue via a maleimide or an iodoacetamide to form a carbon-sulfur bond. In certain embodiments, the CRM is conjugated to the conjugatable cysteine residue via a disulphide to form a disulfide bond. Additional examples of suitable thiol-reactive group include, dienyl sulfone, α-haloacyl, or other thiol-reactive conjugation partner. See, for details, Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671.

For example, the fusion polypeptide or the polypeptide complex having a conjugatable residue such as NNAA can be conjugated to a CRM such that a stable linkage can be formed between the NNAA of the fusion polypeptide and the CRM. For example, NNAAs containing keto group or aldehyde or β-diketomoieties can react with a hydrazide- or O-alkylhydroxylamine-, hydroxylamine-containing agents to form a hydrazone or an O-alkylated oxime linkage. For another example, NNAAs containing an azide group can react with an alkyne derivative to form a stable triazole linker by copper (I) catalyzed [3+2] cycloaddition (and vice versa). For another example, NNAAs containing an azide group can be ligated with an appropriate water soluble phosphine-containing agent to form an amide linkage by a Staudinger ligation. Further, a thioester moiety in an NNAA can react with an amine-containing agent to form amide linkage. The fusion polypeptides provided herein incorporated with an NNAA can be conjugated with an agent via cycloaddition reactions, such as (4+2) cycloaddition between diene and dienophile (Diels-Alder reaction), (3+2) cycloaddtion via 1, 3-dipolar Huisgen cycloaddition, and (3+2) cycloaddtion via Nitrone-olefin cycloaddition. Cycloaddition methods suitable for antibody conjugation have been described in, for example, WO05003294, US20120004183, WO06009901, WO07130453 and U.S. Pat. No. 6,737,236.

For another example, the fusion polypeptide or the polypeptide complex may be conjugated to biotin, then indirectly conjugated to CRM that is conjugated to avidin. For still another example, the fusion polypeptide or the polypeptide complex may be linked to a coupling agent which further links to the CRM. Examples of the coupling agents include bifunctional moieties such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and his-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulphide linkage.

Additional methods for the conjugation of CRM to fusion polypeptides, or polypeptide complexes are found, for example, in U.S. Pat. Nos. 5,208,020; 6,411,163; WO2005037992; WO2005081711; and WO2006/034488, which are incorporated herein by reference to the entirety. Specific examples of methods of preparing the conjugates of the present disclosure are also included in the experimental part of the present disclosure.

The fusion polypeptide complexes, and conjugates thereof provided herein have significant better efficacy in promoting body weight loss, reducing food intake, and lowering fasting blood glucose level than GLP-1 alone, GDF15 alone, or their respective conjugates. The fusion polypeptide complexes, and conjugates thereof provided herein provided similar or even better efficacy than Semaglutide with less systematic exposure, indicating a potentially better safety profile and potentially improved therapeutic index.

Pharmaceutical Composition

In another aspect, the present disclosure also provides a pharmaceutical composition comprising the fusion polypeptide, polypeptide complex, or conjugate provided herein and a pharmaceutically acceptable carrier.

The term "pharmaceutically acceptable" indicates that the designated carrier, vehicle, diluent, excipient(s), and/or salt is generally chemically and/or physically compatible with the other ingredients comprising the formulation, and physiologically compatible with the recipient thereof.

A "pharmaceutically acceptable carrier" refers to an ingredient in a pharmaceutical formulation, other than an active ingredient, which is bioactivity acceptable and non-toxic to a subject. Pharmaceutical acceptable carriers for use in the pharmaceutical compositions disclosed herein may include, for example, pharmaceutically acceptable liquid, gel, or solid carriers, aqueous vehicles, nonaqueous vehicles, antimicrobial agents, isotonic agents, buffers, antioxidants, anesthetics, suspending/dispending agents, sequestering or chelating agents, diluents, adjuvants, excipients, or non-toxic auxiliary substances, other components known in the art, or various combinations thereof.

Suitable components may include, for example, antioxidants, fillers, binders, disintegrants, buffers, preservatives, lubricants, flavorings, thickeners, coloring agents, emulsifiers or stabilizers such as sugars and cyclodextrins. Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a pharmaceutical composition provided herein decreases oxidation of the polypeptide complex or the bispecific polypeptide complex. This reduction in oxidation prevents or reduces loss of binding affinity, thereby improving protein stability and maximizing shelf-life. Therefore, in certain embodiments, compositions are provided that comprise the fusion polypeptide, the polypeptide complex or the conjugate disclosed herein and one or more antioxidants such as methionine.

To further illustrate, pharmaceutical acceptable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcelluose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable non-toxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The pharmaceutical compositions can be a liquid solution, suspension, emulsion, pill, capsule, tablet, sustained release formulation, or powder. Oral formulations can include standard carriers such as pharmaceutical grades of mannitol, lactose, starch, magnesium stearate, polyvinyl pyrollidone, sodium saccharine, cellulose, magnesium carbonate, etc.

In embodiments, the pharmaceutical compositions are formulated into an injectable composition. The injectable pharmaceutical compositions may be prepared in any conventional form, such as for example liquid solution, suspension, emulsion, or solid forms suitable for generating liquid solution, suspension, or emulsion. Preparations for injection may include sterile and/or non-pyretic solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile and/or non-pyretic emulsions. The solutions may be either aqueous or nonaqueous.

In certain embodiments, unit-dose parenteral preparations are packaged in an ampoule, a vial or a syringe with a needle. All preparations for parenteral administration should be sterile and not pyretic, as is known and practiced in the art.

In certain embodiments, a sterile, lyophilized powder is prepared by dissolving the fusion polypeptide, the polypeptide complex or the conjugate as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the fusion polypeptide, the polypeptide complex, or the conjugate provided herein or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the sterile and/or non-pyretic water or other liquid suitable carrier is added to lyophilized powder. The precise amount depends upon the selected therapy being given, and can be empirically determined.

Administration of the pharmaceutical composition as described herein may be via any route known to be effective by the physician of ordinary skill. One example is peripheral parenteral administration by a sterile syringe or some other mechanical device such as an infusion pump. In certain embodiments, peripheral parenteral route is intravenous, intramuscular, subcutaneous, or intraperitoneal routes of administration.

In certain embodiments, the fusion polypeptide, the polypeptide complex, or the conjugate described herein is formulated in a form suitable for non-parenteral routes administration, such as oral, rectal, nasal, or lower respiratory routes administration.

In certain embodiments, the fusion polypeptide, the polypeptide complex, or the conjugate described herein is formulated in a solid formulation such as lyophilization or spray drying, which is then reconstituted in a suitable diluent solution prior to administration. Standard pharmaceutical formulation techniques, such as those described in Remington: The Science and Practice of Pharmacy (D. B. Troy, Editor, 21st Edition, Lippincott, Williams & Wilkins, 2006), may be employed. Alternatively, the fusion polypeptide, the polypeptide complex, or the conjugate described herein can be formulated for administration through the lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, transdermal, or pulmonary route. As a still further option, the fusion polypeptide, the polypeptide complex, or the conjugate described herein can be formulated for administration through transdermal administration, for example, by needle-free injection or from a patch, optionally an iontophoretic patch, or transmucosal, for example, buccal, administration.

Method of Treatment

In another aspect, the present disclosure provides a method of preventing or treating a metabolic disorder in a subject in need thereof, comprising administering a therapeutically effective amount of the fusion polypeptide provided herein, the polypeptide complex provided herein, or the conjugate provided herein.

Therapeutic methods are also provided, comprising: administering a therapeutically effective amount of the fusion polypeptide, the polypeptide complex or the conjugate provided herein to a subject in need thereof, thereby treating or preventing a condition or a disorder. In certain embodiments, the subject has been identified as having a disorder or condition likely to respond to the fusion polypeptide, the polypeptide complex or the conjugate provided herein.

In certain embodiments, the metabolic disorder is diabetes, obesity, non-alcoholic steatohepatitis (NASH), cardiovascular disorders like dyslipidemia, atherosclerosis, alcoholic steatohepatitis (ASH), diabeticnephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

For example, a metabolic condition or disorder that can be treated or ameliorated using the fusion polypeptide, the polypeptide complex or the conjugate provided herein, includes a condition where a human subject has a fasting blood glucose level of 125 mg/dL or greater, for example 130, 135, 140, 145, 150, 155, 160, 165, 170, 175, 180, 185, 190, 195, 200 or greater than 200 mg/dL. Blood glucose levels can be determined in the fed or fasted state, or at random. The metabolic condition or disorder can also comprise a condition in which a subject is at increased risk of developing a metabolic condition. For a human subject, such conditions include a fasting blood glucose level of 100 mg/dL. Conditions that can be treated using a pharmaceutical composition comprising a GDF15 mutant polypeptide can also be found in the American Diabetes Association Standards of Medical Care in Diabetes Care-2011, American Diabetes Association, Diabetes Care Vol. 34, No. Supplement 1, SI 1-S61, 2010, incorporated herein by reference.

The therapeutically effective amount of the fusion polypeptide, the polypeptide complex and the conjugate provided herein will depend on various factors known in the art, such as for example body weight, age, past medical history, present medications, state of health of the subject and potential for cross-reaction, allergies, sensitivities and adverse side-effects, as well as the administration route and extent of disease development. Dosages may be proportionally reduced or increased by one of ordinary skill in the art (e.g., physician or veterinarian) as indicated by these and other circumstances or requirements. The therapeutically effective amount can be an amount of the fusion polypeptide, the polypeptide complex and the conjugate provided herein, that elicits a biological or medicinal response in a tissue system, animal, or human being sought by a researcher, medical doctor, or other clinician, which includes alleviation or amelioration of the symptoms of the disease or disorder being treated, i.e., an amount that supports an observable level of one or more desired biological or medicinal response, for example lowering blood glucose, insulin, triglyceride, or cholesterol levels; reducing body weight; or improving glucose tolerance, energy expenditure, or insulin sensitivity.

In certain embodiments, the fusion polypeptide, the polypeptide complex or the conjugate provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the fusion polypeptide, the polypeptide complex or the conjugate provided herein is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

The fusion polypeptide, the polypeptide complex or the conjugate provided herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes.

The fusion polypeptide, the polypeptide complex or the conjugate may be administered alone or in combination with one or more additional therapeutic means or agents.

In certain embodiments, when used for treating a metabolic disease, the fusion polypeptide, the polypeptide complex or the conjugate provided herein may be administered in combination with any other therapeutic agent for use in the treatment of a metabolic disease or any medical disorder that related. "Administered in combination" as used herein includes administration simultaneously as part of the same pharmaceutical composition, simultaneously as separate compositions, or at different timings as separate compositions. A composition administered prior to or after another agent is considered to be administered "in combination" with that agent as the phrase is used herein, even if the composition and the second agent are administered via different routes. Where possible, additional therapeutic agents administered in combination with the fusion polypeptide, the polypeptide complex or the conjugate provided herein are administered according to the schedule listed in the product information sheet of the additional therapeutic agent, or according to the Physicians' Desk Reference (Physicians' Desk Reference, 70th Ed (2016)) or protocols well known in the art. A non-limiting list of examples of compounds that can be administered in combination with a pharmaceutical composition comprising a GDF15 polypeptide, construct comprising a GDF15 polypeptide or a mutant form thereof, include rosiglitizone, pioglitizone, repaglinide, nateglitinide, metform in, exenatide, stiagliptin, pramlintide, glipizide, glimeprirideacarbose, and miglitol.

Kit

Also provided are kits for practicing the disclosed methods. Such kits can comprise a pharmaceutical composition such as those described herein, including nucleic acids encoding the fusion polypeptides, the polypeptide complex, or the conjugate provided herein, vectors and cells comprising such nucleic acids, and pharmaceutical compositions comprising such nucleic acid-containing compounds, which can be provided in a sterile container. Optionally, instructions on how to employ the provided pharmaceutical composition in the treatment of a metabolic disorder can also be included or be made available to a patient or a medical service provider.

In one aspect, a kit comprises (a) a pharmaceutical composition comprising a therapeutically effective amount of a fusion polypeptide, a polypeptide complex, or a conjugate, or construct comprising the aforementioned polypeptides or a mutant form thereof; and (b) one or more containers for the pharmaceutical composition. Such a kit can also comprise instructions for the use thereof; the instructions can be tailored to the precise metabolic disorder being treated. The instructions can describe the use and nature of the materials provided in the kit. In certain embodiments, kits include instructions for a patient to carry out administration to treat a metabolic disorder, such as elevated glucose levels, elevated insulin levels, diabetes, obesity, non-alcoholic steatohepatitis (NASH), cardiovascular disorders like dyslipidemia, atherosclerosis, alcoholic steatohepatitis (ASH), diabeticnephropathy, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

Instructions can be printed on a substrate, such as paper or plastic, etc, and can be present in the kits as a package insert, in the labeling of the container of the kit or components thereof (e.g., associated with the packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, such as over the internet, are provided. An example of this embodiment is a kit that includes a web address where the instructions can be viewed and/or from which the instructions can be downloaded. Often it will be desirable that some or all components of a kit are packaged in suitable packaging to maintain sterility. The components of a kit can be packaged in a kit containment element to make a single, easily handled unit, where the kit containment element, e.g., box or analogous structure, may or may not be an airtight container, e.g., to further preserve the sterility of some or all of the components of the kit.

Example 1: Recombinant Expression of Fusion Proteins

The GLP-1/GDF15 fusion proteins listed in Table 1 were produced from bacterial E. coli expression system, using BL21(DE3) derivative strain. The DNA coding for the GLP-1/GDF15 fusion precursors was codon optimized for E. coli expression, de novo synthesized and subcloned into PET derivative expression vectors (Novagen). Amino acid substitutions were accomplished by modification of the corresponding genetic codes. Overexpression of GLP-1/GDF15 precursor as inclusion bodies was induced with 0.5 mM isopropyl b-d-thiogalactoside (IPTG) when the cell density reached an OD600 of 2.0 in Terrific Broth (TB) medium. The cells were harvested after protein induction at 37° C. for 20-22 hours. The quality of inclusion bodies was analyzed with microscopic imaging.

Control fusion proteins were also prepared using the same methods described above. The control compounds included the following:

Example 2: Refolding and Purification

Cells were harvested as described in Example 1 and lysed in 20 mM Tris pH8.0, 0.15M NaCl buffer by cell disruptor (900 bar, for twice). The insoluble fractions, containing the fusion proteins, were collected and washed in the same buffer twice by centrifugation (8,000×g, for 30 min). The 8M urea with 10 mM DTT buffer was then used to solubilize the inclusion bodies. After 0.5 hours, the solutions were diluted 20-fold with refolding buffer. The refolding samples were stirred at the room temperature for 12 hours. After removing tag by protease, the proteins were loaded on to anion exchange chromatography using Source 30Q resin or Q Sepharose Fast flow resin GE healthcare) running with gradient elution with 20 mM Tris 9.0 and 0.5 M NaCl. In some instances, further polishing was performed by reverse phase chromatography using Source 30RPC resin (GE Healthcare) operated with 50 mM Tris pH 8.0 and Ethanol. The samples in each step were characterized by LC/MS to confirm the correct molecular weight.

Example 3: Preparation of GLP1-GDF15 Fusion Compounds with CRMs

The GLP1-GDF15 fusion proteins obtained in Example 2 were used in this Example for further conjugation. To a solution of a GLP1-GDF15 fusion protein (90 mg) in NaOH or 20 mM Tris pH9.5 was added with CRM reagent (i.e. HOOC—(CH2)16-CO-gGlu-2XADO, HOOC—(CH2)16-CO-gGlu-2XADO-EDA-CO—CH2, or HOOC—(CH2)20-CO-gGlu-2XADO-EDA-CO—CH2) (10 mg) in organic solvent dropwise. The reaction was stirred at room temperature for 1 h. Then the product was applied to anion exchange chromatography using Source 30Q resin (GE healthcare). This provided the compounds as listed in Table 2 as shown above.

The conjugated fusion proteins were detected and characterized by LC-MS method with Waters BioAccord LC-MS system, or by UPLC with Waters Acquity UPLC system, using conditions optimized for different conjugates, following the supplier's manuals.

TABLE A

| SEQ ID NO | Mutations in GLP-1** | Linker | Mutations in GDF15# |
|---|---|---|---|
| 383 | 8G, 34R, 22E, 36G (SEQ ID NO: 243) | (GQEPGAQP)6(GAQP)8 (SEQ ID NO: 5) | N3Q, M57L, V87R (SEQ ID NO: 452) |
| 384 | del7-8$, 34R, 22E, 36G (SEQ ID NO: 450) | (GQEPGAQP)6(GAQP)8 (SEQ ID NO: 5) | N3Q, M57L (SEQ ID NO: 247) |
| 400 | 8G, 34R, 22E, 36G (SEQ ID NO: 243) | (GAQP)8(CQEPGAQP) (GQEPGAQP)5 (SEQ ID NO: 438) | N3Q, M57L, V87R (SEQ ID NO: 452) |
| 401 | del7-8$, 34R, 22E, 36G (SEQ ID NO: 450) | (GAQP)8(CQEPGAQP) (GQEPGAQP)5 (SEQ ID NO: 439) | N3Q, M57L (SEQ ID NO: 247) |
| 406 | 8G, 34R, 22E, 36G (SEQ ID NO: 243) | (GAQP)8(GQEPGQCP) (GQEPGAQP)5 (SEQ ID NO: 444) | N3Q, M57L, V87R (SEQ ID NO: 452) |
| 407 | del7-8$, 34R, 22E, 36G (SEQ ID NO: 450) | (GAQP)8(GQEPGQCP) (GQEPGAQP)5 (SEQ ID NO: 445) | N3Q, M57L (SEQ ID NO: 247) |

$: del7-8 in GLP-1 means deletion of $7^{th}$ and $8^{th}$ amino acids counting from the N-terminus relative to the amino acid sequence of GLP-1 (1-37), which corresponds to the $1^{st}$ and $2^{nd}$ amino acids from the N-terminus relative to SEQ ID NO: 242.

Control fusion protein conjugates were also prepared using the same methods described above. The control compounds included the following:

TABLE B

| Molecule Code (MLC) | Fusion polypeptide SEQ ID NO | Conjugation residue | Moiety |
|---|---|---|---|
| 113 | 400 | 33C of Linker; (64C of fusion polypeptide) | HOOC—(CH2)16-CO-gGlu-2XADO |
| 114 | 401 | 33C of Linker; (62C of fusion polypeptide) | HOOC—(CH2)16-CO-gGlu-2XADO |
| 119 | 406 | 39C of Linker; (70C of fusion polypeptide) | HOOC—(CH2)16-CO-gGlu-2XADO |
| 120 | 407 | 39C of Linker; (68C of fusion polypeptide) | HOOC—(CH2)16-CO-gGlu-2XADO |

Example 4: Acylation Specificity of 4 Lysines (K62, K69, K91, K107) in Native GDF15

Methods

To a solution of native GDF15 (i.e. the mature domain) (90 mg) in NaOH was added with protractor (10 mg) in organic solvent dropwise. The reaction was stirred at room temperature for 1 h. 8M Urea and 20 mM DTT were mixed with the reaction mixture followed by adding *Achromobacter* protease I (API) with 1:10 mass ratio and it was applied to LC/MS the next day. API protease is a lysine-specific endopeptidase and cleaved all lysine residues without acylation except 69K since 69K is followed by proline. When the lysine is acylated with protractor, it was not cleaved by API protease.

Result

The analysis on the API digested fragments on LC/MS was summarized in Table 4. K62 was not acylated under the reaction condition. Therefore K62 was not a conjugatable residue and presence of K62 in the fusion compounds would not cause unspecific acylation on K62 when adding protractor on to a specific position other than K62. Furthermore, K69 was acylated with only around 14%, and therefore could also be considered as not a conjugatable residue due to the low acylation rate. 14% acylated K69 may be removed by chromatography method, and the purified product could still be homogenous. All 91K was acylated and 107K was acylated with 42%, therefore 91K and 107 need to be mutated, for example, to R or Q to prevent unspecific acylation on these two sites. The same acylation specificity was also observed for the fusion proteins containing GDF15.

TABLE 4

| Lysine position on GDF15 | Acylation percentage |
|---|---|
| 62K | 0% |
| 69K | ~14% |
| 91K | 100% |
| 107K | ~42% |

Example 5: In Vitro Activities of Fusion Proteins and Conjugates

Method:

The in vitro GLP-1 activities of fusion protein and conjugates were measured using a BHK cell line overexpressing human GLP-1 receptor and CRE luciferase reporter. Tested fusion proteins and conjugates were measured at 1 nM or 100 nM top concentration with 3-fold serial dilutions with or without 1% human serum albumin (HSA), respectively. After cells were treated with molecules for 4 hours, luciferase activities were measured by Steadylite plus kit (Perkin Elmer, 6066751).

The in vitro GDF15 activities of fusion proteins and conjugates were assessed using a BHK cell line overexpressing both human GFRAL, c-Ret receptor and SRE luciferase reporter. Tested fusion proteins and conjugates were measured at 5 nM or 100 nM top concentration with 3-fold serial dilutions with or without 1% HSA, respectively. After cells were treated with molecules for 3 hours, luciferase activities were measured by Steadylite plus kit (Perkin Elmer, 6066751).

The activity of each protein and conjugate was represented by $EC_{50}$, derived from non-linear regression analysis. Data for a few exemplary protein conjugates were summarized in below Table 3, with Semaglutide (Novo Nordisk, lot JP51144) and Native GDF15 as controls.

TABLE 3

In vitro activities of fusion proteins and conjugates in the absence of HSA.

| Molecule Code (MLC) | Fusion polypeptide SEQ ID NO | Conjugatable Lysine/Cysteine position* | GLP-1 activity (EC50, pM) | GDF15 activity (EC50, pM) |
|---|---|---|---|---|
| Semaglutide (JP51144) | | | 5.4 | n/a |
| Native GDF15 | (SEQ ID NO: 248) | | n/a | 8.1 |
| 002 | (SEQ ID NO: 249) | 26K of GLP-1; (20K of fusion polypeptide) | 13.1 | 17.9 |
| 004 | (SEQ ID NO: 251) | 26K of GLP-1; (20K of fusion polypeptide) | 8.3 | 17.3 |
| 005 | (SEQ ID NO: 252) | 12K of Linker; (29K away from N terminal of GDF15) | 3.0 | 20.3 |
| 006 | (SEQ ID NO: 253) | 36K of GLP-1; (30K of fusion polypeptide) | 28.7 | 11.6 |

TABLE 3-continued

In vitro activities of fusion proteins and conjugates in the absence of HSA.

| Molecule Code (MLC) | Fusion polypeptide SEQ ID NO | Conjugatable Lysine/Cysteine position* | GLP-1 activity (EC50, pM) | GDF15 activity (EC50, pM) |
|---|---|---|---|---|
| 007 | (SEQ ID NO: 254) | 1K of Linker; (40K away from N terminal of GDF15) | 5.9 | 9.5 |
| 008 | (SEQ ID NO: 255) | 6K of linker; (35K away from N terminal of GDF15) | 4.3 | 15.3 |
| 009 | (SEQ ID NO: 256) | 15K of linker; (26K away from N terminal of GDF15) | 1.8 | 24.6 |
| 100 | (SEQ ID NO: 387) | None | 3.1 | 29.9 |
| 023 | (SEQ ID NO: 270) | None | 4.0 | 62.8 |
| 022 | (SEQ ID NO: 269) | None | 6.7 | 59.2 |
| 020 | (SEQ ID NO: 267) | None | 6.6 | 55.9 |
| 003 | (SEQ ID NO: 250) | None | 7.8 | 55.0 |
| 021 | (SEQ ID NO: 268) | None | 5.7 | 67.3 |
| 019 | (SEQ ID NO: 266) | None | 8.0 | 80.5 |
| 096 | (SEQ ID NO: 383) | None | 1.3 | >5000 |
| 097 | (SEQ ID NO: 384) | None | >900 | 32.9 |
| 102 | (SEQ ID NO: 389) | None | 2.5 | 29 |
| 012 | (SEQ ID NO: 259) | 12K of linker; (29K away from N terminal of GDF15) | 3.5 | 32.8 |
| 043 | (SEQ ID NO: 326) | 26K of GLP-1; (20K of fusion polypeptide) | 1.8 | 39 |
| 124 | (SEQ ID NO: 326) | None | 2.5 | 27.5 |
| 013 | (SEQ ID NO: 260) | 1K of linker; (80K away from N terminal of GDF 15) | 6.9 | 48.8 |
| 030 | (SEQ ID NO: 277) | 15K of linker; (66K away from N terminal of GDF 15) | 0.9 | 52.3 |
| 047 | (SEQ ID NO: 330) | 41K of linker; (40K away from N terminal of GDF 15) | 1.0 | 59.4 |
| 064 | (SEQ ID NO: 359) | 51K of linker; (30K away from N terminal of GDF 15) | 1.3 | 116.5 |
| 016 | (SEQ ID NO: 263) | 52K of linker; (29K away from N terminal of GDF 15) | 2.5 | 110.5 |
| 018 | (SEQ ID NO: 265) | 52K of linker; (29K away from N terminal of GDF 15) | 3.3 | 75.5 |
| 017 | (SEQ ID NO: 264) | 55K of linker; (26K away from N terminal of GDF 15) | 2.8 | 77.6 |
| 026 | (SEQ ID NO: 273) | 55K of linker; (26K away from N terminal of GDF 15) | 6.6 | 56.1 |
| 027 | (SEQ ID NO: 274) | 55K of linker; (26K away from N terminal of GDF 15) | 6.6 | 45.4 |
| 046 | (SEQ ID NO: 329) | 60K of linker; (21K away from N terminal of GDF 15) | 1.0 | 78.9 |
| 103 | (SEQ ID NO: 390) | 71K of linker; (10K away from N terminal of GDF 15) | 0.89 | 79.2 |
| 104 | (SEQ ID NO: 391) | 76K of linker; (5K away from N terminal of GDF 15) | 0.88 | 79.4 |
| 045 | (SEQ ID NO: 328) | 1K of linker; (80K away from N terminal of GDF 15) 55K of linker; (26K away from N terminal of GDF 15) | 1.2 | 113.7 |
| 074 | (SEQ ID NO: 369) | 41C of linker; (40C away from N terminal of GDF 15) | 0.94 | 41.1 |

TABLE 3-continued

In vitro activities of fusion proteins and conjugates in the absence of HSA.

| Molecule Code (MLC) | Fusion polypeptide SEQ ID NO | Conjugatable Lysine/Cysteine position* | GLP-1 activity (EC50, pM) | GDF15 activity (EC50, pM) |
| --- | --- | --- | --- | --- |
| 075 | (SEQ ID NO: 369) | 41C of linker; (40C away from N terminal of GDF 15) | 1.3 | 48.6 |
| 087 | (SEQ ID NO: 378) | 41C of linker; (40C away from N terminal of GDF 15) | 1.4 | 23.8 |
| 088 | (SEQ ID NO: 378) | 41C of linker; (40C away from N terminal of GDF 15) | 1.6 | 30.2 |
| 083 | (SEQ ID NO: 376) | 39C of linker; (42C away from N terminal of GDF 15) | 1.7 | 52.4 |
| 084 | (SEQ ID NO: 376) | 39C of linker; (42C away from N terminal of GDF 15) | 1.3 | 70.5 |
| 089 | (SEQ ID NO: 379) | 39C of linker; (42C away from N terminal of GDF 15) | 1.2 | 42.9 |
| 090 | (SEQ ID NO: 379) | 39C of linker; (42C away from N terminal of GDF 15) | 1.5 | 23.6 |
| 085 | (SEQ ID NO: 377) | 37C of linker; (44C away from N terminal of GDF 15) | 1.5 | 22.0 |
| 086 | (SEQ ID NO: 377) | 37C of linker; (44C away from N terminal of GDF 15) | 1.1 | 32.4 |
| 080 | (SEQ ID NO: 374) | 35C of linker; (46C away from N terminal of GDF 15) | 1.6 | 86.8 |
| 081 | (SEQ ID NO: 374) | 35C of linker; (46C away from N terminal of GDF 15) | 1.2 | 69.8 |
| 091 | (SEQ ID NO: 380) | 35C of linker; (46C away from N terminal of GDF 15) | 2.0 | 34.9 |
| 092 | (SEQ ID NO: 380) | 35C of linker; (46C away from N terminal of GDF 15) | 2.2 | 48.6 |
| 093 | (SEQ ID NO: 381) | 33C of linker; (48C away from N terminal of GD 15) | 1.4 | 54.8 |
| 105 | (SEQ ID NO: 392) | 17C of linker; (64C away from N terminal of GDF 15) | 10.0 | 50.0 |
| 107 | (SEQ ID NO: 394) | 25C of linker; (56C away from N terminal of GDF 15) | 1.1 | 59.3 |
| 111 | (SEQ ID NO: 398) | 51C of linker; (30C away from N terminal of GDF 15) | 11.0 | 54.9 |

TABLE C

In vitro activities of fusion protein conjugates in presence of 1% HSA

| Molecule Code (MLC) | Fusion polypeptide SEQ ID NO | Conjugatable Lysine/Cysteine position* | GLP-1 activity ($EC_{50}$, pM, 1% HSA) | GDF15 activity ($EC_{50}$, pM, 1% HSA) |
| --- | --- | --- | --- | --- |
| Semaglutide (JP51144) | | | 396.9 | n/a |
| Native GDF15 | (SEQ ID NO: 248) | | n/a | 11.3 |
| 127 | (SEQ ID NO: 482) | 26C of GLP-1 (20C of fusion polypeptide) | 872.3 | 72.8 |
| 122 | (SEQ ID NO: 472) | 5C of Linker; (76C away from N terminal of GDF 15) | 434.2 | 70.2 |

TABLE C-continued

In vitro activities of fusion protein conjugates in presence of 1% HSA

| Molecule Code (MLC) | Fusion polypeptide SEQ ID NO | Conjugatable Lysine/Cysteine position* | GLP-1 activity ($EC_{50}$, pM, 1% HSA) | GDF15 activity ($EC_{50}$, pM, 1% HSA) |
|---|---|---|---|---|
| 105 | (SEQ ID NO: 392) | 17C of Linker; (64C away from N terminal of GDF 15) | 168.1 | 55.55 |
| 107 | (SEQ ID NO: 394) | 25C of Linker; (56C away from N terminal of GDF 15) | 39.9 | 58 |
| 093 | (SEQ ID NO: 381) | 33C of Linker; (48C away from N terminal of GDF 15) | 27.3 | 67.6 |
| 089 | (SEQ ID NO: 379) | 39C of Linker; (42C away from N terminal of GDF 15) | 24.35 | 66.2 |
| 087 | (SEQ ID NO: 378) | 41C of Linker; (40C away from N terminal of GDF 15) | 24.39 | 49.22 |
| 111 | (SEQ ID NO: 398) | 51C of Linker; (30C away from N terminal of GDF 15) | 7.52 | 193.5 |
| 126 | (SEQ ID NO: 481) | 73C of Linker; (8C away from N terminal of GDF 15) | 9.67 | 1668 |
| 123 | (SEQ ID NO: 473) | 79C of Linker; (2C away from N terminal of GDF 15) | 9.53 | 1355 |

Conclusion:

As shown in table 3, most of the fusion proteins and conjugates showed similar or same magnitude of activities to Semaglutide or native GDF15 in respective assays without HSA supplement. MLC096 and MLC097 were used as negative controls. MLC096 contains a GDF15 variant having N3Q, M57L, and V87R substitutions, in which V87R was known to abolish GDF15 activities. MLC097 contains a GLP-1 variant having deletion of the $7^{th}$ and $8^{th}$ residues, and therefore were expected to have abolished GLP-1 activities. The comparison shows that, despite of the mutations in the GLP-1 (except deletion of the $7^{th}$ and $8^{th}$ residues) and/or GDF15 (except V87R), the fusion, and/or the conjugation, the tested fusion proteins and conjugates retained biological activities of the GLP-1 and GDF15, respectively. However, the potencies of the fusion conjugates appeared to exhibit different extent of right shifts in the presence of 1% HSA (Table C), implying fatty acid position determines ratio of GLP-1 and GDF15 activities. The GLP-1 activity dropped significantly when fatty acid position is on the GLP-1, such as observed with MLC127. In contrast, when fatty acid is conjugated on the linker, the GLP-1 activity was restored significantly (as observed with MLC122 versus MLC127). In particular, the GLP-1 activity further improved when the fatty acid position is some residues away from the C-terminal of GLP-1, as observed with MLC122, MLC 105, MLC107, and so on. Similarly, the GDF15 activity is significantly improved when fatty acid position is at least some residues away from the N-terminal of GDF15, such as observed with MLC123, MLC126 (2 or 8 residues away from N-terminal of GDF15), versus with MLC111 (30 residues away from N-terminal of GDF15).

Example 6: In Vivo Activities of Fusion Protein Conjugates

Part I: Lysine Conjugated Compounds
Method:

10 week old male C57BL/6 mice were injected everyday subcutaneously with 15 nmol/kg of the fusion protein conjugates (i.e., MLC002, MLC 004, MLC 005, MLC 006, MLC 007, MLC 008, and MLC 009) for 14 days. Food intake and body weight were measured daily and five animals were used for each treatment group. Body weight (BW) was monitored for each individual animal, but food intake for each group animals was measured together. Day 1 and Day 14 are first day and last day of molecule dosage. % BW loss=100*(BW on Day n-BW on Day 1)/(BW on Day 1). Cumulative food intake on Day n represents sum of food intake from Day 1 to Day n. Data are indicated as mean values and standard error (SEM) or pooled values. Statistical analysis was performed by One-way ANOVA. Body weight reduction on Day 11 is calculated by −1*(% BW loss−% BW loss of vehicle group); Cumulative food intake reduction is calculated by −100*(cumulative food intake-cumulative food intake of vehicle)/cumulative food intake of vehicle.

TABLE 6

Food intake and body weight reduction in C57 mice at Day11

| Molecule Code (MLC) | Cumulative food intake reduction at Body 15 nmol/kg (% reduction compared to vehicle)(Day11) | weight reduction at 15 nmol/kg (% reduction compared to vehicle)(Day11) |
|---|---|---|
| Semaglutide | 23.2 | 7.2 |
| 002 | 7.5 | 5.0 |

TABLE 6-continued

Food intake and body weight reduction in C57 mice at Day11

| Molecule Code (MLC) | Cumulative food intake reduction at 15 nmol/kg (% reduction compared to vehicle)(Day11) | Body weight reduction at 15 nmol/kg (% reduction compared to vehicle)(Day11) |
| --- | --- | --- |
| 004 | 21.8 | 13.9 |
| 005 | 9.1 | 12.6 |
| 006 | 23.0 | 9.3 |
| 007 | 21.8 | 11.3 |
| 008 | 19.5 | 10.9 |
| 009 | 23.9 | 14.6 |

Conclusion:

Most of the fusion protein conjugates exhibited enhanced and persistent BW reduction, and comparable food intake to Semaglutide (FIG. 1A-F). All fusion protein conjugates except MLC002 showed similar or much better BW reduction efficacy than Semaglutide (see FIGS. 1A and 1B). MLC004, MLC007 and MLC009 exhibited statistically significantly enhanced BW loss efficacy than Semaglutide (JP51144) (see FIG. 1C and Table 6).

Part II: Unconjugated Fusion Proteins

Method:

As described in the above method, a daily dose of 30 nmol/kg of the unconjugated fusion proteins (i.e., MLC100, MLC023, MLC022, MLC020, MLC003, MLC124, MLC021, MLC019, MLC102) were administered to C57BL/6 for 10 days. Data were calculated as above method. Day 1 and Day 10 are first day and last day of administration.

TABLE 7

Food intake and body weight reduction in C57 mice at Day11

| Molecule Code (MLC) | Cumulative food intake reduction at 30 nmol/kg (% reduction compared to vehicle)(Day11) | Body weight reduction at 30 nmol/kg (% reduction compared to vehicle)(Day11) | Linker length (amino acids) |
| --- | --- | --- | --- |
| 020 (SEQ ID NO: 267) | 26.0 | 17.0 | 40 |
| 021 (SEQ ID NO: 268) | 48.7 | 22.1 | 80 |
| 022 (SEQ ID NO: 269) | 30.0 | 10.4 | 24 |
| 023 (SEQ ID NO: 270) | 31.7 | 12.5 | 12 |
| 003 (SEQ ID NO: 250) | 25.3 | 15.5 | 40 |
| 019 (SEQ ID NO: 266) | 48.6 | 23.0 | 80 |
| 124 (SEQ ID NO: 326) | 38.0 | 23.0 | 60 |
| 100 (SEQ ID NO: 387) | 26.3 | 9.9 | 4 |
| 102 (SEQ ID NO: 389) | 36.9 | 29.3 | 120 |

Figure 2:
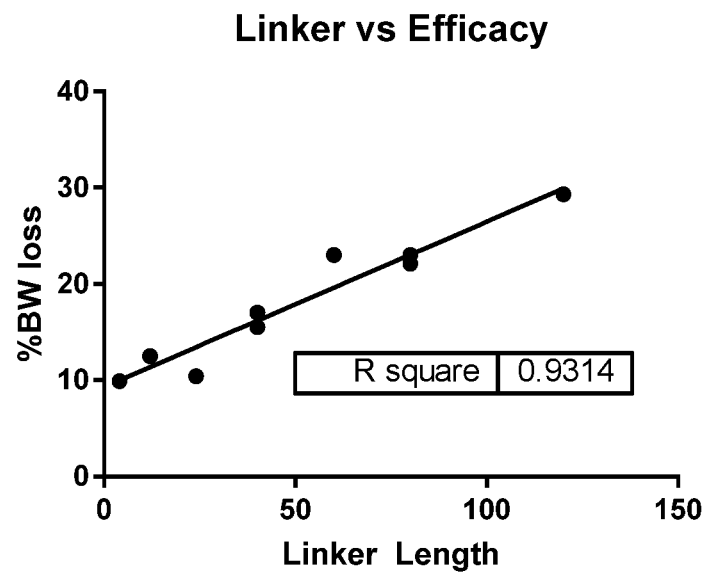
FIG. 2 shows proportional correlation between linker length and body weight loss.

Conclusion:

Linker lengths appeared to be relevant to the in vivo efficacy of the unconjugated fusion proteins. Molecules having a linker of at least 60 residues (e.g. MLC124), or of at least 80 residues (e.g. MLC019 and MLC021), or of at least 120 residues (e.g. MLC021) showed the most significant results among all the tested fusion proteins as shown in Table 7 and FIG. 2. Meanwhile, K69R, K91R, K107R substitutions at GDF15 in the fusion proteins did not show a negative effect on in vivo efficacy.

Part III: Fusion Protein Conjugates

Method:

As described in the above method, a daily dose of 30 nmol/kg of the fusion protein conjugates (i.e., MLC004, MLC013, MLC012, MLC017, MLC018, MLC026, MLC027, MLC064, MLC030, MLC043, MLC045, MLC046, MLC047, MLC074, MLC075, MLC080, MLC081, MLC083, MLC084, MLC091, MLC092, MLC085, MLC086, MLC087, MLC088, MLC089, MLC090, MLC093, MLC103, MLC104) were administered to C57BL/6 mice for 10 days. Data were calculated in the same way as described above. Day 1 and Day 10 are first day and last day of the administration.

MLC014 was used as a negative control. MLC014 has an amino acid sequence of SEQ ID NO: 261, which contains a linker fused to the N terminal of GDF15, with a CRM conjugated to the lysine residue in the linker. Tirzepatide was also used as a control. Tirzepatide is a dual GIP/GLP-1 receptor agonist engineered from the glucose-dependent insulinotropic polypeptide (GIP) sequence that has GIPR activity equal to that of native GIP but is somewhat less potent than GLP-1 at the GLP-1R.

TABLE 8

Food intake and body weight reduction in C57BL/6 mice at Day11

| Compound name or Molecule Code (MLC) | Cumulative food intake reduction at 30 nmol/kg (% reduction compared to vehicle) (Day11) | Body weight reduction at 30 nmol/kg (% reduction compared to vehicle) (Day11) |
| --- | --- | --- |
| Semaglutide | 20.9 | 2.6 |
| Tirzepatide | 23.0 | 10.5 |
| 014 (GDF15 alone) | 27.3 | 9.5 |
| 004 | 35.0 | 18.3 |
| 013 | 45.2 | 21.4 |
| 012 | 37.2 | 30.6 |
| 017 | 52.3 | 25.4 |
| 018 | 48.1 | 23.5 |

TABLE 8-continued

Food intake and body weight reduction in C57BL/6 mice at Day11

| Compound name or Molecule Code (MLC) | Cumulative food intake reduction at 30 nmol/kg (% reduction compared to vehicle) (Day11) | Body weight reduction at 30 nmol/kg (% reduction compared to vehicle) (Day11) |
| --- | --- | --- |
| 026 | 41.0 | 24.7 |
| 027 | 40.7 | 19.1 |
| 064 | 43.6 | 24.0 |
| 030 | 29.1 | 22.0 |
| 043 | 30.5 | 17.4 |
| 045 | 27.8 | 20.6 |
| 046 | 41.4 | 24.6 |
| 047 | 51.2 | 24.7 |

TABLE 8-continued

Food intake and body weight reduction in C57BL/6 mice at Day11

| Compound name or Molecule Code (MLC) | Cumulative food intake reduction at 30 nmol/kg (% reduction compared to vehicle) (Day11) | Body weight reduction at 30 nmol/kg (% reduction compared to vehicle) (Day11) |
|---|---|---|
| 103 | 36.2 | 23.3 |
| 104 | 29.4 | 22.7 |
| 074 | 39.9 | 20.0 |
| 075 | 46.2 | 20.7 |
| 080 | 33.2 | 17.2 |
| 081 | 39.0 | 21.5 |
| 083 | 50.5 | 21.6 |
| 084 | 36.2 | 20.7 |
| 091 | 38.1 | 22.7 |
| 092 | 33.9 | 22.2 |
| 085 | 40.1 | 23.8 |
| 086 | 34.8 | 24.4 |
| 087 | 31.8 | 22.7 |
| 088 | 34.8 | 22.4 |
| 089 | 29.9 | 24.6 |
| 090 | 44.4 | 24.5 |
| 093 | 43.8 | 26.2 |

Conclusion:

On Day 11, almost all fusion protein conjugates in Table 8 exhibited better BW reduction efficacy than Semaglutide, MLC014 or Tirzepatide, along with better food intake suppression, which suggests that improved in vivo activities can be observed in most fusion protein conjugates. The tested fusion protein conjugates have conjugation of CRM at a variety of positions, e.g. ranging from position 26 on GLP1 until to the position on linker which is 5 or 2 amino acid residues away from GDF15, yet they were all effective.

Example 7: Pharmacokinetic Measurement of Fusion Protein Conjugates

Method:

6-8 week old male C57BL/6 mice were administered in a single subcutaneous dose of 30 nmol/kg of the fusion protein conjugates or unconjugated fusion proteins (i.e., MLC002, MLC004, MLC005, MLC006, MLC007, MLC008, MLC009, MLC013, MLC017, MLC047, MLC074, MLC075, MLC089, MLC093, MLC003 and MLC019) (n=3/group). Plasma samples were collected pre-dose (−5 min), 0.5 hr, 1 hr, 2 hr, 4 hr, 6 hr, 8 hr, 12 hr, 24 hr, 48 hr and 72 hr after the injection. The concentrations of the fusion protein conjugates in the plasma were measured by an ELISA assay which has immunoreactivity towards both GDF15 and intact N-terminal of GLP-1. Based on the graph showing plasma concentration of each protein versus time after subcutaneous injection, the pharmacokinetic parameters (including $T_{max}$, $C_{max}$, $T_{1/2}$, AUC) were calculated by WinNonlin software.

Figure 3A:
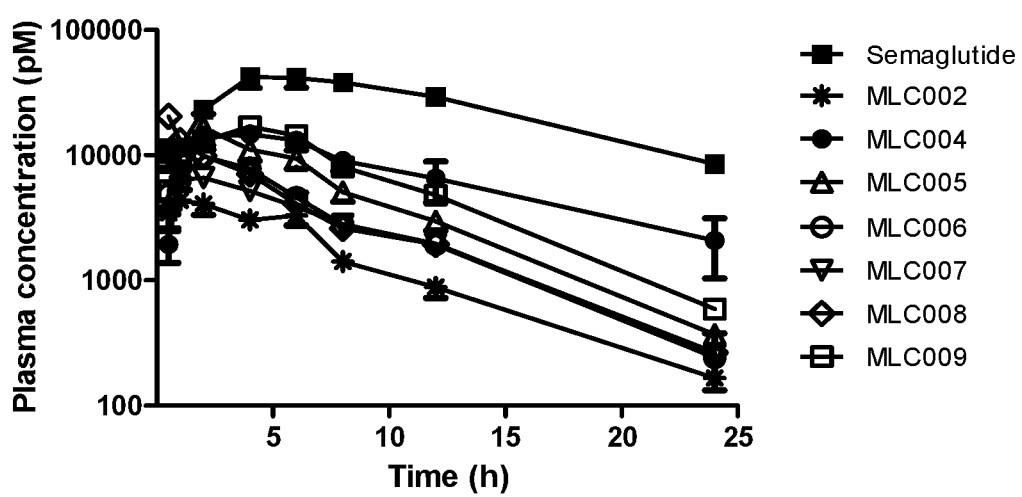
FIGS. 3A-3C show Pharmacokinetic measurement of fusion proteins. Each fusion protein was injected subcutaneously into C57BL/6 mice (n=3/group) once and plasma samples were collected at designed time points and analyzed by ELISA method. Plasma concentrations are indicated as mean values and standard error (SEM).
Figure 3B:
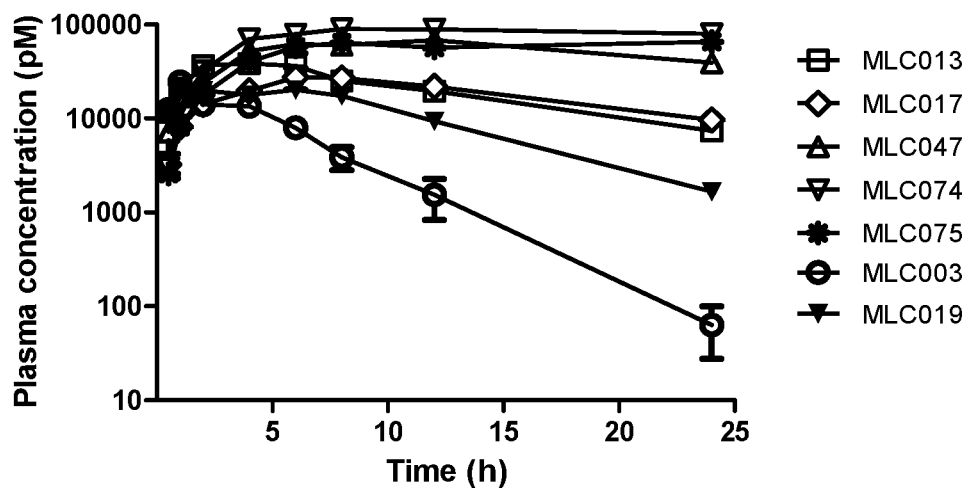
Figure 3C:
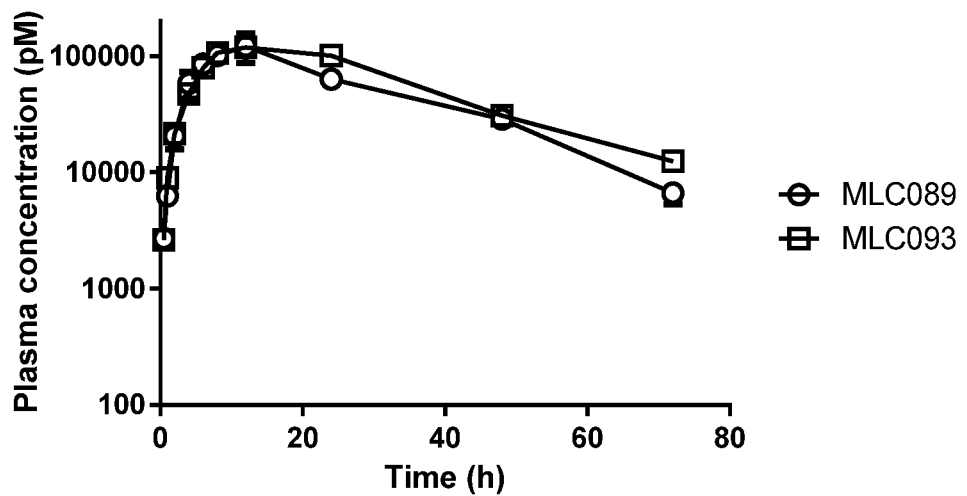

Conclusion:

As shown in Table 5 and FIG. 3, MLC004, MLC013, MLC017 (SEQ ID NO: 264), MLC047, MLC074, MLC075, MLC089 and MLC093 showed similar or even better half-lives to Semaglutide, while the rest molecules exhibited shorter half-lives. Fatty acid conjugation position appears to be relevant to drug exposure reflected by $C_{max}$ and AUC of MLC047, MLC074, MLC075, MLC089, and MLC093. MLC003 and MLC019 have much shorter half-lives and exposures than MLC002 and MLC004, indicating fatty acid conjugation increases protein stabilities in vivo. Meanwhile, fusion proteins having a linker with a length of 80 amino acid residues have longer $T_{1/2}$ than those having a linker with a length of 40 amino acid residues, whether or not conjugated with a fatty acid. Despite of having lower $C_{max}$ and AUC than Semaglutide, most of the fusion protein conjugates showed much greater efficacy than Semaglutide in efficacy study, indicating additive or synergistic effect coming from GLP1 and GDF15 moieties, and from the general construct of the fusion polypeptide.

TABLE 5

Pharmacokinetic parameters of fusion proteins in mouse.

| Molecule Code (MLC) | $T_{max}$ (hr) | $C_{max}$ (nmol/L) | Terminal $t_{1/2}$ (hr) | $AUC_{0-24\,h}$ (hr * nmol/L) |
|---|---|---|---|---|
| Semaglutide (JP51144) | 6.7 | 43.1 | 7.4 | 614.7 |
| 002 | 1.2 | 4.6 | 5.0 | 36.2 |
| 004 | 3.3 | 15.1 | 7.4 | 174.5 |
| 005 | 2.0 | 16.7 | 4.2 | 117.2 |
| 006 | 2.7 | 9.9 | 4.4 | 71.9 |
| 007 | 0.5 | 10.4 | 4.7 | 63.8 |
| 008 | 0.7 | 20.8 | 4.2 | 82.2 |
| 009 | 3.3 | 17.0 | 4.2 | 157.8 |
| 013 | 3.3 | 38.5 | 8.9 | 503.5 |
| 017 | 7.3 | 29.4 | 11.1 | 438.5 |
| 047 | 10.7 | 71.9 | 9.3 | 1246.8 |
| 074 | 10.7 | 102.0 | 18.0 | 1824.7 |
| 075 | 13.3 | 69.8 | 20.4 | 1275.3 |
| 089 | 10.7 | 115.6 | 14.7 | 1982.2 |
| 093 | 16.0 | 120.4 | 15.9 | 2163.7 |
| 003 | 1.0 | 24.7 | 3.5 | 107.4 |
| 019 | 4.0 | 23.7 | 4.8 | 263.9 |

Example 8: Additive or Synergistic Effect of the GLP-1/GDF15 Fusion Protein and Conjugate Method:

10 week old male C57BL/6 mice were injected everyday subcutaneously with 30 nmol/kg of the unconjugated fusion proteins (i.e., MLC096, MLC097 and MLCO21) for 10 days. Food intake and body weight were measured daily and five animals were used for each treatment group. Body weight (BW) was monitored for each individual animal, but food intake for each group animals was measured together. Day 1 and Day 10 are first day and last day of molecule dosage. % BW loss=100*(BW on Day n-BW on Day 1)/(BW on Day 1). Cumulative food intake on Day n represents sum of food intake from Day 1 to Day n. Data are indicated as mean values and standard error (SEM) or pooled values. Statistical analysis was performed by One-way ANOVA.

As discussed above, MLC096 and MLC097 were used as negative controls, as they contained known inactivating mutation in GDF15 or GLP-1.

Figure 7A:
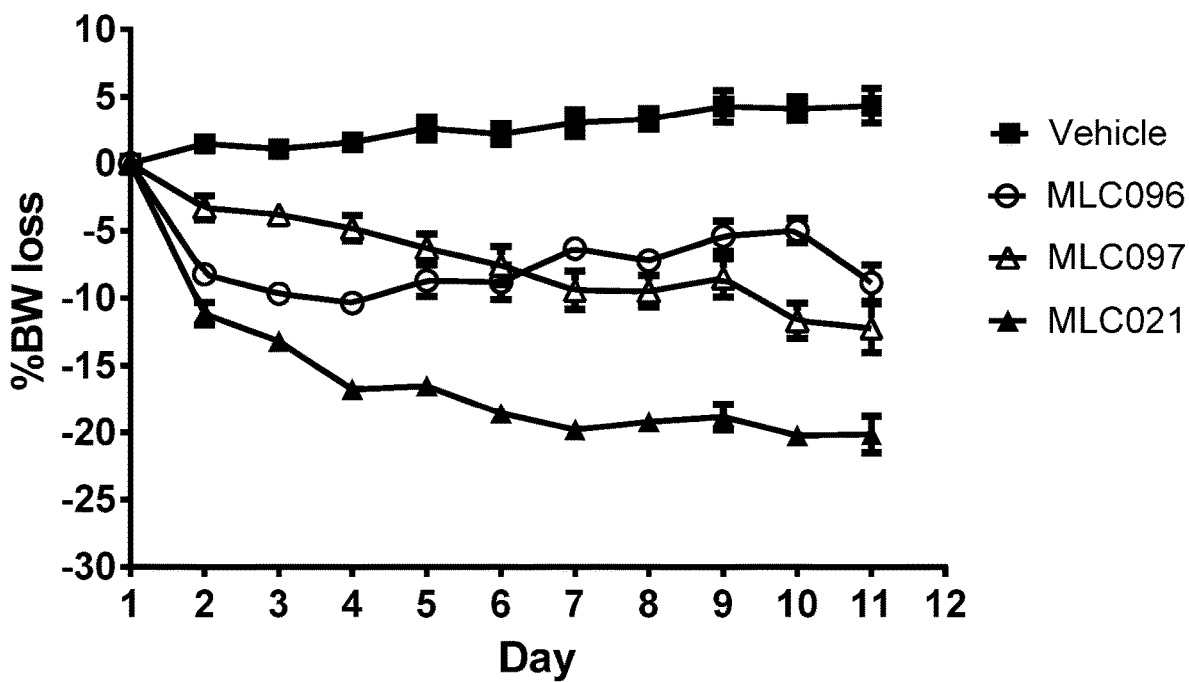
FIGS. 7A-7B show In vivo efficacy in C57 lean mice. To evaluate the body weight and food intake effects of the fusion proteins, 10 week old male C57BL/6J mice were dosed everyday subcutaneously with 30 nmol/kg protein for 10 days. Food intake and body weight were measured daily.
Figure 7B:
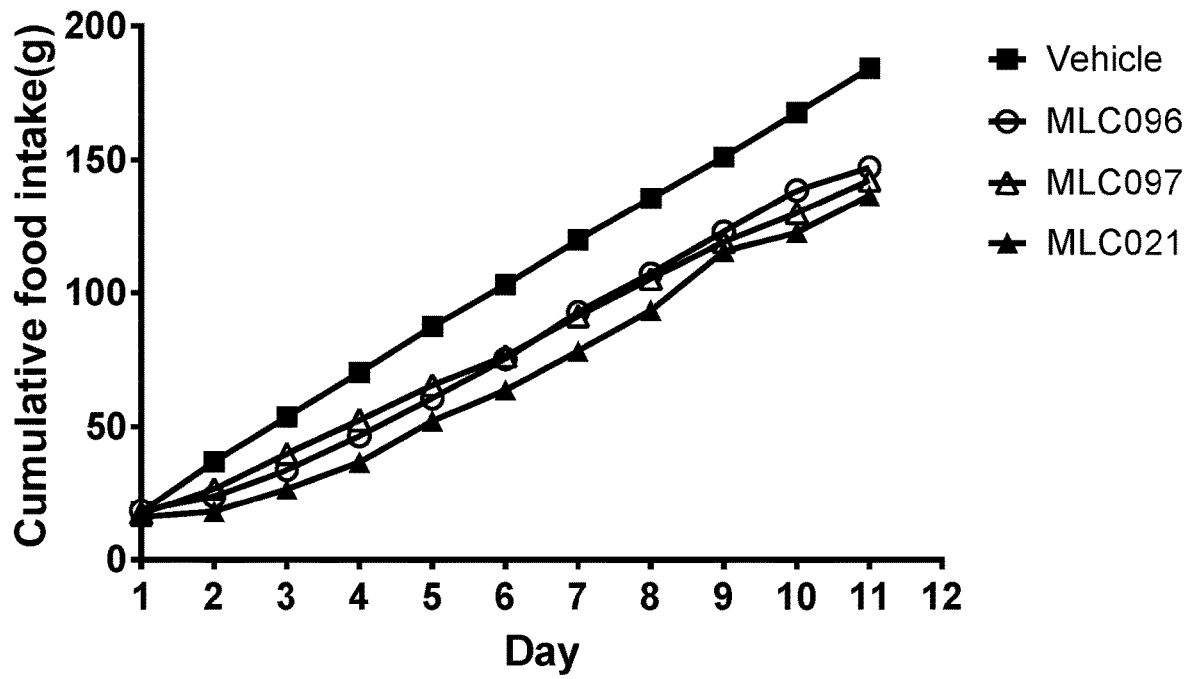

Conclusion:

Unconjugated fusion protein MLC021 showed much better body weight reduction efficacy along with decreased food intake compared to the negative controls MLC096 and MLC097 (see FIG. 7).

In study using db/db mice, fusion protein conjugates (MLC013 and MLC047) showed better efficacy than Semaglutide and GDF15 derivative (MLC014) (see FIG. 5). Fusion protein conjugates (MLC089, MLC090 and MLC093) exhibited better efficacy than Semaglutide and GDF15 derivative (MLC014) (see FIG. 8). Similarly, in DIO study, fusion protein conjugates (MLC089 and MLC093) showed better efficacy than Semaglutide and GDF15 derivative (MLC014) (see FIG. 6). In a separate DIO study, fusion protein conjugate MCL093 also demonstrated better efficacy than corresponding control molecules having inactivated GLP-1 or GDF15 mutants, i.e. MLC114 and MLC113, respectively (FIG. 9A-FIG. 9G). All the data indicate additive or synergistic effect in GLP1-GDF15 conjugates.

Example 9: Efficacy Study in Disease Model

Selected fusion protein conjugates are assessed in disease animal models (DIO mice, db/db mice, etc.) to determine body weight, food intake, glucose efficacy with dose responses. Some biomarkers are also measured, including fasting insulin, plasma triglyceride, cholesterol, liver triglyceride, and inflammatory biomarkers (ALT, AST and CRP).

Method:

8 week old male db/db mice were injected everyday subcutaneously with designated proteins for 14 days. Age matched lean mice were used as control. Food intake and body weight were measured daily and five animals were used for each treatment group. Fasting glucose were tested on designated days as shown in each figure. Body weight was monitored for each individual animal, but food intake for each group animals was measured together. Day 1 and Day 14 are first day and last day of molecule dosage. % BW loss=100*(BW on Day n-BW on Day 1)/(BW on Day 1). Cumulative food intake on Day n represents sum of food intake from Day 1 to Day n. Terminal blood was collected and EDTA-2K plasma was prepared and frozen at −80° C. for biomarker measurement. Liver was also collected and frozen in liquid nitrogen and store at −80° C. Data are indicated as mean values and standard error (SEM) or pooled values. Statistical analysis was performed by One-way ANOVA.

Figure 4A:
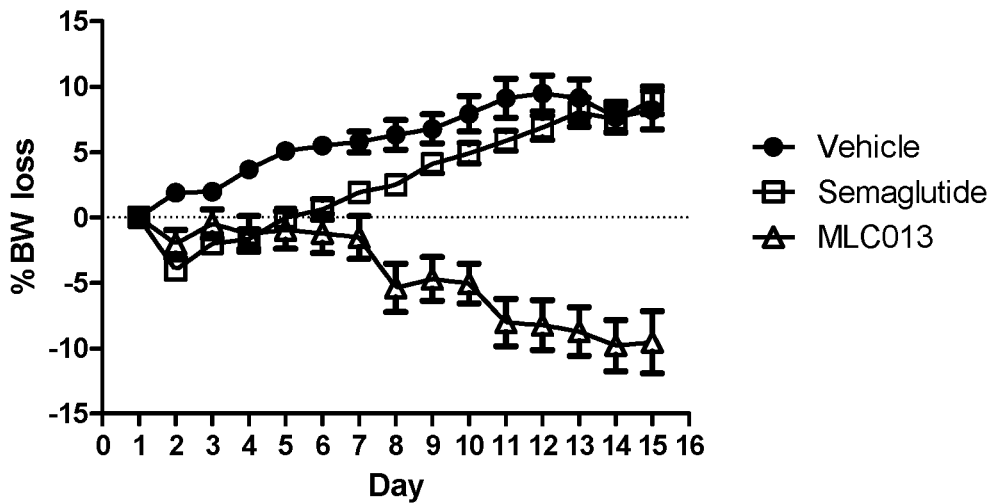
FIGS. 4A-4D show In vivo efficacy in db/db mice. To evaluate the body weight, food intake and glucose effects of the fusion proteins, 8 week old male db/db mice were dosed everyday subcutaneously with 30 nmol/kg protein for 14 days.
Figure 4B:
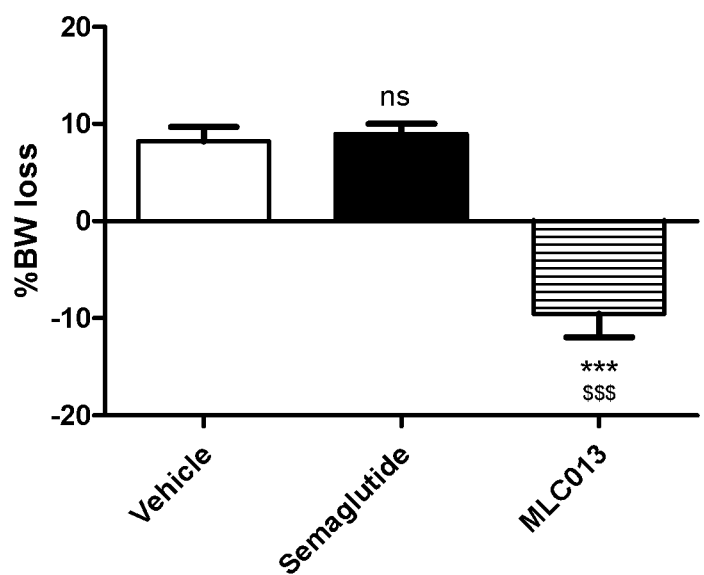
Figure 4C:
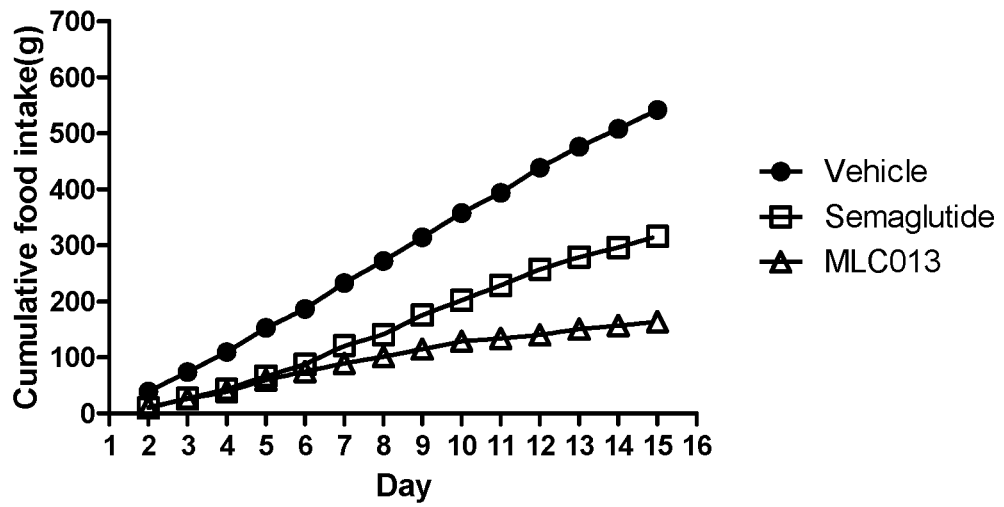
Figure 4D:
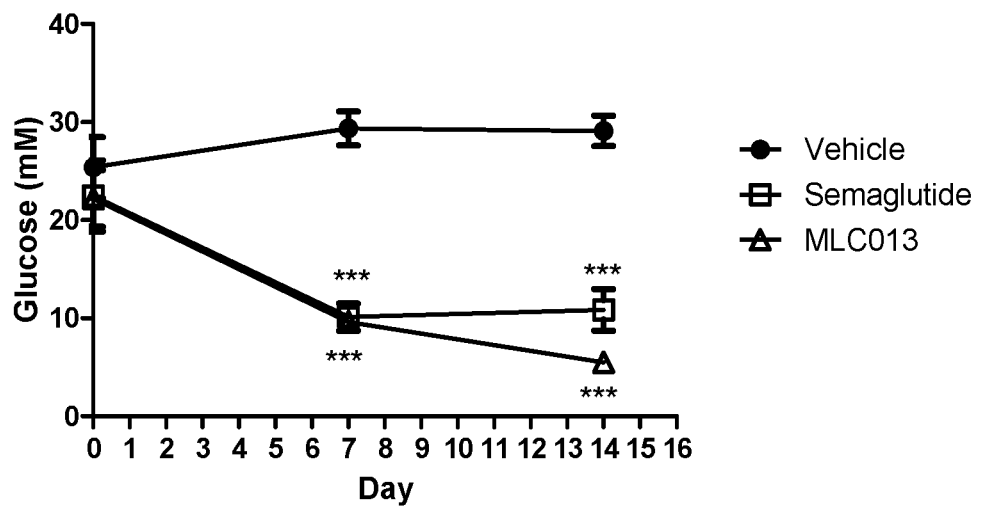
Figure 5A:
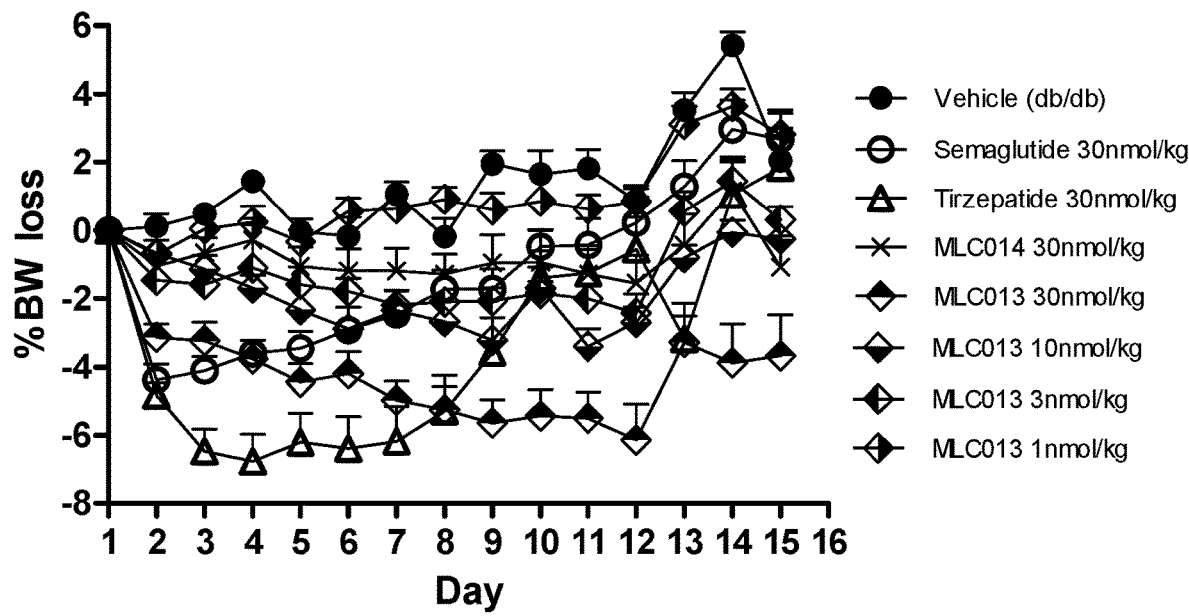
FIGS. 5A-5F show In vivo efficacy in db/db mice. To evaluate the body weight, food intake and glucose effects of the fusion proteins, 8 week old male db/db mice were dosed everyday subcutaneously with different concentrations of proteins for 14 days.
Figure 5B:
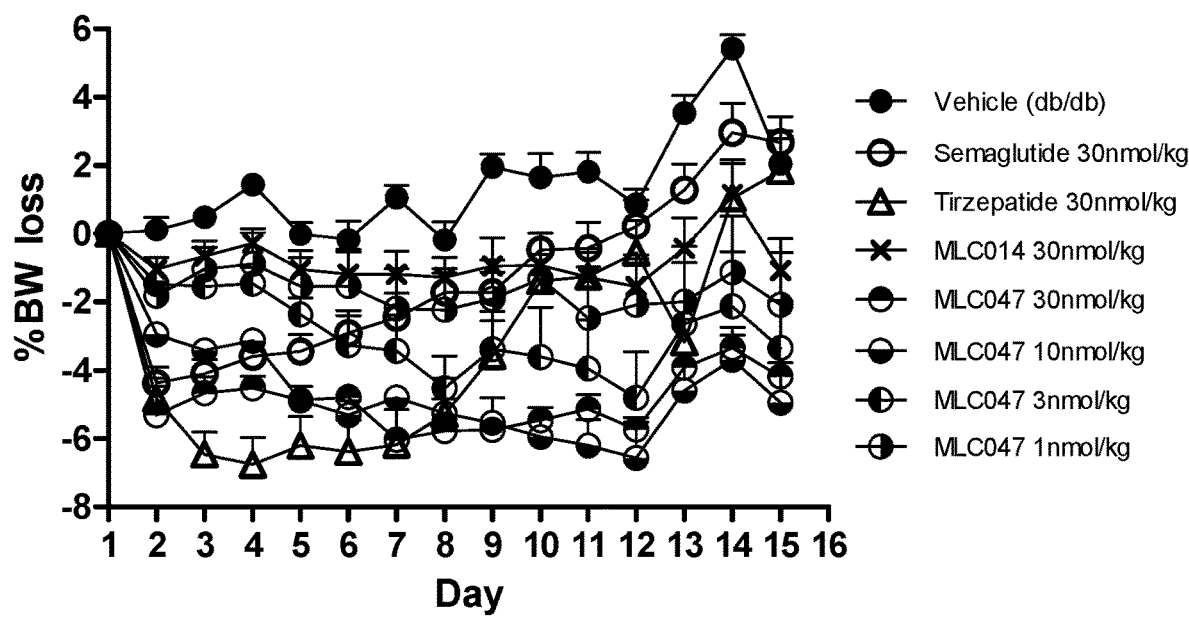
Figure 5C:
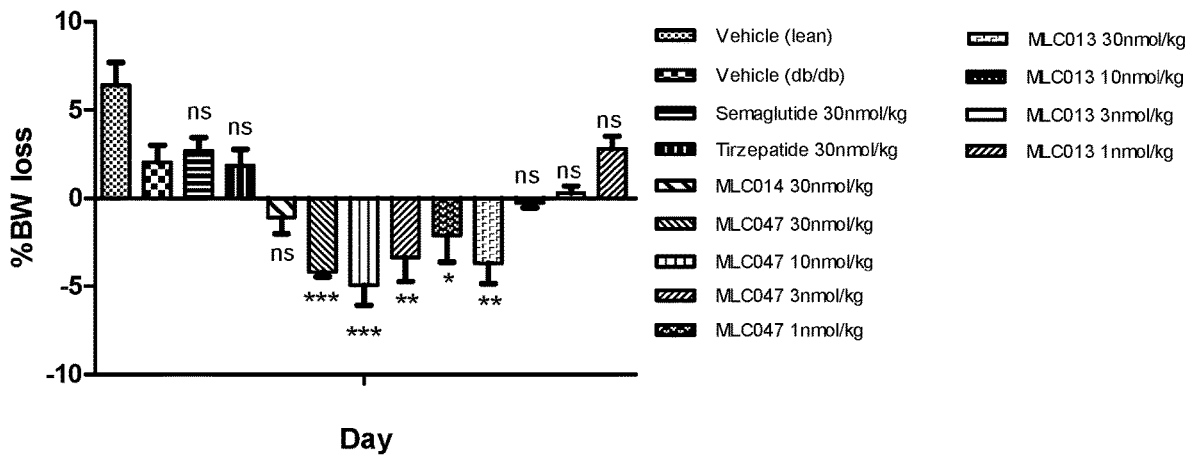
Figure 5D:
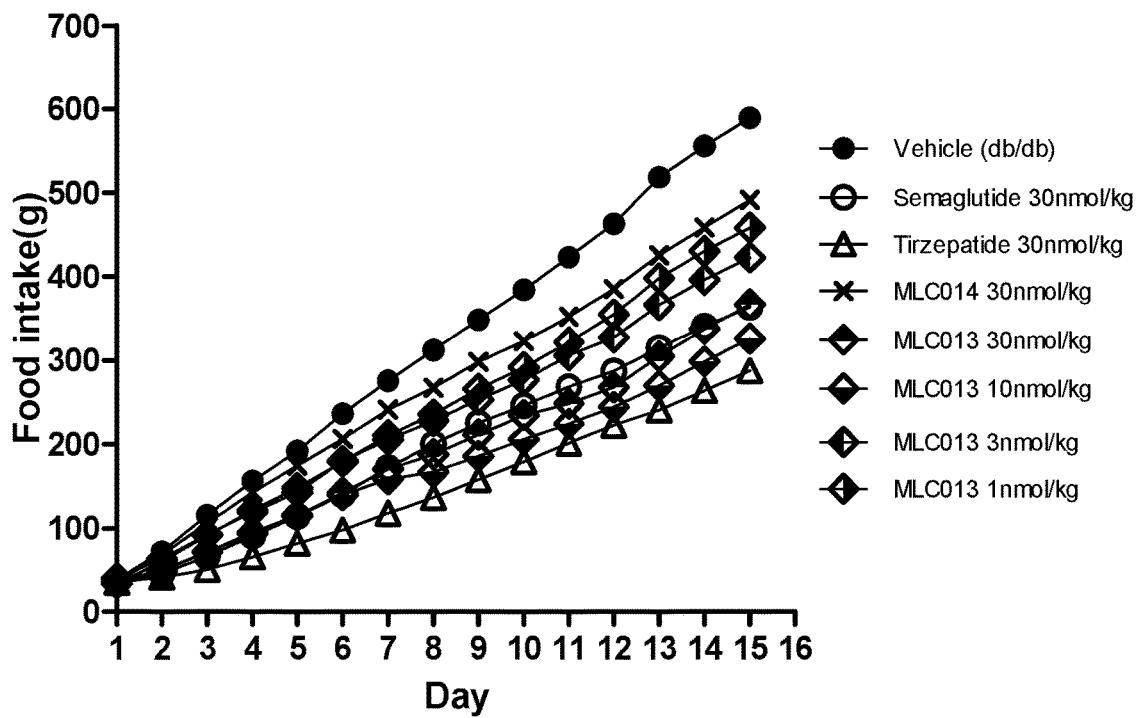
Figure 5E:
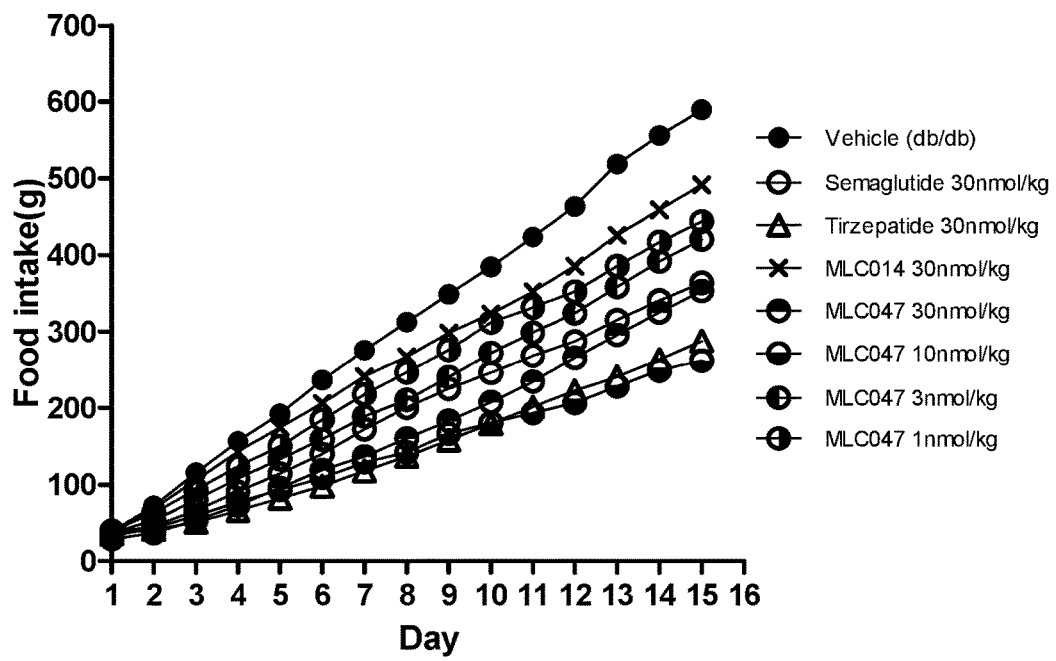
Figure 5F:
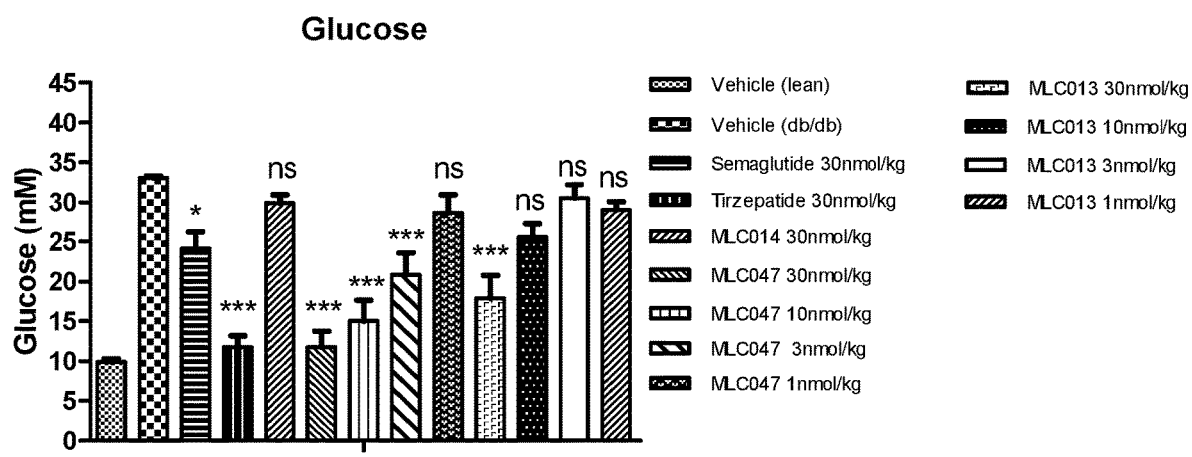
Figure 8A:
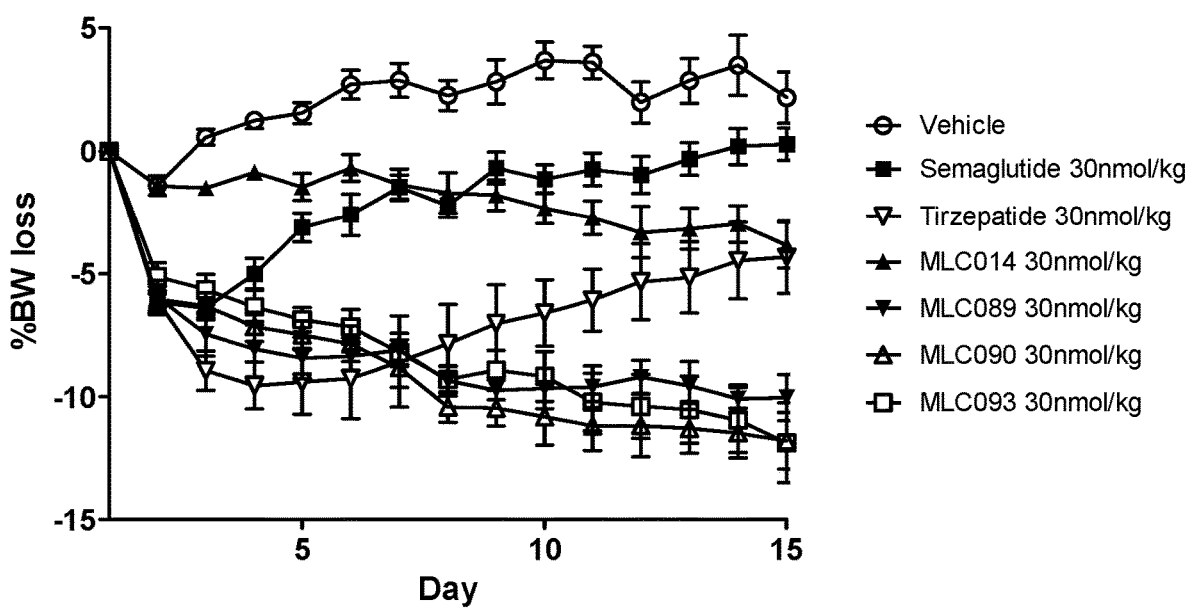
FIGS. 8A-8I show In vivo efficacy in db/db mice. To evaluate the body weight, food intake and glucose effects of the fusion proteins, 8 week old male db/db mice were dosed everyday subcutaneously with different concentrations of proteins for 14 days.
Figure 8B:
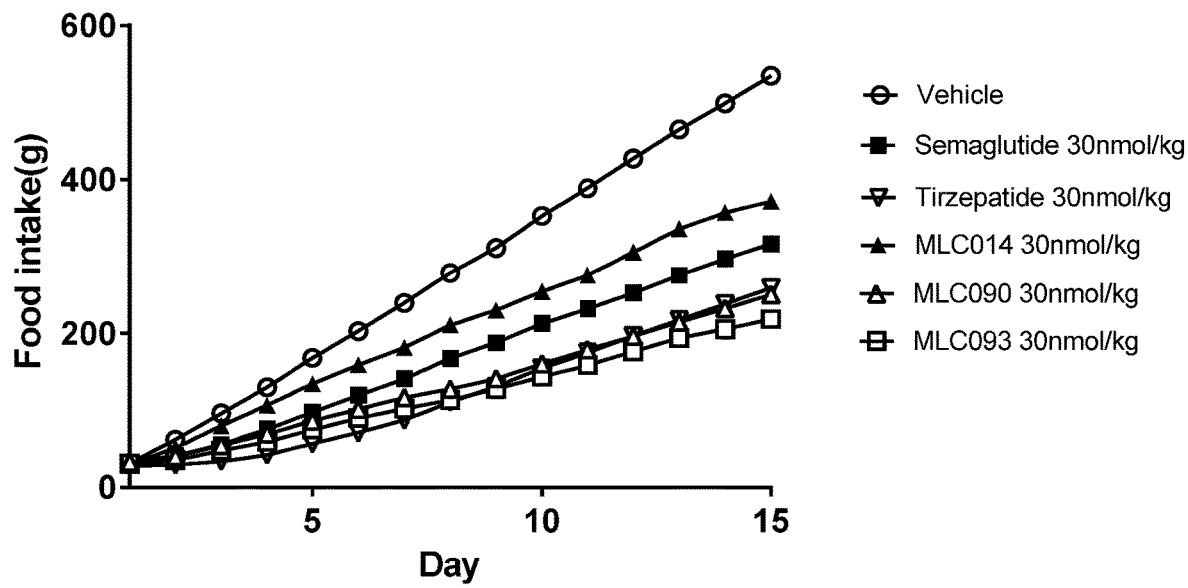
Figure 8C:
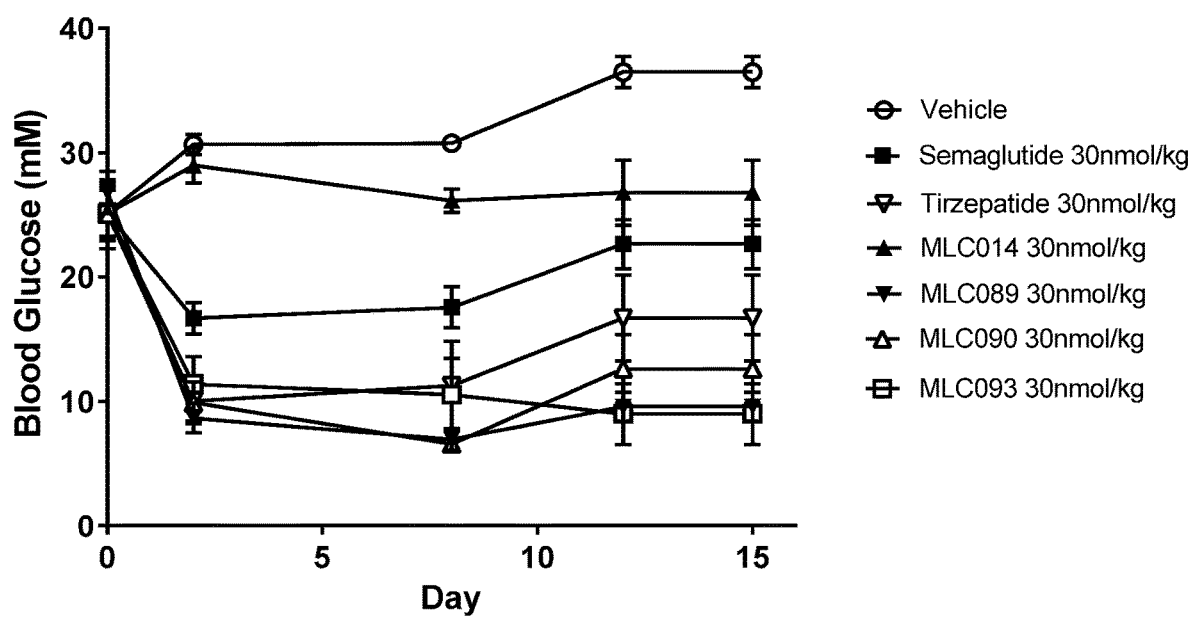
Figure 8D:
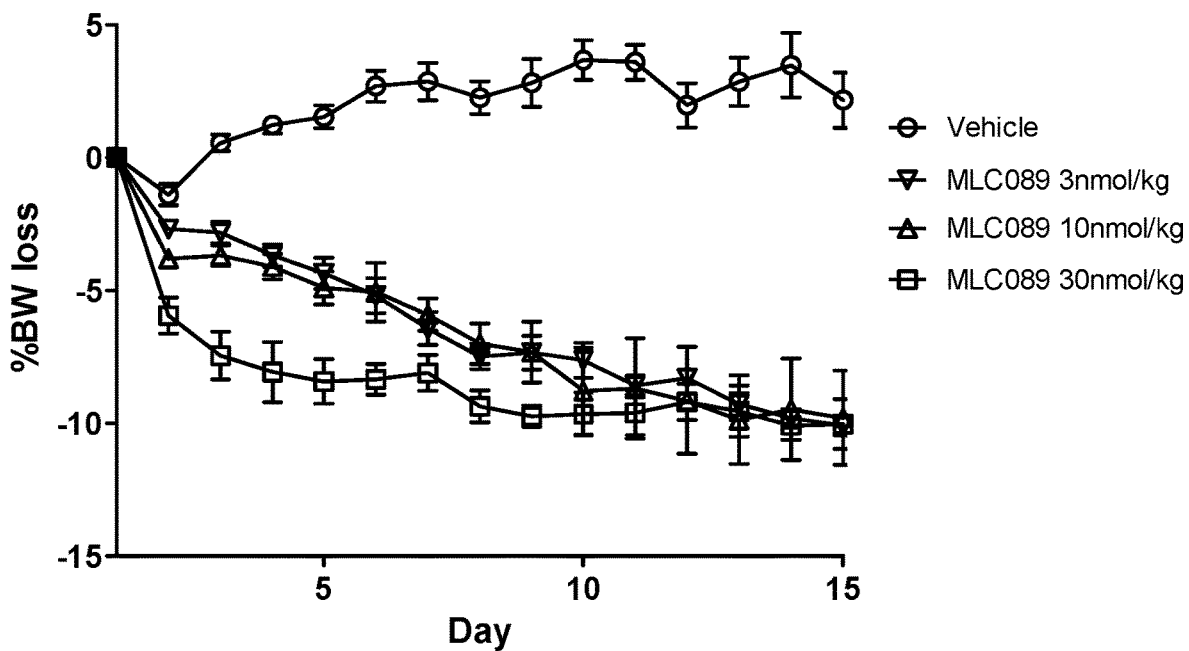
Figure 8E:
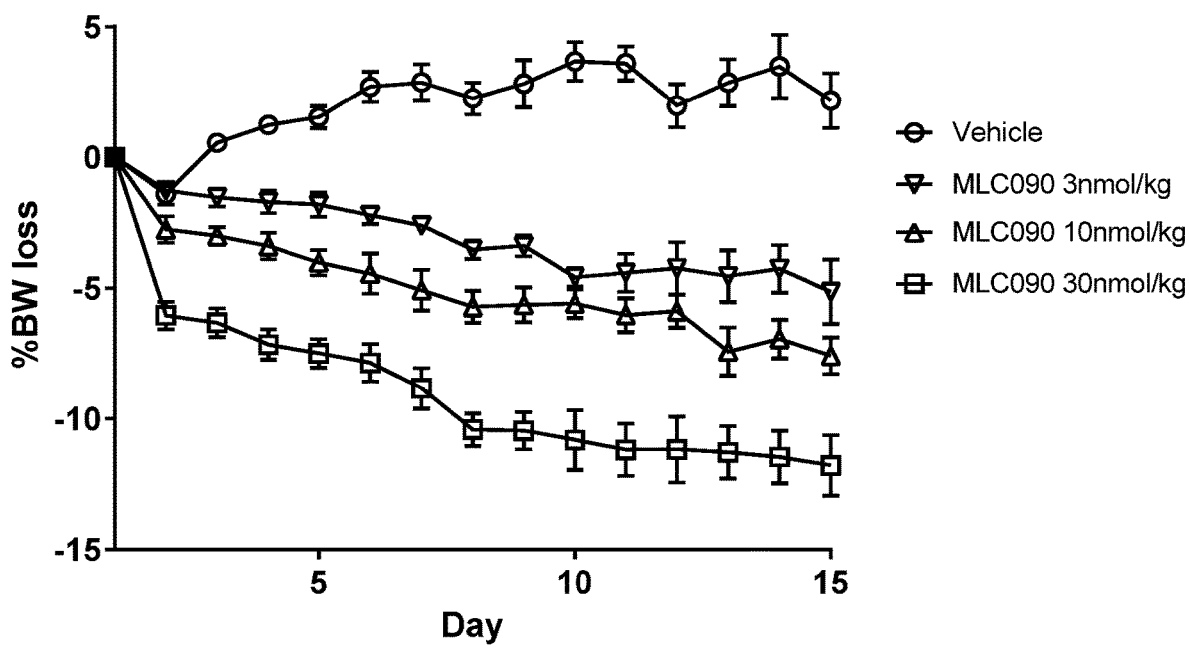
Figure 8F:
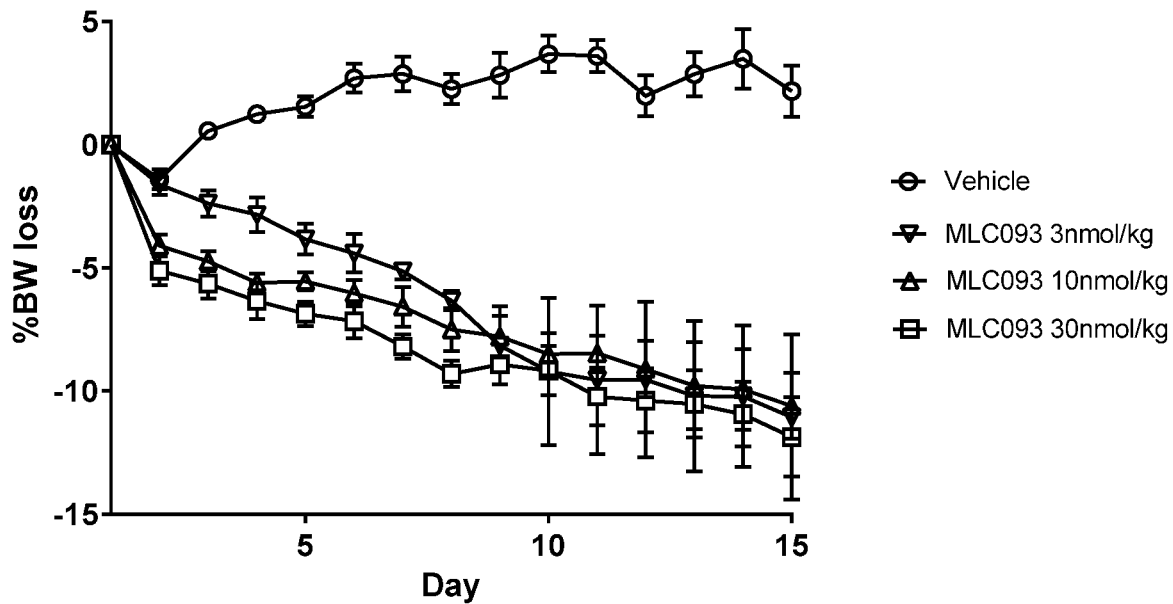
Figure 8G:
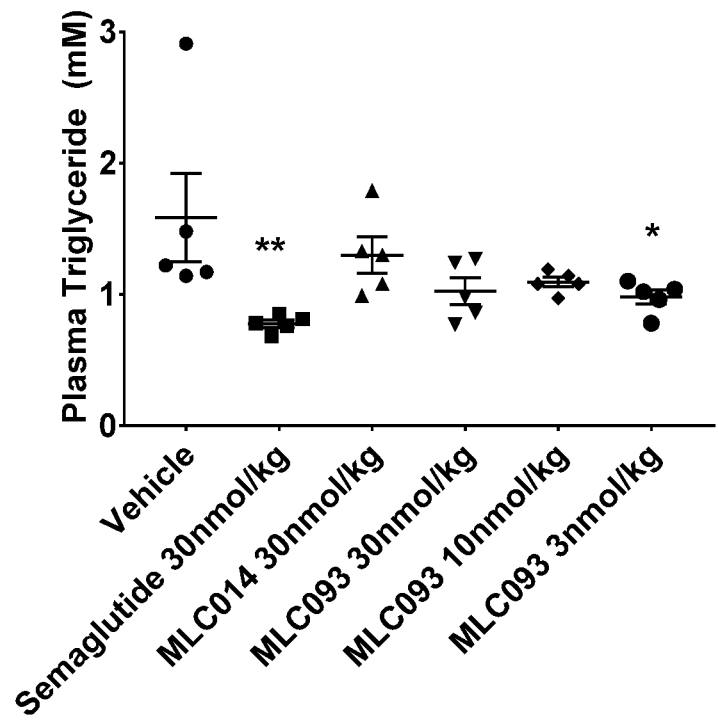
Figure 8H:
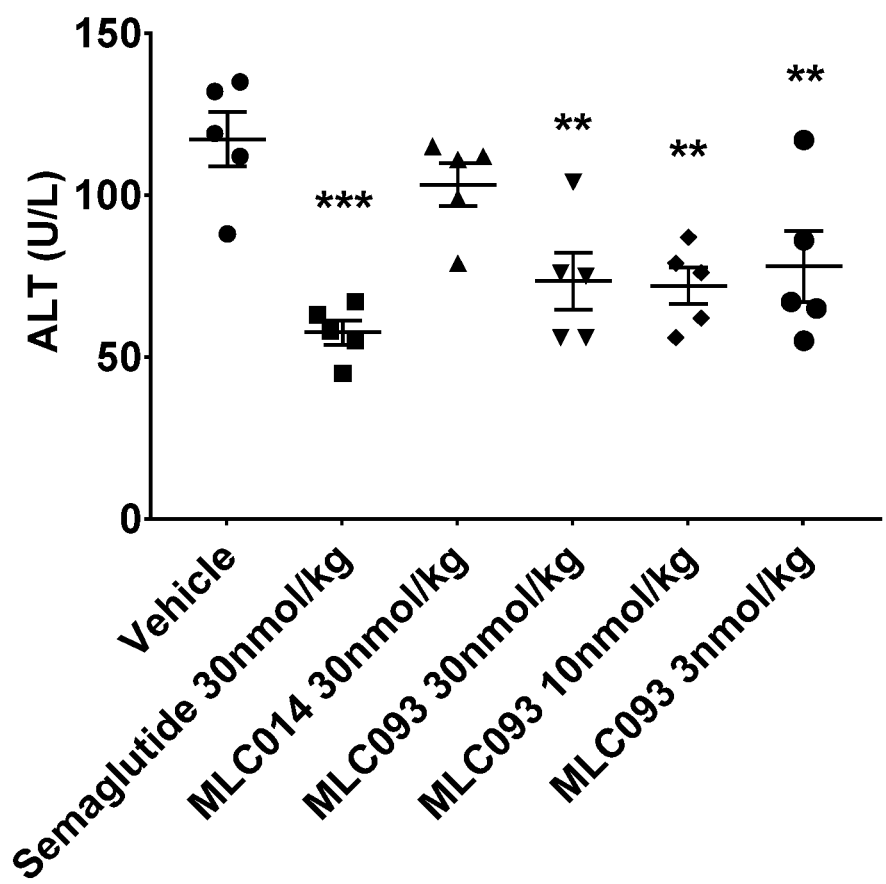
Figure 8I:
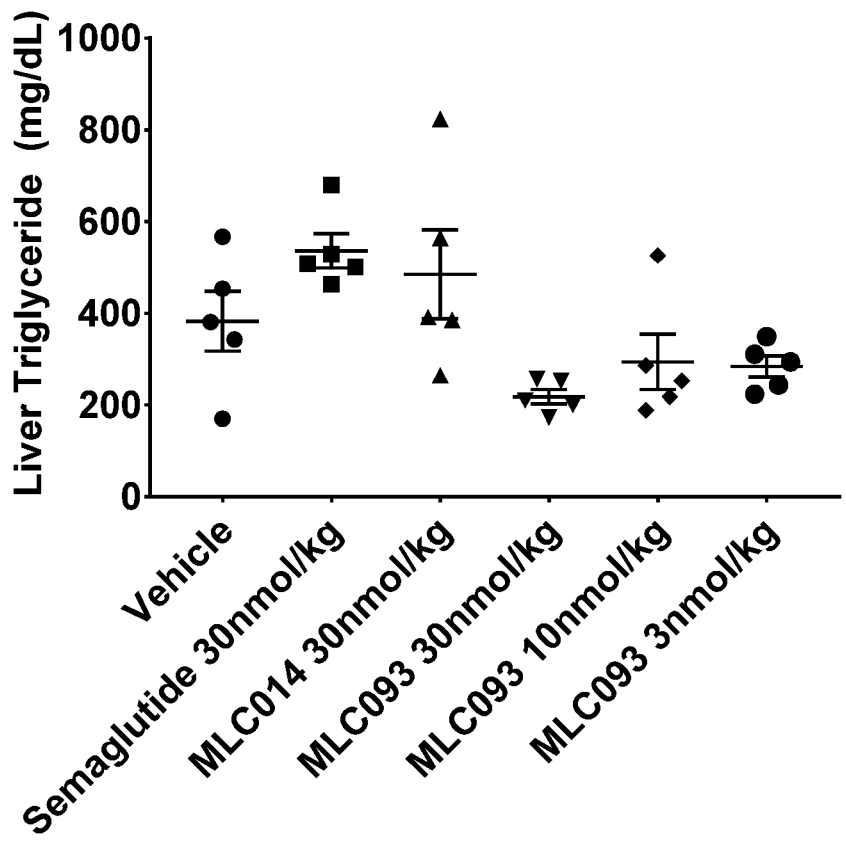

Conclusion:

In db/db study, as shown in FIGS. 4A, 4B and 4C, fusion protein conjugate MLC013 showed sustainable and much better effect on body weight loss and food intake suppression than Semaglutide. Meanwhile, MLC013 has comparable glucose lowering effect to Semaglutide (see FIG. 4D). As shown in FIG. 5A-E, 30 nmol/kg fusion protein conjugates MLC013 and MLC047 showed sustainable and much better effect on body weight loss and food intake suppression than Semaglutide, Tirzepatide and GDF15 derivative (MLC014). All fusion protein conjugates exhibited dose-dependent efficacy. In FIG. 5F, higher doses of fusion protein conjugates can reach similar level or even better effect on glucose control to Tirzepatide or Semaglutide. As shown in FIG. 8A-C, 30 nmol/kg fusion protein conjugates MLC089, MLC090 and MLC093 had more body weight loss, food intake suppression and glycemic control than Semaglutide, Tirzepatide and MLC014. In FIG. 8D-F, different doses (3, 10 and 30 nmol/kg) were tested and all measured doses showed good efficacy on body weight loss. ML093 also induced the reduction of plasma triglyceride and ALT concentration and demonstrated a trend in reducing liver triglyceride content (FIG. 8G-I).

Method:

17 week old DIO male C57BL/6 mice (~45 g) were injected everyday subcutaneously with designated proteins (i.e., MLC089, MLC093) for 28 days. Food intake and body weight were measured daily and five animals were used for each treatment group. Fasting glucose was also monitored on designated days. Body weight and glucose were monitored for each individual animal, but food intake for each group animals was measured together. Day 1 and Day 28 are first day and last day of molecule dosage. % BW loss=100* (BW on Day n-BW on Day 1)/(BW on Day 1). Cumulative food intake on Day n represents sum of food intake from Day 1 to Day n. Terminal blood was collected and EDTA-2K plasma was prepared and frozen at −80 C for biomarker measurement. Liver was also collected and frozen in liquid nitrogen and store at −80 C. Data are indicated as mean values and standard error (SEM) or pooled values.

Figure 6A:
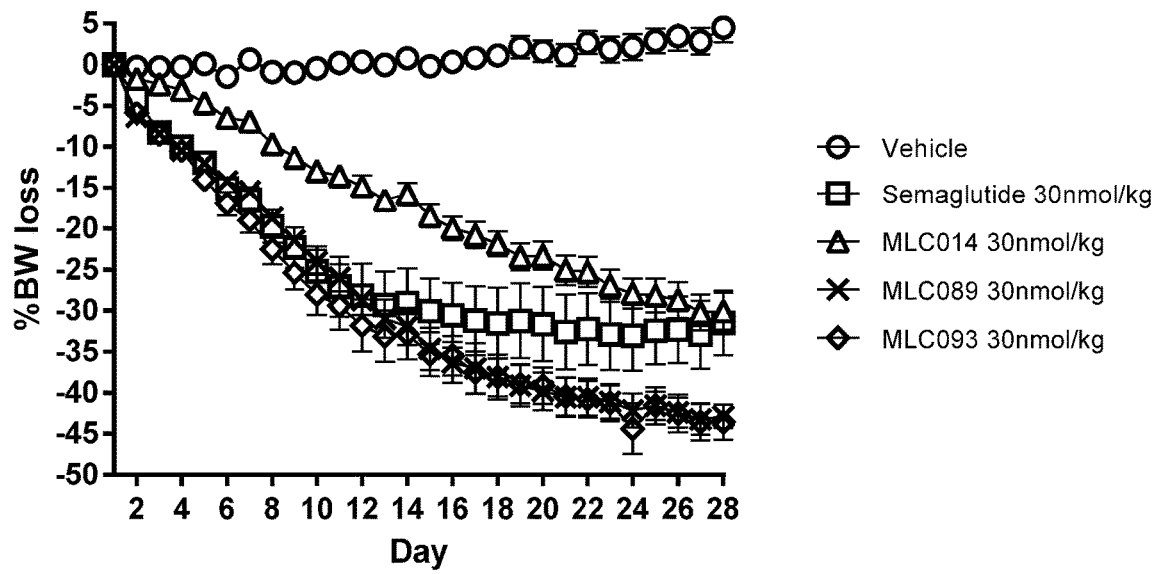
FIGS. 6A-6E show In vivo efficacy in DIO mice. To evaluate the body weight, food intake and glucose effects of the fusion proteins, 17 week old DIO mice (C57BL/6 mice on high fat diet for 13 weeks) were dosed everyday subcutaneously with different concentrations of proteins for 28 days.
Figure 6B:
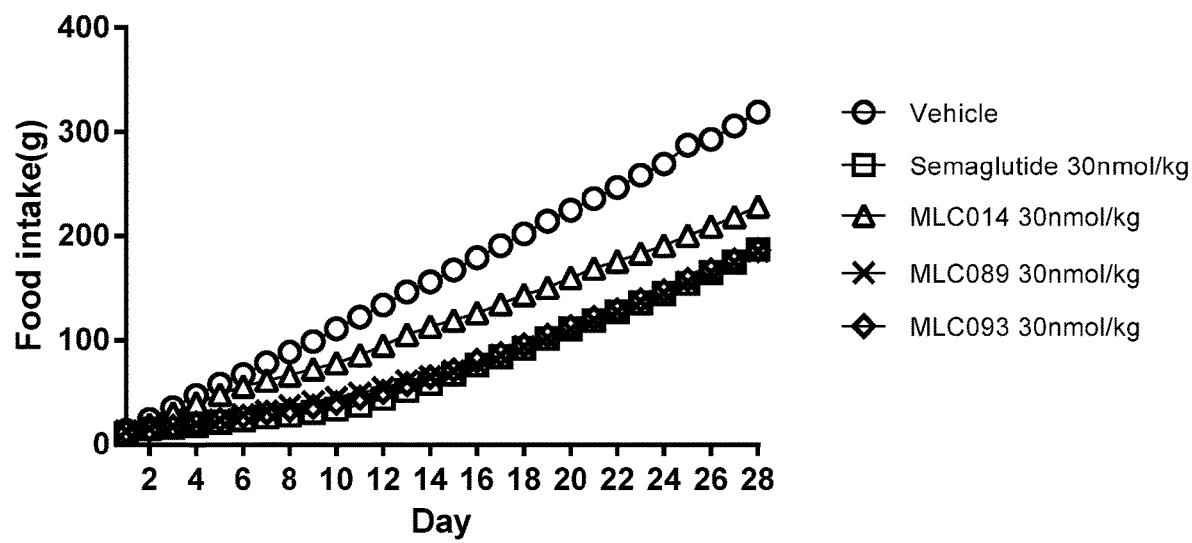
Figure 6C:
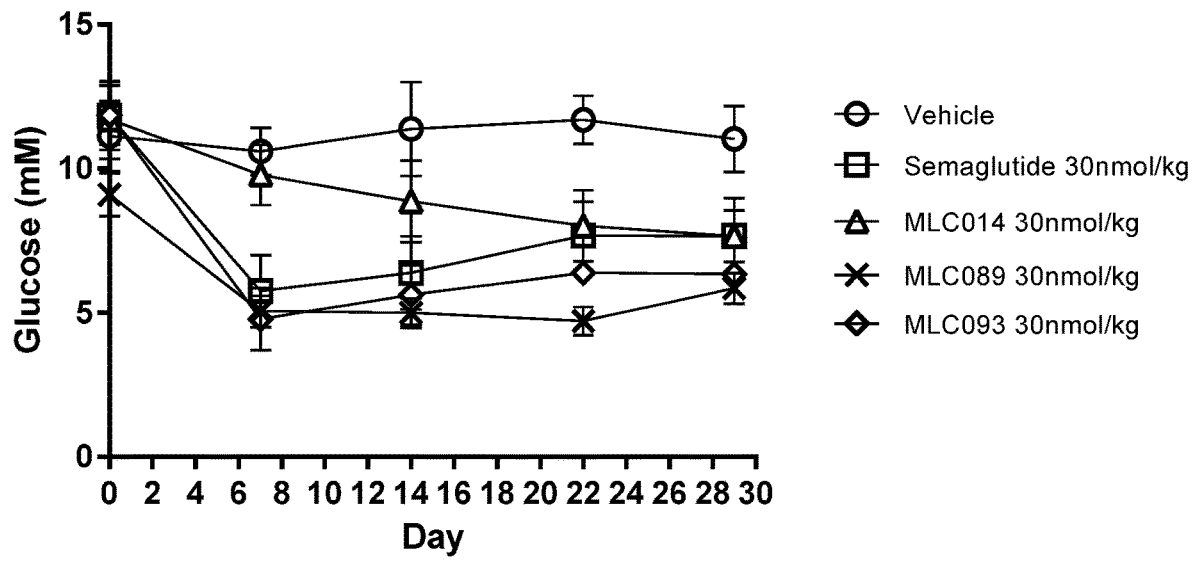
Figure 6D:
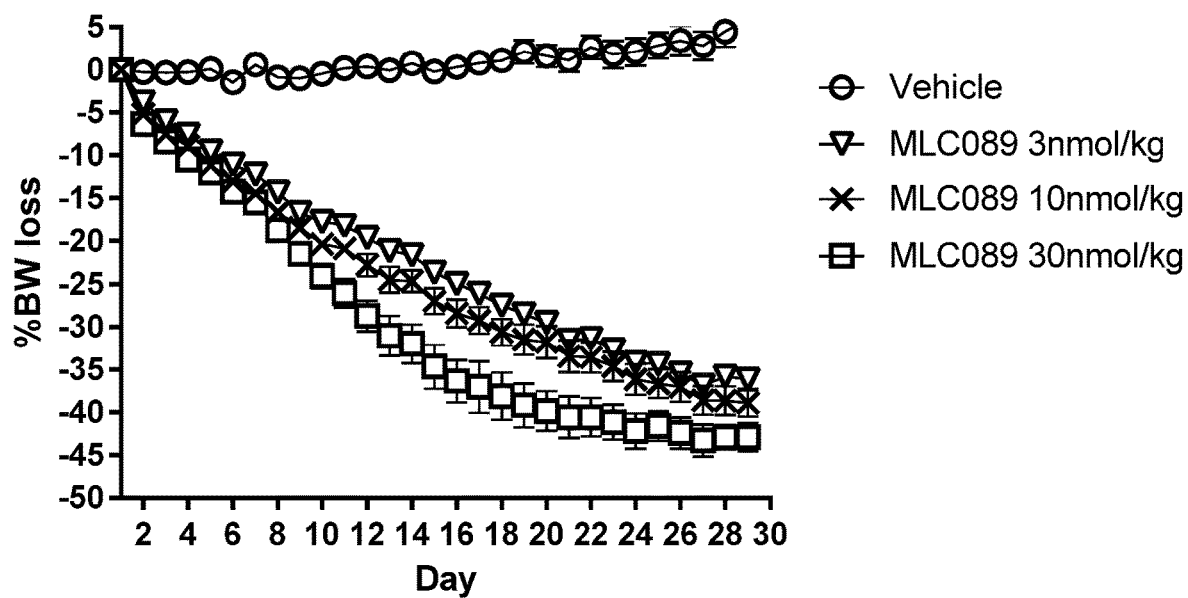
Figure 6E:
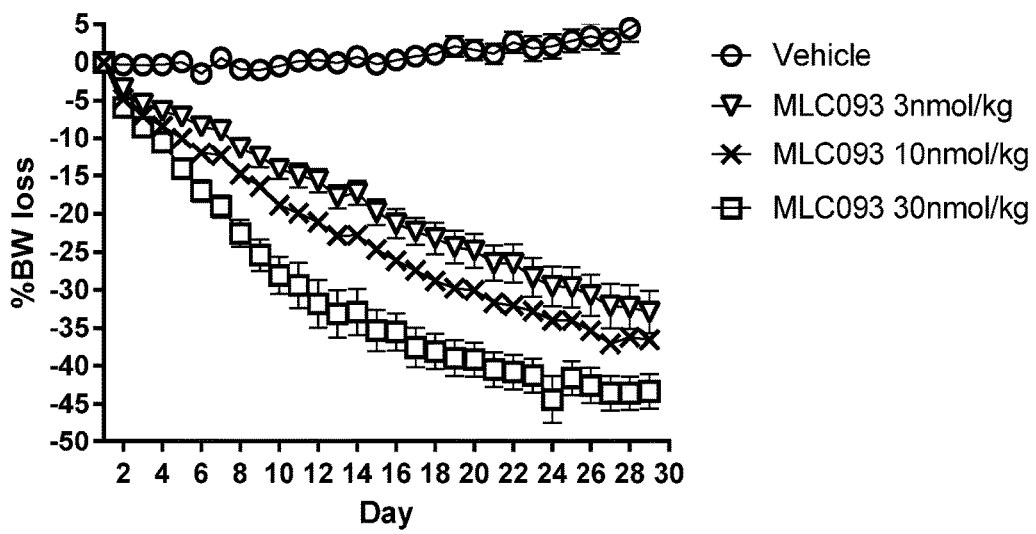

Conclusion:

In DIO study, as shown in FIGS. 6A and 6B, fusion protein conjugates (MLC089 and MLC093) at 30 nmol/kg showed much better body weight reduction efficacy than Semaglutide and GDF15 derivative (MLC014), along with similar food intake suppression to Semaglutide. In FIG. 6C, fasting glucose in MLC089 and MLC093 groups reached similar level to Semaglutide. Both MLC089 and MLC093 showed dose dependent efficacy on body weight reduction (see FIGS. 6D and 6E).

Figure 9A:
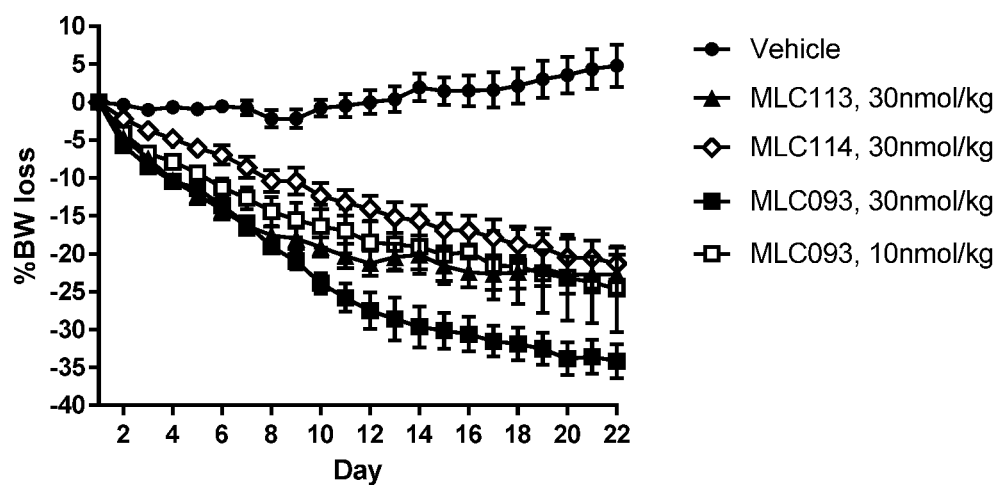
FIGS. 9A-9G show In vivo efficacy in DIO mice. To evaluate the body weight, food intake and glucose effects of the fusion proteins, 17 week old DIO mice (C57BL/6 mice on high fat diet for 13 weeks) were dosed everyday subcutaneously with different concentrations of proteins for 22 days.
Figure 9B:
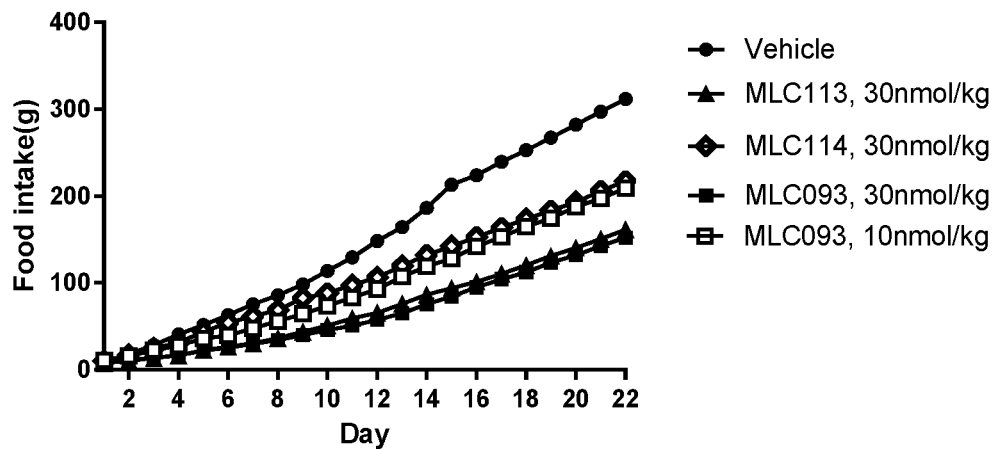
Figure 9C:
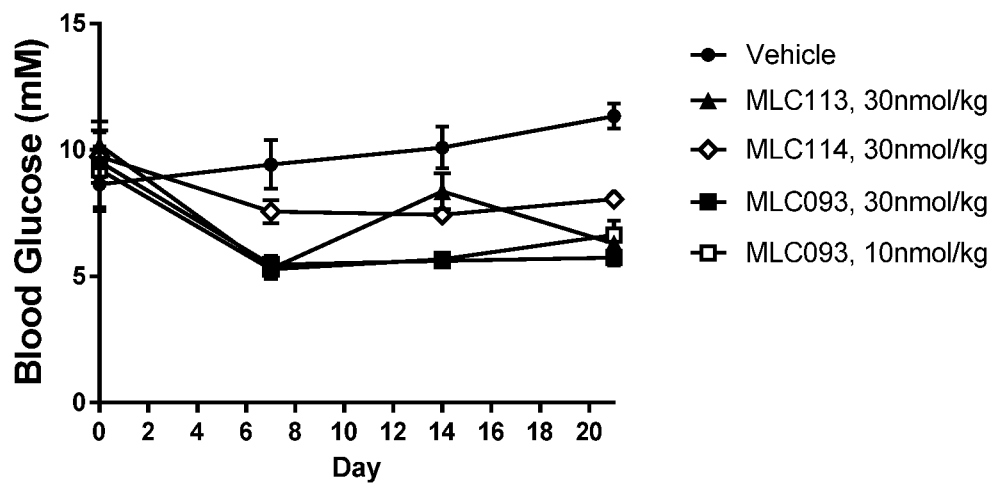
Figure 9D:
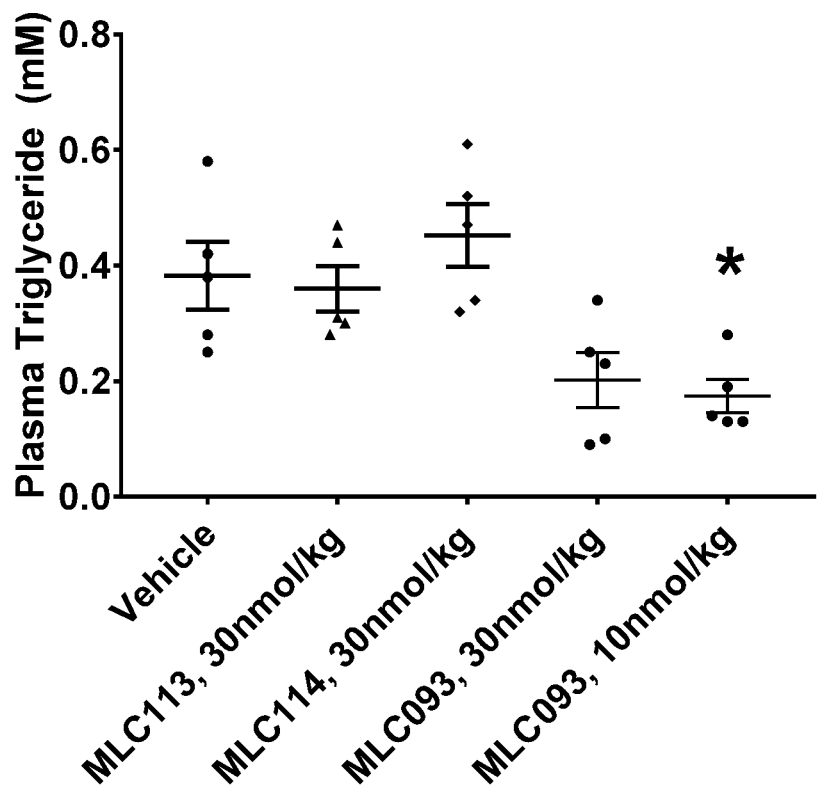
Figure 9E:
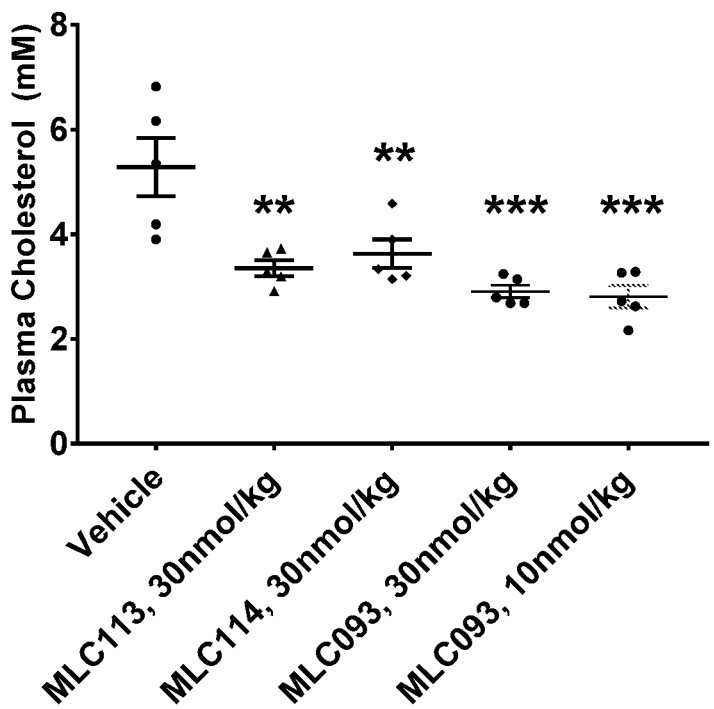
Figure 9F:
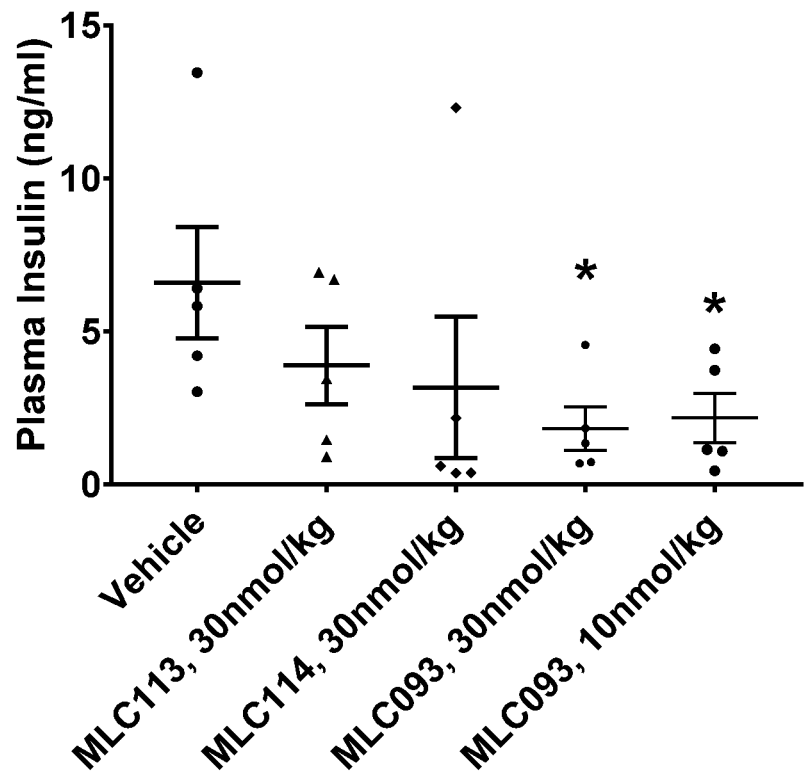
Figure 9G:
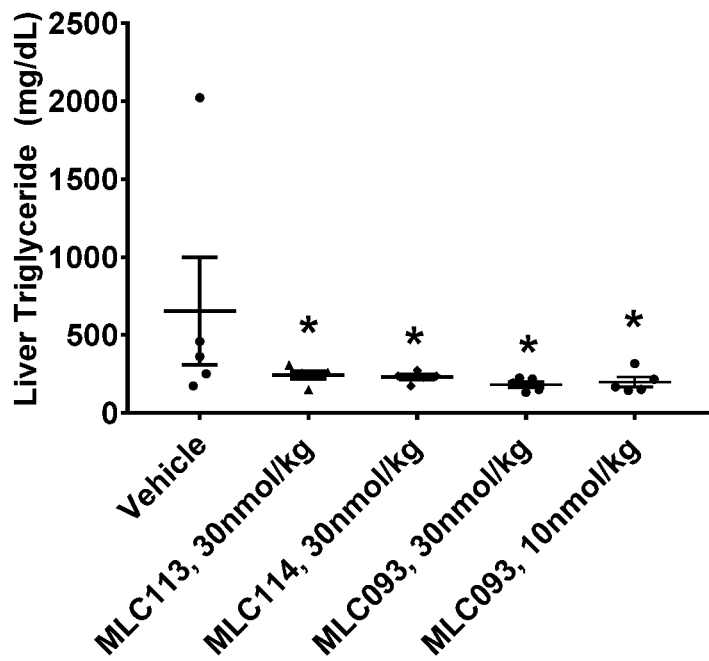

In a separate DIO study, fusion protein conjugate MLC093 demonstrated better body weight reduction, food intake suppression and glucose control than corresponding control molecules having inactivated GLP-1 or GDF15 mutants, i.e. MLC114 and MLC113, respectively (FIG. 9A-C). MLC093 also showed therapeutic efficacy in reducing plasma triglyceride, cholesterol and insulin levels, as well as reduction of liver triglyceride contents (see FIG. 9D-G), relative to vehicle control or corresponding control molecules MLC114 and MLC113.

Method:

Naïve male spontaneously obese cynomolgus monkeys with BMI>40 kg/m$^2$ were injected every three days subcutaneously with designated protein MLC093 for 49 days. Body weight was measured once a week and food intake was measured daily for each monkey. Six animals were used for vehicle or MLC093 1 nmol/kg treamment group and seven animals were used for MLC093 3 nmol/kg or MLC093 10 nmol/kg treamment group. Day 1 and Day 49 are first day and last day of molecule dosage. % BW loss=100*(BW on Day n-BW on Day 1)/(BW on Day 1). Cumulative food intake on Day n represents sum of food intake from Day 1 to Day n. Data are indicated as mean values and standard error (SEM) or pooled values.

Figure 10A:
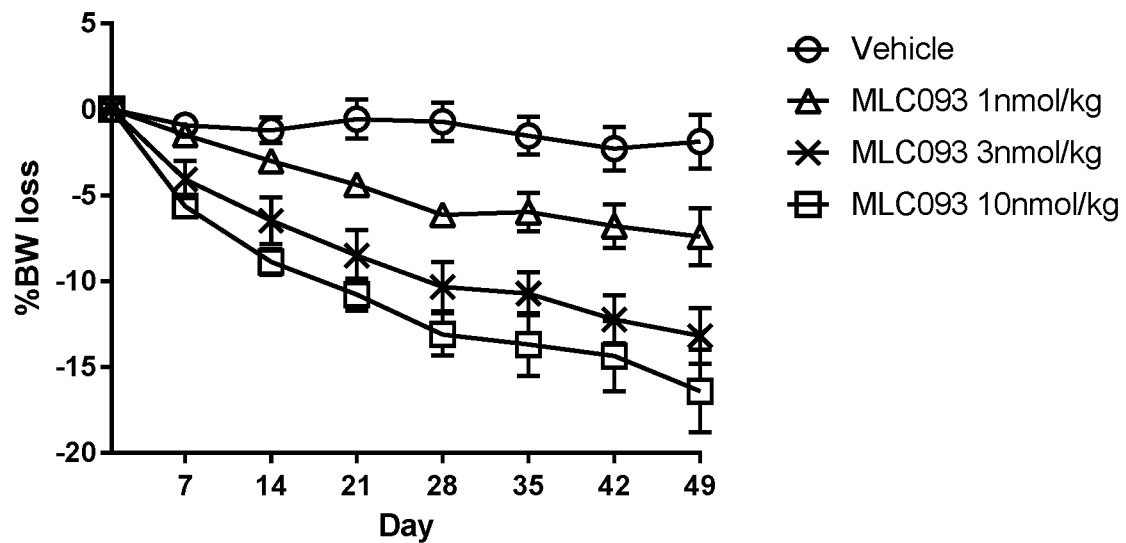
FIGS. 10A-10B show In vivo efficacy in obese monkey. Naïve male spontaneously obese cynomolgus monkeys were injected every three days subcutaneously with designated protein MLC093 with different concentrations for 49 days.
Figure 10B:
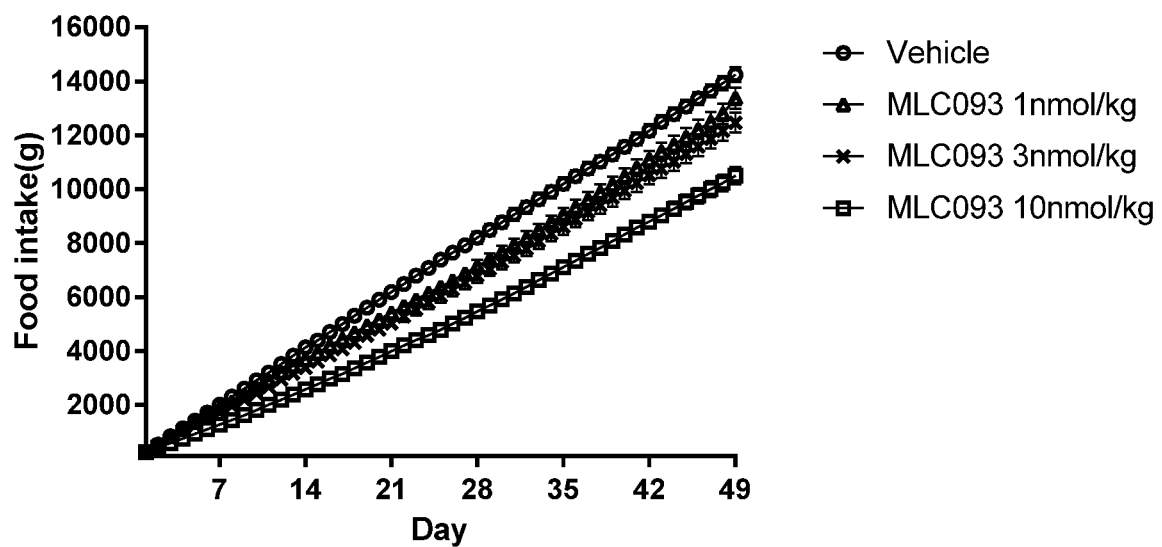

Conclusion:

In obese monkey study, as shown in FIGS. 10A and 10B, different doses (1, 3 and 10 nmol/kg) of fusion protein conjugate MLC093 were tested and all measured doses showed good efficacy on body weight loss and food intake suppression.

Example 10: Stability Study

To test the stability, the different conjugated fusion proteins were formulated in buffers with different compositions (pH6, 7, 7.4 and 8.0) and stored at 4° C. and 37° C. or 40° C. for 2 weeks. The % High Molecular Weight aggregate (HMW) and % Low Molecular Weight (LMW) were analyzed by size exclusion chromatography (SEC)-HPLC. The concentration and modifications were analyzed by reverse phase (RP)-UPLC and LC/MS.

TABLE D

Physical and chemical stability of fusion protein conjugates

| Molecule Code (MLC) | Condition | HMW % | | | Main peak % | | | LMW % | | |
|---|---|---|---|---|---|---|---|---|---|---|
| | | Day 0 | Day 7 | Day 14 | Day 0 | Day 7 | Day 14 | Day 0 | Day 7 | Day 14 |
| 093 | 4.65 mg/mL at 4° C. | 0 | 0 | 0 | 99.56 | 99.46 | 99.6 | 0.43 | 0.51 | 0.39 |
| | 4.65 mg/mL at 37° C. | 0 | 0.53 | 0.8 | 99.56 | 98.86 | 98.6 | 0.43 | 0.56 | 0.53 |
| | 20 mg/mL at 4° C. | 0 | 0 | 0 | 99.6 | 99.49 | 99.24 | 0.38 | 0.49 | 0.44 |
| | 20 mg/mL at 37° C. | 0 | 1.03 | 1.81 | 99.6 | 98.38 | 97.64 | 0.38 | 0.53 | 0.55 |
| | 20 mg/mL at 40° C. | 0.56 | NA | 2.26 | 98.83 | NA | 96.76 | 0.54 | NA | 0.84 |

Conclusion:

As shown in table D, fusion protein conjugates (MLC093) showed high physical and chemical stability at 4° C., 37° C. and 40° C.

Example 11: PK Study in Non-Human Primates

Method:

Cynomolgus monkeys were administrated in a single subcutaneous dose of 5 nmol/kg of the fusion protein conjugates (i.e., MLC004, MLC013, MLC047, MLC093, MLC089, MLC090) (n=2/group). Plasma samples were collected pre-dose (−5 min), 2 hr, 4 hr, 6 hr, 8 hr, 24 hr, 48 hr, 72 hr, 96 hr, 120 hr, 144 hr, 216 hr, 288 hr, 360 hr, 432 hr and 504 hr after the injection. The concentrations of the fusion protein conjugates in the plasma were measured by an ELISA assay which has immunoreactivity towards both GDF15 and intact N-terminal of GLP-1. Based on the graph showing plasma concentration of each protein versus time after subcutaneous injection, the pharmacokinetic parameters (including $T_{max}$, $C_{max}$, $T_{1/2}$, AUC) were calculated by WinNonlin software.

Conclusion:

As shown in Table 9, conjugates having fatty acid at different conjugation positions may have different monkey PK profile. MLC004, MLC013 and MLC047 are conjugates having fatty acid conjugated to a lysine residue. Among the three molecules, MLC047, having fatty acid conjugated to the 41$^{st}$ residue on the linker (41K) showed the longest half life and the highest AUC. MLC089, MLC093 and MLC090 are conjugates having fatty acid conjugated to a cysteine residue (i.e. 39C of the linker, 33C of the linker and 39C of the linker, respectively). All three molecules showed half life above 40 hours, which makes them promising for weekly administration.

TABLE 9

Pharmacokinetic parameters of fusion proteins in monkey.

| Molecule Code (MLC) | $T_{max}$ (hr) | $C_{max}$ (nmol/L) | Terminal $t_{1/2}$ (hr) | $AUC_{0-96\ h}$ (hr * nmol/L) |
|---|---|---|---|---|
| 004 | 8 | 32.1 | 13 | 790 |
| 013 | 7 | 41.3 | 26 | 1435 |
| 047 | 16 | 30.1 | 40 | 1541 |
| 089 | 8 | 70.5 | 54 | 3413 |
| 093 | 16 | 56.2 | 41 | 3843 |
| 090 | 7 | 36.0 | 40 | 1987 |

Example 12: Immunogenicity Assessment

Selected fusion protein conjugates are also assessed for immunogenicity by in silico (iTope and TCED methods) and ex vivo (EpiScreen) methods.

The invention claimed is:

1. A fusion polypeptide comprising, from N terminus to C terminus, GLP-1, a polypeptide linker and GDF15, wherein the polypeptide linker has a length of at least 80 amino acid residues;

wherein the GLP-1 comprises the amino acid sequence of $X_7X_8$EGTFTSDVSSYLE$X_{22}$QAA$X_{26}X_{27}$ FIAWLV$X_{34}$G$X_{36}$G (SEQ ID NO: 325), wherein: the $X_7$ is H; the $X_8$ is A, G, S, V, or Aib; the $X_{22}$ is G, or E; the $X_{26}$ is K, or R; the $X_{27}$ is E; the $X_{34}$ is R, or K, and the $X_{36}$ is K, R, or G; and wherein the GDF15 comprises a combination of substitutions selected from the group consisting of: 1) N3Q, M57L, K69R, K107R, and K91R; 2) N3Q, K69R, K107R, and K91R; 3) K69R, K107R, and K91R; 4) N3Q, M57L, K107R, and K91R; 5) N3Q, K107R, and K91R; 6) K107R, and K91R; 7) N3Q, M57L, K69R, and K91R; 8) Deletion of the first three amino acid residues from the N-terminus of GDF-15 and M57L; 9) N3Q, M57L, M86L, K69R, K107R, K91R; 10) N3Q, M57L; 11) M57L; and 12) M57L, K69R, K107R, K91R, relative to the amino acid sequence of SEQ ID NO: 248, wherein the fusion polypeptide comprises only one conjugatable residue, in which the conjugatable residue is present in the polypeptide linker;

wherein the conjugatable residue is introduced to a position ranging from the $5^{th}$ to the $51^{st}$ residues in the amino acid sequence of the polypeptide linker, with the N terminal residue in the polypeptide linker being the $1^{st}$ residue.

2. The fusion polypeptide of claim 1, wherein the conjugatable residue is cysteine.

3. The fusion polypeptide of claim 2, wherein the GDF15 comprises an amino acid sequence selected from the group consisting of: SEQ ID NO: 247, SEQ ID NO: 246, and SEQ ID NO: 271, and/or the GLP-1 comprises an amino acid sequence selected from the group consisting of: SEQ ID NO: 243, SEQ ID NO: 336, and SEQ ID NO: 478.

4. The fusion polypeptide of claim 3, wherein the fusion polypeptide comprises an amino acid sequence selected from the group consisting of: SEQ ID NOs: 369, 374-381, 392-399, 402-405, 472, 477, and 481.

5. The fusion polypeptide of claim 1, wherein the conjugatable residue is lysine.

6. The fusion polypeptide of claim 5, wherein the $X_{26}$ is R and the $X_{34}$ is R, and wherein the GDF15 comprises substitutions of K91 and K107 to arginine residue, relative to SEQ ID NO: 248.

7. The fusion polypeptide of claim 6, wherein the GDF15 comprises the amino acid sequence of SEQ ID NO: 246 and/or the GLP-1 comprises the amino acid sequence of SEQ ID NO: 244.

8. The fusion polypeptide of claim 7, wherein the fusion polypeptide comprises an amino acid sequence selected from the group consisting of: SEQ ID NOs: 255-256, 258-259, 262, 277-278, 282-283, 330, 359-360, and 370-373.

9. The fusion polypeptide of claim 1, wherein the first conjugatable residue is at least 30 amino acid residues away (inclusive of the conjugatable residue) from the most N-terminal residue of the GDF15.

10. A polypeptide complex comprising a dimer of the fusion polypeptide of claim 1.

11. A polynucleotide encoding the fusion polypeptide of claim 1.

12. A vector comprising the polynucleotide of claim 11.

13. A host cell comprising the vector of claim 12.

14. A conjugate comprising the fusion polypeptide of claim 1 or a dimer of the fusion polypeptide, and a clearance-reducing moiety (CRM), wherein the CRM is conjugated to the conjugatable residue in the fusion polypeptide or in the dimer of the fusion polypeptide, wherein the CRM comprise an albumin-binding moiety.

15. The conjugate of claim 14, wherein the albumin-binding moiety comprises a structure of: *-A-B-C-D-E, wherein A, B, C, D and E are interconnected via amide bonds, and the * end of A is connected to a reactive group of the conjugatable residue on the polypeptide complex, and wherein:

A is selected from a bond,

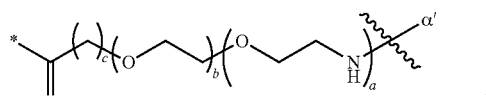

and

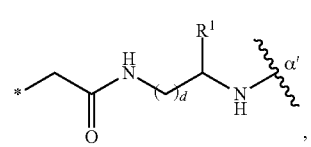

, a, b, c and d are independently an integer from 0 to 4, $R^1$ is hydrogen or —COOH;

B is selected from a bond,

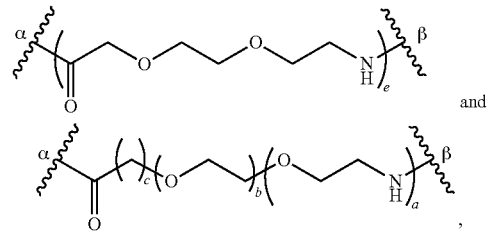

and

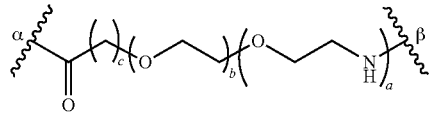

, e is an integer from 1 to 4, wherein position α is linked to the position α',

C is a bond or

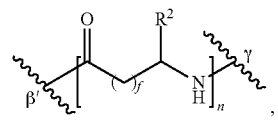

, $R^2$ is —CH$_2$SO$_3$H or —COOH, f is an integer from 1 to 4, n is an integer from 1 to 25, wherein when B is not a bond, then position β' is linked to position β, or when B is a bond, then position β' is linked to position α';

D is selected from a bond,

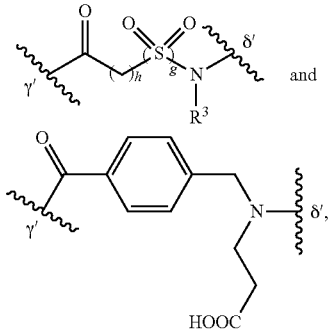

and

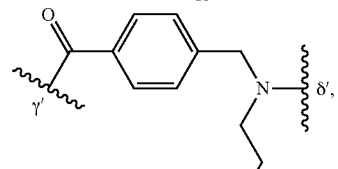

, g and h are independently 0 or 1, and $R^3$ is H or —CH$_2$COOH, wherein:
when B is not a bond and C is a bond, then position γ' is linked to position β;
when C is not a bond, then position γ' is linked to position γ; and
when B is a bond and C is a bond, then position γ' is linked to position α';

E is an acidic group having a formula:

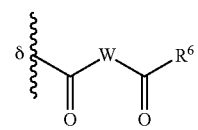

(I)

wherein W represents —(CR$^4$R$^5$)$_j$—,
$R^4$ and $R^5$ are independently selected from the group consisting of hydrogen, halogen, cyano, hydroxyl, alkyl, alkenyl, alkynyl, cycloalkyl, heterocyclyl, aryl, heteroaryl, hydroxyalkyl, amino, aminoalkyl, carboxyl, carboxylalkyl, alkoxy, aryloxy, and carboxamide, $R^6$ is selected from hydroxyl or $NR^7R^8$;

$R^7$ and $R^8$ are independently selected from the group consisting of hydrogen, alkyl, hydroxyl, and

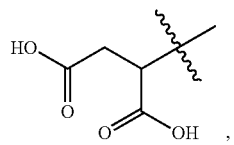 [SMILES: *C(CC(=O)O)C(=O)O]

and l is an integer from 10 to 20, and wherein:

when D is not a bond, then position δ is linked to position δ', when C is not a bond and D is a bond, then position δ is linked to position γ, when B is not a bond, C is a bond and D is a bond, then position δ is linked to position β, when A is not a bond, and all of B, C, and D are bonds, then position δ is linked to position α'.

16. The conjugate of claim 14, wherein the conjugatable residue is lysine, and the CRM comprises the structure of below formula:

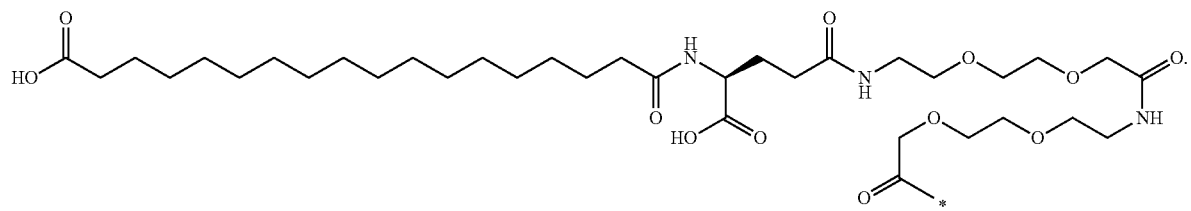 [SMILES: CC(=O)COCCOCCNC(=O)COCCOCCNC(=O)CC[C@H](NC(=O)CCCCCCCCCCCCCCCCC(=O)O)C(=O)O]

17. The conjugate of claim 16, wherein conjugate comprises a dimer of the fusion polypeptide comprising the amino acid sequence of SEQ ID NO: N, and wherein the dimer comprises two CRMs each of which is covalently attached to the m$^{th}$ residue counting in a direction from N terminus to C terminus in the respective fusion polypeptide monomer, with one CRM attached to one residue, wherein the m$^{th}$ residue is lysine (i.e. Km), and wherein:

a) N is 255, m is 37, and Km is K37;
b) N is 262, m is 43, and Km is K43;
c) N is 277, m is 46, and Km is K46;
d) N is 278, m is 43, and Km is K43;
e) N is 282, m is 46, and Km is K46;
f) N is 283, m is 43, and Km is K43;
g) N is 330, m is 71, and Km is K71;
h) N is 340, m is 43, and Km is K43;
i) N is 341, m is 46, and Km is K46;
j) N is 359, m is 82, and Km is K82;
k) N is 360, m is 82, and Km is K82;
l) N is 370, m is 66, and Km is K66;
m) N is 371, m is 60, and Km is K60;
n) N is 372, m is 56, and Km is K56; or
o) N is 373, m is 52, and Km is K52.

18. The conjugate of claim 14, wherein the conjugatable residue is a cysteine residue, and the CRM comprises the structure of below formula:

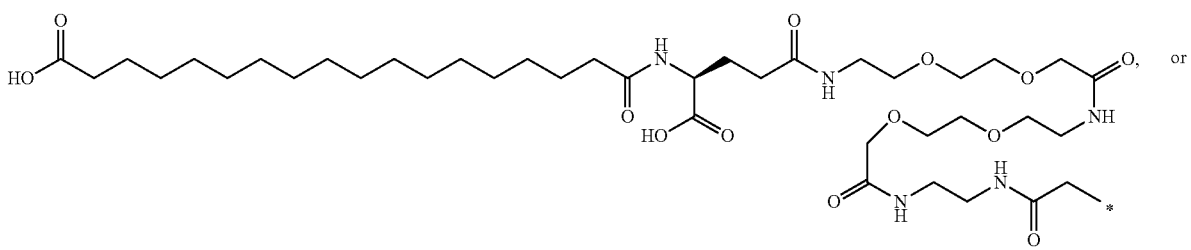

-continued

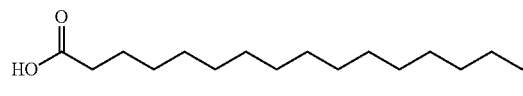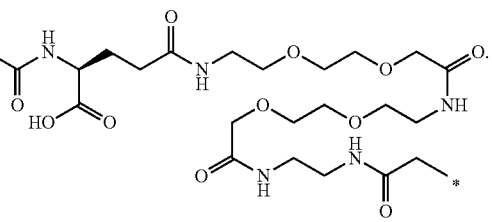

19. The conjugate of claim 14, wherein conjugate provided herein comprises a dimer of the fusion polypeptide comprising the amino acid sequence of SEQ ID NO: Y, and wherein the dimer comprises two CRMs each of which is covalently attached to the $z^{th}$ residue counting in a direction from N terminus to C terminus in the respective fusion polypeptide monomer, with one CRM attached to one residue, wherein the $z^{th}$ residue is cysteine (i.e. Cz), and wherein:
- a) Y is 369, z is 72, and Cz is C72;
- b) Y is 374, z is 66, and Cz is C66;
- c) Y is 375, z is 82, and Cz is C82;
- d) Y is 376, z is 70, and Cz is C70;
- e) Y is 377, z is 68, and Cz is C68;
- f) Y is 378, z is 72, and Cz is C72;
- g) Y is 379, z is 70, and Cz is C70;
- h) Y is 380, z is 66, and Cz is C66;
- i) Y is 381, z is 64, and Cz is C64;
- j) Y is 392, z is 48, and Cz is C48;
- k) Y is 393, z is 52, and Cz is C52;
- l) Y is 394, z is 56, and Cz is C56;
- m) Y is 395, z is 62, and Cz is C62;
- n) Y is 396, z is 56, and Cz is C56;
- o) Y is 397, z is 76, and Cz is C76;
- p) Y is 398, z is 82, and Cz is C82;
- q) Y is 399, z is 60, and Cz is C60;
- r) Y is 402, z is 64, and Cz is C64;
- s) Y is 403, z is 70, and Cz is C70;
- t) Y is 404, z is 64, and Cz is C64;
- u) Y is 405, z is 70, and Cz is C70;
- v) Y is 472, z is 36, and Cz is C36; or
- w) Y is 477, z is 64, and Cz is C64.

20. A pharmaceutical composition comprising the conjugate of claim 14, and a pharmaceutically acceptable carrier.

21. A method of treating a metabolic disorder in a subject in need thereof, comprising administering a therapeutically effective amount of the conjugate of claim 14.

22. The method of claim 21, wherein the metabolic disorder is diabetes, obesity, non-alcoholic steatohepatitis (NASH), cardiovascular disorders like dyslipidemia, artherosclerosis, alcoholic steatohepatitis (ASH), diabetic nephropathy, gestational diabetes, metabolic syndrome such as metabolic syndrome X, nonalcoholic fatty liver disease (NAFLD), end-stage liver disease, hepatic steatosis (fatty liver), liver cirrhosis, or primary biliary cirrhosis (PBC).

23. The fusion polypeptide of claim 1, wherein the $X_7$ is H, the $X_8$ is G, the $X_{22}$ is E; the $X_{26}$ is K, or R; the $X_{27}$ is E; the $X_{34}$ is K, or R, and the $X_{36}$ is R, or G.

24. The fusion polypeptide of claim 1, wherein the GLP-1 comprises no more than 5 substitutions relative to SEQ ID NO: 242 while retaining substantial biological activity of SEQ ID NO: 242, and wherein the $X_7$ is H; the $X_8$ is A, G, or Aib; the $X_{22}$ is G, or E; the $X_{26}$ is R; the $X_{27}$ is E; the $X_{34}$ is R, and the $X_{36}$ is G.

25. The fusion polypeptide of claim 1, wherein the GLP-1 comprises an amino acid sequence selected from the group consisting of SEQ ID NO: 243, SEQ ID NO: 244, SEQ ID NO: 336, and SEQ ID NO: 478.

26. The fusion polypeptide of claim 1, wherein the GDF15 comprises an amino acid sequence selected from the group consisting of SEQ ID NO: 246, SEQ ID NO: 247, SEQ ID NO: 271, SEQ ID NO: 290, SEQ ID NO: 293, SEQ ID NO: 295, SEQ ID NO: 451, and SEQ ID NO: 480.

* * * * *